US008273762B2

(12) United States Patent
Apodaca et al.

(10) Patent No.: US 8,273,762 B2
(45) Date of Patent: Sep. 25, 2012

(54) HEXAHYDRO-PYRROLO-ISOQUINOLINE COMPOUNDS

(75) Inventors: Richard Apodaca, La Jolla, CA (US); Ann J. Barbier, Cambridge, MA (US); Nicholas I. Carruthers, Poway, CA (US); Leslie A. Gomez, San Diego, CA (US); John M. Keith, San Diego, CA (US); Timothy W. Lovenberg, San Diego, CA (US); Ronald L. Wolin, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 297 days.

(21) Appl. No.: 12/792,675

(22) Filed: Jun. 2, 2010

(65) Prior Publication Data
US 2010/0240648 A1   Sep. 23, 2010

Related U.S. Application Data

(62) Division of application No. 11/424,734, filed on Jun. 16, 2006, now Pat. No. 7,754,882.

(60) Provisional application No. 60/691,958, filed on Jun. 17, 2005.

(51) Int. Cl.
C07D 487/02 (2006.01)
A61K 31/4353 (2006.01)

(52) U.S. Cl. ............................ 514/294; 546/94; 546/111

(58) Field of Classification Search .................... 546/94, 546/111; 514/294
See application file for complete search history.

(56) References Cited

U.S. PATENT DOCUMENTS

| 4,113,869 | A | 9/1978 | Gardner |
| 6,162,417 | A | 12/2000 | Goodman et al. |
| 2006/0194837 | A1 | 8/2006 | Carruthers |
| 2006/0287292 | A1 | 12/2006 | Carruthers |

FOREIGN PATENT DOCUMENTS

| EP | 0130069 A | 1/1985 |
| EP | 1113007 A1 | 7/2001 |
| WO | WO 01/32624 A1 | 5/2001 |

OTHER PUBLICATIONS

Alves-Rodrigues, A. et al. Pharmacological Characterisation of the Histamine $H_3$ Receptor in the Rat Hippocampus. Brain Res. 1998, 788(1-2), 179-186.
Arrang, J.-M. et al. Auto-Inhibition of Brain Histamine Release by a Novel Class ($H_3$) of Histamine Receptor. Nature (London) 1983, 302(5911), 832-837.
Berge, S.M. et al. Pharmaceutical Salts. J. Pharm. Sci., 1977, 66(1):1-19.
Blandizzi, C. et al. Histamine $H_3$ Receptors Mediate Inhibition of Noradrenaline Release from Intestinal Symphathetic Nerves. Br. J. Pharmacol. 2000, 129(7), 1387-1396.
Bonnet, U. Moclobemide: E volution, Pharmacodynamic, and Pharmacokinetic Properties. CNS Drug Rev. 2002, 8(3), 283-308.
Chen, Z. Effect of histamine H3-receptor antagonist clobenpropit on spatial memory of radial maze performance in rats. Acta Pharmacol. Sin. 2000, 21(10), 905-910.
Cheng, Y-C et al.: Relationship Between the Inhibition Constant ($K_1$) and the Concentration of Inhibitor Which Causes 50 Per Cent Inhibition ($I_{50}$) of an Enzymatic Reaction*. Biochemical Pharmacology, vol. 22 (1973), 3099-3108.
Darmani, N.A. And S.L. Reeves. The Mechanims by which the Selective 5-$HT_{1A}$ Receptor Antagonist S-(-)UH 301 Produces Head-Twitches in Mice. Pharmacol., Biochem. Behav. 1996, 55(1), 1-10.
Fink, K. et al. Involvement of Presynaptic $H_3$ Receptors in the Inhibitory Effect of Histamine on Serotonin Release in the Rat Brain Cortex. Naunyn-Schmiedeberg's Arch. Pharmacol. 1990, 342(5), 513-519.
Fox, G.B. et al. Effects of Histamine $H_3$ Receptor Ligands GT-2331 and Ciproxifan in a Repeated Acquisition Avoidance Response in the Spontaneously Hypertensive Rat Pup. Behav. Brain Res. 2002, 131(1-2), 151-161.
Fox, G.B. et al. Differential in Vivo Effects of $H_3$ Receptor Ligands in a New Mouse Dipsogenia Model. Pharmacol., Biochem. Behav. 2002, 72, 741-750.
Griffiths, R.I. et al. Medical Resource Use and Cost of Venlaxafine or Tricyclic Antidepressant Therapy. Pharmacoeconomics 1999, 15(5), 495-505.
Hatta, E. et al. Activation of Histamine $H_3$ Receptors Inhibits Carrier-Mediated Norepinephrine Release in a Human Model of Protracted Myocardial Infarction. J. Pharmacol. Exp. Ther. 1997, 283(2), 494-500.
Hill, S.J. et al. International Union of Pharmacology. XIII. Classification of Histamine Receptors. Pharmacol. Rev. 1997, 49(3), 253-278.
Kelly, S.A. et al.: A convergent approach to huperzine A and analogues. Org. Biomol. Chem. 2003, 1, 2865-2876.
Kraly, F.S. et al. $H_1$, $H_2$, and $H_3$ Receptors Contribute to Drinking Elicited by Exogenous Histamine and Eating in Rats. Pharmacol., Biochem. Behav. 1996, 53(2), 347-354.
Laitinen, K.S.M. et al. Endogenous Serotonin Modulates Histamine Release in the Hypothalamus as Measured by in Vivo Microdialysis. Eur. J. Pharmacol. 1995, 285(2), 159-164.
Lamberti, C. et al. Antidepressant-like Effects of Endogenous Histamine and of Two Histamine $H_1$ Receptor Agonists in the Mouse Forced Swim Test. Br. J. Pharmacol. 1998, 123(7), 1331-1336.
Leurs, R. et al. Histamine Homologues Discriminating between Two Functional H3 Receptor Assays. Evidence for $H_3$ Receptor Homogeneity? J. Pharmacol. Exp. Ther. 1996, 276(3), 1009-1015.
Lin, J.-S. et al. Involvement of Histaminergic Neurons in Arousal Mechanisms Demonstrated with $H_3$-Receptor Ligands in the Cat. Brain Res. 1990, 523(2), 325-330.
Lovenberg, T.W. et al. Cloning and Functional Expression of the Human Histamine $H_3$ Receptor. Molec. Pharmacol. 1999, 55(6), 1101-1107.

(Continued)

Primary Examiner — Rita Desai
(74) Attorney, Agent, or Firm — Michael J. Atkins

(57) ABSTRACT

Certain hexahydro-pyrrolo-isoquinoline compounds are histamine $H_3$ receptor and serotonin transporter modulators useful in the treatment of histamine $H_3$ receptor- and serotonin-mediated diseases.

17 Claims, 1 Drawing Sheet

OTHER PUBLICATIONS

Lovenberg, T.W. Cloning of Rat Histamine H3 Receptor Reveals Distinct Species Pharmacological Profiles. *J. Pharmacol. Exp. Ther.* 2000, 293, 771-778.

Maryanoff, B.E. et al.: Pyrroloisoquinoline Antidepressants. 2. In-Depth Exploration of Structure-Activity Relationships. *J. Med. Chem.*, vol. 30(8) (1987), 1433-1454. XP000941930.

Maryanoff, B.E. et al.: Pyrroloisequinoline Antidepressants. 3. A Focus on Serotonin. *J. Med. Chem*, vol. 33 (1990), 2793-2797. XP002398543.

Menza, M.A. et al. Modafinil Augmentation of Antidepressant Treatment in Depression. *J. Clin. Psych.* 2000, 61(5), 378-381.

Monti, J.M. et al. Effects of Selective Activation or Blockade of the Histamine $H_3$ Receptor on Sleep and Wakefulness. *Eur. J. Pharmacol.* 1991, 205(3), 283-287.

Monti, J.M. et al. Sleep and Waking during Actue Histamine $H_3$ Agonist BP 2.94 or H3 Antagonist Carboperamide (MR 16155) Administration in Rats. *Neuropsychopharmacology* 1996, 15(1), 31-35.

Miyazaki, S. et al. Effects of Thioperamide on the cholinergic system and the step-through passive avoidance test in mice. *Meth. Find. Exp. Clin. Pharmacol.* 1995, 17(10), 653-658.

Miyazaki, S. et al. Effects of Thioperamide, A Histamine $H_3$-Receptor Antagonist, on a Scopolamine-Induced Learning Deficit Using an Elevated Plus-Maze Test in Mice. *Life Sci.* 1995, 57(23), 2137-2144.

Olver, J.S. et al. Third Generation Anti-depressants: Do They Offer Advantages over the SSRIs? *CNS Drugs* 2001, 15(12), 941-954.

Orsetti, M. et al. Histamine $H_3$-Receptor Antagonism Improves Memory Retention and Reverses the Cognitive Deficit Induced by Scopolamine in a Two-Trial Place Recognition Task. *Behav. Brain Res.* 2001, 124(2), 235-242.

Parent, M. et al. Analysis of Amino Acids and Catecholamines, 5-Hydroxytryptamine and Their Metabolites in Brain Areas in the Rat Using in Vivo Microdialysis. Methods 2001, 23(1), 11-20.

Perez-Garcia, C. et al. Effects of Histamine $H_3$ Receptor Ligands in Experimental Models of Anxiety and Depression. *Psychopharmacology* 1999, 142(2), 215-220.

Riemann, D. et al. Sleep and Sleep-Wake Manipulations in Bipolar Depression. *Neuropsychobiology* 2002, 45(Suppl. 1), 7-12.

Schlicker, E. et al. Histamine H3 Receptor-Mediated Inhibition of Serotonin Release in the Rat Brain Cortex. *Naunyn-Schmiedeberg's Arch. Pharmacol.* 1988, 337(5), 588-590.

Sharpley, A.L., and P.J. Cowen. Effects of Pharmacologic Treatments on the Sleep of Depressed Patients. *Biol. Psych.* 1995, 37(2), 85-98.

Tomita, T. et al.: Structure-Activity Relationships of Dopamine- and Norepinephrine-Uptake Inhibitors. Chem. Pharm. Bull., vol. 38(6), (1990), 1563-1569. XP 002047151.

Greene et al Protective Groups in Organic Synthesis 3DR ED 1990 TW Greene & PGM Wuts Eds John Wiley & Sons 1999.

Mcomie Protective Groups in Organic Chemistry 1973 Plenum Press JFW Mcomie Eds.

Dorwald et al Side Reactions in Organic Synthesis 2005 Wiley VCH Weinheim PG IX Preface.

PCT Search Report for PCT/US/2006/023552 Dated Sep. 29, 2008.

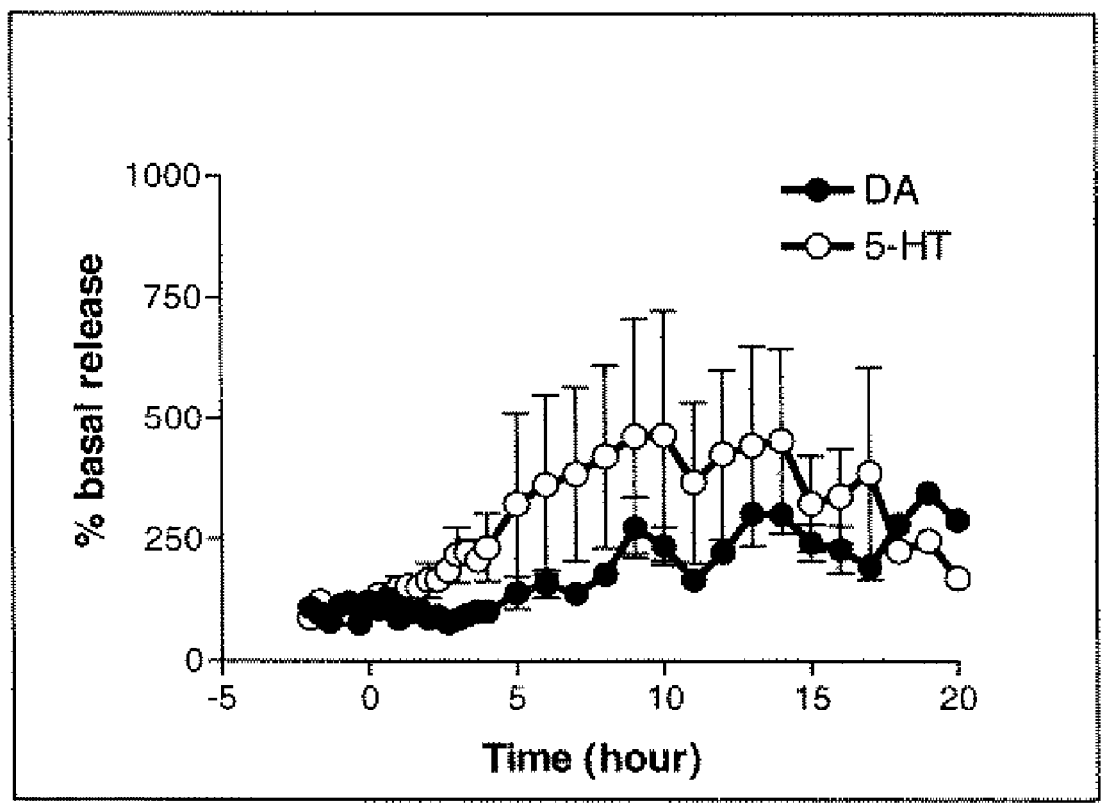

HEXAHYDRO-PYRROLO-ISOQUINOLINE COMPOUNDS

CROSS REFERENCE TO RELATED APPLICATION

This application is a divisional of U.S. Ser. No. 11/424,734 filed on Jun. 16, 2006 now U.S. Pat. No. 7,754,882, which claims the benefit under 35 USC §119(e) of the following provisional application: U.S. Ser. No. 60/691,958 filed on Jun. 17, 2005. The complete disclosures of the aforementioned related U.S. patent applications are hereby incorporated herein by reference for all purposes.

FIELD OF THE INVENTION

There is provided by the present invention compounds that are modulators of the histamine $H_3$ receptor and the serotonin transporter. More particularly, there is provided by the present invention hexahydro-pyrrolo-isoquinoline compounds and methods for using them to treat disorders and conditions mediated by the histamine $H_3$ receptor and the serotonin transporter. As a consequence of these activities the compounds of the present invention will have therapeutic utility for the treatment of depression and a range of related disorders.

BACKGROUND OF THE INVENTION

Depression is a chronic illness with an estimated lifetime prevalence of 17%. The total annual cost of depression in the USA is estimated at $44 billion. As such, it represents a major health problem with a serious pharmacoeconomic impact (Griffiths, R. I. et al. *Pharmacoeconomics* 1999, 15(5), 495-505). Although the biochemical basis of depression is not completely elucidated, the most commonly accepted hypothesis states that depression occurs when monoaminergic neurotransmission in the brain is impaired. This theory is largely based on the observation that compounds that improve noradrenergic and/or serotoninergic neurotransmission often have beneficial effects in depression. Such an improvement in monoaminergic neurotransmission can be achieved in several ways. The biological effect of noradrenaline is terminated by two mechanisms: reuptake from the synaptic cleft into the neuron via the norepinephrine transporter (NET), and degradation by monoamine oxidase (MAO). For serotonin, reuptake in the neuron via the serotonin transporter (SERT) likewise limits its availability in the synaptic cleft.

Currently, clinical treatment of depression relies mainly on four types of drugs: 1) MAO inhibitors; 2) tricyclic antidepressants (TCA); 3) selective serotonin reuptake inhibitors (SSRI); and 4) other drugs such as reboxetine and venlafaxine. MAOs have long been used as second-line drugs because of their potentially dangerous side effects, and more recently, reversible MAO-A selective inhibitors with improved profiles have been described (Bonnet, U. *CNS Drug Rev.* 2002, 8(3), 283-308). TCAs such as amitryptiline display complex pharmacological activities. They inhibit reuptake of noradrenaline and serotonin via their respective transporters, but also have affinity at muscarinic and histamine $H_1$ receptors. Thus, their efficacy in treating depression is counterbalanced by numerous unwanted side effects. The SSRIs, which represent the largest and most successful group of antidepressants, show a higher selectivity for the SERT than for the NET, although the exact affinity ratio varies from drug to drug. This class of drugs is characterized by a milder side-effect profile than the MAO-inhibitors or the TCAs. Other drugs have been described, such as reboxetine, which preferentially targets the NET, and venlafaxine, which has dual activity at the SERT and NET (Olver, J. S. et al. *CNS Drugs* 2001, 15(12), 941-954).

Although remarkable progress has been made in the treatment of depression, there remains opportunity for improvement. The delay between start of treatment and subjective improvement is a case in point. Most drugs do not cause an improvement in the Hamilton Rating Scale for Depression until after several weeks of treatment, potentially leaving the patient subject to severe mental anguish during this time. Currently available drugs have a limited response rate and in most clinical trials only about 30% of patients show clinical improvement (Menza, M. A. et al. *J. Clin. Psych.* 2000, 61(5), 378-381). Psychiatrists frequently have to evaluate several drugs for individual patients before a satisfactory therapeutic response is observed. Consequently there is a significant therapeutic need for drugs with a faster onset of action, improved side effect profiles and higher response ratio.

In order to appreciate the rationale for a combined SERT/$H_3$ antagonist, it is necessary to understand the physiology of the histamine $H_3$ receptor. This receptor was described in 1983 (Arrang, J.-M. et al. *Nature (London)* 1983, 302(5911), 832-837) as a presynaptic, auto-inhibitory receptor on histaminergic neurons with a characteristic pharmacology. Activation of the $H_3$ receptor was shown to decrease the amount of histamine released from the nerve terminals and to inhibit the activity of histidine decarboxylase, the rate-limiting enzyme in the synthesis of histamine. The cloning and characterization of the human $H_3$ receptor made it possible to explore its pharmacology (Lovenberg, T. W. et al. *Molec. Pharmacol.* 1999, 55(6), 1101-1107). It is now known that the $H_3$ receptor is expressed on a variety of neurons and thus, when activated, decreases the release of a number of other neurotransmitters including noradrenaline, dopamine, and acetylcholine (Hill, S. J. et al. *Pharmacol. Rev.* 1997, 49(3), 253-278). For the purpose of this discussion, we will focus on its known effects on the release of the neurotransmitters involved in depression, noradrenaline and serotonin. Although the serotoninergic cell bodies are found in the dorsal raphe nucleus while the histaminergic cells are located in the tuberomammillary nucleus of the hypothalamus, both systems have extensive projections throughout the brain. In several regions, such as the suprachiasmatic nucleus (Laitinen, K. S. M. et al. *Eur. J. Pharmacol.* 1995, 285(2), 159-164) and striatum both neurotransmitters are present. It is known that activation of the $H_3$ receptor leads to a decreased release of serotonin, for instance in rat cortex slices (Fink, K. et al. *Naunyn-Schmiedeberg's Arch. Pharmacol.* 1990, 342(5), 513-519; Schlicker, E. et al. *Naunyn-Schmiedeberg's Arch. Pharmacol.* 1988, 337(5), 588-590). Functional antagonists of the $H_3$ receptor lead to an increased release of noradrenaline in the central (mouse cortex slices, Leurs, R. et al. *J. Pharmacol. Exp. Ther.* 1996, 276(3), 1009-1015; the rat hippocampus, Alvez-Rodrigues, A. et al. *Brain Res.* 1998, 788(1-2), 179-186) and peripheral nervous system (human myocardial nerves, Hatta, E. et al. *J. Pharmacol. Exp. Ther.* 1997, 283(2), 494-500; guinea-pig intestinal sympathetic nerves, Blandizzi, C. et al. *Br. J. Pharmacol.* 2000, 129(7), 1387-1396). However, there is little evidence that $H_3$ receptor antagonists alone are capable of increasing serotonin levels in vivo to those required for antidepressant effects. Microdialysis studies of the effect of $H_3$ antagonists on serotonin levels in the brain of live animals are lacking. There are sparse reports indicating that thioperamide, an $H_3$ receptor antagonist, may have an antidepressant effect per se in the mouse or rat forced swim test (Lamberti, C. et al. *Br. J.*

Pharmacol. 1998, 123(7), 1331-1336; Perez-Garcia, C. et al. Psychopharmacology 1999, 142(2), 215-220).

The rationale for combining $H_3$ receptor blockade and SERT activity in one single molecule is the expectation that both mechanisms will contribute synergistically to enhanced concentrations of serotonin in the synaptic cleft. Antagonism at the $H_3$ receptor will provide increased release of serotonin-containing vesicles into the synaptic cleft, and concomitant blockade of the SERT will decrease the neuronal reuptake of these neurotransmitter molecules. Thus, higher concentrations of serotonin will be achieved, leading to an enhanced therapeutic effect.

Among the prominent vegetative symptoms of depression are disturbed sleep and the daytime fatigue associated with it. Polysomnographic investigations have shown severe disturbances in the sleep architecture of depressed patients. Among the typical abnormalities observed are: discontinuous sleep, decreased slow-wave sleep, shorter latency to REM sleep and an increased intensity and duration of REM sleep (Riemann, D. et al. *Neuropsychobiology* 2002, 45(Suppl. 1), 7-12). It is believed that suppression of REM sleep is involved in antidepressant efficacy. This is illustrated by the dramatic success of overnight deprivation of (REM) sleep (Riemann et al. 2002). Another non-pharmacological treatment for depression, electroconvulsant therapy, likewise decreases REM sleep. Virtually all of the available antidepressant drugs, regardless of their neurochemical mechanism of action, suppress REM sleep, nefazodone (a 5-$HT_{2A}$ antagonist) being the exception (Sharpley, A. L., Cowen, P. J. *Biol. Psych.* 1995, 37(2), 85-98). Antidepressant drugs also affect slow-wave-sleep, although in a less clear manner. $H_3$ antagonists share this REM-sleep suppressing property and one of the main biological effects of histamine $H_3$ antagonists is to improve wakefulness. Administration of $H_3$ antagonists has been shown to decrease REM and non-REM sleep in several animal species. For example, the $H_3$ antagonist carboperamide induces waking in rats (Monti, J. M. et al. *Neuropsychopharmacology* 1996, 15(1), 31-35). Another $H_3$ antagonist, thioperamide, decreased both REM and non-REM sleep in rats (Monti, J. M. et al. *Eur. J. Pharmacol.* 1991, 205(3), 283-287) and cats (Lin, J.-S. et al. *Brain Res.* 1990, 523(2), 325-330). It is of interest to note that although $H_3$ antagonists promote wakefulness, they do so much less potently than amphetamine derivatives. They may thus be considered mild stimulants. The daytime correlate of disturbed sleep is fatigue. Indeed, fatigue and lethargy are prominent symptoms of depression, and there is considerable interest in the use of stimulants to augment antidepressant therapy (Menza et al., 2000). However, most of the available stimulants, like the amphetamine derivatives and methylphenidate, carry a considerable risk of abuse and are not ideal therapeutic choices. Modafinil, a wake-promoting compound of unknown mechanism with a lower addictive potential, is marketed for the treatment of narcolepsy. In a small series of patients it was shown that addition of a low dose of modafinil to traditional antidepressant therapy resulted in a faster onset of action. Fatigue was particularly responsive to this therapy, but the cognitive and physical subscales of the Hamilton Rating Scale for Depression also improved (Menza et al., 2000). The behavioral profile of $H_3$ antagonists (suppression of sleep with no stimulation of locomotor activity and limited addictive potential) is much like that of modafinil. Therefore, a combined $H_3$/SSRI compound would provide symptomatic relief for the fatigue during the first weeks of treatment, before the mood-elevating effect of the SSRI can be noticed.

Depression is also associated with a number of cognitive symptoms such as impaired memory and concentration difficulties. $H_3$ antagonists have been shown to improve memory in a variety of memory tests, including the elevated plus maze in mice (Miyazaki, S. et al. *Life Sci.* 1995, 57(23), 2137-2144), a two-trial place recognition task (Orsetti, M. et al. *Behav. Brain Res.* 2001, 124(2), 235-242), the passive avoidance test in mice (Miyazaki, S. et al. *Meth. Find. Exp. Clin. Pharmacol.* 1995, 17(10), 653-658) and the radial maze in rats (Chen, Z. *Acta Pharmacol. Sin.* 2000, 21(10), 905-910). Also, in the spontaneously hypertensive rat, an animal model for the learning impairments in attention-deficit disorders, $H_3$ antagonists were shown to improve memory (Fox, G. B. et al. *Behav. Brain Res.* 2002, 131(1-2), 151-161). Although no human studies are available, the evidence indicates that a combined SERT/$H_3$ antagonist will provide additional benefit in combating the cognitive impairments associated with depression.

In summary, the combination of $H_3$ receptor antagonism with SERT activity will result in the production of drugs with an improved antidepressant profile compared to an SSRI alone. These drugs will be especially efficacious in ameliorating the symptoms of fatigue, disturbed sleep and memory loss associated with depression.

The features and advantages of the invention are apparent to one of ordinary skill in the art. Based on this disclosure, including the summary, detailed description, background, examples, and claims, one of ordinary skill in the art will be able to make modifications and adaptations to various conditions and usages. Publications described herein are incorporated by reference in their entirety.

References cited herein, including U.S. Patent Appl. No. 60/637,173, U.S. patent application Ser. No. 11/300,880, and U.S. Provisional Appl. No. 60/692,003, are incorporated by reference in their entirety.

SUMMARY OF THE INVENTION

The invention features a compound of formula (I):

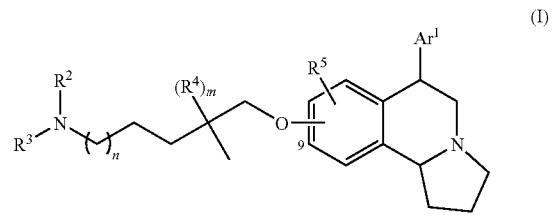

wherein n is 0 or 1;

m is 0, 1, or 2;

$R^2$ and $R^3$ are independently selected from —H, or from the group consisting of:

A) —$C_{1-6}$alkyl, —$C_{3-6}$alkenyl, —$C_{3-6}$alkynyl, —$C_{3-7}$cycloalkyl, —$C_{1-6}$alkyl$C_{3-7}$cycloalkyl, benzyl;

B) phenyl or pyridyl, optionally fused at two adjacent carbon ring members to a three- or four-membered hydrocarbon moiety to form a fused five- or six-membered aromatic ring, which moiety has one carbon atom replaced by >O, >S, >NH, or >N($C_{1-4}$alkyl), and which moiety has up to one additional carbon atom optionally replaced by —N═;

C) a 4-8 membered heterocyclic ring, said heterocyclic ring having a carbon atom which is the point of attachment, having 1 or 2 heteroatom members selected from >O, >S(O)$_{0-2}$, and >NH, and having 0 or 1 double bonds; and D) a monocyclic aromatic hydrocarbon group having five or six ring atoms, having a carbon atom which is the point of attachment, having one carbon atom replaced by >O, >S, >NH, or >N($C_{1-4}$alkyl), having up to one additional carbon atom optionally replaced by —N=, and optionally benzofused or pyridofused;

where each of A)-D) is optionally mono-, di-, or tri-substituted with a moiety selected from the group consisting of —OH, —$C_{1-4}$alkylOH, —$OC_{1-6}$alkyl, —CN, —$NO_2$, —N($R^d$)$R^e$ (wherein $R^d$ and $R^e$ are independently —H or —$C_{1-6}$alkyl), —C(O)N($R^d$)$R^e$, —N($R^d$)C(O)$R^d$, —N($R^d$)$SO_2C_{1-6}$alkyl, —C(O)$C_{1-6}$alkyl, —S(O)$_{0-2}$—$C_{1-6}$alkyl, —$SO_2$N($R^d$)$R^e$, —$SCF_3$, halo, —$CF_3$, —$OCF_3$, —COOH, —$COOC_{1-6}$alkyl, —OC(O)N($R^d$)$R^e$, and —OC(O)O$R^d$;

or, alternatively, $R^2$ and $R^3$ may be taken together with the nitrogen to which they are attached to form a 4-8 membered heterocyclic ring, said heterocyclic ring having 0 or 1 additional heteroatom members separated from the nitrogen of attachment by at least one carbon member and selected from >O, >S(O)$_{0-2}$, >NH, and >N$R^f$, having 0 or 1 double bonds, having 0, 1, or 2 carbon members separated from the nitrogen of attachment by at least one carbon member which is a carbonyl, optionally benzo or pyrido fused, optionally having one carbon member that forms a bridge, and having 0-5 carbon member substituents $R^{ff}$, $R^f$ is selected from the group consisting of —$C_{1-6}$alkyl optionally mono-, di-, or tri-substituted with halo, —$C_{3-6}$alkenyl, —$C_{3-6}$alkynyl, —$C_{3-7}$cycloalkyl, —$C_{1-6}$alkyl$C_{3-7}$cycloalkyl, —$C_{2-6}$alkylOH, —C(O)N($R^g$)$R^h$ (wherein $R^g$ and $R^h$ are independently —H or —$C_{1-6}$alkyl), —C(O)$R^i$ (where $R^i$ is —$C_{1-6}$alkyl, —$C_{3-8}$cycloalkyl, phenyl, or 5- or 6-membered aromatic heterocyclyl, each optionally mono-, di-, or tri-substituted with —$C_{1-3}$alkyl, —OH, —$OC_{1-6}$alkyl, —$CF_3$, or halo), —S(O)$_{0-2}$—$C_{1-6}$alkyl, and —$COOC_{1-6}$alkyl;

$R^{ff}$ is selected from the group consisting of —$C_{1-6}$alkyl optionally mono-, di-, or tri-substituted with halo, —$C_{2-6}$alkenyl, —$C_{2-6}$alkynyl, —$C_{3-7}$cycloalkyl, —$C_{1-6}$alkyl$C_{3-7}$cycloalkyl, halo, —OH, —$C_{1-6}$alkylOH, —$OC_{1-6}$alkyl, —$OC_{2-3}$alkylO—, —CN, —$NO_2$, —N($R^g$)$R^h$ (wherein $R^g$ and $R^h$ are independently —H or —$C_{1-6}$alkyl), —C(O)N($R^g$)$R^h$, —N($R^g$)C(O)$R^g$, —N($R^g$)$SO_2C_{1-6}$alkyl, —C(O)$R^i$ (where $R^i$ is —$C_{1-6}$alkyl, —$C_{3-8}$cycloalkyl, phenyl, or 5- or 6-membered aromatic heterocyclyl, each optionally mono-, di-, or tri-substituted with —$C_{1-3}$alkyl, —OH, —$OC_{1-6}$alkyl, —$CF_3$, or halo), —S(O)$_{0-2}$—$C_{1-6}$alkyl, —$SO_2$N($R^y$)$R^z$, —$SCF_3$, —$OCF_3$, —COOH, and —$COOC_{1-6}$alkyl;

$R^4$ is —OH, —$OC_{1-6}$alkyl, —$CF_3$, —$C_{1-6}$alkyl, or halo; two $R^4$ substituents may be taken together to form methylene or ethylene; or one of $R^4$ is taken together with $R^2$ to form methylene, ethylene, or propylene; wherein each methylene, ethylene, or propylene is optionally substituted with —OH, —$OC_{1-6}$alkyl, —$SC_{1-6}$alkyl, —$CF_3$, —$C_{1-6}$alkyl, amino, or halo;

$R^5$ is selected from the group consisting of —H, —$C_{1-6}$alkyl, —OH, —$OC_{1-6}$alkyl, —$SC_{1-6}$alkyl, and halo;

$Ar^1$ is an aryl or heteroaryl ring selected from the group consisting of:

a) phenyl, optionally mono-, di-, or tri-substituted with $R^j$ or di-substituted on adjacent carbons with —$OC_{1-4}$alkyleneO— optionally mono- or di-substituted with fluoro, —(CH$_2$)$_{2-3}$NH—, —(CH$_2$)$_{1-2}$NH(CH$_2$)—, —(CH$_2$)$_{2-3}$N($C_{1-4}$alkyl)-, or —(CH$_2$)$_{1-2}$N($C_{1-4}$alkyl)(CH$_2$)—;

$R^j$ is selected from the group consisting of

1) —OH, —$C_{1-6}$alkyl, —$OC_{1-6}$alkyl optionally mono-, di-, or tri-substituted with halo, —$C_{2-6}$alkenyl, —$OC_{3-6}$alkenyl, —$C_{2-6}$alkynyl, —$OC_{3-6}$alkynyl, —$C_{3-6}$cycloalkyl, —$OC_{3-6}$cycloalkyl, —CN, —$NO_2$, —N($R^k$)$R^l$ (wherein $R^k$ and $R^l$ are independently —H or —$C_{1-6}$alkyl), —N($R^k$)COR$^l$, —N($R^k$)$SO_2C_{1-6}$alkyl, —C(O)$C_{1-6}$alkyl, —S(O)$_{0-2}$—$C_{1-6}$alkyl, —C(O)N($R^m$)$R^n$ (wherein $R^m$ and $R^n$ are independently —H or —$C_{1-6}$alkyl, or $R^m$ and $R^n$ taken together with their nitrogen of attachment form a 4-8 membered heterocyclic ring having 1 or 2 heteroatom members selected from >O, >S(O)$_{0-2}$, >NH, and >N$C_{1-6}$alkyl, having 0 or 1 double bonds, having 0 or 1 carbonyl members), —$SO_2$N($R^m$)$R^n$, —$SCF_3$, halo, —$CF_3$, —COOH, —$COOC_{1-6}$alkyl, and —$COOC_{3-7}$cycloalkyl; and 2) a 4-8 membered saturated or partially saturated heterocyclic ring, having 1 or 2 heteroatom members selected from >O, >S(O)$_{0-2}$, >NH, and >N$C_{1-6}$alkyl, having 0 or 1 carbonyl members; said ring optionally mono-, di-, or tri-substituted with $R^p$;

$R^p$ is a substituent independently selected from the group consisting of: —OH, —$C_{1-6}$alkyl, —$OC_{1-6}$alkyl, phenyl, —CN, —$NO_2$, —N($R^q$)$R^r$ (wherein $R^q$ and $R^r$ are independently —H, —$C_{1-6}$alkyl, or —$C_{2-6}$alkenyl), —C(O)N($R^q$)$R^r$, —N($R^q$)C(O)$R^r$, —N($R^q$)$SO_2C_{1-6}$alkyl, —C(O)$C_{1-6}$alkyl, —S(O)$_{0-2}$—$C_{1-6}$alkyl, —$SO_2$N($R^q$)$R^r$, —$SCF_3$, halo, —$CF_3$, —$OCF_3$, —$OCHF_2$, —COOH, and —$COOC_{1-6}$alkyl;

b) phenyl or pyridyl fused at two adjacent carbon ring members to a three membered hydrocarbon moiety to form a fused five membered aromatic ring, which moiety has one carbon atom replaced by >O, >S, >NH, or >N($C_{1-4}$alkyl) and which moiety has up to one additional carbon atom optionally replaced by —N=, the fused rings optionally mono-, di-, or tri-substituted with $R^t$;

$R^t$ is a substituent independently selected from the group consisting of: —OH, —$C_{1-6}$alkyl, —$OC_{1-6}$alkyl, phenyl, —CN, —$NO_2$, —N($R^u$)$R^v$ (wherein $R^u$ and $R^v$ are independently —H or —$C_{1-6}$alkyl), —C(O)N($R^u$)$R^v$, —N($R^u$)C(O)$R^v$, —N($R^u$)$SO_2C_{1-6}$alkyl, —C(O)$C_{1-6}$alkyl, —S(O)$_{0-2}$—$C_{1-6}$alkyl, —$SO_2$N($R^u$)$R^v$, —$SCF_3$, halo, —$CF_3$, —$OCF_3$, —$OCHF_2$, —COOH, and —$COOC_{1-6}$alkyl;

c) phenyl fused at two adjacent ring members to a four membered hydrocarbon moiety to form a fused six membered aromatic ring, which moiety has 0, 1, or 2 carbon atoms replaced by —N=, the fused rings optionally mono-, di-, or tri-substituted with $R^t$;

d) a monocyclic aromatic hydrocarbon group having five ring atoms, having a carbon atom which is the point of attachment, having one carbon atom replaced by >O, >S, >NH, or >N($C_{1-4}$alkyl), having up to one additional carbon atom optionally replaced by —N=, optionally mono- or di-substituted with $R^t$, and optionally benzofused or pyridofused at two adjacent carbon atoms, where the benzofused or pyridofused moiety is optionally mono-, di-, or tri-substituted with $R^t$; and e) a monocyclic aromatic hydrocarbon group having six ring atoms, having a carbon atom which is the point of attachment, having one or two carbon atoms replaced by —N=, optionally mono- or di-substituted with $R^t$, and optionally benzofused or pyridofused at two adjacent carbon atoms, where the benzofused or pyridofused moiety is optionally mono- or di-substituted with $R^t$;

and enantiomers, diastereomers, hydrates, solvates thereof, and pharmaceutically acceptable salts, esters, and amides thereof.

The invention also features a compound of formulae (II) or (III):

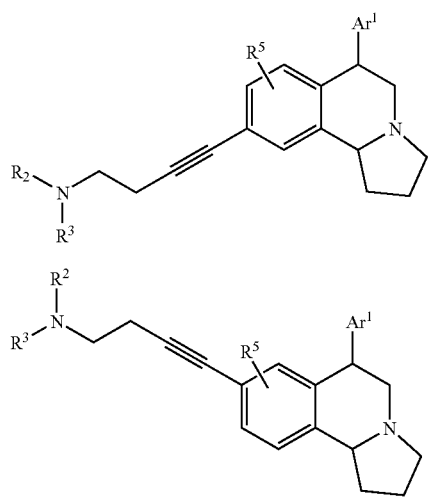

wherein
$R^2$, $R^3$, $R^5$, and $Ar^1$ are as defined for formula (I);
and enantiomers, diastereomers, hydrates, solvates thereof, and pharmaceutically acceptable salts, esters, and amides thereof.

Isomeric forms of the compounds of formulae (I), (II), and (III), and of their pharmaceutically acceptable salts, esters, and amides, are encompassed within the present invention, and reference herein to one of such isomeric forms is meant to refer to at least one of such isomeric forms. One of ordinary skill in the art will recognize that compounds according to this invention may exist, for example in a single isomeric form whereas other compounds may exist in the form of a regioisomeric mixture.

The invention also features pharmaceutical compositions containing such compounds and methods of using such compounds and compositions in the treatment or prevention of disease states mediated by the histamine $H_3$ receptor and the serotonin transporter.

Compounds of the present invention are useful in combination with other therapeutic agents as a combination therapy method, including use in combination with $H_1$ receptor antagonists, $H_2$ receptor antagonists, $H_3$ receptor antagonists, and neurotransmitter modulators such as serotonin-norepinephrine reuptake inhibitors, selective serotonin reuptake inhibitors (SSRIs), noradrenergic reuptake inhibitors, non-selective serotonin re-uptake inhibitors (NSSRIs), acetylcholinesterase inhibitors, and modafinil.

Additional features and advantages of the invention will become apparent from the detailed description and examples below, and the appended claims.

BRIEF DESCRIPTION OF DRAWINGS

FIG. 1 shows the results of measuring levels of serotonin and dopamine in the cortex of freely moving rats after subcutaneous injection of 1 mg/kg of Example 8A.

DETAILED DESCRIPTION

Particular preferred compounds of the invention comprise a compound of formula (I), or an enantiomer, diastereomer, hydrate, solvate thereof, or a pharmaceutically acceptable salt, amide or ester thereof, wherein n, m, $R^{2-5}$, and $Ar^1$ have any of the meanings defined hereinabove and equivalents thereof, or at least one of the following assignments and equivalents thereof. Such assignments may be used where appropriate with any of the definitions, claims or embodiments defined herein:

Preferably, n is 0 or 1.
Preferably, m is 0.
Preferably, $R^2$ and $R^3$ are independently selected from —H, or optionally substituted, from the group consisting of:

A) methyl, ethyl, isopropyl, butyl, pentyl, hexyl, allyl, propargyl, cyclopropyl, cyclobutyl, cyclopentyl, cyclohexyl, cyclopropylmethyl, benzyl, B) phenyl, pyridyl, 4-, 5-, 6- or 7-benzoxazolyl, 4-, 5-, 6- or 7-benzothiophenyl, 4-, 5-, 6- or 7-benzofuranyl, 4-, 5-, 6- or 7-indolyl, 4-, 5-, 6- or 7-benzthiazolyl, 4-, 5-, 6- or 7-benzimidazolyl, 4-, 5-, 6- or 7-indazolyl, imidazo[1,2-a]pyridin-5, 6, 7 or 8-yl, pyrazolo[1,5-a]pyridin-4, 5, 6 or 7-yl, 1H-pyrrolo[2,3-b]pyridin-4, 5 or 6-yl, 1H-pyrrolo[3,2-c]pyridin-4, 6 or 7-yl, 1H-pyrrolo[2,3-c]pyridin-4, 5 or 7-yl, 1H-pyrrolo[3,2-b]pyridin-5, 6 or 7-yl, C) azetidinyl, pyrrolidinyl, piperidinyl, and D) furanyl, oxazolyl, isoxazolyl, 1,2,3-oxadiazolyl, 1,2,4-oxadiazolyl, 1,2,5-oxadiazolyl, 1,3,4-oxadiazolyl, thiophenyl, thiazolyl, isothiazolyl, pyrrolyl, imidazolyl, pyrazolyl, 1,2,3-triazolyl, 1,2,4-triazolyl, 3-indoxazinyl, 2-benzoxazolyl, 2- or 3-benzothiophenyl, 2- or 3-benzofuranyl, 2- or 3-indolyl, 2-benzthiazolyl, 2-benzimidazolyl, and 3-indazolyl.

More preferably, $R^2$ and $R^3$, optionally substituted, are independently selected from methyl, ethyl, isopropyl, pyrrolidinyl, piperidinyl, 2-benzothiazolyl, and methoxyethyl.

Even more preferably, $R^2$ and $R^3$ are, independently, ethyl, isopropyl, methoxyethyl, or 2-benzothiazolyl.

In a preferred embodiment, $R^2$ and $R^3$, optionally substituted, are taken together with the nitrogen to which they are attached to form a ring selected from the group consisting of azetidinyl, pyrrolidinyl, piperidinyl, morpholinyl, thiomorpholinyl, piperazinyl, homopiperidinyl, 1,3-dihydro-isoindol-2-yl, 5,6-dihydro-4H-pyrimidin-1-yl, and 1,1-dioxo-1$\lambda^6$-thiomorpholin-4-yl.

Preferably, $R^2$ and $R^3$ are taken together with the nitrogen to which they are attached to form a 4-8 membered heterocyclic ring, said heterocyclic ring selected from piperidine, pyrrolidine, and morpholine, said ring substituted with 1 or 2 substituents $R^{ff}$.

Preferably, $R^{ff}$ is selected from the group consisting of methyl, ethyl, isopropyl, butyl, hexyl, —$CF_3$, —$CHF_2$, vinyl, allyl, propargyl, cyclopropyl, cyclopentyl, cyclopropylmethyl, cyclobutylethyl, bromo, chloro, fluoro, iodo, —OH, hydroxymethyl, hydroxyethyl, methoxy, ethoxy, isopropoxy, pentyloxy, —$O(CH_2)_2O$—, —$O(CH_2)_3O$—, —CN, amino, methylamino, dimethylamino, diethylamino, diethylcarbamoyl, methanesulfanyl, methanesulfonyl, methanesulfonamido, —$C(O)R^i$, —COOH, and ethoxycarbonyl.

More preferably, $R^{ff}$ is selected from the group consisting of methyl, fluoro, —OH, —$CF_3$, hydroxymethyl, hydroxyethyl, dimethylamino, ethoxycarbonyl, and —$O(CH_2)_2O$—.

Preferably, $R^i$ is selected from the group consisting of methyl, pyridyl, isopropyl, cyclobutyl, cyclopropyl, N-methylpyrrolyl, and 1-methylimidazolyl.

More preferably, $R^2$ and $R^3$ are taken together with the nitrogen to which they are attached to form azetidinyl, 2-methylpyrrolidinyl, 3-hydroxypyrrolidinyl, 3-dimethylaminopyrrolidinyl, 2,5-dimethylpyrrolidinyl, 2-trifluoromethylpyrrolidinyl, 2-hydroxymethylpyrrolidinyl, piperidinyl, 4-fluoropiperidinyl, 3,3-difluoropiperidinyl, 4,4-difluoropiperidinyl, 3-trifluoromethylpiperidinyl, 4-trifluoromethylpiperidinyl, 1,4-dioxa-8-aza-spiro[4.5]dec-8-yl, morpholinyl, 4-cyanopiperidinyl, 4-carboethoxypiperidinyl, 3-hydroxipiperidinyl, 4-hydroxypiperidinyl, 2-hydroxymethylpiperidinyl, 3-hydroxymethylpiperidinyl, 4-hydroxymethylpiperidinyl, 4-hydroxyethylpiperidinyl, 3-methylmorpholin-4-yl, 3-hydroxymethylmorpholin-4-yl, 2-hydroxymethylmorpholin-4-yl, 2,6-dimethylmorpholin-4-yl, 1,3-dihydro-isoindol-2-yl, 5,6-dihydro-4H-pyrimidin-1-yl, 1,1-dioxo-1$\lambda^6$-thiomorpholin-4-yl, or 2-methylmorpholin-4-yl.

Even more preferably, $R^2$ and $R^3$ are taken together with the nitrogen to which they are attached to form 4-fluoropiperidinyl, morpholinyl, or 3-methylmorpholin-4-yl.

Preferably, $R^4$ is methoxy, ethoxy, isopropoxy, pentyloxy, —$CF_3$, methyl, ethyl, propyl, isobutyl, pentyl, chloro, or fluoro.

More preferably, $R^4$ is hydroxy, methyl, methoxy, fluoro, or —$CF_3$.

Preferably, two $R^4$ are taken together to form methylene.

Preferably, $R^2$ and one of $R^4$ are taken together form methylene, ethylene, or propylene, each optionally substituted with —OH, —$OC_{1-6}$alkyl, —$SC_{1-6}$alkyl, —$CF_3$, —$C_{1-6}$ alkyl, amino, or halo.

More preferably, $R^2$ and one of $R^4$ are taken together form methylene or ethylene.

Preferably, $R^5$ is hydrogen, methyl, ethyl, isopropyl, hexyl, hydroxyl, methoxy, ethoxy, isopropoxy, methylsulfanyl, bromo, chloro, fluoro, or iodo.

More preferably, $R^5$ is hydrogen.

Preferably, $Ar^1$, optionally substituted, is selected from the group consisting of:

a) phenyl, 5-, 6-, 7-, 8-benzo-1,4-dioxanyl, 4-, 5-, 6-, 7-benzo-1,3-dioxolyl, 4-, 5-, 6-, 7-indolinyl, 4-, 5-, 6-, 7-isoindolinyl, 1,2,3,4-tetrahydro-quinolin-4, 5, 6 or 7-yl, 1,2,3,4-tetrahydro-isoquinolin-4, 5, 6 or 7-yl, b) 4-, 5-, 6- or 7-benzoxazolyl, 4-, 5-, 6- or 7-benzothiophenyl, 4-, 5-, 6- or 7-benzofuranyl, 4-, 5-, 6- or 7-indolyl, 4-, 5-, 6- or 7-benzthiazolyl, 4-, 5-, 6- or 7-benzimidazolyl, 4-, 5-, 6- or 7-indazolyl, imidazo[1,2-a]pyridin-5, 6, 7 or 8-yl, pyrazolo[1,5-a]pyridin-4, 5, 6 or 7-yl, 1H-pyrrolo[2,3-b]pyridin-4, 5 or 6-yl, 1H-pyrrolo[3,2-c]pyridin-4, 6 or 7-yl, 1H-pyrrolo[2,3-c]pyridin-4, 5 or 7-yl, 1H-pyrrolo[3,2-b]pyridin-5, 6 or 7-yl, c) naphthyl, 5-, 6-, 7- or 8-isoquinolinyl, 5-, 6-, 7- or 8-quinolinyl, 5-, 6-, 7- or 8-quinoxalinyl, 5-, 6-, 7- or 8-quinazolinyl, d) furanyl, oxazolyl, isoxazolyl, 1,2,3-oxadiazolyl, 1,2,4-oxadiazolyl, 1,2,5-oxadiazolyl, 1,3,4-oxadiazolyl, thiophenyl, thiazolyl, isothiazolyl, pyrrolyl, imidazolyl, pyrazolyl, 1,2,3-triazolyl, 1,2,4-triazolyl, 3-indoxazinyl, 2-benzoxazolyl, 2- or 3-benzothiophenyl, 2- or 3-benzofuranyl, 2- or 3-indolyl, 2-benzthiazolyl, 2-benzimidazolyl, 3-indazolyl, and e) pyridinyl, pyridinyl-N-oxide, pyrazinyl, pyrimidinyl, pyridazinyl, 1-, 3- or 4-isoquinolinyl, 2-, 3- or 4-quinolinyl, 2- or 3-quinoxalinyl, 2- or 4-quinazolinyl, [1,5], [1,6], [1,7], or [1,8]naphthyridin-2-, 3-, or 4-yl, [2,5], [2,6], [2,7], [2,8]naphthyridin-1-, 3-, or 4-yl.

More preferably, $Ar^1$, optionally substituted, is selected from the group consisting of phenyl, pyridyl, pyrazinyl, thiazolyl, pyrazolyl, and thiophenyl.

Even more preferably, $Ar^1$ is selected from the group consisting of phenyl, 2-methoxyphenyl, 3-methoxyphenyl, 4-methoxyphenyl, 2,4-dimethoxyphenyl, 2,5-dimethoxyphenyl, 3,4-dimethoxyphenyl, 3,5-dimethoxyphenyl, 3,4,5-trimethoxyphenyl, 2-methylphenyl, 3-methylphenyl, 4-methylphenyl, 4-ethylphenyl, 3-ethynylphenyl, 4-ethynylphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 3-iodophenyl, 4-iodophenyl, 2-trifluoromethylphenyl, 3-trifluoromethylphenyl, 4-trifluoromethylphenyl, 3-trifluoromethoxyphenyl, 4-trifluoromethoxyphenyl, 4-difluoromethoxyphenyl, 3-cyanophenyl, 4-cyanophenyl, 3-acetylphenyl, 4-acetylphenyl, 3,4-difluorophenyl, 3,4-dichlorophenyl, 2,3-difluorophenyl, 2,3-dichlorophenyl, 2,4-difluorophenyl, 2,4-dichlorophenyl, 2,5-dichlorophenyl, 3,5-dichlorophenyl, 3-nitrophenyl, 4-nitrophenyl, 3-chloro-4-fluorophenyl, 3-chloro-4-methoxyphenyl, 3-chloro-4-difluoromethoxyphenyl, 3-fluoro-4-chlorophenyl, benzo[1,3]dioxol-4 or 5-yl, 2-hydroxyphenyl, 3-hydroxyphenyl, 4-hydroxyphenyl, 4-hydroxy-2-methylphenyl, 4-hydroxy-3-fluorophenyl, 3,4-dihydroxyphenyl, 4-aminophenyl, 4-dimethylaminophenyl, 4-carbamoylphenyl, 4-fluoro-3-methylphenyl, 4-methanesulfanylphenyl, 4-methanesulfinylphenyl, 4-methanesulfonylphenyl, 4-trifluoromethanesulfanylphenyl, thiophen-2-yl, thiophen-3-yl, 2-pyridinyl, 3-pyridinyl, 4-pyridinyl, 2-chloro-5-pyridinyl, 2-dimethylamino-5-pyridinyl, 2-methoxy-5-pyridinyl, 2-thiomethyl-5-pyridinyl, 2-hydroxy-5-pyridinyl, oxazol-5-yl, thiazol-5-yl, thiazol-2-yl, 2H-pyrazol-3-yl, pyrazin-2-yl, 1-naphthyl, 2-naphthyl, 4-imidazol-1-ylphenyl, 4-pyrazol-1-ylphenyl, 1H-indol-5-yl, 1H-benzimidazol-5-yl, benzo[b]thiophen-7-yl, and 4-biphenyl.

In a particular embodiment, $Ar^1$, optionally substituted with halo, is 4-methoxyphenyl or 4-methanesulfanylphenyl.

Preferably, $Ar^1$ is cis to the pyrrolidine ring of formula (I).

Preferably, the $R^3R^2N$-containing ether substituent of formula (I) is at the 9-position.

With respect to compounds of formulae (II) and (III), preferably, $R^2$ and $R^3$ are taken together with the nitrogen to which they are attached to form piperidinyl, 4-fluoropiperidinyl, morpholinyl, or 3-methylmorpholin-4-yl.

Preferably, $Ar^1$ is 4-methoxyphenyl or 4-methylsulfanylphenyl.

Preferably, $R^5$ is —H.

It is understood that some compounds referred to herein are chiral and/or have diastereomeric or geometric isomeric centers, for example cis- and trans-isomers. The present invention encompasses all such isomers, including optical isomers, such as stereoisomers and racemic mixtures, diastereomers, regioisomers, and geometric isomers that possess the activity that characterizes the compounds of this invention. Compounds of the invention may exist as single enantiomers, mixtures of enantiomers, or racemic mixtures. In certain embodiments, the absolute configuration of a single enantiomer may be unknown. Compounds of the invention may exist as a single diastereomers, or as a mixture of diastereomers. In addition, certain compounds referred to herein can exist in solvated as well as unsolvated forms. It is understood that this invention encompasses all such solvated and unsolvated forms that possess the activity that characterizes the compounds of this invention.

Compounds according to the present invention that have been modified to be detectable by some analytic technique are also within the scope of this invention. The compounds of the present invention may be labeled with radioactive elements such as $^{125}I$, $^{18}F$, $^{11}C$, $^{64}Cu$, and the like for use in imaging or for radioactive treatment of patients. An example of such compounds is an isotopically labeled compound, such as an $^{18}F$ isotopically labeled compound that may be used as a probe in detection and/or imaging techniques, such as positron emission tomography (PET) and single-photon emission computed tomography (SPECT). Preferably, compounds of the present invention labeled with $^{18}F$ or $^{11}C$ may be used as a positron emission tomography (PET) molecular probe for studying disorders mediated by the histamine $H_3$ receptor and the serotonin transporter. Another example of such compounds is an isotopically labeled compound, such as a deuterium and/or tritium labeled compound that may be used in reaction kinetic studies. The compounds described herein may be reacted with appropriate functionalized radioactive reagents using conventional chemistry to provide radiolabeled compounds.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with a compound of formulae (I), (II), or (III), or with a compound that converts to a compound of formulae (I), (II), or (III) in vivo after administration to the patient. Conventional procedures for the selection and preparation of suitable prodrug derivatives are described, for example, in "Design of Prodrugs", ed. H. Bundgaard, Elsevier, 1985. In addition to salts, the invention provides the esters, amides, and other protected or derivatized forms of the described compounds.

Preferred compounds, which are hexahydro-pyrrolo-isoquinoline compounds, are selected from the group consisting of:

| EX | CHEMICAL NAME |
|---|---|
| 1A | Cis-6-Phenyl-9-(3-piperidin-1-yl-propoxy)-1,2,3,5,6,10b-hexahydro-pyrrolo[2,1a]isoquinoline; |
| 1B | Trans-6-Phenyl-9-(3-piperidin-1-yl-propoxy)-1,2,3,5,6,10b-hexahydro-pyrrolo[2,1a]isoquinoline; |
| 1C | Trans-6-Phenyl-7-(3-piperidin-1-yl-propoxy)-1,2,3,5,6,10b-hexahydro-pyrrolo[2,1a]isoquinoline; |
| 2A | Cis-6-(4-Nitro-phenyl)-9-(3-piperidin-1-yl-propoxy)-1,2,3,5,6,10b-hexahydro-pyrrolo[2,1-a]isoquinoline; |
| 2B | Trans-6-(4-Nitro-phenyl)-9-(3-piperidin-1-yl-propoxy)-1,2,3,5,6,10b-hexahydro-pyrrolo[2,1-a]isoquinoline; |
| 2C | Trans-6-(4-Nitro-phenyl)-7-(3-piperidin-1-yl-propoxy)-1,2,3,5,6,10b-hexahydro-pyrrolo[2,1-a]isoquinoline; |
| 3 | Cis-4-[9-(3-Piperidin-1-yl-propoxy)-1,2,3,5,6,10b-hexahydro-pyrrolo[2,1-a]isoquinolin-6-yl]-phenylamine; |
| 4A | Cis-6-(3-Nitro-phenyl)-9-(3-piperidin-1-yl-propoxy)-1,2,3,5,6,10b-hexahydro-pyrrolo[2,1-a]isoquinoline; |
| 4B | Trans-6-(3-Nitro-phenyl)-9-(3-piperidin-1-yl-propoxy)-1,2,3,5,6,10b-hexahydro-pyrrolo[2,1-a]isoquinoline; |
| 4C | Cis-6-(3-nitro-phenyl)-7-(3-piperidin-1-yl-propoxy)-1,2,3,5,6,10b-hexahydro-pyrrolo[2,1-a]isoquinoline; |
| 4D | Trans-6-(3-nitro-phenyl)-7-(3-piperidin-1-yl-propoxy)-1,2,3,5,6,10b-hexahydro-pyrrolo[2,1-a]isoquinoline; |
| 5A | Cis-9-(3-Piperidine-1-yl-propoxy)-6-p-tolyl-1,2,3,5,6,10b-hexahydro-pyrrolo[2,1-a]isoquinoline; |
| 5B | Trans-9-(3-Piperidine-1-yl-propoxy)-6-p-tolyl-1,2,3,5,6,10b-hexahydro-pyrrolo[2,1-a]isoquinoline; |
| 5C | Trans-7-(3-Piperidine-1-yl-propoxy)-6-p-tolyl-1,2,3,5,6,10b-hexahydro-pyrrolo[2,1-a]isoquinoline; |
| 6A | Cis-6-(3,4-Dichloro-phenyl)-9-(3-piperidin-1-yl-propoxy)-1,2,3,5,6,10b-hexahydro-pyrrolo[2,1-a]isoquinoline; |
| 6B | Trans-6-(3,4-Dichloro-phenyl)-9-(3-piperidin-1-yl-propoxy)-1,2,3,5,6,10b-hexahydro-pyrrolo[2,1-a]isoquinoline; |
| 6C | Cis-6-(3,4-Dichloro-phenyl)-7-(3-piperidin-1-yl-propoxy)-1,2,3,5,6,10b-hexahydro-pyrrolo[2,1-a]isoquinoline; |
| 7A | Cis-9-(3-Piperidin-1-yl-propoxy)-6-(4-trifluoromethyl-phenyl)-1,2,3,5,6,10b-hexahydro-pyrrolo[2,1-a]isoquinoline; |
| 7B | Trans-9-(3-Piperidin-1-yl-propoxy)-6-(4-trifluoromethyl-phenyl)-1,2,3,5,6,10b-hexahydro-pyrrolo[2,1-a]isoquinoline; |
| 7C | Trans-7-(3-Piperidin-1-yl-propoxy)-6-(4-trifluoromethyl-phenyl)-1,2,3,5,6,10b-hexahydro-pyrrolo[2,1-a]isoquinoline; |
| 8A | Cis-6-(4-Methoxy-phenyl)-9-(3-piperidin-1-yl-propoxy)-1,2,3,5,6,10b-hexahydro-pyrrolo[2,1-a]isoquinoline; |
| 8B | 1S,6R-6-(4-Methoxy-phenyl)-9-(3-piperidin-1-yl-propoxy)-1,2,3,5,6,10b-hexahydro-pyrrolo[2,1-a]isoquinoline; |
| 8C | 1R,6S-6-(4-Methoxy-phenyl)-9-(3-piperidin-1-yl-propoxy)-1,2,3,5,6,10b-hexahydro-pyrrolo[2,1-a]isoquinoline; |
| 8D | Trans-6-(4-Methoxy-phenyl)-9-(3-piperidin-1-yl-propoxy)-1,2,3,5,6,10b-hexahydro-pyrrolo[2,1-a]isoquinoline; |
| 8E | Cis-6-(4-Methoxy-phenyl)-7-(3-piperidin-1-yl-propoxy)-1,2,3,5,6,10b-hexahydro-pyrrolo[2,1-a]isoquinoline; |
| 8F | Trans-6-(4-Methoxy-phenyl)-7-(3-piperidin-1-yl-propoxy)-1,2,3,5,6,10b-hexahydro-pyrrolo[2,1-a]isoquinoline; |
| 9A | Cis-4-[9-(3-Piperidin-1-yl-propoxy)-1,2,3,5,6,10b-hexahydro-pyrrolo[2,1-a]isoquinolin-6-yl]-phenol; |
| 9B | Trans-4-[7-(3-Piperidin-1-yl-propoxy)-1,2,3,5,6,10b-hexahydro-pyrrolo[2,1-a]isoquinolin-6-yl]-phenol; |

-continued

| EX | CHEMICAL NAME |
|---|---|
| 10A | Cis-6-(3-Methoxy-phenyl)-9-(3-piperidin-1-yl-propoxy)-1,2,3,5,6,10b-hexahydro-pyrrolo[2,1-a]isoquinoline; |
| 10B | Trans-6-(3-Methoxy-phenyl)-9-(3-piperidin-1-yl-propoxy)-1,2,3,5,6,10b-hexahydro-pyrrolo[2,1-a]isoquinoline; |
| 10C | Trans-6-(3-Methoxy-phenyl)-7-(3-piperidin-1-yl-propoxy)-1,2,3,5,6,10b-hexahydro-pyrrolo[2,1-a]isoquinoline; |
| 11A | Cis-6-(3-Chloro-phenyl)-9-(3-piperidin-1-yl-propoxy)-1,2,3,5,6,10b-hexahydro-pyrrolo[2,1-a]isoquinoline; |
| 11B | Trans-6-(3-Chloro-phenyl)-9-(3-piperidin-1-yl-propoxy)-1,2,3,5,6,10b-hexahydro-pyrrolo[2,1-a]isoquinoline; |
| 11C | Trans-6-(3-Chloro-phenyl)-7-(3-piperidin-1-yl-propoxy)-1,2,3,5,6,10b-hexahydro-pyrrolo[2,1-a]isoquinoline; |
| 12A | Cis-6-(2-Chloro-phenyl)-9-(3-piperidin-1-yl-propoxy)-1,2,3,5,6,10b-hexahydro-pyrrolo[2,1-a]isoquinoline; |
| 12B | Trans-6-(2-Chloro-phenyl)-9-(3-piperidin-1-yl-propoxy)-1,2,3,5,6,10b-hexahydro-pyrrolo[2,1-a]isoquinoline; |
| 12C | Cis-6-(2-Chloro-phenyl)-7-(3-piperidin-1-yl-propoxy)-1,2,3,5,6,10b-hexahydro-pyrrolo[2,1-a]isoquinoline; |
| 12D | Trans-6-(2-Chloro-phenyl)-7-(3-piperidin-1-yl-propoxy)-1,2,3,5,6,10b-hexahydro-pyrrolo[2,1-a]isoquinoline; |
| 13A | Cis-6-(2-Methoxy-phenyl)-9-(3-piperidin-1-yl-propoxy)-1,2,3,5,6,10b-hexahydro-pyrrolo[2,1-a]isoquinoline; |
| 13B | Trans-6-(2-Methoxy-phenyl)-9-(3-piperidin-1-yl-propoxy)-1,2,3,5,6,10b-hexahydro-pyrrolo[2,1-a]isoquinoline; |
| 14A | Cis-6-(4-Fluoro-phenyl)-9-(3-piperidin-1-yl-propoxy)-1,2,3,5,6,10b-hexahydro-pyrrolo[2,1-a]isoquinoline; |
| 14B | Trans-6-(4-Fluoro-phenyl)-9-(3-piperidin-1-yl-propoxy)-1,2,3,5,6,10b-hexahydro-pyrrolo[2,1-a]isoquinoline; |
| 14C | Trans-6-(4-Fluoro-phenyl)-7-(3-piperidin-1-yl-propoxy)-1,2,3,5,6,10b-hexahydro-pyrrolo[2,1-a]isoquinoline; |
| 15 | Cis-3-[9-(3-piperidin-1-yl-propoxy)-1,2,3,5,6,10b-hexahydro-pyrrolo[2,1-a]isoquinolin-6-yl]-phenol; |
| 16 | Cis-2-[9-(3-Piperidin-1-yl-propoxy)-1,2,3,5,6,10b-hexahydro-pyrrolo[2,1-a]isoquinolin-6-yl]-phenol; |
| 17 | Cis-9-(3-Piperidin-1-yl-propoxy)-6-(4-trifluoromethoxy-phenyl)-1,2,3,5,6,10b-hexahydro-pyrrolo[2,1-a]isoquinoline; |
| 18 | Cis-6-(3,4-Dimethoxy-phenyl)-9-(3-piperidin-1-yl-propoxy)-1,2,3,5,6,10b-hexahydro-pyrrolo[2,1-a]isoquinoline; |
| 19 | Cis-6-(2,4-Dimethoxy-phenyl)-9-(3-piperidin-1-yl-propoxy)-1,2,3,5,6,10b-hexahydro-pyrrolo[2,1-a]isoquinoline; |
| 20 | Cis-6-(2,5-dimethoxy-phenyl)-9-(3-piperidin-1-yl-propoxy)-1,2,3,5,6,10b-hexahydro-pyrrolo[2,1-a]isoquinoline; |
| 21 | Cis-6-(3,5-Dimethoxy-phenyl)-9-(3-piperidin-1-yl-propoxy)-1,2,3,5,6,10b-hexahydro-pyrrolo[2,1-a]isoquinoline; |
| 22 | Cis-6-(3,4,5-Trimethoxy-phenyl)-9-(3-piperidin-1-yl-propoxy)-1,2,3,5,6,10b-hexahydro-pyrrolo[2,1-a]isoquinoline; |
| 23 | Cis-9-(3-Piperidin-1-yl-propoxy)-6-thiophen-2-yl-1,2,3,5,6,10b-hexahydro-pyrrolo[2,1-a]isoquinoline; |
| 24A | Cis-9-(3-Piperidin-1-yl-propoxy)-6-thiophen-3-yl-1,2,3,5,6,10b-hexahydro-pyrrolo[2,1-a]isoquinoline; |
| 24B | Trans-9-(3-piperidin-1-yl-propoxy)-6-thiophen-3-yl-1,2,3,5,6,10b-hexahydro-pyrrolo[2,1-a]isoquinoline; |
| 25 | Cis-9-(3-Piperidin-1-yl-propoxy)-6-pyridin-2-yl-1,2,3,5,6,10b-hexahydro-pyrrolo[2,1-a]isoquinoline; |
| 26 | Cis-9-(3-Piperidin-1-yl-propoxy)-6-pyridin-3-yl-1,2,3,5,6,10b-hexahydro-pyrrolo[2,1-a]isoquinoline; |
| 27A | Cis-9-(3-Piperidin-1-yl-propoxy)-6-pyridin-4-yl-1,2,3,5,6,10b-hexahydro-pyrrolo[2,1-a]isoquinoline; |
| 27B | Trans-9-(3-Piperidin-1-yl-propoxy)-6-pyridin-4-yl-1,2,3,5,6,10b-hexahydro-pyrrolo[2,1-a]isoquinoline; |
| 28 | Cis-7-(1-Isopropyl-piperidin-4-yloxy)-4-(4-methoxy-phenyl)-2-methyl-1,2,3,4-tetrahydro-isoquinoline; |
| 29 | Cis-9-(1-Isopropyl-piperidin-4-ylmethoxy)-6-(4-methoxy-phenyl)-1,2,3,5,6,10b-hexahydro-pyrrolo[2,1-a]isoquinoline; |
| 30 | Cis-Dimethyl-{4-[9-(3-piperidin-1-yl-propoxy)-1,2,3,5,6,10b-hexahydro-pyrrolo[2,1-a]isoquinolin-6-yl]-phenyl}-amine; |
| 31 | Cis-9-(3-Piperidin-1-yl-propoxy)-6-m-tolyl-1,2,3,5,6,10b-hexahydro-pyrrolo[2,1-a]isoquinoline; |
| 32 | Cis-6-(3-Iodo-phenyl)-9-(3-piperidin-1-yl-propoxy)-1,2,3,5,6,10b-hexahydro-pyrrolo[2,1-a]isoquinoline; |
| 33 | Cis-9-(3-Piperidin-1-yl-propoxy)-6-(3-trimethylsilanylethynyl-phenyl)-1,2,3,5,6,10b-hexahydro-pyrrolo[2,1-a]isoquinoline; |
| 34 | Cis-6-(3-Ethynyl-phenyl)-9-(3-piperidin-1-yl-propoxy)-1,2,3,5,6,10b-hexahydro-pyrrolo[2,1-a]isoquinoline; |
| 35A | Cis-6-(4-Iodo-phenyl)-9-(3-piperidin-1-yl-propoxy)-1,2,3,5,6,10b-hexahydro-pyrrolo[2,1-a]isoquinoline; |
| 35B | Trans-6-(4-Iodo-phenyl)-9-(3-piperidin-1-yl-propoxy)-1,2,3,5,6,10b-hexahydro-pyrrolo[2,1-a]isoquinoline; |

-continued

| EX | CHEMICAL NAME |
|---|---|
| 36 | Cis-9-(3-Piperidin-1-yl-propoxy)-6-(4-trimethylsilanylethynyl-phenyl)-1,2,3,5,6,10b-hexahydro-pyrrolo[2,1-a]isoquinoline; |
| 37 | Cis-6-(4-Ethynyl-phenyl)-9-(3-piperidin-1-yl-propoxy)-1,2,3,5,6,10b-hexahydro-pyrrolo[2,1-a]isoquinoline; |
| 38 | Cis-6-(4-Methoxy-phenyl)-9-(3-morpholin-4-yl-propoxy)-1,2,3,5,6,10b-hexahydro-pyrrolo[2,1-a]isoquinoline; |
| 39A | Cis-6-(4-Methylsulfanyl-phenyl)-9-(3-piperidin-1-yl-propoxy)-1,2,3,5,6,10b-hexahydro-pyrrolo[2,1-a]isoquinoline; |
| 39B | Trans-6-(4-Methylsulfanyl-phenyl)-9-(3-piperidin-1-yl-propoxy)-1,2,3,5,6,10b-hexahydro-pyrrolo[2,1-a]isoquinoline; |
| 39C | 6-(4-Methylsulfanyl-phenyl)-7-(3-piperidin-1-yl-propoxy)-1,2,3,5,6,10b-hexahydro-pyrrolo[2,1-a]isoquinoline; |
| 40 | Cis-6-(4-Bromo-phenyl)-9-(3-piperidin-1-yl-propoxy)-1,2,3,5,6,10b-hexahydro-pyrrolo[2,1-a]isoquinoline; |
| 41A | Cis-4-[9-(3-Piperidin-1-yl-propoxy)-1,2,3,5,6,10b-hexahydro-pyrrolo[2,1-a]isoquinolin-6-yl]-benzonitrile; |
| 41B | Trans-4-[9-(3-Piperidin-1-yl-propoxy)-1,2,3,5,6,10b-hexahydro-pyrrolo[2,1-a]isoquinolin-6-yl]-benzonitrile; |
| 42 | Trans-6-(4-Bromo-phenyl)-8-(3-piperidin-1-yl-propoxy)-1,2,3,5,6,10b-hexahydro-pyrrolo[2,1-a]isoquinoline; |
| 43 | Cis-4-[8-(3-Piperidin-1-yl-propoxy)-1,2,3,5,6,10b-hexahydro-pyrrolo[2,1-a]isoquinolin-6-yl]-benzonitrile; |
| 44 | Trans-6-Phenyl-8-(3-piperidin-1-yl-propoxy)-1,2,3,5,6,10b-hexahydro-pyrrolo[2,1-a]isoquinoline; |
| 45 | Cis-6-Phenyl-8-(3-piperidin-1-yl-propoxy)-1,2,3,5,6,10b-hexahydro-pyrrolo[2,1-a]isoquinoline; |
| 46 | Cis-6-(4-Methoxy-phenyl)-9-[3-(3S-methyl-morpholin-4-yl)-propoxy]-1,2,3,5,6,10b-hexahydro-pyrrolo[2,1-a]isoquinoline; |
| 47 | Cis-9-[3-(4-Fluoro-piperidin-1-yl)-propoxy]-6-(4-methoxy-phenyl)-1,2,3,5,6,10b-hexahydro-pyrrolo[2,1-a]isoquinoline; |
| 48A | Cis-6-(4-imidazol-1-yl-phenyl)-9-(3-morpholin-4-yl-propoxy)-1,2,3,5,6,10b-hexahydro-pyrrolo[2,1-a]isoquinoline; |
| 48B | Trans-6-(4-Imidazol-1-yl-phenyl)-9-(3-morpholin-4-yl-propoxy)-1,2,3,5,6,10b-hexahydro-pyrrolo[2,1-a]isoquinoline; |
| 49 | Cis-9-(3-Morpholin-4-yl-propoxy)-6-(4-pyrazol-1-yl-phenyl)-1,2,3,5,6,10b-hexahydro-pyrrolo[2,1-a]isoquinoline; |
| 50A | Cis-9-(3-Morpholin-4-yl-propoxy)-6-pyrazin-2-yl-1,2,3,5,6,10b-hexahydro-pyrrolo[2,1-a]isoquinoline; |
| 50B | Trans-9-(3-Morpholin-4-yl-propoxy)-6-pyrazin-2-yl-1,2,3,5,6,10b-hexahydro-pyrrolo[2,1-a]isoquinoline; |
| 51A | Cis-5-[9-(3-Morpholin-4-yl-propoxy)-1,2,3,5,6,10b-hexahydro-pyrrolo[2,1-a]isoquinolin-6-yl]-pyridin-2-ol; |
| 51B | Trans-5-[9-(3-Morpholin-4-yl-propoxy)-1,2,3,5,6,10b-hexahydro-pyrrolo[2,1-a]isoquinolin-6-yl]-pyridin-2-ol; |
| 52 | Cis-9-(3-Morpholin-4-yl-propoxy)-6-thiazol-5-yl-1,2,3,5,6,10b-hexahydro-pyrrolo[2,1-a]isoquinoline; |
| 53 | Cis-9-(3-Morpholin-4-yl-propoxy)-6-thiazol-2-yl-1,2,3,5,6,10b-hexahydro-pyrrolo[2,1-a]isoquinoline; |
| 54 | Cis-9-(3-Morpholin-4-yl-propoxy)-6-(2H-pyrazol-3-yl)-1,2,3,5,6,10b-hexahydro-pyrrolo[2,1-a]isoquinoline; |
| 55 | Cis-6-Imidazo[1,2-a]pyridin-3-yl-9-(3-morpholin-4-yl-propoxy)-1,2,3,5,6,10b-hexahydro-pyrrolo[2,1-a]isoquinoline; |
| 56 | Cis-9-(3-Morpholin-4-yl-propoxy)-6-thiophen-3-yl-1,2,3,5,6,10b-hexahydro-pyrrolo[2,1-a]isoquinoline; |
| 57 | Cis-9-(3-Morpholin-4-yl-propoxy)-6-thiophen-2-yl-1,2,3,5,6,10b-hexahydro-pyrrolo[2,1-a]isoquinoline; |
| 58 | Cis-3-[9-(3-Morpholin-4-yl-propoxy)-1,2,3,5,6,10b-hexahydro-pyrrolo[2,1-a]isoquinolin-6-yl]-benzonitrile; |
| 59 | Cis-9-(3-Morpholin-4-yl-propoxy)-6-pyridin-3-yl-1,2,3,5,6,10b-hexahydro-pyrrolo[2,1-a]isoquinoline; |
| 60 | Cis-9-(3-Morpholin-4-yl-propoxy)-6-pyridin-2-yl-1,2,3,5,6,10b-hexahydro-pyrrolo[2,1-a]isoquinoline; |
| 61 | Cis-9-(3-Morpholin-4-yl-propoxy)-6-(4-trifluoromethylsulfanyl-phenyl)-1,2,3,5,6,10b-hexahydro-pyrrolo[2,1-a]isoquinoline; |
| 62 | Cis-9-(3-Morpholin-4-yl-propoxy)-6-(3-trifluoromethylsulfanyl-phenyl)-1,2,3,5,6,10b-hexahydro-pyrrolo[2,1-a]isoquinoline; |
| 63 | Cis-6-(4-Methylsulfanyl-phenyl)-9-(3-morpholin-4-yl-propoxy)-1,2,3,5,6,10b-hexahydro-pyrrolo[2,1-a]isoquinoline; |
| 64 | Cis-6-(3-Chloro-4-methoxy-phenyl)-9-(3-morpholin-4-yl-propoxy)-1,2,3,5,6,10b-hexahydro-pyrrolo[2,1-a]isoquinoline; |
| 65 | Cis-6-(3-Fluoro-4-methoxy-phenyl)-9-(3-morpholin-4-yl-propoxy)-1,2,3,5,6,10b-hexahydro-pyrrolo[2,1-a]isoquinoline; |
| 66A | Cis-6-(4-Chloro-phenyl)-9-(3-piperidin-1-yl-propoxy)-1,2,3,5,6,10b-hexahydro-pyrrolo[2,1-a]isoquinoline; |
| 66B | Trans-6-(4-Chloro-phenyl)-9-(3-piperidin-1-yl-propoxy)-1,2,3,5,6,10b-hexahydro-pyrrolo[2,1-a]isoquinoline; |
| 67 | Cis-9-(3-Piperidin-1-yl-propoxy)-6-(3-trifluoromethyl-phenyl)-1,2,3,5,6,10b-hexahydro-pyrrolo[2,1-a]isoquinoline; |

| EX | CHEMICAL NAME |
|---|---|
| 68 | 6-Biphenyl-4-yl-9-(3-morpholin-4-yl-propoxy)-1,2,3,5,6,10b-hexahydro-pyrrolo[2,1-a]isoquinoline; |
| 69 | 9-(3-Morpholin-4-yl-propoxy)-6-naphthalen-2-yl-1,2,3,5,6,10b-hexahydro-pyrrolo[2,1-a]isoquinoline; |
| 70 | 9-(3-Morpholin-4-yl-propoxy)-6-quinolin-7-yl-1,2,3,5,6,10b-hexahydro-pyrrolo[2,1-a]isoquinoline; |
| 71 | 6-(1H-Indol-5-yl)-9-(3-morpholin-4-yl-propoxy)-1,2,3,5,6,10b-hexahydro-pyrrolo[2,1-a]isoquinoline; |
| 72 | 6-(1H-Benzoimidazol-5-yl)-9-(3-morpholin-4-yl-propoxy)-1,2,3,5,6,10b-hexahydro-pyrrolo[2,1-a]isoquinoline; |
| 73 | 6-(1H-Benzoimidazol-2-yl)-9-(3-morpholin-4-yl-propoxy)-1,2,3,5,6,10b-hexahydro-pyrrolo[2,1-a]isoquinoline; |
| 74 | 6-(1-Methyl-1H-benzoimidazol-2-yl)-9-(3-morpholin-4-yl-propoxy)-1,2,3,5,6,10b-hexahydro-pyrrolo[2,1-a]isoquinoline; |
| 75 | 9-(3-Morpholin-4-yl-propoxy)-6-naphthalen-1-yl-1,2,3,5,6,10b-hexahydro-pyrrolo[2,1-a]isoquinoline; |
| 76 | 6-Benzo[b]thiophen-7-yl-9-(3-morpholin-4-yl-propoxy)-1,2,3,5,6,10b-hexahydro-pyrrolo[2,1-a]isoquinoline; |
| 77 | 6-(6-Chloro-pyridin-3-yl)-9-(3-morpholin-4-yl-propoxy)-1,2,3,5,6,10b-hexahydro-pyrrolo[2,1-a]isoquinoline; |
| 78 | Dimethyl-{5-[9-(3-morpholin-4-yl-propoxy)-1,2,3,5,6,10b-hexahydro-pyrrolo[2,1-a]isoquinolin-6-yl]-pyridin-2-yl}-amine; |
| 79 | 6-(6-Methoxy-pyridin-3-yl)-9-(3-morpholin-4-yl-propoxy)-1,2,3,5,6,10b-hexahydro-pyrrolo[2,1-a]isoquinoline; |
| 80 | 9-(3-Morpholin-4-yl-propoxy)-6-oxazol-5-yl-1,2,3,5,6,10b-hexahydro-pyrrolo[2,1-a]isoquinoline; |
| 81 | 6-(1H-Imidazol-2-yl)-9-(3-morpholin-4-yl-propoxy)-1,2,3,5,6,10b-hexahydro-pyrrolo[2,1-a]isoquinoline; |
| 82 | 6-(1-Methyl-1H-imidazol-2-yl)-9-(3-morpholin-4-yl-propoxy)-1,2,3,5,6,10b-hexahydro-pyrrolo[2,1-a]isoquinoline; |
| 83 | 6-(3H-Imidazol-4-yl)-9-(3-morpholin-4-yl-propoxy)-1,2,3,5,6,10b-hexahydro-pyrrolo[2,1-a]isoquinoline; |
| 84 | 6-(3-Methyl-3H-imidazol-4-yl)-9-(3-morpholin-4-yl-propoxy)-1,2,3,5,6,10b-hexahydro-pyrrolo[2,1-a]isoquinoline; |
| 85 | 6-(3-Chloro-4-difluoromethoxy-phenyl)-9-(3-morpholin-4-yl-propoxy)-1,2,3,5,6,10b-hexahydro-pyrrolo[2,1-a]isoquinoline; |
| 86 | (4-{3-[6-(4-Methoxy-phenyl)-1,2,3,5,6,10b-hexahydro-pyrrolo[2,1-a]isoquinolin-9-yloxy]-propyl}-morpholin-2-yl)-methanol; |
| 87 | (4-{3-[6-(4-Methoxy-phenyl)-1,2,3,5,6,10b-hexahydro-pyrrolo[2,1-a]isoquinolin-9-yloxy]-propyl}-morpholin-3-yl)-methanol; |
| 88 | 6-(3,5-Bis-trifluoromethyl-phenyl)-9-(3-piperidin-1-yl-propoxy)-1,2,3,5,6,10b-hexahydro-pyrrolo[2,1-a]isoquinoline; |
| 89 | (1R,6S)-6-(4-Methylsulfanyl-phenyl)-9-(3-morpholin-4-yl-propoxy)-1,2,3,5,6,10b-hexahydro-pyrrolo[2,1-a]isoquinoline; |
| 90 | (1S,6R)-6-(4-Methylsulfanyl-phenyl)-9-(3-morpholin-4-yl-propoxy)-1,2,3,5,6,10b-hexahydro-pyrrolo[2,1-a]isoquinoline; |
| 91 | (1S,6R)-6-(4-Methoxy-phenyl)-9-(3-morpholin-4-yl-propoxy)-1,2,3,5,6,10b-hexahydro-pyrrolo[2,1-a]isoquinoline; |
| 92 | (1R,6S)-6-(4-Methoxy-phenyl)-9-(3-morpholin-4-yl-propoxy)-1,2,3,5,6,10b-hexahydro-pyrrolo[2,1-a]isoquinoline; |
| 93 | Trans-6-(4-Methoxy-phenyl)-9-(3-morpholin-4-yl-propoxy)-1,2,3,5,6,10b-hexahydro-pyrrolo[2,1-a]isoquinoline; |
| 94 | (1R,6R)-6-(4-Methoxy-phenyl)-9-(3-morpholin-4-yl-propoxy)-1,2,3,5,6,10b-hexahydro-pyrrolo[2,1-a]isoquinoline; |
| 95 | (1S,6S)-6-(4-Methoxy-phenyl)-9-(3-morpholin-4-yl-propoxy)-1,2,3,5,6,10b-hexahydro-pyrrolo[2,1-a]isoquinoline; |
| 96A | Cis-6-(4-methoxy-phenyl)-9-(4-piperidin-1-yl-but-1-ynyl)-1,2,3,5,6,10b-hexahydro-pyrrolo[2,1-a]isoquinoline; |
| 96B | Trans-6-(4-methoxy-phenyl)-9-(4-piperidin-1-yl-but-1-ynyl)-1,2,3,5,6,10b-hexahydro-pyrrolo[2,1-a]isoquinoline; |
| 97A | Cis-6-(4-methylsulfanyl-phenyl)-8-(4-piperidin-1-yl-but-1-ynyl)-1,2,3,5,6,10b-hexahydro-pyrrolo[2,1-a]isoquinoline; |
| 97B | Trans-6-(4-methylsulfanyl-phenyl)-8-(4-piperidin-1-yl-but-1-ynyl)-1,2,3,5,6,10b-hexahydro-pyrrolo[2,1-a]isoquinoline; |
| 98A | Cis-6-(4-methylsulfanyl-phenyl)-9-(4-piperidin-1-yl-but-1-ynyl)-1,2,3,5,6,10b-hexahydro-pyrrolo[2,1-a]isoquinoline; and |
| 98B | Trans-6-(4-methylsulfanyl-phenyl)-9-(4-piperidin-1-yl-but-1-ynyl)-1,2,3,5,6,10b-hexahydro-pyrrolo[2,1-a]isoquinoline. |

The features and advantages of the invention are apparent to one of ordinary skill in the art. Based on this disclosure, including the summary, detailed description, background, examples, and claims, one of ordinary skill in the art will be able to make modifications and adaptations to various conditions and usages. Publications described herein are incorporated by reference in their entirety. Where chemical symbols are used, it is understood that they are read from left to right, and that otherwise their spatial orientation has no significance.

The compounds as described above may be made according to processes within the skill of the art and/or that are described in the schemes and examples that follow. To obtain the various compounds herein, starting materials may be employed that carry the ultimately desired substituents though the reaction scheme with or without protection as appropriate. This may be achieved by means of conventional protecting groups, such as those described in "Protective Groups in Organic Chemistry", ed. J. F. W. McOmie, Plenum Press, 1973; and T. W. Greene & P. G. M. Wuts, "Protective Groups in Organic Synthesis", $3^{rd}$ ed., John Wiley & Sons, 1999. The protecting groups may be removed at a convenient subsequent stage using methods known from the art. Alternatively, it may be necessary to employ, in the place of the ultimately desired substituent, a suitable group that may be carried through the reaction scheme and replaced as appropriate with the desired substituent. Such compounds, precursors, or prodrugs are also within the scope of the invention. Reactions may be performed between the melting point and the reflux temperature of the solvent, and preferably between 0° C. and the reflux temperature of the solvent.

The hexahydro-pyrrolo-isoquinoline compounds of formulae (I), (II), and (III) may be prepared by a number of reaction schemes. Access to compounds of formula (I) is described in Schemes A-C. Persons skilled in the art will recognize that certain compounds are more advantageously produced by one scheme as compared to the other. In addition, synthetic sequences described in U.S. Pat. Appl. No. 60/637,173 are incorporated by reference and may be applied to the preparation of compounds of formula (I).

SCHEME A

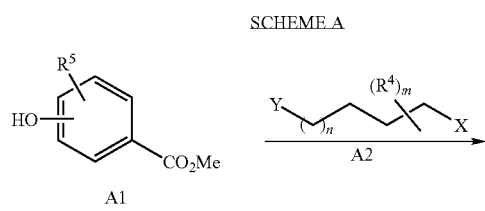

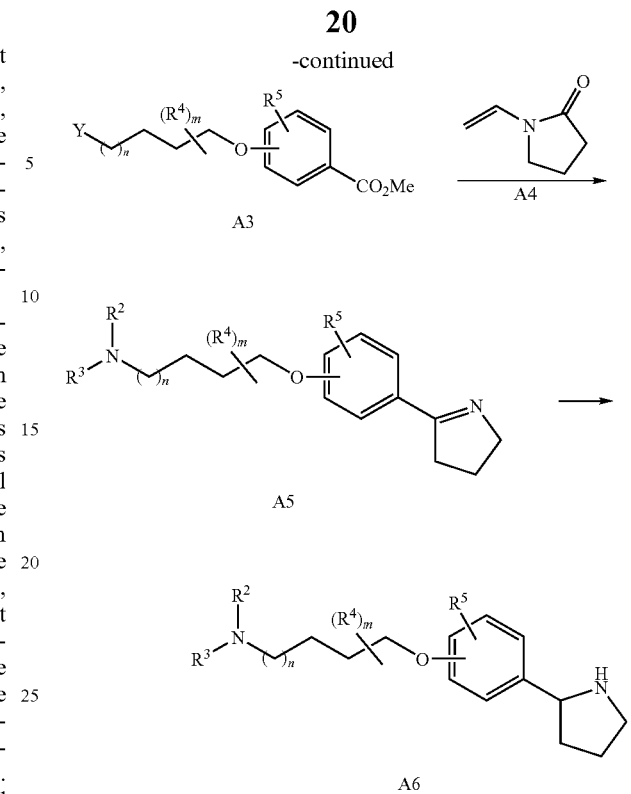

Referring to Scheme A, methyl 3-hydroxybenzoate derivatives A1 may be alkylated with reagents A2, where Y is Cl, OH, a protected alcohol, or $NR^2R^3$, to form ethers A3. Where X is a suitable leaving group, such as Br, I, or OTs, alkylations may be performed by Williamson ether synthesis, using a suitable base such as $K_2CO_3$, $Na_2CO_3$, or NaH, in a solvent such as acetonitrile, with or without catalytic KI or NaI. Alternatively, where X is OH, and Y is a protected hydroxyl or $NR^2R^3$, ethers of formula A3 may be prepared under Mitsunobu conditions. Where Y is Cl, ethers A3 may be converted to the corresponding amines (where Y is $NR^2R^3$) using standard methods. Alternatively, where Y is OH or protected hydroxyl, the amine group $NR^2R^3$ may be installed at a later stage in the synthesis.

Esters of formula A3 are condensed with N-vinylpyrrolidin-2-one to form imines of formula A5, which are subsequently reduced, preferably with $LiAlH_4$, to pyrrolidines A6.

SCHEME B

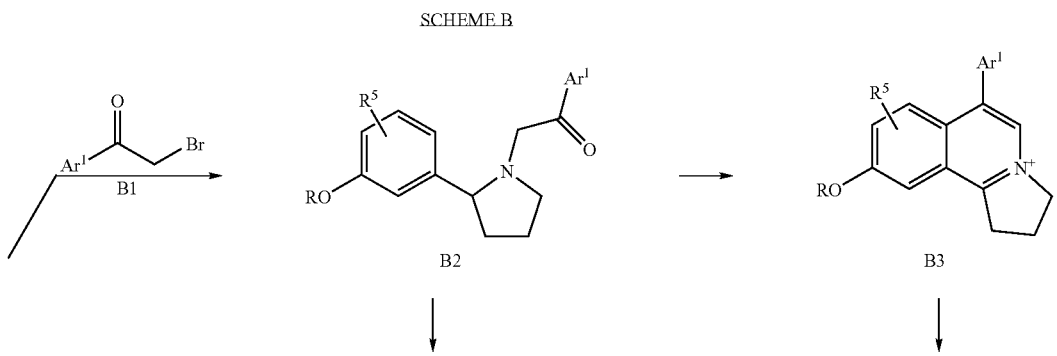

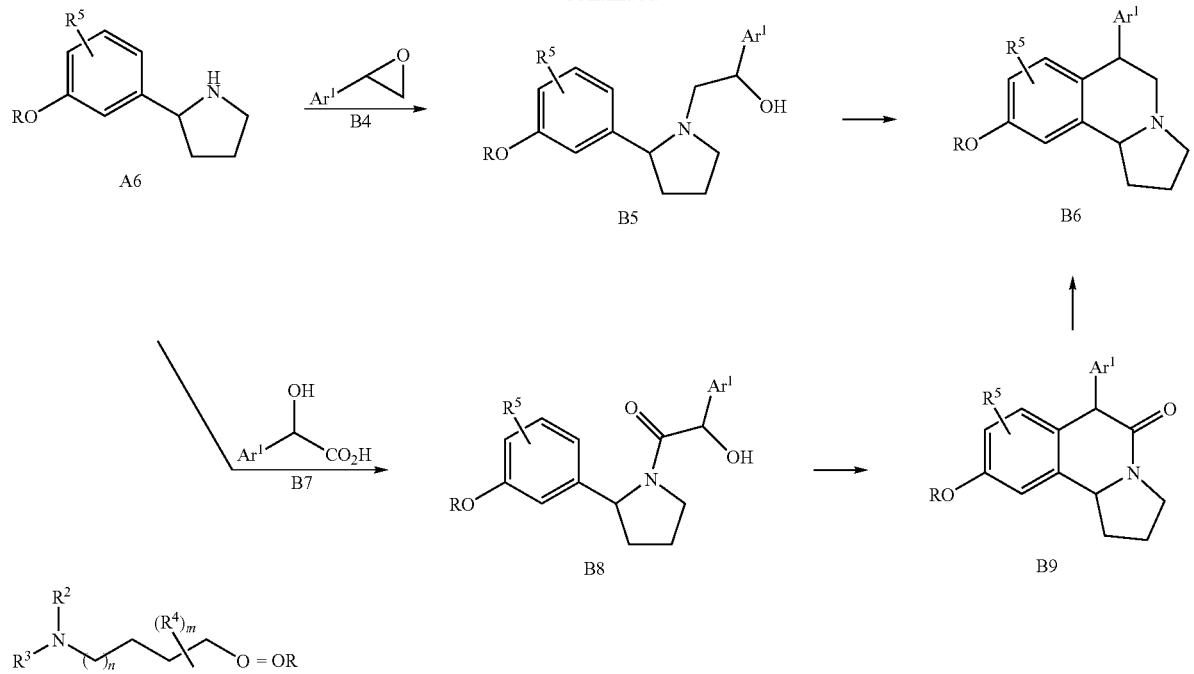

Referring to Scheme B, alkylation of pyrrolidines A6 with alpha-haloketones B1 to form ketones B2 is accomplished in the presence of a tertiary amine base such as Et₃N or iPr₂NEt, in a suitable solvent such as THF or CH₂Cl₂. Cyclization to form tetrahydroisoquinolinium salts B3 is effected by exposure to a suitable protic or Lewis acid, such as methanesulfonic acid (MSA), trifluoroacetic acid, AlCl₃, TiCl₄, or BF₃·OEt₂ with or without a solvent such as CH₂Cl₂. Preferred conditions are neat MSA or MSA in CH₂Cl₂. The intermediate salts B3 may be reduced using standard reducing agents such as NaCNBH₃ in an acidic methanol medium to form tricyclic amines B6.

Alternatively, pyrrolidines A6 may be reacted with styrene oxides B4 to form alcohols B5. Ketones B2 may also be reduced by known methods, including NaBH₄, to the corresponding alcohols B5. Treatment of the intermediate alcohols B5 with MSA in CH₂Cl₂ provides cyclic species B6 directly. Where the OR group has been left as OH, the amino side chain may be installed at this stage using methods described above or methods known in the art. Alternatively, the OR group may be carried through the sequence as a suitably substituted 3-hydroxypropyloxy or 4-hydroxybutyloxy group (protected or unprotected as appropriate), and the terminal hydroxyl group may be converted to the desired amine functionality at an appropriate point during the synthetic sequence using standard methods such as those described above.

In another embodiment, pyrrolidines A6 may be coupled with mandelic acid derivatives B7 to form amides B8. Cyclization to form tricyclic amides B9 is performed as described above. Reduction of the carbonyl to provide compounds of formula B6 is accomplished with a reducing agent such as BH₃, in a solvent such as THF.

Although Scheme B is depicted to produce regioisomers B6 in which the OR substituent is at the 9-position of the tricyclic ring system, those skilled in the art will recognize that cyclization of compounds of formula B2, B5, and B8 may also provide regioisomers where the OR substituent is in the 7-position. Such regioisomers may be converted to compounds of formula (I) according to the procedures described above.

SCHEME C

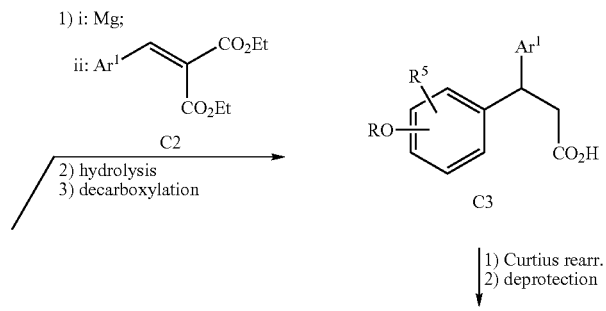

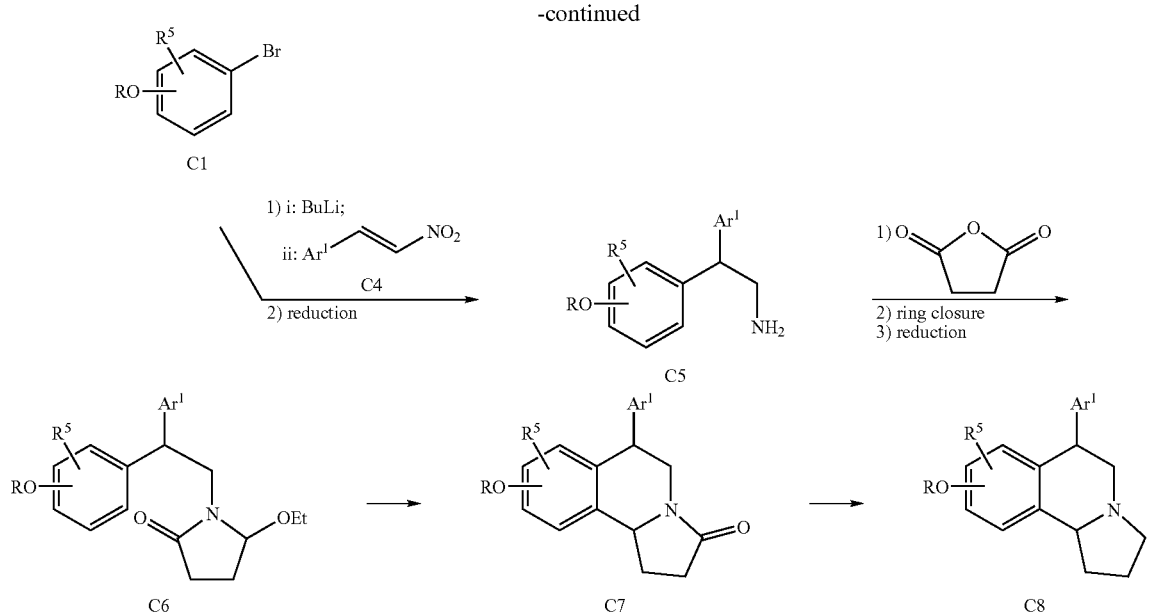

Compounds of formula C8, where OR is defined as in Scheme B, are alternatively prepared according to Scheme C. Intermediates of formula C1 may be commercially available or may be prepared by a variety of methods. Those skilled in the art will recognize that the amine side chain of compounds of formula (I) may be installed at an appropriate point during the sequence using standard methods including those described in Schemes A and B. If required, a protected amino group or surrogate may be used and later transformed into the amino group —$NR^2R^3$.

Formation of the aryl Grignard reagent, followed by reaction with malonic ester analogs C2, hydrolysis of the resulting diester, and decarboxylation provide acids of formula C3. Hydrolysis may be performed using methods known to one skilled in the art, including KOH in EtOH. Decarboxylation is typically accomplished through the application of heat. Curtius rearrangement, preferably using $Et_3N$ and diphenylphosphoryl azide in a suitable solvent, installs a protected amine functionality. Where the solvent is t-BuOH, a Boc protecting group results. The protecting group may be subsequently removed under standard conditions, such as TFA in DCM, to form amines of formula C5.

Alternatively, halogen-metal exchange of the aryl bromides C1, followed by reaction with nitroalkenes C4, and subsequent reduction of the nitro group will provide amines of formula C5 directly. Reduction of the nitro group is accomplished using procedures well-known to those skilled in the art. Reaction of amines C5 with succinic anhydride, followed by ring closure, gives rise to the corresponding succinimides (structure not shown). The ring closure may preferably be accomplished using acetyl chloride, with or without the application of heat. Succinimides C6 are then reduced to hemiaminals C6 using a suitable reducing agent, such as $NaBH_4$, in a solvent such as dioxane.

Reaction under acidic conditions, such as MSA, leads to formation of the tricyclic system of compounds of formula C7. The lactam ring may be reduced to form compounds of formula C8 using a suitable reducing agent, such as $BH_3$, in a solvent such as THF. Where OR is OMe, the methyl protecting group may be removed at the C7 or C8 stage and replaced by the amine-containing side chain described in formula (I).

Compounds of formulae (II) and (III) are prepared according to procedures described above and those described in U.S. patent application Ser. No. 11/300,880 and U.S. Patent Appl. No. 60/692,003, as well as those described in the Examples below.

Compounds prepared according to the schemes described above may be obtained as single enantiomers, diastereomers, or regioisomers, or as racemic mixtures or mixtures of enantiomers, diastereomers, or regioisomers. Where regioisomeric or diastereomeric mixtures are obtained, isomers may be separated using conventional methods such as chromatography or crystallization. Where racemic (1:1) and non-racemic (not 1:1) mixtures of enantiomers are obtained, single enantiomers may be isolated using conventional separation methods known to one skilled in the art. Particularly useful separation methods may include chiral chromatography, recrystallization, resolution, diastereomeric salt formation, or derivatization into diastereomeric adducts followed by separation.

For therapeutic use, salts of the compounds of the present invention are those that are pharmaceutically acceptable. However, salts of acids and bases that are non-pharmaceutically acceptable may also find use, for example, in the preparation or purification of a pharmaceutically acceptable compound. All salts, whether pharmaceutically acceptable or not are included within the ambit of the present invention.

Pharmaceutically acceptable salts, esters, and amides of compounds according to the present invention refer to those salt, ester, and amide forms of the compounds of the present invention which would be apparent to the pharmaceutical chemist, i.e., those which are non-toxic and which would favorably affect the pharmacokinetic properties of said compounds of the present invention. Those compounds having favorable pharmacokinetic properties would be apparent to the pharmaceutical chemist, i.e., those which are non-toxic and which possess such pharmacokinetic properties to provide sufficient palatability, absorption, distribution, metabolism and excretion. Other factors, more practical in nature, which are also important in the selection, are cost of raw materials, ease of crystallization, yield, stability, hygroscopicity and flowability of the resulting bulk drug.

Examples of acids that may be used in the preparation of pharmaceutically acceptable salts include the following: acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Compounds of the present invention containing acidic protons may be converted into their therapeutically active non-toxic metal or amine addition salt forms by treatment with appropriate organic and inorganic bases. Appropriate base salt forms comprise, for example, the ammonium salts; the alkali and earth alkaline metal salts (e.g. lithium, sodium, potassium, magnesium, calcium salts, which may be prepared by treatment with, for example, magnesium hydroxide, calcium hydroxide, potassium hydroxide, zinc hydroxide, or sodium hydroxide); and amine salts made with organic bases (e.g. primary, secondary and tertiary aliphatic and aromatic amines such as L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine). See, e.g., S. M. Berge, et al., "Pharmaceutical Salts", J. Pharm. Sci., 1977, 66:1-19, which is incorporated herein by reference.

Pharmaceutically acceptable esters and amides are those that are within a reasonable benefit/risk ratio, pharmacologically effective and suitable for contact with the tissues of patients without undue toxicity, irritation, or allergic response. Representative pharmaceutically acceptable amides of the invention include those derived from ammonia, primary $C_{1-6}$alkyl amines and secondary di($C_{1-6}$alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$alkyl primary amines, and di($C_{1-2}$alkyl)amines.

Representative pharmaceutically acceptable esters of the invention include $C_{1-7}$alkyl, $C_{5-7}$cycloalkyl, phenyl, substituted phenyl, and phenyl$C_{1-6}$alkyl-esters. Preferred esters include methyl esters. Furthermore, examples of suitable esters include such esters where one or more carboxyl substituents is replaced with p-methoxybenzyloxy-carbonyl, 2,4,6-trimethylbenzyloxy-carbonyl, 9-anthryloxycarbonyl, $CH_3SCH_2COO-$, tetrahydrofur-2-yloxycarbonyl, tetrahydropyran-2-yloxy-carbonyl, fur-2-yloxycarbonyl, benzoyl methoxy-carbonyl, p-nitrobenzyloxy-carbonyl, 4-pyridylmethoxycarbonyl, 2,2,2-trichloroethoxycarbonyl, 2,2,2-tribromoethoxycarbonyl, t-butyloxycarbonyl, t-amyloxycarbonyl, diphenylmethoxycarbonyl, triphenylmethoxycarbonyl, adamantyloxycarbonyl, 2-benzyloxyphenyloxycarbonyl, 4-methylthiophenyloxycarbonyl, or tetrahydropyran-2-yloxycarbonyl.

The compounds of the present invention are modulators of the histamine $H_3$ receptor and of the serotonin transporter, and as such, the compounds are useful in the treatment of histamine $H_3$ and serotonin-mediated disease states. Compounds of the present invention possess serotonin transporter and $H_3$ receptor modulating activity. As such modulators, the compounds may act as antagonists or agonists. The effect of an antagonist may also be produced by an inverse agonist.

The compounds of the present invention are useful in methods for treating or preventing neurologic or CNS disorders including sleep/wake and arousal/vigilance disorders (e.g. insomnia, jet lag, and disturbed sleep), attention deficit hyperactivity disorders (ADHD), attention-deficit disorders, learning and memory disorders, learning impairment, memory impairment, memory loss, cognitive dysfunction, migraine, neurogenic inflammation, dementia, mild cognitive impairment (pre-dementia), Alzheimer's disease, epilepsy, narcolepsy with or without associated cataplexy, cataplexy, disorders of sleep/wake homeostasis, idiopathic somnolence, excessive daytime sleepiness (EDS), circadian rhythym disorders, sleep/fatigue disorders, fatigue, drowsiness associated with sleep apnea, sleep impairment due to perimenopausal hormonal shifts, Parkinson's-related fatigue, MS-related fatigue, depression-related fatigue, chemotherapy-induced fatigue, work-related fatigue, lethargy, eating disorders, obesity, motion sickness, vertigo, schizophrenia, substance abuse, bipolar disorders, manic disorders and depression. Said methods comprise the step of administering to a mammal suffering therefrom an effective amount of at least one compound of the present invention.

Particularly, as modulators of the histamine $H_3$ receptor and the serotonin transporter, the compounds of the present invention may be used in the treatment or prevention of depression, disturbed sleep, fatigue, lethargy, cognitive impairment, memory impairment, memory loss, learning impairment, and attention-deficit disorders.

The present invention also contemplates a method of treating or preventing a disease or condition mediated by the histamine $H_3$ receptor and the serotonin transporter with a combination therapy, comprising administering at least one compound of the present invention in combination with one or more therapeutic agents. Suitable therapeutic agents include: $H_1$ receptor antagonists, $H_2$ receptor antagonists, $H_3$ receptor antagonists, and neurotransmitter modulators such as serotonin-norepinephrine reuptake inhibitors, selective serotonin reuptake inhibitors (SSRIs), noradrenergic reuptake inhibitors, non-selective serotonin re-uptake inhibitors (NSSRIs), acetylcholinesterase inhibitors, and modafinil. In a particular embodiment, a combination therapy method includes administering at least one compound of present invention and administering modafinil, for example, for the treatment of narcolepsy, excessive daytime sleepiness (EDS), Alzheimer's disease, depression, attention-deficit disorders, MS-related fatigue, post-anesthesia grogginess, cognitive impairment, schizophrenia, spasticity associated with cerebral palsy, age-related memory decline, idiopathic somnolence, or jet-lag.

The present invention also contemplates a method for the treatment or prevention of a disease selected from the group consisting of: depression, disturbed sleep, fatigue, lethargy, cognitive impairment, memory impairment, memory loss, learning impairment, and attention-deficit disorders in mammals, comprising the step of administering to a mammal suffering therefrom an effective amount of a compound having both $H_3$ receptor modulating activity and serotonin transporter modulating activity. Preferably, said compound has an $H_3$ receptor binding activity of at least 20 nM in the human $H_3$ binding assay. Preferably, said compound has a serotonin transporter binding activity of at least 20 nM in the human SERT binding assay. Preferably, the ratio of the $H_3$ receptor binding activity in the human $H_3$ binding assay and the serotonin transporter binding activity in the human SERT binding assay for said compound is between 10:1 and 1:10.

Compounds of the present invention may be administered in pharmaceutical compositions to treat patients (humans and other mammals) with disorders mediated by the $H_3$ receptor and serotonin transporter. Thus, the invention features pharmaceutical compositions containing at least one compound of the present invention and a pharmaceutically acceptable carrier. A composition of the invention may further include at least one other therapeutic agent (for example, a combination formulation or combination of differently formulated active agents for use in a combination therapy method).

The present invention also features methods of using or preparing or formulating such pharmaceutical compositions. The pharmaceutical compositions can be prepared using conventional pharmaceutical excipients and compounding techniques known to those skilled in the art of preparing dosage forms. It is anticipated that the compounds of the invention can be administered by oral, parenteral, rectal, topical, or ocular routes, or by inhalation. Preparations may also be designed to give slow release of the active ingredient. The preparation may be in the form of tablets, capsules, sachets, vials, powders, granules, lozenges, powders for reconstitution, liquid preparations, or suppositories. Preferably, compounds may be administered by intravenous infusion or topical administration, but more preferably by oral administration.

For oral administration, the compounds of the invention can be provided in the form of tablets or capsules, or as a solution, emulsion, or suspension. Tablets for oral use may include the active ingredient mixed with pharmaceutically acceptable excipients such as inert diluents, disintegrating agents, binding agents, lubricating agents, sweetening agents, flavoring agents, coloring agents and preservatives agents. Suitable inert fillers include sodium and calcium carbonate, sodium and calcium phosphate, lactose, starch, sugar, glucose, methyl cellulose, magnesium stearate, mannitol, sorbitol, and the like; typical liquid oral excipients include ethanol, glycerol, water and the like. Starch, polyvinyl-pyrrolidone, sodium starch glycolate, microcrystalline cellulose, and alginic acid are suitable disintegrating agents. Binding agents may include starch and gelatin. The lubricating agent, if present, will generally be magnesium stearate, stearic acid or talc. If desired, the tablets may be coated with a material such as glyceryl monostearate or glyceryl distearate to delay absorption in the gastrointestinal tract, or may be coated with an enteric coating. Capsules for oral use include hard gelatin capsules in which the active ingredient is mixed with a solid, semi-solid, or liquid diluent, and soft gelatin capsules wherein the active ingredient is mixed with water, an oil such as peanut oil or olive oil, liquid paraffin, a mixture of mono and di-glycerides of short chain fatty acids, polyethylene glycol 400, or propylene glycol.

Liquids for oral administration may be suspensions, solutions, emulsions or syrups or may be presented as a dry product for reconstitution with water or other suitable vehicles before use. Compositions of such liquid may contain pharmaceutically-acceptable excipients such as suspending agents (for example, sorbitol, methyl cellulose, sodium alginate, gelatin, hydroxyethylcellulose, carboxymethylcellulose, aluminium stearate gel and the like); non-aqueous vehicles, which include oils (for example, almond oil or fractionated coconut oil), propylene glycol, ethyl alcohol or water; preservatives (for example, methyl or propyl p-hydroxybenzoate or sorbic acid); wetting agents such as lecithin; and, if needed, flavoring or coloring agents.

The compounds of this invention may also be administered by non-oral routes. The compositions may be formulated for rectal administration as a suppository. For parenteral use, including intravenous, intramuscular, intraperitoneal, or subcutaneous routes, the compounds of the invention will generally be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit dose form such as ampules or disposable injection devices, in multi-dose forms such as vials from which the appropriate dose may be withdrawn, or in a solid form or pre-concentrate that can be used to prepare an injectable formulation. Another mode of administration of the compounds of the invention may utilize a patch formulation to affect transdermal delivery. The compounds of this invention may also be administered by inhalation, via the nasal or oral routes using a spray formulation consisting of the compound of the invention and a suitable carrier.

Methods are known in the art for determining effective doses for therapeutic and prophylactic purposes for the pharmaceutical compositions or the drug combinations of the present invention, whether or not formulated in the same composition. The specific dosage level required for any particular patient will depend on a number of factors, including severity of the condition being treated, the route of administration, and the weight of the patient. For therapeutic purposes, "effective dose" or "effective amount" refers to that amount of each active compound or pharmaceutical agent, alone or in combination, that elicits the biological or medicinal response in a tissue system, animal, or human that is being sought by a researcher, veterinarian, medical doctor, or other clinician, which includes alleviation of the symptoms of the disease or disorder being treated. For prophylactic purposes (i.e., inhibiting the onset or progression of a disorder), the term "effective dose" or "effective amount" refers to that amount of each active compound or pharmaceutical agent, alone or in combination, that inhibits in a subject the onset or progression of a disorder as being sought by a researcher, veterinarian, medical doctor, or other clinician, the delaying of which disorder is mediated, at least in part, by the modulation of the histamine $H_3$ receptor and/or the serotonin transporter. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both drugs are administered in an amount that is sub-therapeutic or sub-prophylactic if administered alone, but are therapeutic or prophylactic when administered together. Combinations of three or more drugs are analogously possible. Methods of combination therapy include co-administration of a single formulation containing all active agents; essentially contemporaneous administration of more than one formulation; and administration of two or more active agents separately formulated.

It is anticipated that the daily dose (whether administered as a single dose or as divided doses) will be in the range 0.01 to 1000 mg per day, more usually from 1 to 500 mg per day, and most usually from 10 to 200 mg per day. Expressed as dosage per unit body weight, a typical dose will be expected to be between 0.0001 mg/kg and 15 mg/kg, especially between 0.01 mg/kg and 7 mg/kg, and most especially between 0.15 mg/kg and 2.5 mg/kg.

Preferably, oral doses range from about 0.05 to 200 mg/kg, daily, taken in 1 to 4 separate doses. Some compounds of the invention may be orally dosed in the range of about 0.05 to about 50 mg/kg daily, others may be dosed at 0.05 to about 20 mg/kg daily, while still others may be dosed at 0.1 to about 10 mg/kg daily. Infusion doses can range from about 1 to 1000 µg/kg/min of inhibitor, admixed with a pharmaceutical carrier over a period ranging from several minutes to several days. For topical administration compounds of the present invention may be mixed with a pharmaceutical carrier at a concentration of about 0.1% to about 10% of drug to vehicle.

EXAMPLES

In order to illustrate the invention, the following examples are included. These examples do not limit the invention. They are only meant to suggest a method of practicing the invention. Those skilled in the art may find other methods of practicing the invention, which are obvious to them. However, those methods are deemed to be within the scope of this invention.

Protocol for Preparative Reversed-Phase HPLC

Gilson®
Column: YMC-Pack ODS-A, 5 µm, 75×30 mm
Flow rate: 25 mL/min
Detection: $\lambda$=220 & 254 nm
Gradient (acetonitrile/water, 0.05% trifluoroacetic acid)
1) 0.0 min 15% acetonitrile/85% water
2) 20.0 min 99% acetonitrile/1% water Protocol for HPLC (Reversed-Phase)

Method A:
Hewlett Packard Series 1100
Column: Agilent ZORBAX® Bonus RP, 5 µm, 4.6×250 mm
Flow rate: 1 mL/min
Detection: $\lambda$=220 & 254 nm
Gradient (acetonitrile/water, 0.05% trifluoroacetic acid)
1) 0.0 min 1% acetonitrile/99% water
2) 20.0 min 99% acetonitrile/1% water
Method B:
Hewlett Packard HPLC
Column: Agilent ZORBAX® Eclipse XDB-C8, 5 µm, 4.6×150 mm
Flow rate: 1 mL/min
Detection: $\lambda$=220 & 254 nm
Gradient (acetonitrile/water, 0.05% trifluoroacetic acid)
1) 0.0 min 1% acetonitrile/99% water
2) 8.0 min 99% acetonitrile/1% water
3) 12.0 min 99% acetonitrile/1% water Protocol for Preparative SFC Thar Technologies®
Column: Chiracel AD, 10 µm, 250×20 mm
Flow rate: 37 gm/min
Detection: $\lambda$=220 & 254 nm
Mobile phase: Isocratic 30% IPA/70% $CO_2$
Pressure: 150 Bar
Temperature: 35° C.

Protocol for Analytical SFC

Jasco®
Column: Chiracel AD, 10 µm, 250×4.6 mm
Flow rate: 1 gm/min
Detection: $\lambda$=220 & 254 nm
Mobile phase: Isocratic 30% IPA/70% $CO_2$
Pressure: 150 Bar
Temperature: 35° C.

Mass spectra were obtained on an Agilent series 1100 MSD using electrospray ionization (ESI) in positive mode unless otherwise indicated. Calculated mass corresponds to the exact mass.

Thin-layer chromatography was performed using Merck silica gel 60 $F_{254}$ 2.5 cm×7.5 cm 250 µm or 5.0 cm×10.0 cm 250 µm pre-coated silica gel plates. Preparative thin-layer chromatography was performed using EM Science silica gel 60 $F_{254}$ 20 cm×20 cm 0.5 mm pre-coated plates with a 20 cm×4 cm concentrating zone.

NMR spectra were obtained on either a Bruker model DPX400 (400 MHz), DPX500 (500 MHz), or DPX600 (600 MHz) spectrometer. The format of the $^1$H NMR data below is: chemical shift in ppm down field of the tetramethylsilane reference (multiplicity, coupling constant J in Hz, integration).

Normal phase flash column chromatography (FCC) was typically performed with RediSep® silica gel columns using 2 M ammonia in methanol/dichloromethane as eluent.

Chiral chromatography was performed using SFC HPLC (Chiralpak AD-h column), IPA/MeOH/$CO_2$, or by chiral HPLC (21×250 mm Chiracel AD-H, 5 µM (Chiral Technologies), 0.2% diethylamine in EtOH, 8 mL/min). Where a potential chiral center is designated with a solid bond (not bold or hashed), the structure is meant to refer to a racemic mixture, a mixture of enantiomers, or a single enantiomer as described. Where a single enantiomer is described without enantiomeric designation at the chiral center, it is understood that the absolute configuration of the single enantiomer is unknown.

Example 1-(A-C)

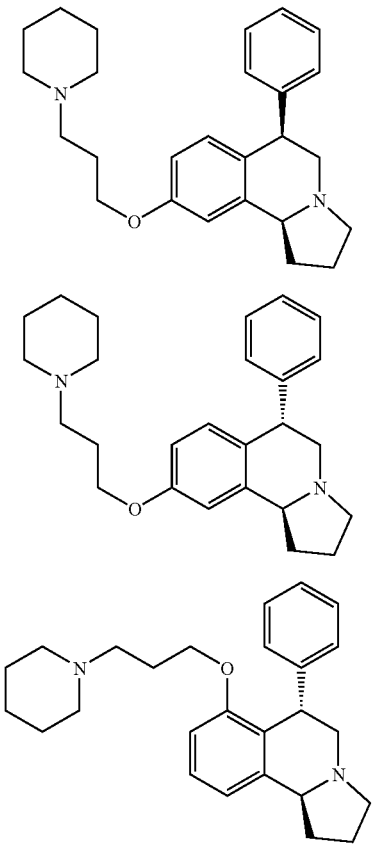

1A: Cis-6-Phenyl-9-(3-piperidin-1-yl-propoxy)-1,2,3,5,6,10b-hexahydro-pyrrolo[2,1a]isoquinoline 1B: Trans-6-Phenyl-9-(3-piperidin-1-yl-propoxy)-1,2,3,5,6,10b-hexahydro-pyrrolo[2,1a]isoquinoline 1C: Trans-6-Phenyl-7-(3-piperidin-1-yl-propoxy)-1,2,3,5,6,10b-hexahydro-pyrrolo[2,1a]isoquinoline Step 1. 3-(3-Chloro-propoxy)-benzoic acid methyl ester. A mixture of methyl 3-hydroxybenzoate (100.4 g, 0.657 mol), 1-bromo-3-chloropropane (78 mL, 0.789 mol), and $K_2CO_3$ (136.4 g, 0.986 mol) in acetone (430 mL) was heated to 60° C. for 42 h. The reaction mixture was cooled to 0° C. and then treated with diethyl ether (500 mL). The resultant mixture was filtered and concentrated to give a viscous oil. Short-path distillation (bp=134-136° C. at 1 torr) gave the product as colorless oil (138.85 g, 92%). $^1$H NMR (acetone-$d_6$): 7.58 (dt, J=1.4, 7.7, 1H), 7.53 (dd, J=1.5, 2.6, 1H), 7.40 (t, J=8.0, 1H), 7.18 (ddd, J=0.9, 2.7, 8.3, 1H), 4.18 (t, J=5.9, 2H), 3.87 (s, 3H), 3.80 (t, J=6.5, 2H), 2.24 (quint, J=6.2, 2H).

Step 2. 3-(3-Iodo-propoxy)-benzoic acid methyl ester. A mixture of NaI (318.4 g, 2.12 mol) and 3-(3-chloro-propoxy)-benzoic acid methyl ester (138.5 g, 0.606 mol) in acetone (1.2 L) was heated to 60° C. for 2 d. The reaction mixture was concentrated and then diluted with $CH_2Cl_2$ (1 L) and water (500 mL). After mixing thoroughly, the layers were separated and the organic layer was washed with water (2×500 mL) and brine (1×200 mL), dried ($MgSO_4$), filtered and concentrated to give the desired product as a pale-yellow oil (190.95 g, 98%). The product was protected from light by wrapping the flask in aluminum foil. bp=154° C. at 1 torr. $^1$H NMR (acetone-$d_6$): 7.61 (d, J=7.6, 1H), 7.56 (s, 1H), 7.44 (t, J=8.0, 1H), 7.23 (d, J=8.1, 1H), 4.16 (t, J=5.6, 2H), 3.89 (s, 3H), 3.48 (t, J=6.7, 2H), 2.31 (m, 2H).

Step 3. 3-(3-Piperidin-1-yl-propoxy)-benzoic acid methyl ester. A mixture of 3-(3-iodo-propoxy)-benzoic acid methyl ester (190.9 g, 0.596 mol), $Na_2CO_3$ (94.9 g, 0.894 mol), and piperidine (80 mL, 0.80 mol) in dry ethanol (400 mL) was protected from light with aluminum foil, and was heated to 60° C. under nitrogen for 22 h. The reaction mixture was diluted with $CH_2Cl_2$ (1 L), washed with water (4×600 mL) and brine (1×300 mL), dried ($K_2CO_3$), and concentrated to give the crude product as a biphasic (solid/liquid) mixture. Purification by Kugelrohr distillation (bp=215° C. at 1 torr) yielded a pale-yellow oil (143.4 g, 87%). MS (ESI): exact mass calcd for $C_{16}H_{23}NO_3$, 277.2; m/z found, 278.2 [M+H]$^+$. $^1$H NMR (DMSO-$d_6$): 7.51 (d, J=7.6, 1H), 7.4 (m, 2H), 7.18 (m, 1H), 4.02 (t, J=6.4, 2H), 3.83 (s, 3H), 2.37 (t, J=7.0, 2H), 2.30 (br s, 4H), 1.84 (m, 2H), 1.46 (m, 4H), 1.35 (br m, 2H).

Step 4. 1-{3-[3-(4,5-Dihydro-3H-pyrrol-2-yl)-phenoxy]-propyl}-piperidine. To a 0° C. solution of NaH (95%, 17.4 g, 0.723 mol) in dry THF (500 mL) was added a solution of 3-(3-piperidin-1-yl-propoxy)-benzoic acid methyl ester (143.2 g, 0.516 mol) and N-vinylpyrrolidin-2-one (66.0 mL, 0.620 mol) in dry THF (172 mL), via cannula, over the course of 18 min. The resultant mixture was stirred at 0° C. for 1 h (until gas evolution subsided) before heating to reflux for 5 h. The reaction mixture was then cooled to 0° C. and slowly treated with 12 N HCl (150 mL). The THF was removed in vacuo and an additional 12 N HCl (150 mL) and water (220 mL) was added and the mixture heated to 110° C. under nitrogen for 2 d. The reaction mixture was again cooled to 0° C. before slowly adding a solution of NaOH (150 g, 3.75 mol) in water (400 mL). The aqueous mixture was extracted with $CH_2Cl_2$ (2×500 mL). The combined extracts were washed with brine (1×500 mL), dried ($Na_2CO_3$), filtered and concentrated to give the crude product as a nearly black oil. Kugelrohr distillation of the crude product (bp=226-228° C. at 1 torr) yielded a pale-yellow oil (106.35 g, 72%). MS: exact mass calcd for $C_{18}H_{26}N_2O$, 286.2; m/z found, 287.2 [M+H]$^+$. $^1$H NMR (MeOH-$d_4$): 7.37 (d, J=1.5, 1H), 7.32 (m, 2H), 7.00 (m, 1H), 3.96 (m, 4H), 2.95 (m, 2H), 2.49 (m, 6H), 1.99 (m, 4H), 1.59 (m, 4H), 1.45 (br m, 2H).

Step 5. 1-[3-(3-Pyrrolidin-2-yl-phenoxy)-propyl]-piperidine To a 0° C. mixture of LiAlH$_4$ (14.28 g, 0.376 mol) in dry THF (200 mL) under nitrogen was added a solution of 1-{3-[3-(4,5-dihydro-3H-pyrrol-2-yl)-phenoxy]-propyl}-piperidine (106.4 g, 0.371 mol) in THF (200 mL) via cannula. Once addition was complete, the mixture was allowed to warm to room temperature (rt) and stir for 18 h. The mixture was then cooled to 0° C. and slowly treated with water (14.3 mL), followed by 15% aq. NaOH (14.3 mL), an additional 43 mL of water and 200 mL of THF. The resultant mixture was stirred for 2 h before filtering and concentrating to give a nearly colorless oil (94.4 g, 88%). MS: exact mass calcd for $C_{18}H_{28}N_2O$, 288.2; m/z found, 289.2 [M+H]$^+$. $^1$H NMR (MeOH-$d_4$): 7.20 (t, J=7.8, 1H), 6.9 (d, J=7.8, 2H), 6.77 (dd, J=2.0, 8.2, 1H), 4.91 (s, 1H), 3.97 (m, 3H), 3.13 (m, 1H), 2.90 (m, 1H), 2.49 (m, 6H), 2.16 (m, 1H), 1.95 (m, 4H), 1.7 (m, 1H), 1.60 (m, 4H), 1.47 (br m, 2H).

Step 6. 1-Phenyl-2-{2-[3-(3-piperidin-1-yl-propoxy)-phenyl]-pyrrolidin-1-yl}-ethanol. A solution of 1-[3-(3-pyrrolidin-2-yl-phenoxy)-propyl]-piperidine (3.50 mmol) and styrene oxide (1.0 equiv.) in ethanol (0.5 molar) was heated at reflux until conversion was complete. The ethanol was removed in vacuo and the residue was then either passed through a plug of silica gel (NH$_3$ in MeOH/CH$_2$Cl$_2$) or taken on to the next step without purification to yield 1.12 g (79%)

of the desired product as a mixture of diastereomers (colorless oil). MS: exact mass calcd for $C_{26}H_{36}N_2O_2$, 408.3; m/z found, 409.3 $[M+H]^+$.

Step 7. A solution of 1-phenyl-2-{2-[3-(3-piperidin-1-yl-propoxy)-phenyl]-pyrrolidin-1-yl}-ethanol (1.7 mmol) and MSA (5 mL/g of amino-alcohol) under nitrogen was stirred at rt. When the reaction was complete, the mixture was cooled to 0° C., diluted with 2 N NaOH and extracted with $CH_2Cl_2$. The organic extract was washed with brine, dried ($Na_2CO_3$), filtered and concentrated to give the crude products as a mixture of diastereomers. Purification by column chromatography ($NH_3$ in $MeOH/CH_2Cl_2$) followed by reverse-phase HPLC provided Examples 1 A-C in a combined yield of 41%.

1A: Cis-6-phenyl-9-(3-piperidin-1-yl-propoxy)-1,2,3,5,6,10b-hexahydro-pyrrolo[2,1a]isoquinoline. 18.4 mg (2%) as the TFA salt. MS: exact mass calcd for $C_{26}H_{34}N_2O$, 390.3; m/z found, 391.4 $[M+H]^+$. $^1H$ NMR (MeOH-$d_4$): 7.28 (m, 2H), 7.24 (m, 1H), 7.13 (d, J=7.0, 2H), 6.76 (d, J=2.5, 1H), 6.67 (d, J=8.6, 1H), 6.58 (d, J=8.7, 1H), 4.74 4.25 (m, 1H), 3.97 (t, J=5.8, 2H), 3.72 (m, 1H), 3.45 (m, 3H), 3.17 (m, 2H), 2.83 (m, 2H), 2.73 (m, 1H), 2.15 (m, 6H), 1.83 (d, J=14.7, 2H), 1.67 (m, 3H), 1.40 (m, 1H).

1B: Trans-6-Phenyl-9-(3-piperidin-1-yl-propoxy)-1,2,3,5,6,10b-hexahydro-pyrrolo[2,1a]isoquinoline. 299.0 mg (27%) as the TFA salt. MS: exact mass calcd exact mass calcd for $C_{26}H_{34}N_2O$, 390.3; m/z found, 391.4 $[M+H]^+$. $^1H$ NMR (MeOH-$d_4$): 7.37 (m, 2H), 7.31 (m, 1H), 7.17 (br s, 2H), 6.92 (br m, 3H), 5.10 (br s, 3H), 4.98 (br s, 1H), 4.52 (br s, 1H), 4.14 (t, J=5.6, 2H), 3.77 (br s, 2H), 3.65 (m, 2H), 3.49 (br s, 1H), 2.28 (m, 2H), 2.10 (br s, 2H), 1.96 (d, J=14.6, 2H), 1.90 (m, 3H), 1.54 (m, 1H).

1C: Trans-6-Phenyl-9-(3-piperidin-1-yl-propoxy)-1,2,3,5,6,10b-hexahydro-pyrrolo[2,1a]isoquinoline. 129.8 mg (12%) as the TFA salt. MS: exact mass calcd for $C_{26}H_{34}N_2O$, 390.3; m/z found, 391.4 $[M+H]^+$. $^1H$ NMR (MeOH-$d_4$): 7.38 (m, 4H), 7.10 (d, J=7.3, 2H), 7.01 (d, J=7.8, 1H), 6.97 (d, J=8.2, 1H), 5.00 (s, 4H), 4.76 (m, 2H), 4.11 (d, J=4.6, 1H), 3.7 (m, 4H), 3.30 (m, 3H), 2.75 (br m, 1H), 2.60 (m, 3H), 2.45 (m, 1H), 2.23 (m, 3H), 2.05 (br m, 1H), 1.75 (m, 5H), 1.45 (m, 1H).

Example 2-(A-C)

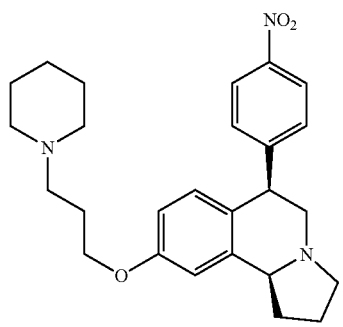
2A

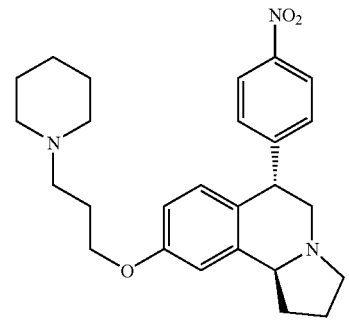
2B

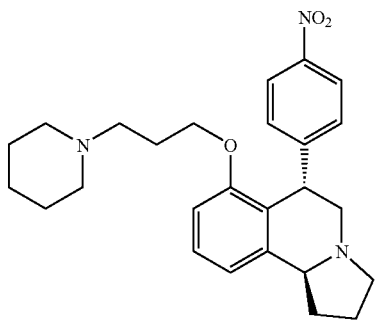
2C

2A: Cis-6-(4-Nitro-phenyl)-9-(3-piperidin-1-yl-propoxy)-1,2,3,5,6,10b-hexahydro-pyrrolo[2,1-a]isoquinoline
2B: Trans-6-(4-Nitro-phenyl)-9-(3-piperidin-1-yl-propoxy)-1,2,3,5,6,10b-hexahydro-pyrrolo[2,1-a]isoquinoline
2C: Trans-6-(4-Nitro-phenyl)-7-(3-piperidin-1-yl-propoxy)-1,2,3,5,6,10b-hexahydro-pyrrolo[2,1-a]isoquinoline Step 1. 1-(4-Nitrophenyl)-2-{2-[3-(3-piperidin-1-yl-propoxy)-phenyl]-pyrrolidin-1-yl}-ethanol. Prepared as described in Example 1, Step 6, on a 3.47 mmol scale, to yield 1.57 g (quant.) of the desired product as a mixture of diastereomers (yellow oil). MS: exact mass calcd for $C_{26}H_{36}N_3O_4$, 453.3; m/z found, 454.2 $[M+H]^+$.

Step 2. Performed as described in Example 1, Step 7, on a 3.47 mmol scale, to give a 3% combined yield of the products 2A, 2B, and 2C.

2A: Cis-6-(4-Nitrophenyl)-9-(3-piperidin-1-yl-propoxy)-1,2,3,5,6,6a,10a,10b-octahydro-pyrrolo[2,1a]isoquinoline. 30.2 mg (1%) as the TFA salt. MS: exact mass calcd for $C_{26}H_{33}N_3O_3$, 435.3; m/z found, 436.1 $[M+H]^+$. $^1H$ NMR (MeOH-$d_4$): 8.17 (d, J=8.8, 2H), 7.44 (d, J=8.6, 2H), 6.82 (d, J=2.5, 1H), 6.72 (dd, J=2.5, 8.7, 1H), 6.56 (d, J=8.7, 1H), 4.50 (m, 1H), 4.00 (t, J=5.7, 2H), 4.81 (br m, 1H), 3.56 (m, 1H), 3.48 (d, J=12.3, 2H), 3.38 (m, 2H), 3.19 (m, 2H), 2.85 (m, 2H), 2.72 (m, 1H), 2.15 (m, 5H), 1.85 (d, J=14.6, 2H), 1.68 (m, 3H), 1.42 (m, 1H).

2B: Trans-6-(4-Nitrophenyl)-9-(3-piperidin-1-yl-propoxy)-1,2,3,5,6,6a,10a,10b-octahydro-pyrrolo[2,1a]isoquinoline. 21.4 mg (1%) as the TFA salt. MS: exact mass calcd for $C_{26}H_{33}N_3O_3$, 435.3; m/z found, 436.5 $[M+H]^+$. $^1H$ NMR (MeOH-$d_4$): 8.23 (d, J=8.8, 2H), 7.43 (m, 3H), 7.02 (d, J=7.8, 1H), 6.95 (br d, J=7.8, 1H), 4.77 (br s, 1H), 3.97 (br s, 1H), 3.70 (br m, 3H), 3.29 (br m, 4H), 2.77 (m, 1H), 2.70 (m, 3H), 2.57 (br m, 1H), 2.22 (br s, 3H), 1.9 (br d, J=14.8, 2H), 1.75 (m, 1H), 1.73 (m, 5H), 1.49 (m, 1H).

2C: Trans-6-(4-Nitrophenyl)-7-(3-piperidin-1-yl-propoxy)-1,2,3,5,6,6a,10a,10b-octahydro-pyrrolo[2,1a]isoquinoline. 28.7 mg (1%) as the TFA salt. MS: exact mass calcd for $C_{26}H_{33}N_3O_3$, 435.3; m/z found, 436.5 $[M+H]^+$. $^1H$ NMR (MeOH-$d_4$): 8.20 (d, J=8.8, 2H), 7.46 (t, J=8.0, 1H), 7.34 (br d, J=6.6, 2H), 7.04 (d, J=7.9, 1H), 7.00 (d, J=8.3, 1H), 4.88 (m, 1H), 3.86 (s, 6H), 4.08 (br s, 1H), 3.88 (br s, 2H), 3.76 (br s, 2H), 3.30 (m, 2H), 2.77 (m, 2H), 2.65 (m, 3H), 2.18 (m, 3H), 1.99 (br m, 1H), 1.82 4H), 1.70 (m, 2H), 1.47 (m, 1H).

Example 3

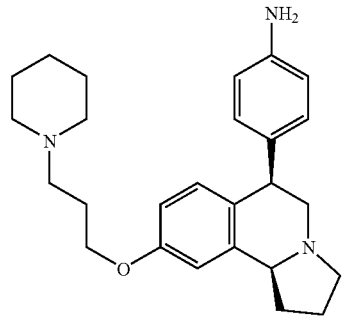

Cis-4-[9-(3-Piperidin-1-yl-propoxy)-1,2,3,5,6,10b-hexahydro-pyrrolo[2,1-a]isoquinolin-6-yl]-phenylamine A mixture of cis-6-(4-nitrophenyl)-9-(3-piperidin-1-yl-propoxy)-1,2,3,5,6,6a,10a,10b-octahydro-pyrrolo[2,1a]isoquinoline (Example 2, 310 mg, 0.71 mmol), PtO$_2$ (20 wt %, 62 mg), and ammonium formate (1.01 g, 16.0 mmol) in ethanol (13 mL) was purged with nitrogen and then heated to 75° C. overnight. The reaction mixture was filtered through a pad of diatomaceous earth and the filtrate was concentrated. Purification by normal phase column chromatography (NH$_3$ in MeOH/CH$_2$Cl$_2$) followed by reverse-phase HPLC gave 19.6 mg (4%) of the desired product as the TFA salt. MS mass calcd for C$_{26}$H$_{35}$N$_3$O, 405.3; found 406.5 [M+H]$^+$. $^1$H NMR (MeOH-d$_4$): 7.28 (m, 4H), 6.78 (d, J=2.5, 1H), 6.69 (m, 1H), 6.55 (d, J=8.7, 1H), 4.74 (m, 1H), 4.37 (m, 1H), 3.97 (t, J=5.8, 2H), 3.76 (m, 1H), 3.46 (m, 3H), 3.33 (m, 2H), 3.18 (m, 2H), 2.83 (m, 2H), 2.69 (m, 1H), 2.13 (m, 5H), 1.83 (d, J=14.6, 2H), 1.65 (m, 3H), 1.40 (m, 1H), 1.89 (t, J=7.3, 1H).

Example 4-(A-D)

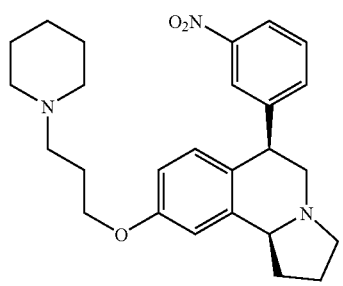

4A

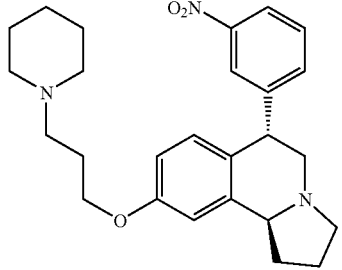

4B

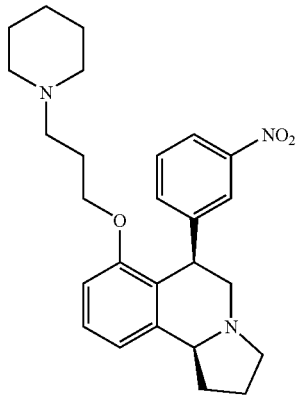

4C

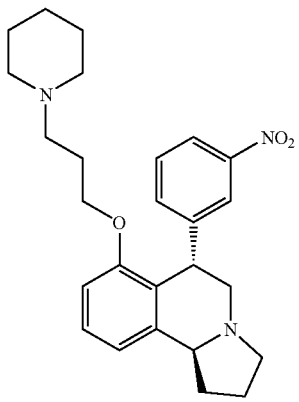

4D

4A: Cis-6-(3-Nitro-phenyl)-9-(3-piperidin-1-yl-propoxy)-1,2,3,5,6,10b-hexahydro-pyrrolo[2,1-a]isoquinoline
4B: Trans-6-(3-Nitro-phenyl)-9-(3-piperidin-1-yl-propoxy)-1,2,3,5,6,10b-hexahydro-pyrrolo[2,1-a]isoquinoline
4C: Cis-6-(3-Nitro-phenyl)-7-(3-piperidin-1-yl-propoxy)-1,2,3,5,6,10b-hexahydro-pyrrolo[2,1-a]isoquinoline
4D: Trans-6-(3-Nitro-phenyl)-7-(3-piperidin-1-yl-propoxy)-1,2,3,5,6,10b-hexahydro-pyrrolo[2,1-a]isoquinoline Step 1. 1-(3-Nitrophenyl)-2-{2-[3-(3-piperidin-1-yl-propoxy)-phenyl]-pyrrolidin-1-yl}-ethanol. Prepared as described in Example 1, Step 6, on a 3.47 mmol scale, to yield 1.31 g (83%) of the desired product as a mixture of diastereomers (yellow oil). MS: exact mass calcd for C$_{26}$H$_{35}$N$_3$O$_4$, 453.3; m/z found, 454.5 [M+H]$^+$.

Step 2. Performed as described in Example 1, Step 7, on a 2.88 mmol scale to give a 34% combined yield of the products 4A, 4B, 4C, and 4D.

4A: Cis-6-(3-Nitro-phenyl)-9-(3-piperidin-1-yl-propoxy)-1,2,3,5,6,10b-hexahydro-pyrrolo[2,1-a]isoquinoline. 73.2 mg (4%) as the TFA salt. MS: exact mass calcd for C$_{26}$H$_{33}$N$_3$O$_3$, 435.3; m/z found, 436.5 [M+H]+. 1H NMR (acetone-d6): 13.30 (br s, 1H), 11.68 (br s, 1H), 11.04 (br s, 1H), 8.23 (m, 1H), 8.16 (s, 1H), 7.80 (d, J=7.6, 1H), 7.73 (m, 1H), 6.98 (d, J=2.4, 1H), 6.79 (m, 1H), 6.67 (d, J=8.6, 1H), 4.93 (br s, 1H), 4.82 (m, 1H), 4.13 (t, J=5.9, 2H), 3.96 (br s, 1H), 3.77 (m, 1H), 3.65 (d, J=11.2, 3H), 3.45 (br s, 1H), 3.35 (br s, 2H), 3.01 (br s, 2H), 2.90 (m, 1H), 2.35 (m, 5H), 1.90 (br s, 4H), 1.75 (m, 1H), 1.5 (m, 1H).

4B: Trans-6-(3-Nitro-phenyl)-9-(3-piperidin-1-yl-propoxy)-1,2,3,5,6,10b-hexahydro-pyrrolo[2,1-a]isoquinoline. 201.4 mg (10%) as the TFA salt. MS: exact mass calcd for $C_{26}H_{33}N_3O_3$, 435.3; m/z found, 436.5 [M+H]+. 1H NMR (acetone-d6): 13.22 (br s, 1H), 11.5 (br s, 1H), 8.16 (m, 1H), 8.09 (s, 1H), 7.69 (m, 1H), 7.64 (m, 1H), 7.01 (br s, 1H), 6.87 (br m, 2H), 5.15 (br s, 1H), 4.83 (br s, 1H), 4.15 (m, 2H), 3.80 (br s, 3H), 3.64 (d, J=11.7, 2H), 3.57 (br s, 1H), 3.33 (s, 2H), 2.99 (s, 2H), 2.38 (br s, 1H), 2.32 (m, 2H), 2.20 (br m, 3H), 1.91 (m, 4H), 1.79 (m, 1H), 1.49 (m, 1H).

4C: Cis-6-(3-Nitro-phenyl)-7-(3-piperidin-1-yl-propoxy)-1,2,3,5,6,10b-hexahydro-pyrrolo[2,1-a]isoquinoline. 38.3 mg (2%) as the TFA salt. MS: exact mass calcd for $C_{26}H_{33}N_3O_3$, 435.3; m/z found, 436.5 [M+H]+. 1H NMR (acetone-d6): 13.56 (br s, 1H), 11.42 (br s, 1H), 8.17 (d, J=7.4, 1H), 8.03 (s, 1H), 7.70 (br m, 2H), 7.40 (m, 1H), 7.06 (d, J=7.8, 1H), 6.95 (d, J=8.1, 1H), 4.94 (m, 2H), 4.01 (s, 1H), 3.83 (m, 1H), 3.74 (m, 1H), 3.48 (br s, 1H), 3.40 (m, 2H), 3.26 (m, 1H), 2.75 (m, 5H), 2.32 (m, 1H), 2.20 (m, 2H), 1.85 (m, 7H), 1.42 (br m, 1H).

4D: Trans-6-(3-Nitro-phenyl)-7-(3-piperidin-1-yl-propoxy)-1,2,3,5,6,10b-hexahydro-pyrrolo[2,1-a]isoquinoline. 369.1 mg (18%) as the TFA salt. MS: exact mass calcd for $C_{26}H_{33}N_3O_3$, 435.3; m/z found, 436.5 [M+H]+. 1H NMR (acetone-d6): 13.29 (br s, 1H), 11.52 (br s, 1H), 8.16 (m, 1H), 8.10 (s, 1H), 7.67 (m, 2H), 7.02 (s, 1H), 6.88 (s, 2H), 6.23 (br s, 1H), 5.08 (s, 1H), 4.83 (br s, 1H), 4.17 (m, 2H), 3.78 (br s, 2H), 3.65 (d, J=11.2, 2H), 3.55 (br s, 1H), 3.35 (s, 2H), 2.99 (s, 2H), 2.70 (br s, 1H), 2.33 (m, 2H), 2.12 (m, 3H), 1.93 (m, 4H), 1.79 (m, 1H), 1.28 (m, 1H).

Example 5-(A-C)

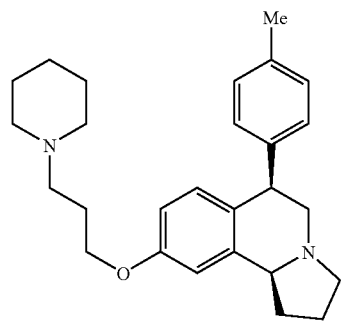

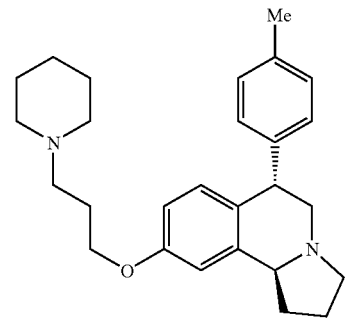

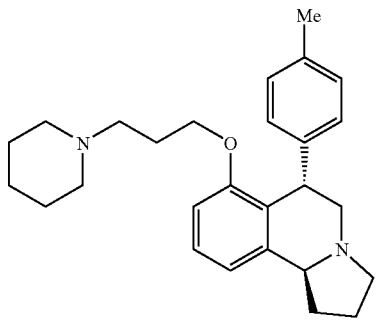

5A: Cis-9-(3-Piperidine-1-yl-propoxy)-6-p-tolyl-1,2,3,5,6,10b-hexahydro-pyrrolo[2,1-a]isoquinoline 5B: Trans-9-(3-Piperidine-1-yl-propoxy)-6-p-tolyl-1,2,3,5,6,10b-hexahydro-pyrrolo[2,1-a]isoquinoline 5C: Trans-7-(3-Piperidine-1-yl-propoxy)-6-p-tolyl-1,2,3,5,6,10b-hexahydro-pyrrolo[2,1-a]isoquinoline Step 1. 2-{2-[3-Piperidin-1-yl-propoxy)-phenyl]-pyrrolidin-1-yl}-1-p-tolyl-ethanol. Prepared as described in Example 1, Step 6, on a 3.47 mmol scale, to yield 1.3 g (87%) of the desired product as a mixture of diastereomers. MS: exact mass calcd for $C_{27}H_{38}N_2O_2$, 422.3; m/z found, 423.4 [M+H]+.

Step 2. Performed as described in Example 1, Step 7, on a 3.08 mmol scale, to give a 19% combined yield of the products 5A, 5B, and 5C.

5A: Cis-9-(3-Piperidine-1-yl-propoxy)-6-p-tolyl-1,2,3,5,6,10b-hexahydro-pyrrolo[2,1-a]isoquinoline. 22.0 mg (1%) as the TFA salt. MS: exact mass calcd for $C_{27}H_{36}N_2O$, 404.3; m/z found, 405.4 [M+H]+. 1H NMR (acetone-d6): 7.09 (d, J=8.0, 2H), 7.04 (d, J=8.0, 2H), 6.82 (m, 1H), 6.66 (m, 1H), 6.53 (d, J=8.7, 1H), 4.79 (m, 1H), 4.40 (m, 1H), 4.00 (t, J=6.0, 2H), 3.82 (m, 1H), 3.50 (m, 3H), 3.30 (m, 1H), 3.25 (m, 1H), 3.18 (t, J=7.6, 2H), 2.79 (m, 3H), 2.22 (s, 3H), 2.17 (m, 4H), 2.09 (m, 1H), 1.76 (m, 4H), 1.67 (m, 1H), 1.39 (m, 1H).

5B: Trans-9-(3-Piperidine-1-yl-propoxy)-6-p-tolyl-1,2,3,5,6,10b-hexahydro-pyrrolo[2,1-a]isoquinolin. 200.1 mg (10%) as the TFA salt. MS: exact mass calcd for $C_{27}H_{36}N_2O$, 404.3; m/z found, 405.4 [M+H]+. 1H NMR (acetone-d6): 12.50 (br s, 1H), 11.21 (br s, 1H), 7.19 (d, J=8.0, 2H), 7.13 (d, J=7.9, 2H), 7.00 (br s, 1H), 6.84 (m, 2H), 5.18 (br s, 1H), 4.54 (s, 1H), 4.17 (m, 2H), 3.87 (m, 1H), 3.67 (m, 4H), 3.61 (br s, 1H), 3.37 (m, 2H), 3.03 (m, 2H), 2.76 (br s, 1H), 2.36 (m, 3H), 2.33 (m, 3H), 2.23 (m, 1H), 2.12 (m, 1H), 1.93 (m, 4H), 1.83 (m, 1H), 1.54 (m, 1H).

5C: Trans-7-(3-Piperidine-1-yl-propoxy)-6-p-tolyl-1,2,3,5,6,10b-hexahydro-pyrrolo[2,1-a]isoquinoline. 153.5 mg (8%) as the TFA salt. MS: exact mass calcd for $C_{27}H_{36}N_2O$, 404.3; m/z found, 405.5 [M+H]+. 1H NMR (acetone-d6): 11.61 (br s, 1H), 10.54 (br s, 1H), 7.42 (m, 1H), 7.14 (d, J=7.4, 2H), 7.07

(m, 1H), 7.02 (d, J=7.3, 2H), 6.98 (d, 8.2, 1H), 5.16 (br s, 1H), 4.79 (s, 1H), 4.17 (m, 1H), 3.97 (m, 1H), 3.89 (m, 2H), 3.80 (m, 1H), 3.50 (m, 1H), 3.34 (m, 2H), 2.89 (m, 1H), 2.69 (m, 1H), 2.60 (m, 3H), 2.30 (s, 2H), 2.27 (m, 3H), 2.18 (m, 1H), 2.06 (m, 1H), 1.77 (m, 5H), 1.75 (m, 1H), 1.45 (m, 1H).

Example 6-(A-B)

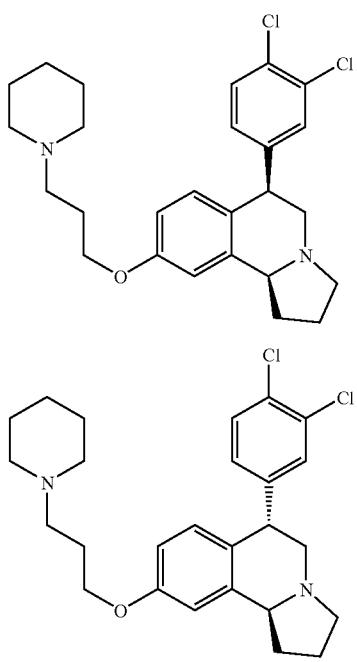

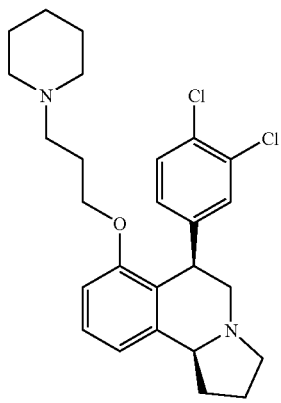

6A: Cis-6-(3,4-Dichloro-phenyl)-9-(3-piperidin-1-yl-propoxy)-1,2,3,5,6,10b-hexahydro-pyrrolo[2,1-a]isoquinoline 6B: Trans-6-(3,4-Dichloro-phenyl)-9-(3-piperidin-1-yl-propoxy)-1,2,3,5,6,10b-hexahydro-pyrrolo[2,1-a]isoquinoline 6C. Cis-6-(3,4-Dichloro-phenyl)-7-(3-piperidin-1-yl-propoxy)-1,2,3,5,6,10b-hexahydro-pyrrolo[2,1-a]isoquinoline Step 1. 2-(3,4-Dichloro-phenyl)-2-{2-[3-(3-piperidin-1-yl-propoxy)-phenyl]-pyrrolidin-1-yl}-ethanol. Prepared as described in Example 1, Step 6, on a 2.53 mmol scale, to yield 0.96 g (80%) of the desired product as a mixture of diastereomers (yellow oil). MS: exact mass calcd for $C_{26}H_{34}Cl_2N_2O_2$, 476.2; m/z found, 477.3 [M+H]+.

Step 2. Performed as described in Example 1, Step 7, on a 2.01 mmol scale, to give a 25% combined yield of the desired products 6A and 6B.

6A: Cis-6-(3,4-Dichloro-phenyl)-9-(3-piperidin-1-yl-propoxy)-1,2,3,5,6,10b-hexahydro-pyrrolo[2,1-a]isoquinoline. 20.0 mg (1%) as the TFA salt. MS: exact mass calcd for $C_{26}H_{32}Cl_2N_2O$, 458.2; m/z found, 459.4 [M+H]+. $^1$H NMR (acetone-$d_6$): 7.61 (d, J=8.3, 1H), 7.51 (m, 1H), 7.32 (m, 1H), 6.95 (m, 1H), 6.79 (m, 1H), 6.68 (d, J=8.7, 1H), 4.90 (m, 1H), 4.66 (m, 1H), 4.12 (t, J=6.0, 2H), 3.93 (m, 1H), 3.70 (m, 1H), 3.61 (m, 2H), 3.51 (m, 1H), 3.38 (m, 1H), 3.29 (t, J=7.6, 2H), 2.89 (m, 3H), 2.27 (m, 5H), 1.93 (m, 4H), 1.79 (m, 1H), 1.49 (m, 1H).

6B: Trans-6-(3,4-Dichloro-phenyl)-9-(3-piperidin-1-yl-propoxy)-1,2,3,5,6,10b-hexahydro-pyrrolo[2,1-a]isoquinoline. 338.0 mg (24%) as the TFA salt. MS: exact mass calcd for $C_{26}H_{32}Cl_2N_2O$, 458.2; m/z found, 459.3 [M+H]+. $^1$H NMR (acetone-$d_6$): 11.35 (br s, 1H), 7.56 (d, J=10.1, 1H), 7.46 (m, 1H), 7.22 (m, 1H), 7.00 (br s, 1H), 6.89 (m, 2H), 5.13 (br s, 1H), 4.69 (br s, 1H), 4.18 (m, 2H), 3.76 (m, 2H), 3.67 (d, J=11.7, 2H), 3.56 (m, 1H), 3.35 (m, 2H), 3.03 (m, 2H), 2.79 (br s, 1H), 2.34 (m, 2H), 2.21 (m, 1H), 2.13 (m, 2H), 1.92 (m, 4H), 1.82 (m, 1H), 1.51 (m, 1H).

6C. Cis-6-(3,4-Dichloro-phenyl)-7-(3-piperidin-1-yl-propoxy)-1,2,3,5,6,10b-hexahydro-pyrrolo[2,1-a]isoquinoline. 85 mg (6%) as the TFA salt. MS: exact mass calcd for $C_{26}H_{32}Cl_2N_2O$, 458.2; m/z found, 459.5 [M+H]+. $^1$H NMR (acetone-$d_6$): 7.41 (m, 3H), 7.06 (m, 2H), 6.98 (d, J=8.2, 1H), 5.09 (br s, 1H), 4.84 (br s, 1H), 4.15 (m, 1H), 3.92 (m, 3H), 3.76 (br s, 1H), 3.43 (m, 3H), 2.85 (m, 2H), 2.68 (m, 3H), 2.23 (m, 4H), 1.84 (m, 6H), 1.46 (m, 1H).

Example 7-(A-C)

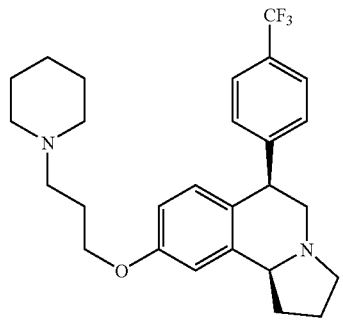

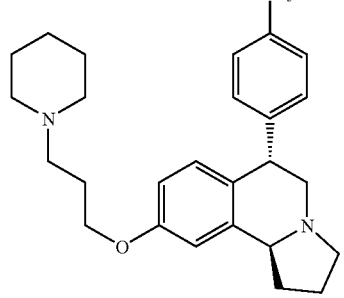

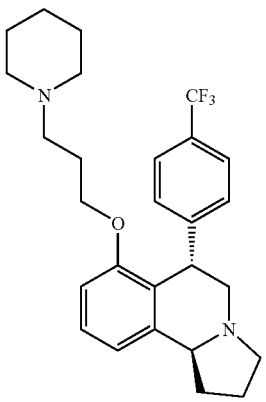

7C

7A: Cis-9-(3-Piperidin-1-yl-propoxy)-6-(4-trifluoromethyl-phenyl)-1,2,3,5,6,10b-hexahydro-pyrrolo[2,1-a]isoquinoline 7B: Trans-9-(3-Piperidin-1-yl-propoxy)-6-(4-trifluoromethyl-phenyl)-1,2,3,5,6,10b-hexahydro-pyrrolo[2,1-a]isoquinoline 7C: Trans-7-(3-Piperidin-1-yl-propoxy)-6-(4-trifluoromethyl-phenyl)-1,2,3,5,6,10b-hexahydro-pyrrolo[2,1-a]isoquinoline Step 1. 2-{2-[3-(3-Piperidin-1-yl-propoxy)-phenyl]-pyrrolidin-1-yl}-2-(4-trifluoromethyl-phenyl)-ethanol. Prepared as described in Example 1, Step 6, on a 3.47 mmol scale, to yield 1.27 g (77%) of the desired product as a mixture of diastereomers (yellow oil). MS: exact mass calcd for $C_{27}H_{35}F_3N_2O_2$, 476.3; m/z found, 477.4 [M+H]$^+$.

Step 2. Performed as described in Example 1, Step 7, on a 2.66 mmol scale, to give a 2% combined yield of the desired products 7A, 7B, and 7C.

7A: Cis-9-(3-Piperidin-1-yl-propoxy)-6-(4-trifluoromethyl-phenyl)-1,2,3,5,6,10b-hexahydro-pyrrolo[2,1-a]isoquinoline. 6.4 mg (0.3%) as the TFA salt. MS: exact mass calcd for $C_{27}H_{33}F_3N_2O$, 458.3; m/z found, 459.5 [M+H]$^+$. $^1$H NMR (acetone-d$_6$): 7.74 (d, J=7.9, 2H), 7.54 (d, J=7.9, 2H), 6.96 (br s, 1H), 6.78 (m, 1H), 6.61 (m, 1H), 4.89 (m, 1H), 4.73 (m, 1H), 4.11 (t, J=6.0, 2H), 3.71 (m, 1H), 3.69 (m, 1H), 3.60 (m, 2H), 3.49 (m, 1H), 3.36 (m, 1H), 3.28 (t, J=7.0, 2H), 2.91 (m, 3H), 2.27 (m, 5H), 1.87 (m, 4H), 1.77 (br s, 1H), 1.50 (m, 1H).

7B: Trans-9-(3-Piperidin-1-yl-propoxy)-6-(4-trifluoromethyl-phenyl)-1,2,3,5,6,10b-hexahydro-pyrrolo[2,1-a]isoquinoline. 16.0 mg (1%) as the TFA salt. MS: exact mass calcd for $C_{27}H_{33}F_3N_2O$, 458.3; m/z found, 459.5 [M+H]$^+$. $^1$H NMR (acetone-d$_6$): 7.70 (d, J=8.1, 2H), 7.49 (d, J=8.0, 2H), 7.01 (br s, 1H), 6.90 (m, 1H), 6.79 (m, 1H), 5.14 (br s, 1H), 4.76 (br s, 1H), 4.16 (m, 2H), 3.75 (m, 2H), 3.65 (m, 2H), 3.55 (m, 1H), 3.34 (m, 2H), 2.99 (m, 2H), 2.78 (m, 1H), 2.33 (m, 2H), 2.22 (m, 1H), 2.13 (m, 1H), 1.94 (m, 6H), 1.81 (m, 1H), 1.52 (m, 1H).

7C: Trans-7-(3-Piperidin-1-yl-propoxy)-6-(4-trifluoromethyl-phenyl)-1,2,3,5,6,10b-hexahydro-pyrrolo[2,1-a]isoquinoline. 16.0 mg (1%) as the TFA salt. MS: exact mass calcd for $C_{27}H_{33}F_3N_2O$, 458.3; m/z found, 459.5 [M+H]$^+$. $^1$H NMR (acetone-d$_6$): 7.56 (d, J=11.3, 2H), 7.40 (t, J=8.0, 1H), 7.34 (d, J=7.9, 2H), 7.06 (d, J=7.8, 1H), 6.96 (d, J=8.2, 1H), 5.01 (br s, 1H), 4.87 (m, 1H), 4.11 (m, 1H), 3.87 (m, 3H), 3.76 (br s, 3H), 3.27 (m, 3H), 2.82 (m, 1H), 2.74 (m, 1H), 2.62 (m, 3H), 2.20 (m, 3H), 2.00 (m, 1H), 1.80 (m, 6H), 1.43 (m, 1H).

Example 8-(A-F)

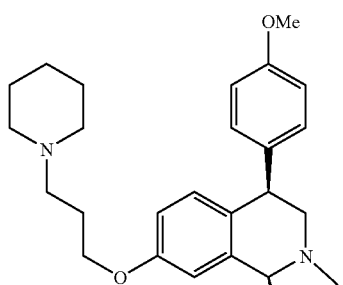

8A,B,C

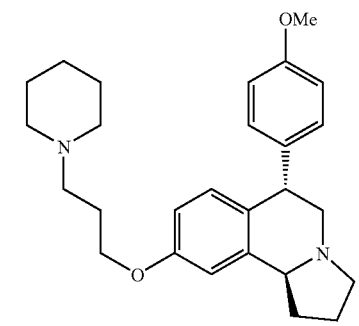

8D

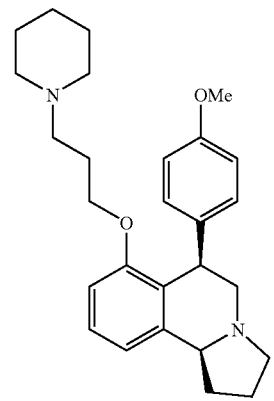

8E

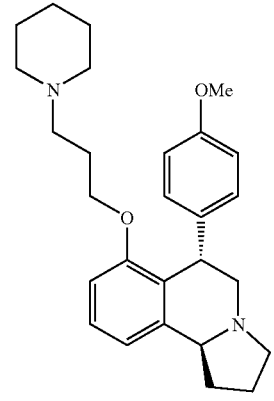

8F

8A: Cis-6-(4-Methoxy-phenyl)-9-(3-piperidin-1-yl-propoxy)-1,2,3,5,6,10b-hexahydro-pyrrolo[2,1-a]isoquinoline 8B: 1S,6R-6-(4-Methoxy-phenyl)-9-(3-piperidin-1-yl-propoxy)-1,2,3,5,6,10b-hexahydro-pyrrolo[2,1-a]isoquinoline 8C: 1R,6S-6-(4-Methoxy-phenyl)-9-(3-piperidin-1-yl-propoxy)-1,2,3,5,6,10b-hexahydro-pyrrolo[2,1-a]isoquinoline 8D: Trans-6-(4-Methoxy-phenyl)-9-(3-piperidin-1-yl-propoxy)-1,2,3,5,6,10b-hexahydro-pyrrolo[2,1-a]isoquinoline 8E: Cis-6-(4-Methoxy-phenyl)-7-(3-piperidin-1-yl-propoxy)-1,2,3,5,6,10b-hexahydro-pyrrolo[2,1-a]isoquinoline 8F: Trans-6-(4-Methoxy-phenyl)-7-(3-piperidin-1-yl-propoxy)-1,2,3,5,6,10b-hexahydro-pyrrolo[2,1-a]isoquinoline Step 1. 1-(4-Methoxy-Phenyl)-2-{2-[3-(3-piperidin-1-yl-propoxy)-phenyl]-pyrrolidin-1-yl}-ethanone. To a solution of 1-[3-(3-pyrrolidin-2-yl-phenoxy)-propyl]-piperidine (6.93 mmol) and triethylamine (3.0 equiv.) in THF (0.1 M) under nitrogen was added 2-bromo-1-(4-methoxyphenyl)-ethanone (1.05-1.20 equiv.) and the reaction mixture was stirred at rt for 30 min. The reaction mixture was diluted with $CH_2Cl_2$ and washed with 1.0 N NaOH followed by brine. The organic solution was dried ($Na_2CO_3$) and concentrated to give the crude product, which was purified by normal phase column chromatography ($NH_3$ in $MeOH/CH_2Cl_2$) to provide 2.21 g (73%) of the desired product as a yellow oil. MS: exact mass calcd for $C_{27}H_{36}N_2O_3$, 436.3; m/z found, 437.4 $[M+H]^+$. $^1H$ NMR (acetone-$d_6$): 7.86 (dd, J=2.1, 6.9, 2H), 7.22 (m, 1H), 7.00 (d, J=1.6, 1H), 6.97 (m, 3H), 6.81 (m, 1H), 4.01 (m, 3H), 3.85 (s, 3H), 3.48 (t, J=8.0, 1H), 3.30 (m, 2H), 2.39 (m, 8H), 2.15 (m, 1H), 1.89 (m, 5H), 1.67 (m, 1H), 1.51 (m, 5H), 1.38 (br m, 1H). Alternatively, the reaction mixture may be concentrated and taken on to the next synthetic step without purification.

Step 2. 1-(4-Methoxy-phenyl)-2-{2-[3-(3-piperidin-1-yl-propoxy)-phenyl]-pyrrolidin-1-yl}-ethanol. To a 0° C. solution of the aminoalcohol obtained from Step 1 (2.29 mmol) in ethanol (0.1 M) was added $NaBH_4$ (1.5 equiv.), and the mixture was allowed to warm to rt. After completion of the reaction, the mixture was diluted with $CH_2Cl_2$ and washed with water and brine. The organic layer was dried ($Na_2CO_3$), filtered and concentrated to give the crude product. Normal phase chromatographic purification ($NH_3$ in $MeOH/CH_2Cl_2$) gave the desired product (820.7 mg, 83%) as a mixture of diastereomers. MS: exact mass calcd for $C_{27}H_{38}N_2O_3$, 438.3; m/z found, 439.4 $[M+H]^+$.

Step 3. Performed as described in Example 1, Step 7, on a 1.72 mmol scale, to give a combined yield of 33% for the four diastereomers.

8A: Cis-6-(4-Methoxy-phenyl)-9-(3-piperidin-1-yl-propoxy)-1,2,3,5,6,10b-hexahydro-pyrrolo[2,1-a]isoquinoline. 27.5 mg (2%) as the TFA salt. MS: exact mass calcd for $C_{27}H_{36}N_2O_2$, 420.3; m/z found, 421.3 $[M+H]^+$. $^1H$ NMR (MeOH-$d_4$): 7.18 (d, J=8.6, 2H), 6.97 (d, J=8.8, 2H), 6.89 (d, J=2.4, 1H), 6.82 (dd, J=2.4, 8.7, 1H), 6.75 (d, J=8.7, 1H), 4.87 (m, 1H), 4.33 (m, 1H), 4.11 (t, J=5.8, 2H), 3.9 (m, 1H), 3.82 (s, 3H), 3.59 (m, 3H), 3.42 (m, 2H), 3.31 (m, 2H), 2.97 (m, 2H), 2.85 (m, 1H), 2.27 (m, 5H), 1.98 (d, J=14.6, 2H), 1.82 (m, 3H), 1.53 (m, 1H). The enantiomers were separated using a Chiralpak® AD column. The first eluting enantiomer was Example 8B: 1S,6R-6-(4-Methoxy-phenyl)-9-(3-piperidin-1-yl-propoxy)-1,2,3,5,6,10b-hexahydro-pyrrolo[2,1-a]isoquinoline. ($[\alpha]_D^{20}$=−66°, c=0.006, $CH_2Cl_2$). The second eluting compound was Example 8C: 1R,6S-6-(4-Methoxy-phenyl)-9-(3-piperidin-1-yl-propoxy)-1,2,3,5,6,10b-hexahydro-pyrrolo[2,1-a]isoquinoline. ($[\alpha]_D^{20}$=+68°, c=0.011, $CH_2Cl_2$).

8D: Trans-6-(4-Methoxy-phenyl)-9-(3-piperidin-1-yl-propoxy)-1,2,3,5,6,10b-hexahydro-pyrrolo[2,1-a]isoquinoline. 101.5 mg (9%) as the TFA salt. MS: exact mass calcd for $C_{27}H_{36}N_2O_2$, 420.3; m/z found, 421.3 $[M+H]^+$. $^1H$ NMR (MeOH-$d_4$): 7.06 (br m, 2H), 6.91 (m, 5H), 4.95 (br s, 1H), 4.46 (br s, 1H), 4.14 (t, J=5.5, 2H), 3.79 (s, 3H), 3.76 (br s, 1H), 3.62 (m, 2H), 3.45 (br s, 1H), 3.33 (m, 2H), 2.98 (t, J=12.4, 2H), 3.74 (br s, 1H), 2.27 (m, 2H), 2.16 (br s, 2H), 1.97 (m, 2H), 1.85 (m, 3H), 1.54 (m, 1H).

8E: Cis-6-(4-Methoxy-phenyl)-7-(3-piperidin-1-yl-propoxy)-1,2,3,5,6,10b-hexahydro-pyrrolo[2,1-a]isoquinoline. 18.0 mg (2%) as the TFA salt. MS: exact mass calcd for $C_{27}H_{36}N_2O_2$, 420.3; m/z found, 421.2 $[M+H]^+$. $^1H$ NMR (MeOH-$d_4$): 7.42 (m, 1H), 7.07 (br s, 2H), 6.98 (m, 4H), 4.56 (br s, 1H), 4.02 (br s, 1H), 3.78 (s, 3H), 3.70 (br m, 3H), 3.38 (m, 1H), 3.30 (m, 3H), 3.20 (m, 1H), 2.73 (br s, 1H), 2.63 (m, 3H), 2.35 (br m, 1H), 2.14 (br m, 3H), 1.80 (m, 4H), 1.69 (m, 3H), 1.49 (m, 1H).

8F: Trans-6-(4-Methoxy-phenyl)-7-(3-piperidin-1-yl-propoxy)-1,2,3,5,6,10b-hexahydro-pyrrolo[2,1-a]isoquinoline. 176.6 mg (20%) as the TFA salt. MS: exact mass calcd for $C_{27}H_{36}N_2O_2$, 420.3; m/z found, 421.2 $[M+H]^+$. $^1H$ NMR (MeOH-$d_4$): 7.37 (t, J=8.0, 1H), 6.96 (d, J=8.0, 3H), 6.92 (d, J=8.2, 1H), 6.87 (d, J=8.7, 2H), 4.78 (m, 1H), 4.66 (s, 1H), 4.08 (br m, 1H), 3.82 (m, 1H), 3.75 (m, 2H), 3.73 (s, 3H), 3.61 (br m, 1H), 3.27 (m, 3H), 2.75 (br m, 1H), 2.58 (m, 3H), 2.41 (m, 1H), 2.1-1.6 (m, 10H), 1.41 (m, 1H).

Example 9-(A-B)

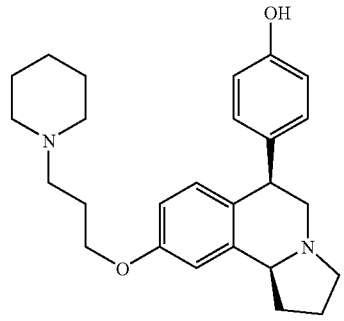

9A

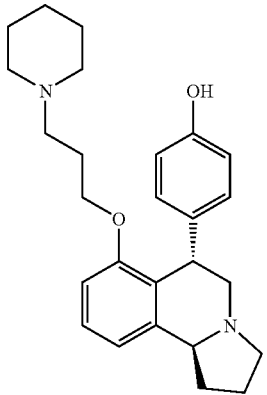

9B

9A: Cis-4-[9-(3-Piperidin-1-yl-propoxy)-1,2,3,5,6,10b-hexahydro-pyrrolo[2,1-a]isoquinolin-6-yl]-phenol 9B: Trans-4-[7-(3-Piperidin-1-yl-propoxy)-1,2,3,5,6,10b-hexahydro-pyrrolo[2,1-a]isoquinolin-6-yl]-phenol Step 1. Acetic acid 4-(2-{2-[3-(3-piperidin-1-yl-propoxy)-phenyl]-pyrrolidin-1-yl}-acetyl)-phenyl ester. Prepared as described in Example 8, Step 1, on a 4.51 mmol scale. Chromatographic purification as described provided 450.1 mg (28%) of the desired product as yellow oil. MS: exact mass calcd for $C_{28}H_{36}N_2O_4$, 464.3; m/z found, 465.4 [M+H]$^+$. $^1$H NMR (acetone-d$_6$): 7.98 (m, 2H), 7.26 (m, 1H), 7.24 (m, 2H), 7.06 (d, J=1.5, 1H), 7.02 (d, J=7.5, 1H), 6.88 (m, 1H), 4.05 (m, 3H), 3.56 (m, 1H), 3.44 (d, J=15.5, 1H), 3.37 (m, 1H), 2.50 (m, 2H), 2.45 (m, 4H), 2.33 (s, 3H), 2.22 (m, 1H), 1.90 (m, 4H), 1.75 (m, 1H), 1.58 (m, 4H), 1.46 (br m, 2H).

Step 2. 4-(1-Hydroxy-2-{2-[3-(3-piperidin-1-yl-propoxy)-phenyl]-pyrrolidin-1-yl}-ethyl)-phenol. Prepared as described in Example 8, Step 2, on a 0.896 mmol scale, to give crude material that was taken on to the next step without purification. MS: exact mass calcd for $C_{26}H_{36}N_2O_3$, 424.3; m/z found, 425.5 [M+H]$^+$.

Step 3. Performed as described in Example 1, Step 7, on a 0.896 mmol scale, to give a combined yield of 16% of two diastereomers.

9A: Cis-4-[9-(3-Piperidin-1-yl-propoxy)-1,2,3,5,6,10b-hexahydro-pyrrolo[2,1-a]isoquinolin-6-yl]-phenol. 27.2 mg (5%) as the TFA salt. MS: exact mass calcd for $C_{26}H_{34}N_2O_2$, 406.3; m/z found, 407.5 [M+H]$^+$. $^1$H NMR (acetone-d$_6$): 12.51 (br s, 1H), 11.35 (br s, 1H), 7.63 (br s, 3H), 7.04 (d, J=8.4, 2H), 6.95 (s, 1H), 6.82 (m, 4H), 5.14 (br s, 1H), 4.44 (br s, 1H), 4.13 (br m, 2H), 3.84 (br s, 1H), 3.64 (m, 5H), 3.34 (br s, 2H), 2.99 (br m, 2H), 2.72 (br s, 1H), 2.30 (m, 2H), 2.17 (br m, 1H), 2.09 (br m, 1H), 1.91 (m, 4H), 1.80 (m, 1H), 1.48 (m, 1H).

9B: Trans-4-[7-(3-Piperidin-1-yl-propoxy)-1,2,3,5,6,10b-hexahydro-pyrrolo[2,1-a]isoquinolin-6-yl]-phenol. 68.8 mg (11%) as the TFA salt. MS: exact mass calcd for $C_{26}H_{34}N_2O_2$, 406.3; m/z found, 407.5 [M+H]$^+$. $^1$H NMR (acetone-d$_6$): 10.96 (br s, 1H), 10.36 (br s, 3H), 9.59 (br s, 1H), 7.39 (m, 1H), 7.03 (d, J=7.5, 1H), 6.94 (m, 4H), 6.77 (d, J=7.8, 2H), 5.13 (br s, 1H), 4.69 (br s, 1H), 4.14 (br m, 1H), 3.84 (m, 4H), 3.49 (br s, 1H), 3.39 (m, 2H), 2.87 (d, J=8.4, 1 H), 2.64 (br m, 3H), 2.53 (br m, 1H), 2.24 (m, 3H), 2.05 (br s, 1H), 1.80 (m, 5H), 1.46 (br m, 1H).

Example 10-(A-C)

10A

10B

10C

10A: Cis-6-(3-Methoxy-phenyl)-9-(3-piperidin-1-yl-propoxy)-1,2,3,5,6,10b-hexahydro-pyrrolo[2,1-a]isoquinoline 10B: Trans-6-(3-Methoxy-phenyl)-9-(3-piperidin-1-yl-propoxy)-1,2,3,5,6,10b-hexahydro-pyrrolo[2,1-a]isoquinoline 10C: Trans-6-(3-Methoxy-phenyl)-7-(3-piperidin-1-yl-propoxy)-1,2,3,5,6,10b-hexahydro-pyrrolo[2,1-a]isoquinoline Step 1. 1-(3-Methoxy-phenyl)-2-{2-[3-(3-piperidin-1-yl-propoxy)-phenyl]-pyrrolidin-1-yl}-ethanone. Prepared as described in Example 8, Step 1, on a 4.33 mmol scale. Chromatographic purification provided 1.37 g (72%) of the desired product as an orange oil. MS: exact mass calcd for $C_{27}H_{36}N_2O_3$, 436.3; m/z found, 437.5 [M+H]$^+$. $^1$H NMR (acetone-d$_6$): 7.44 (m, 2H), 7.28 (m, 1H), 7.21 (m, 1H), 7.07 (d, J=2.6, 1H), 6.97 (m, 2H), 6.79 (m, 1H), 4.07 (d, J=16.3, 1H), 3.98 (m, 2H), 3.83 (s, 3H), 3.45 (m, 3H), 2.54 (m, 3H), 2.47 (m, 3H), 2.37 (m, 1H), 2.19 (m, 1H), 2.00 (m, 3H), 1.82 (m, 2H), 1.63 (m, 4H), 1.45 (m, 2H).

Step 2. 1-(3-Methoxy-phenyl)-2-{2-[3-(3-piperidin-1-yl-propoxy)-phenyl]-pyrrolidin-1-yl}-ethanol. Prepared as described in Example 8, Step 2, on a 1.8 mmol scale, to give 420 mg (53%) of the desired product as a mixture of diastereomers which were not separated. MS: exact mass calcd for $C_{27}H_{38}N_2O_3$, 438.3; m/z found, 439.5 [M+H]$^+$.

Step 3. Performed as described in Example 1, Step 7, on a 0.91 mmol scale, to give a 48% combined yield of the desired products.

10A: Cis-6-(3-Methoxy-phenyl)-9-(3-piperidin-1-yl-propoxy)-1,2,3,5,6,10b-hexahydro-pyrrolo[2,1-a]isoquinoline. 57.3 mg (10%) as the TFA salt. MS: exact mass calcd for $C_{27}H_{36}N_2O_2$, 420.3; m/z found, 421.5 [M+H]$^+$. $^1$H NMR (acetone-d$_6$): 7.32 (t, J=8.1, 1H), 6.93 (m, 2H), 6.91 (m, 2H), 6.78 (dd, J=2.6, 8.7, 1H), 6.68 (d, J=8.7, 1H), 4.91 (m, 1H), 4.54 (dd, J=4.6, 12.1, 1H), 4.12 (t, J=6.0, 2H), 3.88 (m, 1H), 3.78 (5, 3H), 3.64 (m, 3H), 3.47 (m, 1H), 3.38 (m, 1H), 3.30 (m, 2H), 2.93 (m, 3H), 2.31 (m, 4H), 2.86 (m, 1H), 1.84 (m, 4H), 1.78 (m, 1H), 1.50 (m, 1H).

10B: Trans-6-(3-Methoxy-phenyl)-9-(3-piperidin-1-yl-propoxy)-1,2,3,5,6,10b-hexahydro-pyrrolo[2,1-a]isoquinoline. 122.0 mg (21%) as the TFA salt. MS: exact mass calcd for $C_{27}H_{36}N_2O_2$, 420.3; m/z found, 421.5 [M+H]$^+$. $^1$H NMR (acetone-d$_6$): 7.30 (t, J=7.9, 1H), 6.98 (br s, 1H), 6.91 (m, 1H), 6.83 (m, 4H), 5.15 (br s, 1H), 4.57 (br s, 1H), 4.16 (m, 2H), 3.86 (br s, 1H), 3.77 (s, 3H), 3.66 (m, 4H), 3.36 (m, 2H), 3.01 (br s, 2H), 2.75 (m, 1H), 2.34 (m, 2H), 2.22 (m, 1H), 2.15 (m, 1H), 1.91 (m, 4H), 1.80 (m, 1H), 1.55 (m, 1H).

10C: Trans-6-(3-Methoxy-phenyl)-7-(3-piperidin-1-yl-propoxy)-1,2,3,5,6,10b-hexahydro-pyrrolo[2,1-a]isoquinoline. 85.0 mg (14%) as the TFA salt. MS: exact mass calcd for $C_{27}H_{36}N_2O_2$, 420.3; m/z found, 421.5 [M+H]$^+$. $^1$H NMR (acetone-d$_6$): 7.41 (t, J=8.0, 1H), 7.22 (m, 1H), 7.06 (m, 1H), 6.97 (d, J=8.2, 1H), 6.84 (m, 1H), 6.76 (s, 1H), 6.67 (m, 1H), 5.16 (br s, 1H), 4.79 (br s, 1H), 4.16 (br s, 1H), 3.90 (m, 4H), 3.77 (s, 3H), 3.37 (m, 3H), 2.86 (m, 1H), 2.65 (m, 4H), 2.23 (m, 3H), 2.10 (m, 1H), 2.05 (br s, 1H), 1.77 (m, 5H), 1.49 (m, 1H).

Example 11-(A-C)

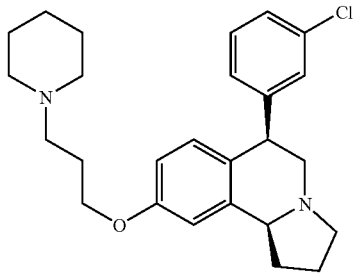

11A

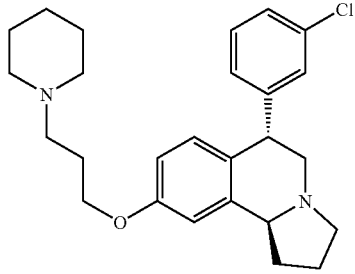

11B

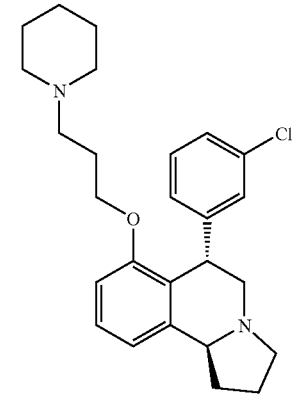

11C

11A: Cis-6-(3-Chloro-phenyl)-9-(3-piperidin-1-yl-propoxy)-1,2,3,5,6,10b-hexahydro-pyrrolo[2,1-a]isoquinoline
11B: Trans-6-(3-Chloro-phenyl)-9-(3-piperidin-1-yl-propoxy)-1,2,3,5,6,10b-hexahydro-pyrrolo[2,1-a]isoquinoline
11C: Trans-6-(3-Chloro-phenyl)-7-(3-piperidin-1-yl-propoxy)-1,2,3,5,6,10b-hexahydro-pyrrolo[2,1-a]isoquinoline Step 1. 1-(3-Chloro-phenyl)-2-{2-[3-(3-piperidin-1-yl-propoxy)-phenyl]-pyrrolidin-1-yl}-ethanone. Prepared as described in Example 8, Step 1, on a 5.63 mmol scale. Chromatographic purification gave 1.35 g (71%) of the desired product as an orange oil. MS: exact mass calcd for $C_{26}H_{33}ClN_2O_2$, 440.2; m/z found, 441.5 [M+H]$^+$. $^1$H NMR (CDCl$_3$): 7.85 (m, 1H), 7.73 (m, 1H), 7.48 (m, 1H), 7.33 (t, J=3.9, 1H), 7.23 (t, J=7.8, 1H), 6.95 (m, 2H), 6.78 (dd, J=1.9, 8.2, 1H), 4.01 (d, J=15.9, 1H), 3.98 (t, J=6.3, 2 H), 3.43 (m, 1H), 3.36 (m, 2H), 2.58 (m, 2H), 2.51 (m, 4H), 2.35 (m, 1H), 2.20 (m, 1H), 2.01 (m, 4H), 1.81 (m, 2H), 1.66 (m, 4H), 1.47 (m, 2H).

Step 2. 1-(3-Chloro-phenyl)-2-{2-[3-(3-piperidin-1-yl-propoxy)-phenyl]-pyrrolidin-1-yl}-ethanol. Prepared as described in Example 8, Step 2, on a 1.83 mmol scale, to give 610 mg (75%) of the desired product as a mixture of diastereomers, which were not separated. MS: exact mass calcd for $C_{26}H_{35}ClN_2O_2$, 442.2; m/z found, 443.5 [M+H]$^+$.

Step 3. Performed as described in Example 1, Step 7, on a 1.35 mmol scale, to give a 16% combined yield of the desired products.

11A: Cis-6-(3-Chloro-phenyl)-9-(3-piperidin-1-yl-propoxy)-1,2,3,5,6,10b-hexahydro-pyrrolo[2,1-a]isoquinoline. 37.0 mg (4%) as the TFA salt. MS: exact mass calcd for $C_{26}H_{33}ClN_2O$, 424.2; m/z found, 425.5 [M+H]$^+$. $^1$H NMR (acetone-d$_6$): 7.45 (m, 2H), 7.33 (m, 2H), 6.97 (m, 1H), 6.81 (dd, J=2.6, 8.7, 1H), 6.68 (d, J=8.7, 1H), 4.95 (m, 2H), 4.63 (m, 1H), 4.14 (m, 2H), 3.98 (m, 1H), 3.72 (m, 3H), 3.55 (m, 1H), 3.46 (m, 1H), 3.36 (m, 2H), 3.01 (m, 2H), 2.91 (m, 1H), 2.36 (m, 5H), 1.94 (s, 3H), 1.80 (m, 1H), 1.52 (m, 1H).

11B: Trans-6-(3-Chloro-phenyl)-9-(3-piperidin-1-yl-propoxy)-1,2,3,5,6,10b-hexahydro-pyrrolo[2,1-a]isoquinoline. 38 mg (4%) as the TFA salt. MS: exact mass calcd for $C_{26}H_{33}ClN_2O$, 424.2; m/z found, 425.5 [M+H]$^+$. $^1$H NMR (acetone-d$_6$): 7.36 (m, 3H), 7.24 (m, 1H), 6.99 (br s, 1H), 6.85 (m, 1H), 6.81 (m, 1H), 5.14 (br s, 2H), 4.65 (br s, 1H), 4.17 (m, 2H), 3.68 (m, 6H), 3.33 (m, 2H), 2.98 (m, 2H), 2.76 (m, 1H), 2.32 (m, 2H), 2.22 (m, 2H), 1.91 (m, 4H), 1.80 (m, 1H), 1.53 (m, 1H).

11C: Trans-6-(3-Chloro-phenyl)-7-(3-piperidin-1-yl-propoxy)-1,2,3,5,6,10b-hexahydro-pyrrolo[2,1-a]isoquinoline. 69 mg (8%) as the TFA salt. MS: exact mass calcd for $C_{26}H_{33}ClN_2O$, 424.2; m/z found, 425.5 [M+H]$^+$. $^1$H NMR (acetone-d$_6$): 7.43 (t, J=8.0, 1H), 7.30 (br s, 2H), 7.26 (s, 1H), 7.07 (m, 2H), 6.99 (d, J=8.2, 1H), 5.15 (br s, 1H), 4.85 (br s, 1H), 4.15 (m, 1H), 3.89 (m, 3H), 3.78 (m, 1H), 3.44 (m, 3H), 2.86 (m, 1H), 2.78 (m, 1H), 2.62 (m, 3H), 2.23 (m, 3H), 2.10 (m, 2H), 1.85 (m, 5H), 1.49 (m, 1H).

Example 12-(A-D)

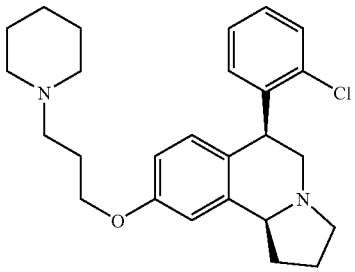

12A

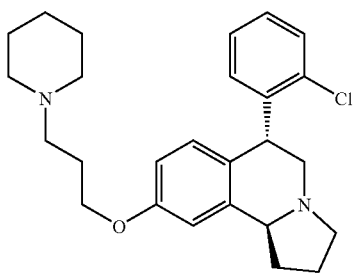

12B

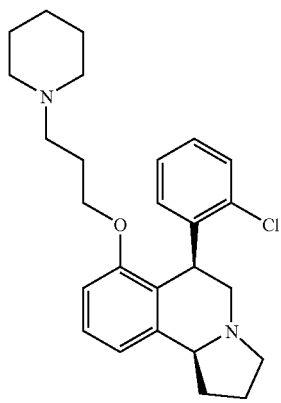

12C

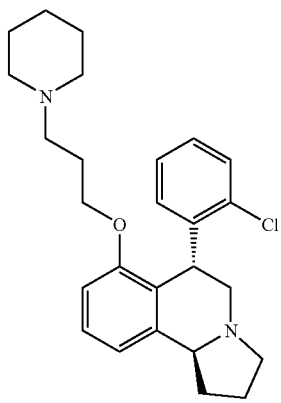

12D

12A: Cis-6-(2-Chloro-phenyl)-9-(3-piperidin-1-yl-propoxy)-1,2,3,5,6,10b-hexahydro-pyrrolo[2,1-a]isoquinoline 12B: Trans-6-(2-Chloro-phenyl)-9-(3-piperidin-1-yl-propoxy)-1,2,3,5,6,10b-hexahydro-pyrrolo[2,1-a]isoquinoline 12C: Cis-6-(2-Chloro-phenyl)-7-(3-piperidin-1-yl-propoxy)-1,2,3,5,6,10b-hexahydro-pyrrolo[2,1-a]isoquinoline 12D: Trans-6-(2-Chloro-phenyl)-7-(3-piperidin-1-yl-propoxy)-1,2,3,5,6,10b-hexahydro-pyrrolo[2,1-a]isoquinoline Step 1. 1-(2-Chloro-phenyl)-2-{2-[3-(3-piperidin-1-yl-propoxy)-phenyl]-pyrrolidin-1-yl}-ethanone. Prepared as described in Example 8, Step 1, on a 5.63 mmol scale. Chromatographic purification gave 1.37 g (72%) of the desired product as an orange oil. MS: exact mass calcd for $C_{26}H_{33}ClN_2O_2$, 440.2; m/z found, 441.5 [M+H]$^+$.

Step 2. 1-(2-Chloro-phenyl)-2-{2-[3-(3-piperidin-1-yl-propoxy)-phenyl]-pyrrolidin-1-yl}-ethanol. Prepared as described in Example 8, Step 2, on a 1.83 mmol scale, to give 375 mg (46%) of the desired product as a mixture of diastereomers, which were not separated. MS: exact mass calcd for $C_{26}H_{35}ClN_2O_2$, 442.2; m/z found, 443.5 [M+H]$^+$.

Step 3. Performed as described in Example 1, Step 7, on a 1.35 mmol scale, to give a 24% combined yield of the desired products.

12A: Cis-6-(2-Chloro-phenyl)-9-(3-piperidin-1-yl-propoxy)-1,2,3,5,6,10b-hexahydro-pyrrolo[2,1-a]isoquinoline. 13.3 mg (2%) as the TFA salt. MS: exact mass calcd for $C_{26}H_{33}ClN_2O$, 424.2; m/z found, 425.5 [M+H]$^+$. $^1$H NMR (acetone-d$_6$): 7.54 (m, 1H), 7.37 (m, 2H), 7.20 (br s, 1H), 7.02 (s, 1H), 6.80 (m, 1H), 6.61 (d, J=8.8, 1H), 5.13 (br s, 1H), 4.86 (br s, 1H), 4.13 (s, 2H), 3.88 (br s, 1H), 3.74 (m, 3H), 3.44 (m, 2H), 3.30 (m, 2H), 2.89 (m, 4H), 2.30 (m, 5H), 1.92 (m, 4H), 1.58 (m, 1H).

12B: Trans-6-(2-Chloro-phenyl)-9-(3-piperidin-1-yl-propoxy)-1,2,3,5,6,10b-hexahydro-pyrrolo[2,1-a]isoquinoline. 53 mg (8%) as the TFA salt. MS: exact mass calcd for $C_{26}H_{33}ClN_2O$, 424.2; m/z found, 425.5 [M+H]$^+$. $^1$H NMR (acetone-d$_6$): 7.51 (m, 1H), 7.35 (m, 1H), 7.29 (m, 1H), 7.08 (m, 2H), 6.87 (m, 2H), 5.15 (m, 1H), 4.99 (m, 1H), 4.71 (m, 2H), 4.19 (m, 2H), 3.76 (m, 2H), 3.65 (m, 2H), 3.35 (m, 2H), 3.00 (m, 2H), 2.82 (br s, 1H), 2.34 (m, 2H), 2.19 (m, 3H), 1.92 (m, 4H), 1.81 (m, 1H), 1.54 (m, 1H).

12C: Cis-6-(2-Chloro-phenyl)-7-(3-piperidin-1-yl-propoxy)-1,2,3,5,6,10b-hexahydro-pyrrolo[2,1-a]isoquinoline. 49.2 mg (7%) as the TFA salt. MS: exact mass calcd for $C_{26}H_{33}ClN_2O$, 424.2; m/z found, 425.5 [M+H]$^+$. $^1$H NMR (acetone-d$_6$): 7.45 (d, J=7.9, 1H), 7.20 (m, 2H), 7.07 (m, 1H), 6.87 (d, J=7.7, 1H), 6.76 (m, 2H), 4.91 (br s, 1H), 3.89 (m, 1H), 3.56 (m, 1H), 3.40 (m, 2H), 3.24 (1H), 3.11 (m, 2H), 3.79 (m, 4H), 2.62 (m, 3H), 2.46 (m, 2H), 2.02 (m, 2H), 1.77 (m, 4H), 1.61 (m, 2H), 1.40 (m, 1H).

12D: Trans-6-(2-Chloro-phenyl)-7-(3-piperidin-1-yl-propoxy)-1,2,3,5,6,10b-hexahydro-pyrrolo[2,1-a]isoquinoline. 50 mg (7%) as the TFA salt. MS: exact mass calcd for $C_{26}H_{33}ClN_2O$, 424.2; m/z found, 425.5 [M+H]$^+$. $^1$H NMR (acetone-d$_6$): 7.57 (d, J=11.4, 1H), 7.43 (m, 1H), 7.31 (m, 1H), 7.08 (m, 2H), 6.97 (d, J=8.2, 1H), 6.73 (br s, 1H), 5.19 (br s, 1H), 5.07 (br s, 1H), 4.29 (m, 1H), 3.86 (m, 4H), 3.53 (m, 2H), 3.38 (m, 1H), 2.89 (m, 1H), 2.69 (m, 4H), 2.30 (m, 3H), 2.10 (m, 1H), 1.90 (m, 1H), 1.87 (m, 5H), 1.51 (m, 1H).

Example 13-(A-B)

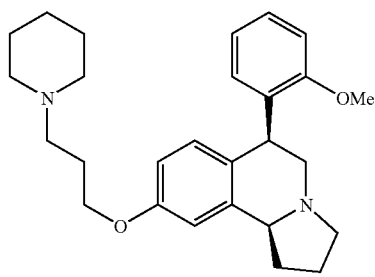

13A

13B

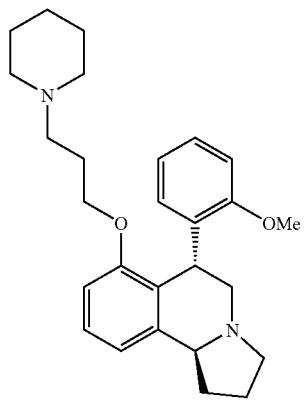

13A: Cis-6-(2-Methoxy-phenyl)-9-(3-piperidin-1-yl-propoxy)-1,2,3,5,6,10b-hexahydro-pyrrolo[2,1-a]isoquinoline 13B: Trans-6-(2-Methoxy-phenyl)-9-(3-piperidin-1-yl-propoxy)-1,2,3,5,6,10b-hexahydro-pyrrolo[2,1-a]isoquinoline Step 1. 1-(2-Methoxy-phenyl)-2-{2-[3-(3-piperidin-1-yl-propoxy)-phenyl]-pyrrolidin-1-yl}-ethanone. Prepared as described in Example 8, Step 1, on a 3.47 mmol scale. Chromatographic purification gave 1.12 g (74%) of the desired product as an orange semi-solid. MS: exact mass calcd for $C_{27}H_{36}N_2O_3$, 436.3; m/z found, 437.5 [M+H]$^+$. $^1$H NMR (CDCl$_3$): 7.63 (dd, J=1.8, 7.7, 1H), 7.40 (m, 1H), 7.18 (m, 1H), 6.94 (m, 3H), 6.87 (d, J=8.3, 1H), 6.75 (m, 1H), 4.10 (d, J=18.0, 1H), 3.96 (t, J=6.4, 2H), 3.72 (s, 3H), 3.52 (m, 3H), 2.50 (m, 2H), 2.45 (m, 4H), 2.16 (m, 1H), 1.97 (m, 3H), 1.84 (m, 2H), 1.75 (m, 1H), 1.60 (m, 4H), 1.44 (m, 2H).

Step 2. 1-(2-Methoxy-phenyl)-2-{2-[3-(3-piperidin-1-yl-propoxy)-phenyl]-pyrrolidin-1-yl}-ethanol. Prepared as described in Example 8, Step 2, on a 2.18 mmol scale, to give 930 mg (97%) of the desired product as a mixture of diastereomers, which were not separated. MS: exact mass calcd for $C_{27}H_{38}N_2O_3$, 438.3; m/z found, 439.6 [M+H]$^+$.

Step 3. Performed as described in Example 1, Step 7, on a 2.05 mmol scale, to give a 20% combined yield of two diastereomers.

13A: Cis-6-(2-Methoxy-phenyl)-9-(3-piperidin-1-yl-propoxy)-1,2,3,5,6,10b-hexahydro-pyrrolo[2,1-a]isoquinoline. 27.3 mg (2%) as the TFA salt. MS: exact mass calcd for $C_{27}H_{36}N_2O_2$, 420.3; m/z found, 421.5 [M+H]$^+$. $^1$H NMR (acetone-d$_6$): 7.35 (m, 1H), 7.14 (br s, 1H), 7.09 (d, J=8.2, 1H), 6.97 (m, 1H), 6.89 (m, 1H), 6.75 (m, 1H), 6.63 (d, J=8.6, 1H), 4.92 (m, 2H), 4.11 (t, J=6.0, 2H), 3.95 (m, 1H), 3.76 (m, 3H), 3.62 (m, 4H), 3.37 (m, 1H), 3.30 (m, 2H), 2.97 (m, 2H), 2.88 (m, 1H), 2.30 (m, 5H), 2.0 (m, 4H), 1.79 (m, 1H), 1.51 (m, 1H).

13B: Trans-6-(2-Methoxy-phenyl)-9-(3-piperidin-1-yl-propoxy)-1,2,3,5,6,10b-hexahydro-pyrrolo[2,1-a]isoquinoline. 235 mg (18%) as the TFA salt. MS: exact mass calcd for $C_{27}H_{36}N_2O_2$, 420.3; m/z found, 421.5 [M+H]$^+$. $^1$H NMR (acetone-d$_6$): 11.54 (br s, 1H), 10.48 (m, 2H), 7.42 (m, 1H), 7.27 (m, 1H), 7.11 (d, J=8.1, 1H), 7.06 (m, 1H), 6.98 (d, J=11.8, 1H), 6.74 (m, 1H), 6.51 (m, 1H), 5.11 (br s, 1H), 4.96 (br s, 1H), 4.13 (m, 1H), 3.98 (s, 3H), 3.89 (m, 2H), 3.70 (m, 1H), 3.43 (m, 2H), 3.33 (m, 1H), 2.87 (m, 1H), 2.62 (m, 3H), 2.25 (m, 3H), 2.03 (m, 1H), 1.82 (m, 5H), 1.48 (m, 1H).

Example 14-(A-C)

14A
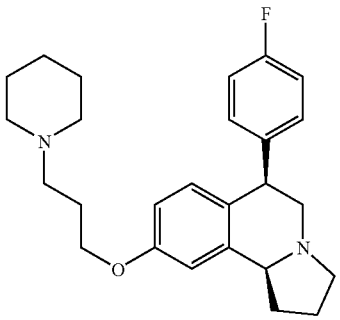

14B
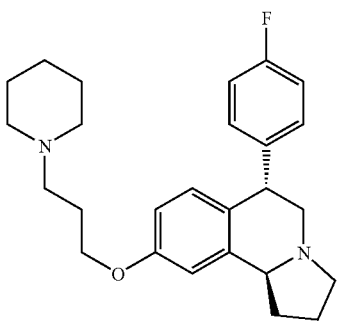

14C
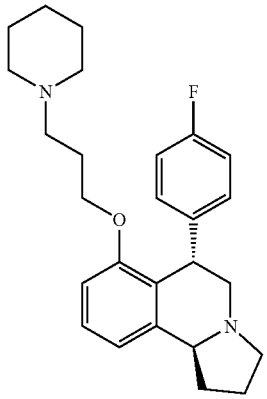

14A: Cis-6-(4-Fluoro-phenyl)-9-(3-piperidin-1-yl-propoxy)-1,2,3,5,6,10b-hexahydro-pyrrolo[2,1-a]isoquinoline 14B: Trans-6-(4-Fluoro-phenyl)-9-(3-piperidin-1-yl-propoxy)-1,2,3,5,6,10b-hexahydro-pyrrolo[2,1-a]isoquinoline 14C: Trans-6-(4-Fluoro-phenyl)-7-(3-piperidin-1-yl-propoxy)-1,2,3,5,6,10b-hexahydro-pyrrolo[2,1-a]isoquinoline Step 1. 1-(4-Fluoro-phenyl)-2-{2-[3-(3-piperidin-1-yl-propoxy)-phenyl]-pyrrolidin-1-yl}-ethanone. Prepared as described in Example 8, Step 1, on a 3.47 mmol scale. Chromatographic purification gave 1.24 g (84%) of the desired product. MS: exact mass calcd for $C_{26}H_{33}FN_2O_2$, 424.3; m/z found, 425.5 [M+H]$^+$. $^1$H NMR (CDCl$_3$): 7.90 (m, 2H), 7.22 (m, 1H), 7.06 (m, 2H), 7.95 (m, 2H), 6.79 (m, 1H), 4.03 (d, J=15.7, 1H), 3.98 (m, 2H), 3.39 (m, 3H), 2.52 (t, J=7.4, 2H), 2.45 (br s, 3H), 2.36 (m, 1H), 2.18 (m, 2H), 2.00 (m, 3H), 1.80 (m, 2H), 1.62 (m, 4H), 1.45 (m, 2H).

Step 2. 1-(4-Fluoro-phenyl)-2-{2-[3-(3-piperidin-1-yl-propoxy)-phenyl]-pyrrolidin-1-yl}-ethanol. Prepared as described in Example 8, Step 2, on a 2.47 mmol scale, to give 980 mg (93%) of the desired product as a mixture of diastereomers and regioisomers, which were not separated. MS: exact mass calcd for $C_{26}H_{35}FN_2O_2$, 426.3; m/z found, 427.5 $[M+H]^+$.

Step 3. Performed as described in Example 1, Step 7, on a 2.23 mmol scale to give a 12% combined yield of the desired products.

14A: Cis-6-(4-Fluoro-phenyl)-9-(3-piperidin-1-yl-propoxy)-1,2,3,5,6,10b-hexahydro-pyrrolo[2,1-a]isoquinoline. 28.0 mg (2%) as the TFA salt. MS: exact mass calcd for $C_{26}H_{33}FN_2O$, 408.3; m/z found, 409.5 $[M+H]^+$. $^1$H NMR (acetone-$d_6$): 7.33 (m, 2H), 7.17 (t, J=8.8, 2H), 6.95 (d, J=2.6, 1H), 6.78 (dd, J=2.6, 8.7, 1H), 6.64 (d, J=8.7, 1H), 4.91 (m, 1H), 4.61 (m, 1H), 4.26 (m, 4H), 4.12 (t, J=6.0, 2H), 3.94 (m, 1H), 3.62 (m, 3H), 3.45 (m, 2H), 3.31 (m, 2H), 2.92 (m, 3H), 2.32 (m, 5H), 1.78 (m, 1H), 1.50 (m, 1H).

14B: Trans-6-(4-Fluoro-phenyl)-9-(3-piperidin-1-yl-propoxy)-1,2,3,5,6,10b-hexahydro-pyrrolo[2,1-a]isoquinoline. 9.7 mg (0.6%) as the TFA salt. MS: exact mass calcd for $C_{26}H_{33}FN_2O$, 408.3; m/z found, 409.5 $[M+H]^+$. $^1$H NMR (acetone-$d_6$): 7.30 (m, 2H), 7.13 (t, J=8.7, 2H), 7.00 (br s, 1H), 6.85 (m, 2H), 5.15 (br s, 1H), 4.63 (br s, 1H), 4.17 (m, 2H), 3.85 (m, 1H), 3.66 (m, 4H), 3.59 (m, 1H), 3.33 (m, 2H), 3.01 (m, 2H), 2.78 (m, 1H), 2.34 (m, 2H), 2.22 (m, 2H), 2.14 (m, 1H), 1.92 (m, 4H), 1.82 (m, 1H), 1.53 (m, 1H).

14C: Trans-6-(4-Fluoro-phenyl)-7-(3-piperidin-1-yl-propoxy)-1,2,3,5,6,10b-hexahydro-pyrrolo[2,1-a]isoquinoline. 124.8 mg (9%) as the TFA salt. MS: exact mass calcd for $C_{26}H_{33}FN_2O$, 408.3; m/z found, 409.5 $[M+H]^+$. $^1$H NMR (acetone-$d_6$): 7.42 (m, 1H), 7.17 (m, 2H), 7.06 (m, 3H), 6.98 (d, J=8.2, 1H), 5.12 (br s, 1H), 4.83 (s, 1H), 4.15 (br s, 1H), 3.89 (m, 3H), 3.77 (m, 1H), 3.43 (m, 3H), 3.78 (m, 5H), 2.24 (m, 4H), 1.85 (m, 6H), 1.49 (m, 1H).

Example 15

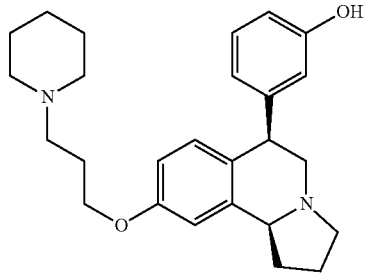

Cis-3-[9-(3-Piperidin-1-yl-propoxy)-1,2,3,5,6,10b-hexahydro-pyrrolo[2,1-a]isoquinolin-6-yl]-phenol To a solution of cis-6-(3-methoxy-phenyl)-9-(3-piperidin-1-yl-propoxy)-1,2,3,5,6,10b-hexahydro-pyrrolo[2,1-a]isoquinoline (27.0 mg, 0.042 mmol) in $CH_2Cl_2$ (0.2 mL) was added $BBr_3$ (1 M in $CH_2Cl_2$, 0.21 mL) and the reaction mixture was stirred at rt for 15 min. The reaction was quenched with water and the mixture was concentrated under a stream of $N_2$. The crude material was purified by reverse-phase HPLC to give 14.1 mg (53%) of the desired product as a TFA salt. MS: exact mass calcd for $C_{26}H_{34}N_2O_2$, 406.3; m/z found, 407.5 $[M+H]^+$. $^1$H NMR (acetone-$d_6$): 7.20 (m, 1H), 6.92 (m, 1H), 6.78 (m, 5H), 4.83 (m, 1H), 4.46 (m, 1H), 4.11 (t, J=7.2, 2H), 3.87 (m, 1H), 3.59 (m, 2H), 3.38 (m, 2H), 3.28 (m, 2H), 2.89 (m, 3H), 2.87 (m, 2H), 2.29 (m, 5H), 1.88 (m, 4H), 1.57 (m, 2H).

Example 16

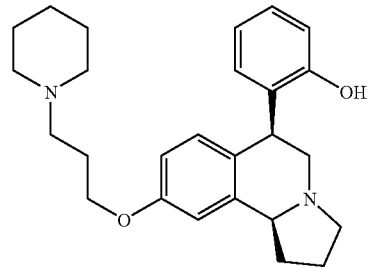

Cis-2-[9-(3-Piperidin-1-yl-propoxy)-1,2,3,5,6,10b-hexahydro-pyrrolo[2,1-a]isoquinolin-6-yl]-phenol Prepared as described in Example 15, on a 0.030 mmol scale, to give 3.6 mg (19%) of the desired product after chromatography. MS: exact mass calcd for $C_{26}H_{34}N_2O_2$, 406.3; m/z found, 407.4 $[M+H]^+$. $^1$H NMR (acetone-$d_6$): 6.87 (m, 7H), 4.92 (br s, 1H), 4.10 (t, J=5.9, 2H), 3.61 (m, 3H), 3.41 (m, 1H), 3.30 (m, 2H), 2.95 (m, 5H), 2.29 (m, 4H), 2.07 (m, 2H), 1.89 (m, 6H), 1.52 (m, 1H).

Example 17

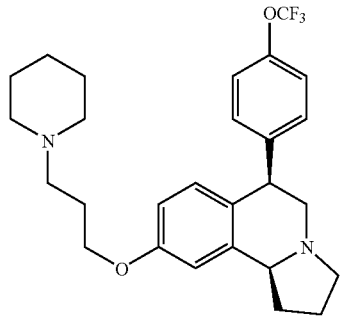

Cis-9-(3-Piperidin-1-yl-propoxy)-6-(4-trifluoromethoxy-phenyl)-1,2,3,5,6,10b-hexahydro-pyrrolo[2,1-a]isoquinoline Step 1. 2-{2-[3-(3-Piperidin-1-yl-propoxy)-phenyl]-pyrrolidin-1-yl}-1-(4-trifluoromethoxy-phenyl)-ethanone. Prepared as described in Example 8, Step 1, on a 3.47 mmol scale, to give 1.35 g (79%) of the desired product as a viscous oil after chromatography ($NH_3$ in MeOH/$CH_2Cl_2$). MS: exact mass calcd for $C_{27}H_{33}F_3N_2O_3$, 474.2; m/z found, 475.5 $[M+H]^+$. $^1$H NMR (MeOH-$d_4$): 7.77 (d, J=8.7, 2H), 7.11 (d, J=8.5, 2H), 7.05 (t, J=7.9, 1H), 6.82 (d, J=1.4, 1H), 6.78 (d, J=7.5, 1H), 6.64 (dd, J=2.3, 8.1, 1H), 3.80 (m, 3H), 3.3 (m, 2H), 2.31 (m, 5H), 2.21 (m, 1H), 1.96 (m, 1H), 1.81 (m, 3H), 1.60 (m, 2H), 1.45 (m, 4H), 1.31 (m, 2H).

Step 2. 9-(3-Piperidin-1-yl-propoxy)-6-(4-trifluoromethoxy-phenyl)-2,3-dihydro-1H-pyrrolo[2,1-a]isoquinolinylium salt. Prepared as described in Example 1, Step 7, on a 1.03 mmol scale, to give 445 mg (85%) of crude product, which was carried forward without purification. MS: exact mass calcd for $C_{27}H_{30}F_3N_2O_2^+$, 471.2; m/z found, 471.5 $[M]^+$.

Step 3. A mixture of isoquinolinium salt (Step 2, 0.878 mmol), bromocresol green (1-5 mg), and $NaCNBH_3$ (approx. 10 equiv.) in methanol (0.1 M) was stirred for 10 min at rt. The mixture was treated with methanolic HCl until the pH=4-5

(indicator turned yellow). More methanolic HCl was added when the solution takes on a green cast. When the reaction was complete, the mixture was diluted with CH$_2$Cl$_2$, and washed with 2 N NaOH, water (×2), and brine. The organic extract was dried (Na$_2$CO$_3$), filtered, and concentrated to provide the crude product. Purification by normal phase column chromatography (NH$_3$ in MeOH/CH$_2$Cl$_2$) followed by reverse-phase HPLC gave the desired compound (311.6 mg, 48%) as the TFA salt. MS: exact mass calcd for C$_{27}$H$_{33}$F$_3$N$_2$O$_2$, 474.3; m/z found, 475.5 [M+H]$^+$. $^1$H NMR (MeOH-d$_4$): 7.53 (d, J=8.6, 2H), 7.46 (d, J=8.1, 2H), 7.05 (d, J=2.4, 1H), 6.97 (dd, J=2.3, 8.7, 1H), 6.84 (d, J=8.7, 1H), 5.03 (m, 1H), 4.65 (m, 1H), 4.25 (t, J=5.7, 2H), 4.01 (m, 1H), 3.74 (m, 3H), 3.57 (m, 2H), 3.45 (m, 2H), 3.11 (m, 2H), 2.95 (m, 1H), 2.41 (m, 5H), 2.10 (m, 2H), 1.99 (m, 3H), 1.69 (m, 1H).

Example 18

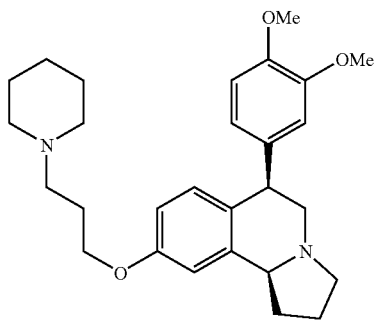

Cis-6-(3,4-Dimethoxy-phenyl)-9-(3-piperidin-1-yl-propoxy)-1,2,3,5,6,10b-hexahydro-pyrrolo[2,1-a]isoquinoline Step 1. 2-Bromo-1-(3,4-dimethoxy-phenyl)-ethanone. To a 0° C. solution of 3,4-dimethoxyacetophenone (5.00 g, 27.8 mmol) in diethyl ether (200 mL) and CHCl$_3$ (30 mL) was added, dropwise over 1.5 h, a solution of Br$_2$ (1.45 mL, 27.8 mmol) in CHCl$_3$ (30 mL). Once the addition was complete, the mixture was stirred for 1 h at 0° C., and then was allowed to warm to rt. The reaction mixture was concentrated and the residue chromatographed (CH$_2$Cl$_2$/hexanes) to give 5.23 g (73%) of the ketone as a pale yellow solid. $^1$H NMR (DMSO-d$_6$): 7.68 (dd, J=2.0, 8.4, 1H), 7.47 (d, J=2.0, 1H), 7.08 (d, J=8.5, 1H), 4.85 (s, 2H), 3.85 (s, 3H), 3.81 (s, 3H).

Step 2. 1-(3,4-Dimethoxy-phenyl)-2-{2-[3-(3-piperidin-1-yl-propoxy)-phenyl]-pyrrolidin-1-yl}-ethanone. Prepared as described in Example 8, Step 1, on a 3.47 mmol scale, to give 1.30 g (77%) of the desired product as a pale yellow oil after chromatography (NH$_3$ in MeOH/CH$_2$Cl$_2$). MS: exact mass calcd for C$_{28}$H$_{38}$N$_2$O$_4$, 466.3; m/z found, 467.5 [M+H]$^+$. $^1$H NMR (MeOH-d$_4$): 7.40 (m, 1H), 7.35 (d, J=2.0, 1H), 7.17 (m, 1H), 6.96 (m, 1H), 6.91 (d, J=7.6, 1H), 6.81 (d, J=8.5, 1H), 6.76 (m, 1H), 3.91 (m, 3H), 3.80 (s, 3H), 3.74 (s, 3H), 3.40 (m, 3H), 2.40 (m, 6H), 2.28 (m, 1H), 2.11 (m, 1H), 1.91 (m, 3H), 2.75 (m, 1H), 2.62 (m, 1H), 1.54 (m, 4H), 1.41 (m, 2H).

Step 3. 6-(3,4-Dimethoxy-phenyl)-9-(3-piperidin-1-yl-propoxy)-2,3-dihydro-1H-pyrrolo[2,1-a]isoquinolinylium salt. Prepared as described in Example 17, Step 2, on a 2.42 mmol scale, to give 1.05 g (89%) of crude product. MS: exact mass calcd for C$_{28}$H$_{35}$N$_2$O$_3$$^+$, 447.3; m/z found, 447.5 [M]$^+$.

Step 4. Prepared as described in Example 17, Step 3, on a 2.16 mmol scale, to give 420.2 mg (27%) of the desired product as the TFA salt after normal phase chromatography and HPLC. MS: exact mass calcd for C$_{28}$H$_{38}$N$_2$O$_3$, 450.3; m/z found, 451.5 [M+H]$^+$. $^1$H NMR (MeOH-d$_4$): 7.12 (d, J=8.4, 1H), 7.03 (d, J=2.3, 1H), 6.95 (m, 3H), 6.90 (d, J=8.7, 1H), 5.02 (m, 1H), 4.51 (m, 1H), 4.25 (t, J=5.7, 2H), 4.01 (m, 1H), 3.97 (s, 3H), 3.93 (s, 3H), 3.74 (d, J=11.9, 3H), 3.45 (m, 2H), 3.10 (m, 2H), 2.92 (m, 1H), 2.43 (m, 5H), 2.10 (d, J=14.9, 2H), 1.97 (m, 3H), 1.68 (m, 1H).

Example 19

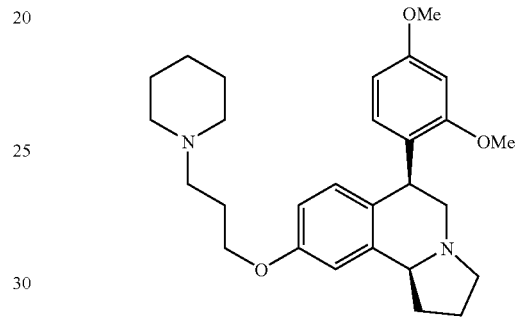

Cis-6-(2,4-Dimethoxy-phenyl)-9-(3-piperidin-1-yl-propoxy)-1,2,3,5,6,10b-hexahydro-pyrrolo[2,1-a]isoquinoline Step 1. 1-(2,4-Dimethoxy-phenyl)-2-{2-[3-(3-piperidin-1-yl-propoxy)-phenyl]-pyrrolidin-1-yl}-ethanone. Prepared as described in Example 8, Step 1, on a 3.47 mmol scale, to give 1.28 g (78%) of the desired product as a pale yellow oil after chromatography (NH$_3$ in MeOH/CH$_2$Cl$_2$). MS: exact mass calcd for C$_{28}$H$_{38}$N$_2$O$_4$, 466.3; m/z found, 467.5 [M+H]$^+$. $^1$H NMR (MeOH-d$_4$): 7.16 (m, 1H), 7.10 (d, J=3.2, 1H), 6.97 (dd, J=3.2, 9.0, 1H), 6.93 (d, J=1.6, 1H), 6.87 (m, 2H), 6.76 (m, 1H), 4.04 (m, 1H), 3.91 (m, 2H), 3.69 (s, 3H), 3.63 (s, 3H), 3.43 (m, 3H), 2.39 (m, 6H), 2.30 (m, 1H), 2.11 (m, 1H), 1.92 (m, 3H), 1.82 (m, 1H), 1.75 (m, 1H), 1.55 (m, 4H), 1.42 (m, 2H).

Step 2. 6-(2,4-Dimethoxy-phenyl)-9-(3-piperidin-1-yl-propoxy)-2,3-dihydro-1H-pyrrolo[2,1-a]isoquinolinylium salt. Prepared as described in Example 17, Step 2, on a 2.90 mmol scale, to give 1.15 g (82%) of crude product. MS: exact mass calcd for C$_{28}$H$_{35}$N$_2$O$_3$$^+$, 447.3; m/z found, 447.5 [M]$^+$.

Step 3. Prepared as described in Example 17, Step 3, on a 2.39 mmol scale, to give 91.9 mg (8%) of the desired product as the TFA salt after chromatography and HPLC. MS: exact mass calcd for C$_{28}$H$_{38}$N$_2$O$_3$, 450.3; m/z found, 451.5 [M+H]$^+$. $^1$H NMR (MeOH-d$_4$): 6.76 (d, J=8.0, 1H), 6.67 (m, 2H), 6.59 (dd, J=2.5, 8.5, 1H), 6.52 (d, J=2.5, 1H), 6.37 (dd, J=2.5, 8.3, 1H), 4.53 (br s, 1H), 3.94 (t, J=6.0, 2H), 3.75 (s, 3H), 3.73 (s, 3H), 2.89 (m, 2H), 2.79 (m, 1H), 2.71 (dd, J=5.5, 11.0, 1H), 2.50 (t, J=7.5, 2H), 2.44 (br s, 3H), 2.31 (m, 1H), 1.93 (m, 3H), 1.85 (m, 2H), 1.60 (m, 4H), 1.46 (br s, 2H).

Example 20

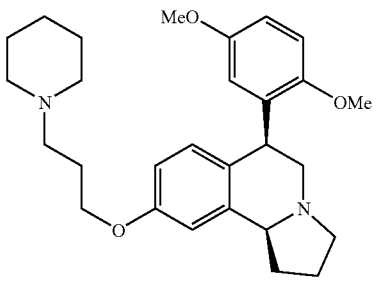

Cis-6-(2,5-Dimethoxy-phenyl)-9-(3-piperidin-1-yl-propoxy)-1,2,3,5,6,10b-hexahydro-pyrrolo[2,1-a]isoquinoline Step 1. 1-(2,5-Dimethoxy-phenyl)-2-{2-[3-(3-piperidin-1-yl-propoxy)-phenyl]-pyrrolidin-1-yl}-ethanone. Prepared as described in Example 8, Step 1, on a 3.47 mmol scale, to give 1.27 g (78%) of the desired product as a pale yellow oil after chromatography ($NH_3$ in $MeOH/CH_2Cl_2$). MS: exact mass calcd for $C_{28}H_{38}N_2O_4$, 466.3; m/z found, 467.5 $[M+H]^+$. $^1H$ NMR (MeOH-$d_4$): 7.14 (m, 1H), 7.09 (d, J=3.2, 1H), 6.97 (dd, J=3.2, 9.0, 1H), 6.93 (d, J=1.6, 1H), 6.88 (m, 1H), 6.75 (m, 1H), 4.03 (d, J=18.4, 1H), 3.91 (m, 2H), 3.69 (s, 3H), 3.63 (s, 3H), 3.43 (m, 3H), 2.40 (m, 6H), 2.30 (m, 1H), 2.15 (m, 1H), 1.90 (m, 3H), 1.80 (m, 1H), 1.75 (m, 1H), 1.55 (m, 4H), 1.41 (m, 2H).

Step 2. 6-(2,5-Dimethoxy-phenyl)-9-(3-piperidin-1-yl-propoxy)-2,3-dihydro-1H-pyrrolo[2,1-a]isoquinolinylium salt. Prepared as described in Example 17, Step 2, on a 2.38 mmol scale, to give 1.01 g (88%) of crude product. MS: exact mass calcd for $C_{28}H_{35}N_2O_3^+$, 447.3; m/z found, 447.5 $[M]^+$.

Step 3. Prepared as described in Example 17, Step 3, on a 2.10 mmol scale, to give 354.4 mg (38%) of the desired product after recrystallization from methanol. MS: exact mass calcd for $C_{28}H_{38}N_2O_3$, 450.3; m/z found, 451.5 $[M+H]^+$. $^1H$ NMR (MeOH-$d_4$): 6.87 (d, J=8.9, 1H), 6.78 (d, J=8.4, 1H), 6.67 (m, 3H), 6.55 (d, J=3.1, 1H), 4.55 (d, 2.9, 1H), 3.99 (m, 2H), 3.84 (s, 3H), 3.57 (s, 3H), 3.15 (m, 1H), 3.03 (m, 1H), 2.91 (m, 1H), 2.70 (m, 1H), 2.3 (m, 8H), 1.51 (m, 4H), 1.40 (m, 2H).

Example 21

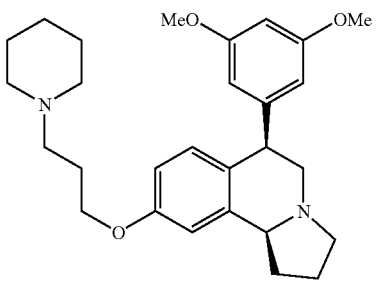

Cis-6-(3,5-Dimethoxy-phenyl)-9-(3-piperidin-1-yl-propoxy)-1,2,3,5,6,10b-hexahydro-pyrrolo[2,1-a]isoquinoline Step 1. 2-Bromo-1-(3,5-dimethoxy-phenyl)-ethanone. Prepared as described in Example 18, Step 1, on a 11.1 mmol scale, to give 2.70 g (85%) of the ketone as a white solid. MS: exact mass calcd for $C_{10}H_{11}BrO_3$, 258.0; m/z found, 281.2 $[M+Na]^+$. $^1H$ NMR (acetone-$d_6$): 7.15 (d, J=2.3, 2H), 6.75 (d, J=2.2, 1H), 4.75 (s, 2H), 3.85 (s, 6H).

Step 2. 1-(3,5-Dimethoxy-phenyl)-2-{2-[3-(3-piperidin-1-yl-propoxy)-phenyl]pyrrolidin-1-yl}-ethanone. Prepared as described in Example 8, Step 1, on a 3.80 mmol scale, to give 1.10 g (90%) of the desired product as a pale yellow oil after chromatography ($NH_3$ in $MeOH/CH_2Cl_2$). MS: exact mass calcd for $C_{28}H_{38}N_2O_4$, 466.3; m/z found, 467.4 $[M+H]^+$. $^1H$ NMR (MeOH-$d_4$): 7.16 (t, J=7.8, 1H), 6.95 (m, 3H), 6.90 (d, J=7.5, 1H), 6.75 (m, 1H), 6.33 (m, 1H), 3.93 (m, 3H), 3.76 (s, 6H), 3.43 (m, 2H), 3.37 (m, 1H), 2.48 (m, 6H), 2.33 (m, 1H), 2.15 (m, 1H), 1.95 (m, 3H), 1.80 (m, 1H), 1.69 (m, 1H), 1.60 (m, 4H), 1.46 (br s, 2H).

Step 3. 6-(3,5-Dimethoxy-phenyl)-9-(3-piperidin-1-yl-propoxy)-2,3-dihydro-1H-pyrrolo[2,1-a]isoquinolinylium salt. Prepared as described in Example 17, Step 2, on a 2.03 mmol scale to give 700 mg (71%) of crude product. The crude product was taken on to the next step without characterization.

Step 4. Prepared as described in Example 17, Step 3, on a 1.45 mmol scale, to give 52.2 mg (5%) of the desired product as the TFA salt. MS: exact mass calcd for $C_{28}H_{38}N_2O_3$, 450.3; m/z found, 451.5 $[M+H]^+$. $^1H$ NMR (MeOH-$d_4$): 6.89 (d, J=2.2, 1H), 6.83 (m, 2H), 6.49 (m, 1H), 6.42 (s, 2H), 4.87 (m, 1H), 4.37 (m, 1H), 4.11 (t, J=5.7, 2H), 3.87 (m, 1H), 3.77 (s, 6H), 3.61 (m, 3H), 3.44 (m, 2H), 3.31 (m, 2H), 2.94 (m, 2H), 2.81 (m, 1H), 2.27 (m, 5H), 1.97 (m, 2H), 1.85 (m, 3H), 1.60 (m, 1H).

Example 22

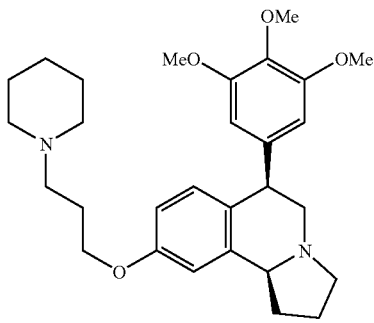

Cis-6-(3,4,5-Trimethoxy-phenyl)-9-(3-piperidin-1-yl-propoxy)-1,2,3,5,6,10b-hexahydro-pyrrolo[2,1-a]isoquinoline Step 1. 2-Bromo-1-(3,4,5-trimethoxy-phenyl)-ethanone. Prepared as described in Example 18, Step 1, on a 9.51 mmol scale, to give 2.23 g (80%) of the ketone as a white solid. MS (electron impact): exact mass calcd for $C_{11}H_{13}BrO_4$, 288.0; m/z found, 288 $[M]^+$. $^1H$ NMR (acetone-$d_6$): 7.35 (s, 2H), 4.76 (s, 2H), 3.90 (s, 6H), 3.81 (s, 3H).

Step 2. 2-{2-[3-(3-Piperidin-1-yl-propoxy)-phenyl]-pyrrolidin-1-yl}-1-(3,4,5-trimethoxy-phenyl)-ethanone. Prepared as described in Example 8, Step 1, on a 3.47 mmol scale, to give 1.47 g (85%) of the desired product as a pale yellow oil after chromatography ($NH_3$ in $MeOH/CH_2Cl_2$). MS: exact mass calcd for $C_{29}H_{40}N_2O_5$, 496.3; m/z found, 497.4

[M+H]+. 1H NMR (MeOH-d4): 7.10 (m, 3H), 6.86 (m, 2H), 6.68 (m, 1H), 3.85 (m, 3H), 3.72 (s, 6H), 3.71 (s, 3H), 3.35 (m, 2H), 3.22 (m, 1H), 2.36 (m, 6H), 2.07 (m, 1H), 1.86 (m, 3H), 1.72 (m, 1H), 1.65 (m, 1H), 1.50 (m, 4H), 1.37 (br s, 2H).

Step 3. 9-(3-Piperidin-1-yl-propoxy)-6-(3,4,5-trimethoxyphenyl)-2,3-dihydro-1H-pyrrolo[2,1-a]isoquinolinylium salt. Prepared as described in Example 17, Step 2, on a 2.76 mmol scale to give 1.17 g (83%) of crude product. MS: exact mass calcd for $C_{29}H_{37}N_2O_4^+$, 477.3; m/z found, 477.5 [M]+.

Step 4. Prepared as described in Example 17, Step 3, on a 2.28 mmol scale, to give 175.0 mg (10%) of the desired product as the TFA salt. MS: exact mass calcd for $C_{29}H_{40}N_2O_4$, 480.3; m/z found, 481.6 [M+H]+. 1H NMR (MeOH-d4): 6.78 (d, J=2.3, 1H), 6.73 (m, 2H), 6.46 (s, 2H), 4.24 (m, 1H), 4.00 (t, J=5.7, 2H), 3.77 (m, 1H), 3.70 (s, 6H), 3.67 (s, 3H), 3.49 (m, 3H), 3.35 (m, 2H), 3.20 (m, 2H), 2.85 (m, 2H), 2.72 (m, 1H), 2.20 (m, 5H), 1.86 (d, J=14.6, 2H), 1.72 (m, 3H), 1.42 (m, 1H).

Example 23

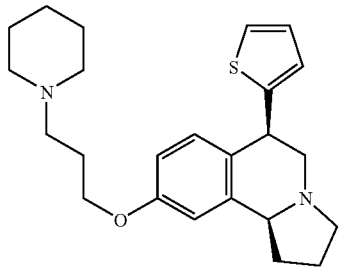

Cis-9-(3-Piperidin-1-yl-propoxy)-6-thiophen-2-yl-1,2,3,5,6,10b-hexahydro-pyrrolo[2,1-a]isoquinoline Step 1. 2-{2-[3-(3-Piperidin-1-yl-propoxy)-phenyl]-pyrrolidin-1-yl}-1-thiophen-2-yl-ethanone. Prepared as described in Example 8, Step 1, on a 3.47 mmol scale, to give 1.24 g (85%) of the desired product as an oil after chromatography (NH3 in MeOH/CH2Cl2). MS: exact mass calcd for $C_{24}H_{32}N_2O_2S$, 412.2; m/z found, 413.6 [M+H]+. 1H NMR (MeOH-d4): 7.75 (m, 2H) 7.18 (t, J=8.0, 1H), 7.09 (dd, J=4.0, 5.0, 1H), 7.0 (m, 1H), 6.94 (d, J=7.6, 1H), 6.77 (m, 1H), 4.88 (s, 1H), 3.96 (m, 2H), 3.88 (d, J=16.4, 1H), 3.47 (d, J=8.8, 1H), 3.42 (d, J=16.0, 1H), 3.37 (m, 1H), 3.34 (s, 2H), 2.43 (m, 7H), 2.18 (m, 1H), 1.94 (m, 3H), 1.86 (m, 1H), 1.76 (m, 1H), 1.59 (m, 4H), 1.45 (br m, 2H).

Step 2. 9-(3-Piperidin-1-yl-propoxy)-6-thiophen-2-yl-2,3-dihydro-1H-pyrrolo[2,1-a]isoquinolinylium salt. Prepared as described in Example 17, Step 2, on a 2.90 mmol scale, to give 1.14 g (92%) of crude product. MS: exact mass calcd for $C_{24}H_{29}N_2OS^+$, 393.2; m/z found, 393.5 [M]+.

Step 3. Prepared as described in Example 17, Step 3, on a 2.90 mmol scale, to give 725.8 mg (41%) of the desired product as the TFA salt. MS: exact mass calcd for $C_{24}H_{32}N_2OS$, 396.2; m/z found, 397.5 [M+H]+. 1H NMR (MeOH-d4): 7.43 (m, 1H), 7.12 (s, 1H), 7.08 (m, 1H), 6.90 (m, 3H), 4.84 (m, 1H), 4.83 (m, 1H), 4.12 (t, J=5.7, 2H), 3.92 (br m, 1H), 3.71 (m, 1H), 3.60 (d, J=11.5, 2H), 3.46 (m, 2H), 3.31 (m, 2H), 2.97 (m, 2H), 2.85 (m, 1H), 2.25 (m, 5H), 1.95 (d, J=14.8, 2H), 1.84 (m, 3H), 1.53 (m, 1H).

Example 24-(A-B)

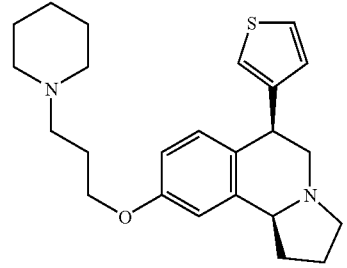

24A

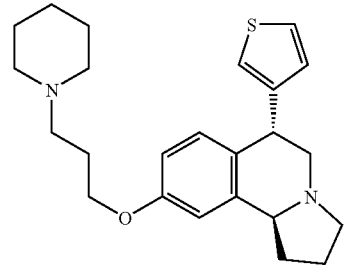

24B

24A: Cis-9-(3-Piperidin-1-yl-propoxy)-6-thiophen-3-yl-1,2,3,5,6,10b-hexahydro-pyrrolo[2,1-a]isoquinoline
24B: Trans-9-(3-Piperidin-1-yl-propoxy)-6-thiophen-3-yl-1,2,3,5,6,10b-hexahydro-pyrrolo[2,1-a]isoquinoline Step 1. 2-Bromo-1-thiophen-3-yl-ethanone. Prepared as described in Example 18, Step 1, on a 39.6 mmol scale, to give 6.89 g (85%) of the ketone as a white solid. 1H NMR (acetone-d6): 8.46 (m, 1H), 7.56 (m, 2H), 4.63 (s, 2H).

Step 2. 2-{2-[3-(3-Piperidin-1-yl-propoxy)-phenyl]-pyrrolidin-1-yl}-1-thiophen-3-yl-ethanone. Prepared as described in Example 8, Step 1, on a 3.47 mmol scale, to give 1.19 g (82%) of the desired product as an oil after chromatography (NH3 in MeOH/CH2Cl2). MS: exact mass calcd for $C_{24}H_{32}N_2O_2S$, 412.2; m/z found, 413.4 [M+H]+. 1H NMR (MeOH-d4): 8.18 (m, 1H), 7.40 (m, 2H), 7.19 (m, 1H), 7.01 (s, 1H), 6.95 (d, J=7.6, 1H), 6.80 (m, 1H), 4.87 (s, 1H), 4.02 (m, 2H), 3.44 (m, 3H), 3.00 (m, 8H), 2.34 (m, 1H), 2.13 (m, 4H), 1.91 (m, 1H), 1.83 (m, 1H), 1.76 (m, 6H), 1.57 (m, 3H).

Step 3. 9-(3-Piperidin-1-yl-propoxy)-6-thiophen-3-yl-2,3-dihydro-1H-pyrrolo[2,1-a]isoquinolinylium salt. Prepared as described in Example 17, Step 2, on a 2.46 mmol scale, to give 779.2 mg (74%) of crude product. The crude product was taken on to the next step without characterization.

Step 4. Performed as described in Example 17, Step 3, on a 1.82 mmol scale, to give the diastereomers in a combined yield of 56%.

24A: Cis-9-(3-Piperidin-1-yl-propoxy)-6-thiophen-3-yl-1,2,3,5,6,10b-hexahydro-pyrrolo[2,1-a]isoquinoline. 587.7 mg (51%) as the TFA salt. MS: exact mass calcd for $C_{24}H_{32}N_2OS$, 396.2; m/z found, 397.5 [M+H]+. 1H NMR (MeOH-d4): 7.44 (m, 1H), 7.36 (s, 1H), 6.92 (d, J=4.4, 1H), 6.86 (d, J=2.2, 1H), 6.76 (m, 2H), 4.84 (m, 1H), 4.58 (m, 1H), 4.06 (t, J=5.8, 2H), 3.85 (m, 1H), 3.55 (m, 3H), 3.35 (m, 2H), 3.26 (m, 2H), 2.93 (m, 2H), 2.78 (m, 1H), 2.23 (m, 5H), 1.91 (m, 2H), 1.82 (m, 3H), 1.51 (m, 1H).

24B: Trans-9-(3-Piperidin-1-yl-propoxy)-6-thiophen-3-yl-1,2,3,5,6,10b-hexahydro-pyrrolo[2,1-a]isoquinoline. 51.2 mg (4%) as the TFA salt. MS: exact mass calcd for $C_{24}H_{32}N_2OS$, 396.2; m/z found, 397.5 [M+H]+. 1H NMR (MeOH-d4): 7.38 (br s, 1H), 6.96 (br s, 1H), 6.94 (br d, J=1.5, 1H), 6.83 (m, 3H), 4.78 (m, 1H), 4.48 (br s, 1H), 4.04 (t, J=5.7, 2H), 3.69 (br m, 2H), 3.51 (d, J=12.0, 3H), 3.33 (br s, 1H), 3.21 (m, 2H), 2.88 (m, 2H), 2.67 (br s, 1H), 2.15 (m, 2H), 2.07 (br m, 3H), 1.87 (d, J=14.5, 2H), 1.73 (m, 3H), 1.46 (m, 1H).

Example 25

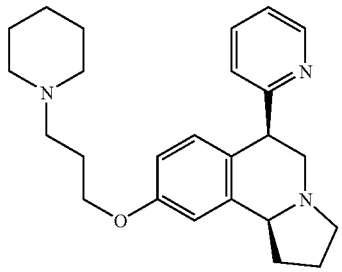

Cis-9-(3-Piperidin-1-yl-propoxy)-6-pyridin-2-yl-1,2,3,5,6,10b-hexahydro-pyrrolo[2,1-a]isoquinoline
Step 1. 2-{2-[3-(3-Piperidin-1-yl-propoxy)-phenyl]-pyrrolidin-1-yl}-1-pyridin-2-yl-ethanone. Prepared as described in Example 8, Step 1, on a 3.47 mmol scale, to give 749.2 mg (52%) of crude product after chromatography (NH$_3$ in MeOH/CH$_2$Cl$_2$). MS: exact mass calcd for $C_{25}H_{33}N_3O_2$, 407.3; m/z found, 408.5 [M+H]$^+$.
Step 2. 9-(3-Piperidin-1-yl-propoxy)-6-pyridin-2-yl-2,3-dihydro-1H-pyrrolo[2,1-a]isoquinolinylium salt. Prepared as described in Example 17, Step 2, on a 1.36 mmol scale to give 243.8 mg (42%) of crude product. MS: exact mass calcd for $C_{25}H_{30}N_3O^+$, 388.2; m/z found, 388.5 [M]$^+$.
Step 3. Prepared as described in Example 17, Step 3, on a 0.575 mmol scale, to give 100.0 mg (23%) of the desired product as the TFA salt. MS: exact mass calcd for $C_{25}H_{33}N_3O$, 391.3; m/z found, 392.5 [M+H]$^+$. $^1$H NMR (MeOH-d$_4$): 8.62 (d, J=4.4, 1H), 8.04 (m, 1H), 7.63 (d, J=7.8, 1H), 7.53 (m, 1H), 6.94 (d, J=2.4, 1H), 6.85 (m, 1H), 6.88 (br s, 1H), 4.88 (m, 1H), 4.72 (m, 1H), 4.13 (t, J=5.8, 2H), 3.88 (br s, 1H), 3.76 (m, 2H), 3.61 (d, J=12.1, 2H), 3.53 (br s, 1H), 2.98 (m, 2H), 2.84 (m, 1H), 2.35 (m, 3H), 2.26 (m, 2H), 1.97 (m, 2H), 1.82 (m, 3H), 1.57 (m, 1H).

Example 26

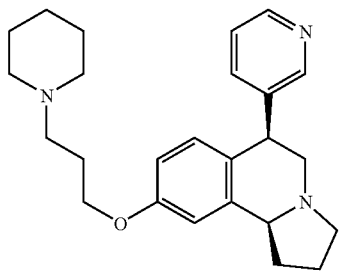

Cis-9-(3-Piperidin-1-yl-propoxy)-6-pyridin-3-yl-1,2,3,5,6,10b-hexahydro-pyrrolo[2,1-a]isoquinoline
Step 1. 2-{2-[3-(3-Piperidin-1-yl-propoxy)-phenyl]-pyrrolidin-1-yl}-1-pyridin-3-yl-ethanone. Prepared as described in Example 8, Step 1, on a 3.47 mmol scale, to give 1.176 g (82%) of crude product after chromatography (NH$_3$ in MeOH/CH$_2$Cl$_2$). MS: exact mass calcd for $C_{25}H_{33}N_3O_2$, 407.3; m/z found, 408.5 [M+H]$^+$.
Step 2. 9-(3-Piperidin-1-yl-propoxy)-6-pyridin-3-yl-2,3-dihydro-1H-pyrrolo[2,1-a]isoquinolinylium salt. Prepared as described in Example 17, Step 2, on a 2.52 mmol scale, to give 749.9 mg (70%) of crude product. MS: exact mass calcd for $C_{25}H_{30}N_3O^+$, 388.2; m/z found, 388.5 [M]$^+$.
Step 3. Prepared as described in Example 17, Step 3, on a 1.77 mmol scale, to give 208.4 mg (16%) of the desired product as the TFA salt. MS: exact mass calcd for $C_{25}H_{33}N_3O$, 391.3; m/z found, 392.5 [M+H]$^+$. $^1$H NMR (MeOH-d$_4$): 8.91 (m, 2H), 8.51 (d, J=8.1, 1H), 8.08 (m, 1H), 6.98 (d, J=2.4, 1H), 6.89 (m, 1H), 6.73 (d, J=8.5, 1H), 4.95 (m, 1H), 4.85 (m, 1H), 4.14 (t, J=5.7, 2H), 3.94 (br s, 1H), 3.75 (m, 1H), 3.61 (d, J=11.2, 3H), 3.48 (m, 1H), 3.22 (m, 2H), 2.98 (m, 2H), 2.88 (m, 1H), 2.30 (m, 5H), 1.96 (d, J=14.6, 2H), 1.83 (m, 3H), 1.54 (m, 1H).

Example 27-(A-B)

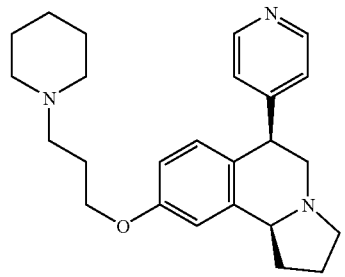

27A

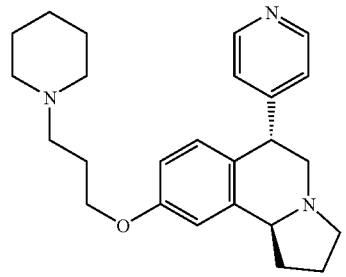

27B

27A: Cis-9-(3-Piperidin-1-yl-propoxy)-6-pyridin-4-yl-1,2,3,5,6,10b-hexahydro-pyrrolo[2,1-a]isoquinoline
27B: Trans-9-(3-Piperidin-1-yl-propoxy)-6-pyridin-4-yl-1,2,3,5,6,10b-hexahydro-pyrrolo[2,1-a]isoquinoline
Step 1. 2-Bromo-1-pyridin-4-yl-ethanone. To a 0° C. solution of 4-acetylpyridine (4.90 g, 41.3 mmol) and 48% HBr (7.0 mL) in acetic acid (46.0 mL) was added, dropwise over 15 min, a solution of Br$_2$ (2.3 mL, 45 mmol) in acetic acid (8.0 mL). After the addition was complete, the mixture was allowed to warm to rt and then was heated at 70° C. for 1 h. The mixture was cooled to 0° C. and treated with diethyl ether. The resultant white solid was isolated by vacuum filtration to give 9.90 g (87%) of the ketone as the HBr salt. MS: exact mass calcd for $C_7H_6BrNO$, 199.0; m/z found, 200.2 [M+H]$^+$.
Step 2. 2-{2-[3-(3-Piperidin-1-yl-propoxy)-phenyl]-pyrrolidin-1-yl}-1-pyridin-4-yl-ethanone. Prepared as described in Example 8, Step 1, on a 6.93 mmol scale, to give crude product that was taken directly to the next step.
Step 3. 9-(3-Piperidin-1-yl-propoxy)-6-pyridin-4-yl-2,3-dihydro-1H-pyrrolo[2,1-a]isoquinolinylium salt. Prepared as described in Example 17, Step 2, on a 6.93 mmol scale to give crude product that was taken directly to the next step.

Step 4. Prepared as described in Example 17, Step 3, on a 6.93 mmol scale, to give the diastereomers in a combined yield of 2.6%.

27A: Cis-9-(3-Piperidin-1-yl-propoxy)-6-pyridin-4-yl-1,2,3,5,6,10b-hexahydro-pyrrolo[2,1-a]isoquinoline. 3.1 mg (0.6%) as the TFA salt. MS: exact mass calcd for $C_{25}H_{33}N_3O$, 391.3; m/z found, 392.4 [M+H]$^+$. $^1$H NMR (MeOH-d$_4$): 8.73 (br s, 2H), 7.66 (br s, 2H), 6.93 (d, J=2.5, 1H), 6.85 (dd, J=2.5, 8.7, 1H), 6.68 (d, J=8.7, 1H), 4.86 (m, 1H; obscured by solvent signal), 4.61 (m, 1H), 4.10 (5.7, 2H), 3.88 (m, 1H), 3.68 (m, 1H), 3.58 (d, J=12.0, 2H), 3.41 (m, 1H), 2.95 (m, 2H), 2.83 (m, 1H), 2.26 (m, 3H), 1.96 (d, J=14.7, 2H), 1.78 (m, 3H), 1.53 (m, 1H).

27B: Trans-9-(3-Piperidin-1-yl-propoxy)-6-pyridin-4-yl-1,2,3,5,6,10b-hexahydro-pyrrolo[2,1-a]isoquinoline. 9.1 mg (2%) as the TFA salt. MS: exact mass calcd for $C_{25}H_{33}N_3O$, 391.3; m/z found, 392.5 [M+H]$^+$. $^1$H NMR (MeOH-d$_4$): 9.03 (br s, 2H), 7.85 (br s, 2H), 6.99 (m, 3H), 4.91 (m, 1H; partially obscured by solvent signal), 4.15 (t, J=5.7, 2H), 3.88 (br s, 2H), 3.70 (m, 1H), 3.60 (d, J=12.2, 3H), 3.48 (br s, 1H), 3.32 (m, 2H; partially obscured by solvent signal), 2.97 (m, 2H), 2.82 (br m, 1H), 2.20 (m, 5H), 1.97 (d, J=14.6, 2H), 1.82 (m, 3H), 1.54 (m, 1H).

Example 28

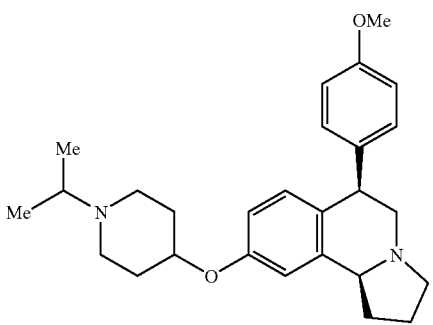

Cis-7-(1-Isopropyl-piperidin-4-yloxy)-4-(4-methoxy-phenyl)-2-methyl-1,2,3,4-tetrahydro-isoquinoline Step 1. 4-(3-Methoxycarbonyl-phenoxy)-piperidine-1-carboxylic acid tert-butyl ester. A solution of 4-hydroxy-piperidine-1-carboxylic acid tert-butyl ester (10.0 g, 49.8 mmol), methyl 3-hydroxybenzoate (9.94 g, 65.3 mmol), and polymer-bound triphenylphosphine (21.5 g, 64.6 mmol) in CH$_2$Cl$_2$ (100 mL) was cooled to 0° C. and treated with di-tert-butyl azodicarboxylate (15.0 g, 65.2 mmol). The mixture was kept at 0° C. for 1.5 h with occasional swirling. The mixture was then allowed to warm to rt and the flask clamped onto a shaker table and the mixture swirled for 4 d. The resin was filtered off and the filtrate was washed with 1 N NaOH and brine. The organic layer was dried (MgSO$_4$), and concentrated to give the crude product as a brown solid. Chromatographic purification (EtOAc/hexanes) gave the desired product as a colorless oil (16.58 g, 99%). $^1$H NMR (acetone-d$_6$): 7.57 (m, 2H), 7.40 (m, 1H), 7.23 (m, 1H), 4.65 (m, 1H), 3.86 (s, 3H), 3.73 (m, 2H), 3.29 (m, 2H), 1.95 (m, 2H), 1.65 (m, 2H), 1.44 (s, 9H).

Step 2. 3-(Piperidin-4-yloxy)-benzoic acid methyl ester. A mixture of 4-(3-methoxycarbonyl-phenoxy)-piperidine-1-carboxylic acid tert-butyl ester (16.5 g, 49.0 mmol) and TFA (50 mL) was stirred under a stream of nitrogen for 1 h. Evolution of gas was evident. The mixture was concentrated to provide the desired product as the TFA salt, (21.7 g, >100%). MS: exact mass calcd for $C_{13}H_{17}NO_3$, 235.1; m/z found, 236.4 [M+H]$^+$. $^1$H NMR (MeOH-d$_4$): 7.60 (m, 2H), 7.39 (m, 1H), 7.23 (m, 1H), 5.08 (s, 4H), 4.76 (m, 1H), 3.88 (s, 3H), 3.39 (m, 2H), 3.22 (m, 2H), 2.16 (m, 2H), 2.02 (m, 2H).

Step 3. 3-(1-Isopropyl-piperidin-4-yloxy)-benzoic acid methyl ester. A mixture of 3-(piperidin-4-yloxy)-benzoic acid methyl ester (TFA salt, 21.7 g, 46.8 mmol), Et$_3$N (39.0 mL, 0.281 mol), and 2-iodopropane (7.1 mL, 70.2 mmol) in THF (95 mL) was heated at 55° C. for 2 d, treated with additional 2-iodopropane (4 mL, 40.1 mmol), and heated for 1 d further. The reaction mixture was diluted with Et$_2$O, washed with 1 N NaOH and brine, dried (Na$_2$CO$_3$), and concentrated to give a yellow oil. Chromatographic purification (EtOAc/hexanes) gave the desired product as a pale-yellow oil (8.17 g, 63%). MS: exact mass calcd for $C_{16}H_{23}NO_3$, 277.2; m/z found, 278.4 [M+H]$^+$. $^1$H NMR (acetone-d$_6$): 7.55 (m, 1H), 7.51 (m, 1H), 7.38 (m, 1H), 7.18 (m, 1H), 4.40 (m, 1H), 3.87 (s, 3H), 2.74 (m, 3H), 2.38 (m, 2H), 1.99 (m, 2H), 1.68 (m, 2H), 1.00 (d, J=6.6, 6H).

Step 4. 4-[3-(4,5-Dihydro-3H-pyrrol-2-yl)-phenoxy]-1-isopropyl-piperidine. Prepared as described in Example 1, Step 4, on a 29.2 mmol scale, to give 5.92 g (71%) of the desired product as a colorless oil after column chromatography (NH$_3$ in MeOH/CH$_2$Cl$_2$). MS: exact mass calcd for $C_{18}H_{26}N_2O$, 286.2; m/z found, 287.5 [M+H]$^+$. $^1$H NMR (MeOH-d$_4$): 7.41 (s, 1H), 7.31 (m, 2H), 7.01 (m, 1H), 4.40 (m, 1H), 3.96 (m, 2H), 2.95 (m, 2H), 2.78 (m, 2H), 2.71 (heptet, J=6.6, 1H), 2.43 (m, 2H), 2.01 (m, 4H), 1.76 (m, 2H), 1.07 (d, J=6.6, 6H).

Step 5. 1-Isopropyl-4-(3-pyrrolidin-2-yl-phenoxy)-piperidine. Prepared as described in Example 1, Step 5, on a 20.4 mmol scale, to give 5.79 g (99%) of the desired product as a colorless oil after column chromatography (NH$_3$ in MeOH/CH$_2$Cl$_2$). A small sample was purified by reverse-phase HPLC to give a clear film (TFA salt). MS: exact mass calcd for $C_{18}H_{28}N_2O$, 288.2; m/z found, 289.5 [M+H]$^+$. $^1$H NMR (MeOH-d$_4$): 7.41 (m, 1H), 7.12 (m, 3H), 4.63 (m, 1H), 3.6-3.3 (m, 8H), 2.45 (m, 2H), 2.24 (m, 5H), 1.95 (m, 1H), 1.40 (m, 6H).

Step 6. 2-{2-[3-(1-Isopropyl-piperidin-4-yloxy)-phenyl]-pyrrolidin-1-yl}-1-(4-methoxy-phenyl)-ethanone. Prepared as described in Example 8, Step 1, on a 3.47 mmol scale, to give 1.28 g (84%) of the desired product as a pale yellow foam after chromatography (NH$_3$ in MeOH/CH$_2$Cl$_2$). MS: exact mass calcd for $C_{27}H_{36}N_2O_3$, 436.3; m/z found, 437.5 [M+H]$^+$. $^1$H NMR (MeOH-d$_4$): 7.82 (dd, J=1.9, 7.0, 2H), 7.22 (m, 1H), 7.06 (d, J=1.3, 1H), 6.97 (d, J=7.5, 1H), 6.91 (dd, J=1.9, 7.0, 2H), 6.86 (m, 1H), 4.86 (s, 1H), 4.61 (br s, 1H), 3.96 (d, J=16.7, 1H), 3.83 (s, 3H), 3.55 (m, 2H), 3.42 (m, 2H), 3.27 (m, 2H), 3.16 (m, 2H), 2.36 (m, 1H), 2.19 (m, 3H), 2.0 (m, 3H), 1.75 (m, 1H), 1.74 (m, 1H), 1.34 (d, J=6.7, 6H).

Step 7. 9-(1-Isopropyl-piperidin-4-yloxy)-6-(4-methoxy-phenyl)-2,3-dihydro-1H-pyrrolo[2,1-a]isoquinolinylium salt. Prepared as described in Example 17, Step 2, on a 2.92 mmol scale, to give 860 mg (65%) of crude product. MS: exact mass calcd for $C_{27}H_{33}N_2O_2^+$, 417.3; m/z found, 417.5 [M]$^+$.

Step 8. Prepared as described in Example 17, Step 3, on a 1.89 mmol scale to give 28.3 mg (3%) of the desired product as the TFA salt. MS: exact mass calcd for $C_{27}H_{36}N_2O_2$, 420.3; m/z found, 421.5 [M+H]$^+$. $^1$H NMR (MeOH-d$_4$): 7.20 (d, J=8.2, 2H), 7.03 (m, 1H), 6.97 (d, J=8.1, 2H), 6.87 (m, 1H), 6.74 (m, 1H), 4.92 (m, 1H), 4.41 (m, 1H), 3.89 (m, 1H), 3.86 (s, 3H), 3.58 (m, 3H), 3.44 (m, 3H), 3.32 (m, 2H), 2.89 (m, 1H), 2.35 (m, 6H), 1.99 (m, 1H), 1.42 (m, 6H).

Example 29

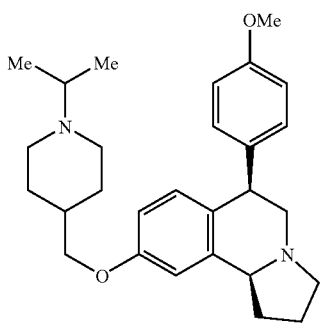

Cis-9-(1-Isopropyl-piperidin-4-ylmethoxy)-6-(4-methoxy-phenyl)-1,2,3,5,6,10b-hexahydro-pyrrolo[2,1-a]isoquinoline. Step 1. 4-(3-Methoxycarbonyl-phenoxymethyl)-piperidine-1-carboxylic acid tert-butyl ester Prepared as described in Example 28, Step 1, on a 45.0 mmol scale, yielding 13.66 g (87%) of the desired product as a colorless oil. MS: exact mass calcd for $C_{19}H_{27}NO_5$, 349.2; m/z found, 372.4 [M+Na]$^+$. $^1$H NMR (acetone-d$_6$): 7.57 (d, J=7.6, 1H), 7.51 (m, 1H), 7.38 (m, 1H), 7.19 (m, 1H), 4.10 (m, 2H), 3.90 (m, 2H), 3.86 (s, 3H), 2.79 (br s, 2H), 1.97 (m, 1H), 1.82 (m, 2H), 1.43 (s, 9H), 1.23 (m, 2H).

Step 2. 3-(Piperidin-4-ylmethoxy)-benzoic acid methyl ester. Prepared as described in Example 28, Step 2, on a 39.0 mmol scale. The crude product was diluted with in 1 N NaOH and extracted with diethyl ether. The organic layer was washed with brine, dried over $Na_2CO_3$, and concentrated to give the desired product as an oil that crystallized on standing (7.14 g, 73%). MS: exact mass calcd for $C_{14}H_{19}NO_3$, 249.1; m/z found, 250.4 [M+H]$^+$. $^1$H NMR (MeOH-d$_4$): 7.66 (d, J=6.8, 1H), 7.60 (s, 1H), 7.45 (m, 1H), 7.22 (d, J=7.3, 1H), 4.98 (s, 1H), 3.98 (s, 3H), 3.92 (d, J=4.6, 2H), 3.18 (d, J=11.4, 2H), 2.72 (t, J=12.0, 2H), 2.02 (br s, 1H), 1.92 (d, J=12.4, 2H), 1.44 (m, 2H).

Step 3. 3-(1-Isopropyl-piperidin-4-ylmethoxy)-benzoic acid methyl ester. A mixture of 3-(piperidin-4-ylmethoxy)-benzoic acid methyl ester (6.82 g, 27.4 mmol), acetone (40 mL), acetic acid (1.6 mL, 27.4 mmol), and NaB(OAc)$_3$H (18.4 g, 86.8 mmol) in THF (110 mL) was stirred for 4.5 h. The mixture was diluted with $CH_2Cl_2$, washed with 1 N NaOH and brine, dried ($Na_2CO_3$), and concentrated to give the crude product. Chromatographic purification (EtOAc/hexanes) yielded the desired product as a pale yellow oil (6.43 g, 81%). MS: exact mass calcd for $C_{17}H_{25}NO_3$, 291.2; m/z found, 292.5 [M+H]$^+$. $^1$H NMR (MeOH-d$_4$): 7.55 (dd, J=1.0, 7.7, 1H), 7.49 (m, 1H), 7.33 (m, 1H), 7.12 (m, 1H), 3.87 (s, 3H), 3.82 (d, J=6.2, 2H), 2.91 (d, J=11.6, 2H), 2.69 (heptet, J=6.6, 1H), 2.18 (m, 2H), 1.83 (d, J=13.2, 2H), 1.77 (m, 1H), 1.40 (m, 2H), 1.05 (d, J=6.6, 6H).

Step 4. 4-[3-(4,5-Dihydro-3H-pyrrol-2-yl)-phenoxymethyl]-1-isopropyl-piperidine. Prepared as described in Example 1, Step 4, on a 21.8 mmol scale, to give 4.92 g (75%) of the desired product as a colorless oil after column chromatography (NH$_3$ in MeOH/CH$_2$Cl$_2$). A small sample was purified by reverse-phase HPLC to give a clear film (TFA salt). MS: exact mass calcd for $C_{19}H_{28}N_2O$, 300.2; m/z found, 301.5 [M+H]$^+$. $^1$H NMR (MeOH-d$_4$): 7.63 (m, 2H), 7.57 (m, 1H), 7.39 (m, 1H), 4.24 (t, J=7.8, 2H), 4.0 (d, J=5.8, 2H), 3.64 (m, 2H), 3.52 (m, 3H), 3.10 (m, 2H), 2.42 (quintet, J=7.9, 2H), 2.17 (m, 3H), 1.76 (m, 2H), 1.37 (m, 6H).

Step 5. 1-Isopropyl-4-(3-pyrrolidin-2-yl-phenoxymethyl)-piperidine. Prepared as described in Example 1, Step 5, on a 20.4 mmol scale, to give 5.79 g (99%) of the desired product as a colorless oil after column chromatography (NH$_3$ in MeOH/CH$_2$Cl$_2$). A small sample was purified by reverse-phase HPLC to give a clear film (TFA salt). MS: exact mass calcd for $C_{19}H_{30}N_2O$, 302.2; m/z found, 303.5 [M+H]$^+$. $^1$H NMR (MeOH-d$_4$, TFA salt): 7.36 (m, 1H), 7.06 (m, 2H), 6.98 (m, 1H), 4.93 (s, 5H), 4.59 (m, 1H), 3.92 (d, J=5.5, 2H), 3.40 (m, 5H), 3.08 (m, 2H), 2.47 (m, 1H), 2.18 (m, 6H), 1.71 (m, 2H), 1.37 (m, 6H).

Step 6. 2-{2-[3-(1-Isopropyl-piperidin-4-ylmethoxy)-phenyl]-pyrrolidin-1-yl}-1-(4-methoxy-phenyl)-ethanone. Prepared as described in Example 8, Step 1, on a 3.31 mmol scale, to give 1.04 g (70%) of the desired product as a pale yellow oil after chromatography (NH$_3$ in MeOH/CH$_2$Cl$_2$). MS: exact mass calcd for $C_{27}H_{36}N_2O_3$, 450.3; m/z found, 451.5 [M+H]$^+$. $^1$H NMR (MeOH-d$_4$): 7.84 (m, 2H), 7.20 (m, 1H), 7.01 (d, J=1.5, 1H), 6.96 (d, J=7.5, 1H), 6.92 (m, 2H), 6.81 (m, 1H), 4.89 (s, 1H), 3.96 (d, J=16.6, 1H), 3.86 (m, 5H), 3.46 (m, 3H), 3.29 (m, 3H), 2.80 (t, J=12.3, 2H), 2.33 (m, 1H), 2.18 (m, 1H), 2.02 (m, 4H), 1.87 (m, 1H), 1.75 (m, 1H), 1.64 (m, 2H), 1.28 (d, J=6.7, 6H).

Step 7. 9-(1-Isopropyl-piperidin-4-ylmethoxy)-6-(4-methoxy-phenyl)-2,3-dihydro-1H-pyrrolo[2,1-a]isoquinolinylium salt. Prepared as described in Example 17, Step 2, on a 2.05 mmol scale, to give 740 mg (77%) of crude product. MS: exact mass calcd for $C_{28}H_{35}N_2O_2^+$, 431.3; m/z found, 431.5 [M]$^+$.

Step 8. Prepared as described in Example 17, Step 3, on a 1.58 mmol scale to give 102.3 mg (12%) of the desired product as the TFA salt. MS: exact mass calcd for $C_{28}H_{38}N_2O_2$, 434.3; m/z found, 435.6 [M+H]$^+$. $^1$H NMR (MeOH-d$_4$): 7.15 (d, J=8.6, 2H), 6.93 (d, J=8.8, 2H), 6.85 (d, J=2.3, 1H), 6.76 (m, 1H), 6.70 (d, J=8.7, 1H), 4.85 (m, 1H), 4.34 (m, 1H), 3.88 (m, 3H), 3.78 (s, 3H), 3.53 (m, 4H), 3.38 (m, 2H), 3.06 (t, J=11.8, 2H), 2.81 (m, 1H), 2.25 (m, 3H), 2.11 (d, J=12.2, 3H), 1.72 (m, 2H), 1.35 (d, J=6.7, 6H).

Example 30

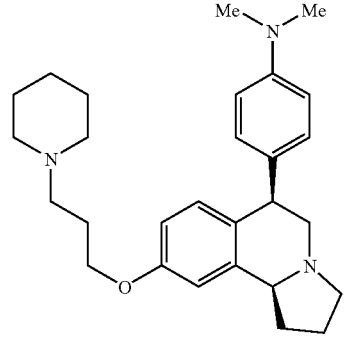

Cis-Dimethyl-{4-[9-(3-piperidin-1-yl-propoxy)-1,2,3,5,6,10b-hexahydro-pyrrolo[2,1-a]isoquinolin-6-yl]-phenyl}-amine Step 1. 1-(4-Dimethylamino-phenyl)-2-{2-[3-(3-piperidin-1-yl-propoxy)-phenyl]-pyrrolidin-1-yl}-ethanone. Prepared as described in Example 8, Step 1, on a 2.70 mmol scale, to give 0.93 g (77%) of the desired product as a viscous oil after chromatography (NH₃ in MeOH/CH₂Cl₂). MS: exact mass calcd for $C_{28}H_{39}F_3N_3O_2$, 449.3; m/z found, 450.5 [M+H]⁺.

Step 2. 6-(4-Dimethylamino-phenyl)-9-(3-piperidin-1-yl-propoxy)-2,3-dihydro-1H-pyrrolo[2,1-a]isoquinolinylium salt. Prepared as described in Example 17, Step 2, on a 2.07 mmol scale, to give 740 mg (83% crude) of the desired product. MS: exact mass calcd for $C_{28}H_{36}N_3O^+$, 430.3; m/z found, 430.5 [M]⁺.

Step 3. Prepared as described in Example 17, Step 3, on a 1.72 mmol scale, to give 87.6 mg (14%) of the desired product as the TFA salt after chromatography (NH₃ in MeOH/CH₂Cl₂) and HPLC. MS: exact mass calcd for $C_{28}H_{39}N_3O$, 433.3; m/z found, 434.5 [M+H]⁺. ¹H NMR (acetone-d₆): 7.19 (d, J=8.6, 2H), 7.03 (d, J=8.7, 2H), 6.95 (m, 1H), 6.80 (m, 1H), 6.72 (d, J=8.7, 1H), 4.94 (m, 1H), 4.49 (m, 1H), 4.15 (t, J=5.9, 2H), 3.98 (br s, 1H), 3.68 (m, 3H), 3.40 (m, 4H), 3.04 (s, 6H), 2.91 (m, 1H), 2.33 (m, 6H), 2.06 (m, 5H), 1.82 (m, 1H), 1.53 (m, 1H).

Example 31

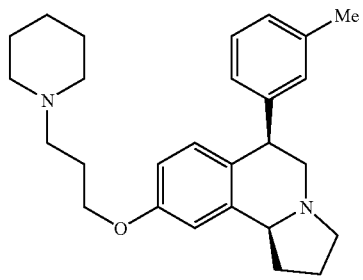

Cis-9-(3-Piperidin-1-yl-propoxy)-6-m-tolyl-1,2,3,5,6,10b-hexahydro-pyrrolo[2,1-a]isoquinoline Step 1. 2-{2-[3-(3-Piperidin-1-yl-propoxy)-phenyl]-pyrrolidin-1-yl}-1-m-tolyl-ethanone. Prepared as described in Example 8, Step 1, on a 2.70 mmol scale, to give 610 mg (54%) of the desired product as an orange oil after chromatography (NH₃ in MeOH/CH₂Cl₂). MS: exact mass calcd for $C_{27}H_{36}N_2O_2$, 420.3; m/z found, 421.5 [M+H]⁺.

Step 2. 9-(3-Piperidin-1-yl-propoxy)-6-m-tolyl-2,3-dihydro-1H-pyrrolo[2,1-a]isoquinolinylium salt. Prepared as described in Example 17, Step 2, on a 1.45 mmol scale, to give 560 mg (96%) of crude product. MS: exact mass calcd for $C_{27}H_{33}N_2O^+$, 401.3; m/z found, 401.5 [M]⁺.

Step 3. Prepared as described in Example 17, Step 3, on a 0.25 mmol scale, to give 3.1 mg (1.3%) of the desired product as the TFA salt after chromatography (NH₃ in MeOH/CH₂Cl₂) and HPLC. MS: exact mass calcd for $C_{27}H_{36}N_2O$, 404.3; m/z found, 405.5 [M+H]⁺. ¹H NMR (acetone-d₆): 7.14 (m, 1H), 7.01 (m, 2H), 6.95 (d, J=7.3, 1H), 6.80 (s, 1H), 6.64 (d, J=8.7, 1H), 6.57 (d, J=8.6, 1H), 4.47 (br s, 1H), 4.32 (m, 1H), 4.00 (m, 2H), 3.52 (br s, 1H), 3.35 (m, 1H), 3.24 (m, 1H), 3.13 (m, 4H), 2.70 (m, 4H), 2.33 (m, 1H), 2.17 (m, 7H), 1.78 (m, 5H), 1.53 (m, 1H).

Example 32

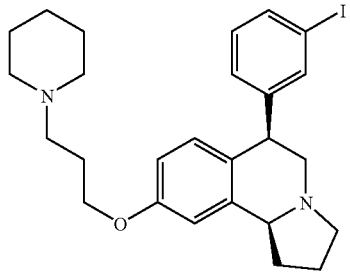

Cis-6-(3-Iodo-phenyl)-9-(3-piperidin-1-yl-propoxy)-1,2,3,5,6,10b-hexahydro-pyrrolo[2,1-a]isoquinoline Step 1. 1-(3-Iodo-phenyl)-2-{2-[3-(3-piperidin-1-yl-propoxy)-phenyl]-pyrrolidin-1-yl}-ethanone. Prepared as described in Example 8, Step 1, on a 3.46 mmol scale, to give 1.0 g (54%) of the desired product as an orange semi-solid after chromatography (NH₃ in MeOH/CH₂Cl₂). MS: exact mass calcd for $C_{26}H_{33}IN_2O_2$, 532.2; m/z found, 533.4 [M+H]⁺. ¹H NMR (CDCl₃): 8.20 (m, 1H), 7.82 (m, 2H), 7.24 (t, J=7.9, 1H), 7.12 (t, J=7.9, 1H), 6.97 (d, J=7.6, 1H), 6.93 (m, 1H), 6.78 (m, 1H), 3.97 (m, 2H), 3.42 (t, J=8.7, 1H), 3.35 (m, 2H), 2.61 (m, 6H), 2.34 (m, 1H), 2.18 (m, 1H), 2.05 (m, 4H), 1.85 (m, 2H), 1.68 (m, 4h), 1.48 (m, 2H).

Step 2. 6-(3-Iodo-phenyl)-9-(3-piperidin-1-yl-propoxy)-2,3-dihydro-1H-pyrrolo[2,1-a]isoquinolinylium salt. Prepared as described in Example 17, Step 2, on a 1.90 mmol scale, to give 800 mg (82%) of crude product. MS: exact mass calcd for $C_{26}H_{30}IN_2O^+$, 513.1; m/z found, 513.4 [M]⁺.

Step 3. Prepared as described in Example 17, Step 3, on a 1.54 mmol scale, to give 165 mg (14%) of the desired product after chromatography and HPLC. MS: exact mass calcd for $C_{26}H_{33}IN_2O$, 516.2; m/z found, 517.4 [M+H]⁺. ¹H NMR (acetone-d₆): 7.76 (d, J=7.8, 1H), 7.69 (s, 1H), 7.38 (m, 1H), 7.26 (m, 1H), 6.97 (m, 1H), 6.81 (m, 1H), 6.67 (d, J=8.7, 1H), 4.91 (m, 1H), 4.59 (m, 1H), 4.14 (m, 2H), 3.71 (br s, 1H), 3.66 (m, 3H), 3.53 (m, 1H), 3.42 (m, 1H), 3.32 (br s, 2H), 2.91 (m, 3H), 2.34 (m, 5H), 1.95 (m, 5H), 1.51 (m, 1H).

Example 33

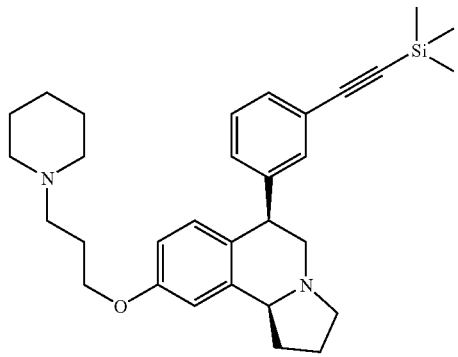

Cis-9-(3-Piperidin-1-yl-propoxy)-6-(3-trimethylsilanylethynyl-phenyl)-1,2,3,5,6,10b-hexahydro-pyrrolo[2,1-a]isoquinoline To a high-pressure reaction vial was added cis-6-(3-iodo-phenyl)-9-(3-piperidin-1-yl-propoxy)-1,2,3,5,6,10b- hexahydro-pyrrolo[2,1-a]isoquinoline (Example 32, 40.0 mg, 0.08 mmol), trimethylsilylacetylene (9.0 mg, 0.093 mmol), Pd(PPh$_3$)$_2$Cl$_2$ (6.0 mg, 0.008 mmol), CuI (2.0 mg, 0.008 mmol), PPh$_3$ (4.0 mg, 0.016 mmol), Et$_2$NH (0.12 mL, 1.2 mmol), and DMF (0.1 mL). The sealed vial was placed in a 120° C. preheated oil bath for 30 min, cooled to rt, concentrated under a stream of nitrogen, and purified by reverse-phase HPLC to give 27.0 mg (47%) of the desired product as a TFA salt. MS: exact mass calcd for C$_{31}$H$_{42}$N$_2$OSi, 486.3; m/z found, 487.6 [M+H]$^+$. $^1$H NMR (acetone-d$_6$): 7.46 (m, 2H), 7.36 (m, 2H), 6.97 (d, J=2.5, 1H), 6.80 (dd, J=2.6, 8.7, 1H), 6.65 (d, J=8.7, 1H), 4.92 (m, 1H), 4.63 (m, 1H), 4.14 (t, J=6.0, 2H), 3.95 (m, 1H), 3.66 (m, 3H), 3.51 (m, 1H), 3.41 (m, 1H), 3.31 (m, 2H), 2.95 (m, 3H), 2.32 (m, 5H), 1.89 (m, 5H), 1.50 (m, 1H), 0.22 (s, 9H).

Example 34

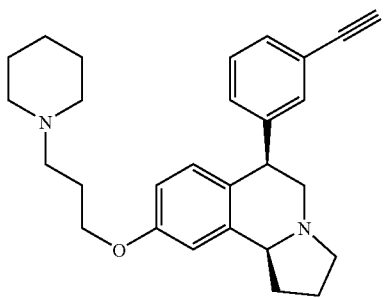

Cis-6-(3-Ethynyl-phenyl)-9-(3-piperidin-1-yl-propoxy)-1,2,3,5,6,10b-hexahydro-pyrrolo[2,1-a]isoquinoline A solution of cis-9-(3-piperidin-1-yl-propoxy)-6-(3-trimethylsilanylethynyl-phenyl)-1,2,3,5,6,10b-hexahydro-pyrrolo[2,1-a]isoquinoline (Example 33, 40.0 mg, 0.082 mmol) and K$_2$CO$_3$ (2.0 mg, 0.008 mmol) in MeOH (4.1 mL, 0.2 M) was stirred for 2 h at rt. The crude reaction mixture was purified directly after filtration by reverse-phase HPLC to give 19.0 mg (36%) of the desired product as a TFA salt. MS: exact mass calcd for C$_{28}$H$_{34}$N$_2$O, 414.3; m/z found, 415.5 [M+H]$^+$. $^1$H NMR (acetone-d$_6$): 7.45 (m, 4H), 6.96 (m, 1H), 6.79 (dd, J=3.2, 10.9, 1H), 6.64 (d, J=10.9, 1H), 4.92 (m, 1H), 4.62 (m, 1H), 4.12 (t, J=7.5, 2H), 3.93 (m, 1H), 3.66 (m, 4H), 3.51 (m, 1H), 3.39 (m, 1H), 3.31 (m, 2H), 2.93 (m, 3H), 2.32 (m, 5H), 1.89 (m, 5H), 1.51 (m, 1H).

Example 35-(A-B)

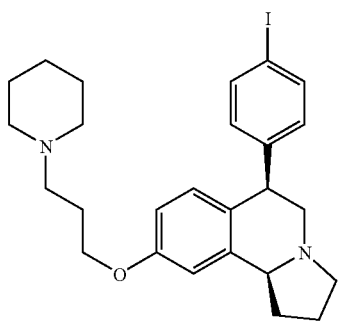

35A

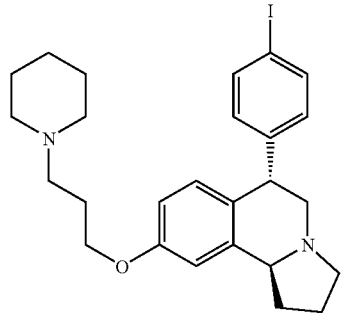

35B

35A: Cis-6-(4-Iodo-phenyl)-9-(3-piperidin-1-yl-propoxy)-1,2,3,5,6,10b-hexahydro-pyrrolo[2,1-a]isoquinoline 35B: Trans-6-(4-Iodo-phenyl)-9-(3-piperidin-1-yl-propoxy)-1,2,3,5,6,10b-hexahydro-pyrrolo[2,1-a]isoquinoline Step 1. 1-(4-Iodo-phenyl)-2-{2-[3-(3-piperidin-1-yl-propoxy)-phenyl]-pyrrolidin-1-yl}-ethanone. Prepared as described in Example 8, Step 1, on a 3.08 mmol scale. The crude product was used without purification in the next step. MS: exact mass calcd for C$_{26}$H$_{33}$IN$_2$O$_2$, 532.2; m/z found, 533.4 [M+H]$^+$.

Step 2. 6-(4-Iodo-phenyl)-9-(3-piperidin-1-yl-propoxy)-2,3-dihydro-1H-pyrrolo[2,1-a]isoquinolinylium salt. Prepared as described in Example 17, Step 2, to give 3.5 g (>100%) of crude product. MS: exact mass calcd for C$_{26}$H$_{30}$IN$_2$O$^+$, 513.1; m/z found, 513.4 [M]$^+$.

Step 3. Performed as described in Example 17, Step 3, to give a combined yield of 20% (over three steps) of two diastereomers.

35A: Cis-6-(4-Iodo-phenyl)-9-(3-piperidin-1-yl-propoxy)-1,2,3,5,6,10b-hexahydro-pyrrolo[2,1-a]isoquinoline. 248.0 mg (13% over 3 steps) as the TFA salt. MS: exact mass calcd for C$_{26}$H$_{33}$IN$_2$O, 516.46; m/z found, 517.4 [M+H]$^+$. $^1$H NMR (acetone-d$_6$): 13.46 (br s, 1H), 11.49 (br s, 1H), 7.89 (d, J=8.3, 2H), 7.12 (d, J=11.6, 2H), 6.96 (m, 1H), 6.80 (dd, J=2.6, 8.7, 1H), 6.65 (d, J=11.2, 1H), 4.91 (m, 1H), 4.59 (dd, J=4.6, 12.1, 1H), 4.14 (t, J=6.0, 2H), 3.96 (m, 1H), 3.69 (m, 3H), 3.41 (m, 4H), 3.00 (m, 2H), 2.91 (m, 1H), 2.33 (m, 5H), 1.91 (m, 4H), 1.80 (m, 1H), 1.53 (m, 1H).

35B: Trans-6-(4-Iodo-phenyl)-9-(3-piperidin-1-yl-propoxy)-1,2,3,5,6,10b-hexahydro-pyrrolo[2,1-a]isoquinoline. 138 mg (7.3% over 3 steps) as the TFA salt. MS: exact mass calcd for C$_{26}$H$_{33}$IN$_2$O, 516.46; m/z found, 517.4 [M+H]$^+$. $^1$H NMR (acetone-d$_6$): 7.74 (d, J=8.2, 2H), 7.09 (d, J=8.3, 2H), 6.98 (m, 1H), 6.80 (m, 2H), 5.15 (br s, 1H), 4.60 (m, 1H), 4.17 (m, 2H), 3.63 (m, 6H), 3.41 (m, 2H), 2.92 (m, 2H), 2.77 (br s, 1H), 2.32 (m, 2H), 2.20 (m, 2H), 1.92 (m, 6H), 1.54 (m, 1H).

Example 36

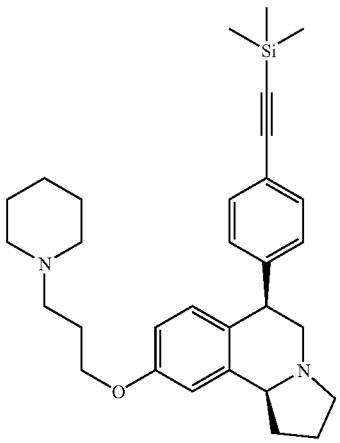

Cis-9-(3-Piperidin-1-yl-propoxy)-6-(4-trimethylsilanylethynyl-phenyl)-1,2,3,5,6,10b-hexahydro-pyrrolo[2,1-a]isoquinoline Performed as described in Example 33, on a 0.27 mmol scale, to yield 131.0 mg (77%) of the desired product as the TFA salt. MS: exact mass calcd for $C_{31}H_{42}N_2OSi$, 486.3; m/z found, 487.6 [M+H]$^+$. $^1$H NMR (acetone-d$_6$): 7.32 (m, 2H), 7.26 (m, 2H), 6.78 (d, J=8.5, 1H), 6.72 (m, 1H), 6.68 (m, 1H), 4.12 (m, 1H), 4.01 (m, 2H), 3.18 (m, 1H), 3.05 (m, 1H), 2.93 (m, 1H), 2.79 (m, 2H), 2.37 (m, 7H), 1.89 (m, 4H), 1.73 (m, 1H), 1.53 (m, 4H), 1.41 (m, 2H), 0.23 (s, 9H).

Example 37

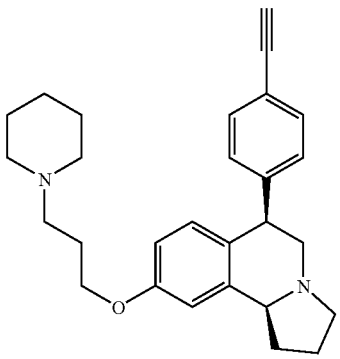

Cis-6-(4-Ethynyl-phenyl)-9-(3-piperidin-1-yl-propoxy)-1,2,3,5,6,10b-hexahydro-pyrrolo[2,1-a]isoquinoline Prepared as described in Example 34, on a 0.18 mmol scale, to yield 43.0 mg (57%) of the desired product as the TFA salt. MS: exact mass calcd for $C_{28}H_{34}N_2O$, 414.3; m/z found, 415.5 [M+H]$^+$. $^1$H NMR (acetone-d$_6$): 7.43 (d, J=8.3, 2H), 7.34 (d, J=8.2, 2H), 6.88 (d, J=9.8, 1H), 6.79 (m, 1H), 6.75 (m, 1H), 4.18 (m, 1H), 4.07 (m, 2H), 3.62 (s, 1H), 3.24 (m, 1H), 3.13 (m, 1H), 3.00 (m, 2H), 2.93 (m, 2H), 2.45 (m, 8H), 1.95 (m, 4H), 1.82 (1H), 1.59 (m, 4H), 1.47 (m, 2H).

Example 38

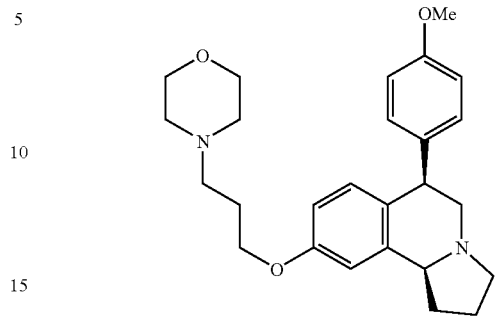

Cis-6-(4-Methoxy-phenyl)-9-(3-morpholin-4-yl-propoxy)-1,2,3,5,6,10b-hexahydro-pyrrolo[2,1-a]isoquinoline Step 1. 3-[3-(tert-Butyl-dimethyl-silanyloxy)-propoxy]-benzoic acid methyl ester. Prepared as described in Example 1, Step 1, on a 0.330 mol scale, using (3-bromopropoxy)-tert-butyldimethylsilane, to give 92.3 g (86%) of the desired product after vacuum distillation (bp 177° C.@1 torr). MS: exact mass calcd for $C_{17}H_{28}O_4Si$, 324.2; m/z found, 325.4 [M+H]$^+$. $^1$H NMR (acetone-d$_6$): 7.56 (m, 1H), 7.52 (m, 1H), 7.40 (m, 1H), 7.18 (m, 1H), 4.14 (t, J=6.0, 2H), 3.86 (s, 3H), 3.84 (t, J=6.0, 2H), 1.98 (m, 2H), 0.88 (s, 9H), 0.05 (s, 6H).

Step 2. 3-[3-(4,5-Dihydro-3H-pyrrol-2-yl)-phenoxy]-propan-1-ol. Prepared as described in Example 1, Step 4, on 0.284 mol scale, to give 33.0 g (52%) of the desired product as a pale-yellow solid after filtering through a plug of silica gel and distilling with a Kugelrohr apparatus. The silyl protecting group was removed during the reaction. MS: exact mass calcd for $C_{13}H_{17}NO_2$, 219.1; m/z found, 220.4 [M+H]$^+$. $^1$H NMR (MeOH-d$_4$): 7.38 (s, 1H), 7.32 (m, 2H), 7.02 (m, 1H), 4.99 (s, 1H), 4.10 (t, J=6.0, 2H), 3.96 (t, J=7.0, 2H), 3.76 (t, J=6.0, 2H), 2.92 (t, J=8.0, 2H), 1.99 (m, 4H).

Step 3. 3-(3-Pyrrolidin-2-yl-phenoxy)-propan-1-ol. Prepared as described in Example 1, Step 5, on a 0.149 mol scale, to give 27.2 g (82%) of the desired product as a colorless oil. MS: exact mass calcd for $C_{13}H_{19}NO_2$, 221.1; m/z found, 222.4 [M+H]$^+$. $^1$H NMR (MeOH-d$_4$): 7.21 (m, 1H), 6.92 (d, J=1.5, 1H), 6.90 (d, J=7.5, 1H), 6.80 (dd, J=2.5, 8.0, 1H), 4.89 (s, 2H), 4.06 (t, J=6.5, 2H), 3.98 (t, J=9.0, 1H), 3.73 (t, J=6.0, 2H), 3.15 (m, 1H), 2.91 (m, 1H), 2.18 (m, 1H), 1.96 (m, 1H), 1.87 (m, 2H), 1.69 (m, 1H).

Step 4. 2-{2-[3-(3-Hydroxy-propoxy)-phenyl]-pyrrolidin-1-yl}-1-(4-methoxy-phenyl)-ethanone. Prepared as described in Example 8, Step 1, on a 82.2 mmol scale, to give 36.59 g (>100%) of the desired product after column chromatography (EtOAc/hexanes). MS: exact mass calcd for $C_{22}H_{27}NO_4$, 369.2; m/z found, 370.4 [M+H]$^+$. $^1$H NMR (acetone-d$_6$): 7.87 (m, 2H), 7.22 (m, 1H), 7.03 (m, 1H), 6.94 (m, 3H), 6.81 (m, 1H), 4.09 (m, 2H), 4.02 (d, J=19.0, 1H), 3.84 (s, 3H), 3.74 (t, J=8.0, 2H), 3.47 (t, J=10.0, 1H), 3.28 (m, 2H), 2.36 (m, 1H), 2.15 (m, 1H), 1.96 (m, 2H), 1.84 (m, 2H), 1.68 (m, 1H).

Step 5. 9-(3-Hydroxy-propoxy)-6-(4-methoxy-phenyl)-2,3-dihydro-1H-pyrrolo[2,1-a]isoquinolinylium salt. Prepared as described in Example 17, Step 2, on an 82.2 mmol scale, to give 30.09 g (95%) of crude product. The product was taken on to the next step without purification. MS: exact mass calcd for $C_{22}H_{24}NO_3{}^+$, 350.2; m/z found, 350.4 [M+H]$^+$.

Step 6. Cis-3-[6-(4-Methoxy-phenyl)-1,2,3,5,6,10b-hexahydro-pyrrolo[2,1-a]isoquinolin-9-yloxy]-propan-1-ol. Prepared as described in Example 17, Step 3, on 78.1 mmol scale, to give 10.09 g (37%) of the desired product after column chromatography (EtOAc) and reverse-phase HPLC. The product was characterized as the TFA salt. MS: exact mass calcd for $C_{22}H_{27}NO_3$, 353.2; m/z found, 354.4 [M+H]$^+$. $^1$H NMR (MeOH-d$_4$): 7.16 (d, J=8.5, 2H), 6.93 (d, J=9.0, 2H), 6.85 (d, J=2.5, 1H), 6.76 (m, 1H), 6.69 (d, J=8.5, 1H), 4.84 (m, 1H), 4.33 (m, 1H), 4.06 (t, J=6.5, 2H), 3.87 (m, 1H), 3.77 (s, 3H), 3.71 (t, J=6.3, 2H), 3.55 (m, 1H), 3.37 (m, 2H), 2.81 (m, 1H), 2.25 (m, 3H), 1.96 (m, 2H).

Step 7. Cis-Methanesulfonic acid 3-[6-(4-methoxy-phenyl)-1,2,3,5,6,10b-hexahydro-pyrrolo[2,1-a]isoquinolin-9-yloxy]-propyl ester. A solution of cis-3-[6-(4-methoxy-phenyl)-1,2,3,5,6,10b-hexahydro-pyrrolo[2,1-a]isoquinolin-9-yloxy]-propan-1-ol (28.5 mmol) and Hunig's base (3 equiv.) in THF (0.2 M) was cooled to 0° C. and treated with methanesulfonyl chloride (2.1 equiv.). The mixture was stirred at 0° C. for 1 h. The mixture was then diluted with methylene chloride, washed with 1 N NaOH and brine, dried (Na$_2$CO$_3$), and concentrated to give the crude product, which was immediately taken on to the next step. MS: exact mass calcd for $C_{22}H_{27}NO_4$, 431.2; m/z found, 432.4 [M+H]$^+$.

Step 8. A mixture of crude cis-methanesulfonic acid 3-[6-(4-methoxy-phenyl)-1,2,3,5,6,10b-hexahydro-pyrrolo[2,1-a]isoquinolin-9-yloxy]-propyl ester (28.5 mmol), Na$_2$CO$_3$ (4 equiv.), KI (0.5 equiv.), and morpholine (7.52 mmol, 10 equiv.) in ethanol (0.2 M) was heated to 50° C. overnight. The mixture was cooled to rt, diluted with CH$_2$Cl$_2$, and filtered. The filtrate was concentrated to give the crude product. Column chromatography (NH$_3$ in MeOH/CH$_2$Cl$_2$) followed by HPLC give the desired product (8.19 g, 68%). The enantiomers were separated using a Chiralcel AD-h column on a SFC HPLC eluting with IPA/MeOH with 0.2% DEA. MS: exact mass calcd for $C_{26}H_{34}N_2O_3$, 422.3; m/z found, 423.5 [M+H]$^+$. $^1$H NMR (MeOH-d$_4$): 7.06 (d, J=8.5, 2H), 6.82 (d, J=8.5, 2H), 6.70 (d, J=2.5, 1H), 6.67 (d, J=8.5, 1H), 6.61 (dd, J=2.5, 8.5 1H), 4.08 (dd, J=8.5, 5.5, 1H), 3.97 (t, J=6.5, 2H), 3.79 (m, 1H), 3.74 (s, 3H), 3.67 (m, 4H), 2.91 (m, 3H), 2.78 (dd, J=5.0, 11.2, 1H), 2.47 (m, 6H), 2.34 (m, 1H), 1.91 (m, 5H).

Example 39-(A-C)

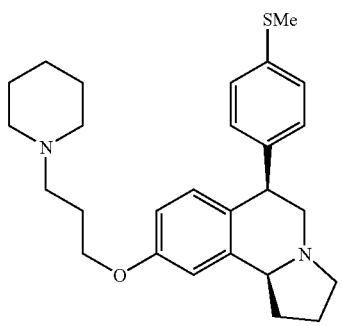

39A

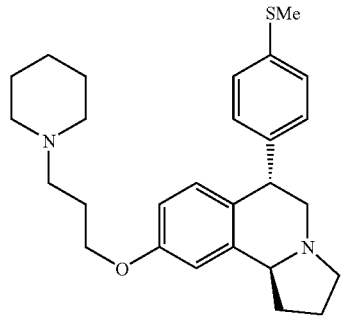

39B

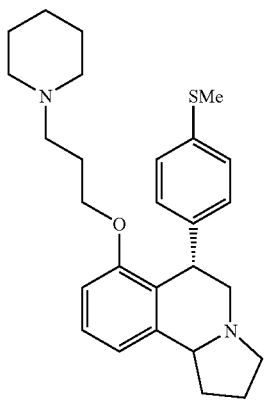

39C

39A: Cis-6-(4-Methylsulfanyl-phenyl)-9-(3-piperidin-1-yl-propoxy)-1,2,3,5,6,10b-hexahydro-pyrrolo[2,1-a]isoquinoline 39B: Trans-6-(4-Methylsulfanyl-phenyl)-9-(3-piperidin-1-yl-propoxy)-1,2,3,5,6,10b-hexahydro-pyrrolo[2,1-a]isoquinoline 39C: 6-(4-Methylsulfanyl-phenyl)-7-(3-piperidin-1-yl-propoxy)-1,2,3,5,6,10b-hexahydro-pyrrolo[2,1-a]isoquinoline Step 1. 5-(3-Methoxy-phenyl)-3,4-dihydro-2H-pyrrole. Prepared as described in Example 1, Step 4, on a 0.24 mol scale, using 3 N HCl in place of 12 N HCl during the workup procedure, to give 37.8 g of the desired product. MS: exact mass calcd for $C_{11}H_{13}NO$, 175.1; m/z found, 176.1 [M+H]$^+$. $^1$H NMR (DMSO-d$_6$): 7.36 (m, 3H), 7.03 (m, 1H), 3.94 (m, J=7.4, 2H), 3.79 (s, 3H), 2.89 (t, J=8.0, 2H), 1.93 (m, 2H).

Step 2. 2-(3-Methoxy-phenyl)-pyrrolidine. A solution of 5-(3-methoxy-phenyl)-3,4-dihydro-2H-pyrrole (0.21 mol) in absolute ethanol (1.2 M) was treated portionwise with NaBH$_4$ (1.0 equiv.). The resultant mixture was stirred at rt overnight. The mixture was cooled to 0° C. and slowly quenched with 1 N HCl. The mixture was acidified to a pH of 1 with 3 N HCl and was stirred at rt for 45 min. The resulting mixture was again cooled to 0° C., and was treated with 1 N NaOH until basic. The aqueous mixture was extracted with CH$_2$Cl$_2$ (×3). The combined extracts were washed with brine, dried (MgSO$_4$), filtered and concentrated to give the crude product. Chromatography (EtOAc/hexanes) gave 37.0 g (99%) of the desired product. MS: exact mass calcd for $C_{11}H_{15}NO$, 177.1; m/z found, 178.1 [M+H]$^+$. $^1$H NMR (DMSO-d$_6$): 7.23 (m, 1H), 7.05 (m, 1H), 6.98 (d, J=7.6, 1H), 6.79 (dd, J=2.8, 8.0, 1H), 4.20 (m, 1H), 3.74 (s, 3H), 3.15 (m, 1H), 3.03 (m, 1H), 2.19 (m, 1H), 1.86 (m, 2H), 1.69 (m, 1H).

Step 3. 2-Hydroxy-1-[2-(3-methoxy-phenyl)-pyrrolidin-1-yl]-2-(4-methylsulfanyl-phenyl)-ethanone. A mixture of 2-(3-methoxy-phenyl)-pyrrolidine (59.2 mmol), hydroxy-(4- methylsulfanyl-phenyl)-acetic acid (1.05 equiv.), O-benzotriazol-1-yl-N,N,N',N'-tetramethyluronium hexafluorophosphate (HATU, 1.2 equiv.), and Hunig's base (1.5 equiv.) in $CH_2Cl_2$ (0.2 M) was stirred at rt overnight under nitrogen. The reaction mixture was filtered to remove a white precipitate and the filtrate was washed with 1 N HCl, water, 1 N NaOH, water, and brine, dried ($MgSO_4$), and concentrated to give the crude product as a mixture of diastereomers. The crude product was purified by normal phase column chromatography (EtOAc/hexanes) to give 29.6 g (37%) of the product as a mixture of diastereomers. MS: exact mass calcd for $C_{20}H_{23}NO_3S$, 357.1; m/z found, 358.1 $[M+H]^+$.

Step 4. 9-Methoxy-6-(4-methylsulfanyl-phenyl)-2,3,6,10b-tetrahydro-1H-pyrrolo[2,1-a]isoquinolin-5-one. A solution of amide from Step 1 (33.3 mmol) and polyphosphoric acid (5 g/g amide) was heated at 105° C. under nitrogen until the starting material was consumed (2 h). The reaction mixture was poured into water and extracted with $CH_2Cl_2$ (×2). The combined extracts were washed with satd. aq. $NaHCO_3$ and brine, dried ($MgSO_4$), and concentrated to provide the crude product. The crude material was purified by chromatography to give 9.3 g (82%) of the product as a mixture of diastereomers and regioisomers. MS: exact mass calcd for $C_{20}H_{21}NO_2S$, 339.1; m/z found, 340.0 $[M+H]^+$.

Step 5. 9-Hydroxy-6-(4-methylsulfanyl-phenyl)-2,3,6,10b-tetrahydro-1H-pyrrolo[2,1-a]isoquinolin-5-one. A solution of amino-ketone (Step 2; 0.15 mmol, 1.0 equiv.) in $CH_2Cl_2$ (0.5 M) was treated dropwise with $BBr_3$ (5.0 equiv.). The reaction mixture was stirred at rt until complete. The reaction was cooled to 0° C. and quenched with water. The crude mixture was sonicated, extracted with $CH_2Cl_2$, washed with brine, dried ($MgSO_4$), and concentrated to give 50 mg (>100%) of the crude product as a mixture of diastereomers and regioisomers. MS: exact mass calcd for $C_{19}H_{19}NO_2S$, 325.1; m/z found, 326.1 $[M+H]^+$.

Step 6. 9-(3-Chloro-propoxy)-6-(4-methylsulfanyl-phenyl)-2,3,6,10b-tetrahydro-1H-pyrrolo[2,1-a]isoquinolin-5-one. Prepared as described in Example 1, Step 1, on a 1.23 mmol scale, to give 330 mg (67%) of the crude product as a mixture of diastereomers and regioisomers after normal phase column chromatography (EtOAc/hexanes). MS: exact mass calcd for $C_{22}H_{24}ClNO_2S$, 401.1; m/z found, 402.0 $[M+H]^+$.

Step 7. 6-(4-Methylsulfanyl-phenyl)-9-(3-piperidin-1-yl-propoxy)-2,3,6,10b-tetrahydro-1H-pyrrolo[2,1-a]isoquinolin-5-one. A solution of amino-ketone (Step 4; 0.82 mmol), $Na_2CO_3$ (1.5 equiv.), KI (0.05 equiv.), and piperidine (1.5 equiv.) in n-butanol (0.3 M) was heated at 100° C. overnight. The reaction mixture was cooled to rt, diluted with $CH_2Cl_2$, and filtered. The filtrate was concentrated to give the crude product (350 mg, 95%) as a mixture of diastereomers and regioisomers. MS: exact mass calcd for $C_{27}H_{34}N_2O_2S$, 450.2; m/z found, 451.2 $[M+H]^+$.

Step 8. To a 0° C. solution of $BH_3$·THF (1 M in THF, 2.5 equiv.) was added a solution of amino-ketone (Step 5, 0.75 mmol, 1 equiv.) in THF (2 M) and the resulting solution was heated at reflux for 1 h. The mixture was cooled to rt, quenched with water, and acidified with 12 N HCl. The THF was removed in vacuo and the aqueous mixture was heated at reflux for 15 min. The reaction mixture was again cooled to rt, made basic with 3 N NaOH, and extracted with $CH_2Cl_2$. The organic extract was washed with brine, dried ($MgSO_4$), and concentrated to give the crude products as a mixture (29%). The products were purified by reverse-phase HPLC.

39A: Cis-6-(4-Methylsulfanyl-phenyl)-9-(3-piperidin-1-yl-propoxy)-1,2,3,5,6,10b-hexahydro-pyrrolo[2,1-a]isoquinoline. 26.0 mg (5%) as the TFA salt. MS: exact mass calcd for $C_{27}H_{36}N_2OS$, 436.3; m/z found, 437.2 $[M+H]^+$. $^1H$ NMR (acetone-$d_6$): 7.30 (d, J=8.4, 2H), 7.23 (d, J=8.2, 2H), 6.95 (m, 1H), 6.78 (m, 1H), 6.67 (d, J=8.6, 1H), 4.89 (m, 1H), 4.54 (m, 1H), 4.13 (t, J=6.0, 2H), 3.93 (m, 1H), 3.64 (m, 2H), 3.39 (m, 2H), 3.29 (m, 2H), 3.15 (m, 2H), 2.91 (m, 3H), 2.51 (s, 3H), 2.29 (m, 3H), 2.23 (m, 1H), 1.92 (m, 4H), 1.79 (m, 1H), 1.47 (m, 1H), 1.32 (m, 2H).

39B: Trans-6-(4-Methylsulfanyl-phenyl)-9-(3-piperidin-1-yl-propoxy)-1,2,3,5,6,10b-hexahydro-pyrrolo[2,1-a]isoquinoline. 82.0 mg (16%) as the TFA salt. MS: exact mass calcd for $C_{27}H_{36}N_2OS$, 436.3; m/z found, 437.2 $[M+H]^+$. $^1H$ NMR (acetone-$d_6$): 13.02 (br s, 1H), 11.64 (br s, 1H), 7.26 (d, J=10.4, 2H), 7.19 (d, J=10.4, 2H), 6.98 (br s, 1H), 6.83 (m, 2H), 5.65 (br s, 2H), 5.07 (br s, 1H), 4.52 (br s, 1H), 4.15 (t, J=5.6, 2H), 3.82 (m, 1H), 3.65 (m, 3H), 3.57 (m, 1H), 3.34 (m, 2H), 2H), 2.99 (m, 2H), 2.74 (m, 1H), 2.49 (s, 3H), 2.32 (m, 2H), 2.20 (m, 2H), 1.92 (m, 4H), 1.84 (m, 1H), 1.52 (m, 1H).

39C: 6-(4-Methylsulfanyl-phenyl)-7-(3-piperidin-1-yl-propoxy)-1,2,3,5,6,10b-hexahydro-pyrrolo[2,1-a]isoquinoline. 39.0 mg (8%) as the TFA salt. MS: exact mass calcd for $C_{27}H_{36}N_2OS$, 436.3; m/z found, 437.2 $[M+H]^+$. $^1H$ NMR (acetone-$d_6$): 11.85 (br s, 1H), 11.31 (br s, 1H), 7.41 (m, 1H), 7.20 (d, J=9.7, 2H), 7.07 (m, 3H), 6.97 (d, 10.3, 1H), 5.13 (br s, 1H), 4.75 (s, 1H), 4.13 (m, 1H), 3.85 (m, 4H), 3.36 (m, 3H), 2.86 (m, 1H), 2.62 (m, 2H), 2.51 (m, 1H), 2.46 (s, 3H), 2.23 (m, 3H), 2.06 (m, 2H), 1.80 (m, 6H), 1.47 (m, 1H).

Example 40

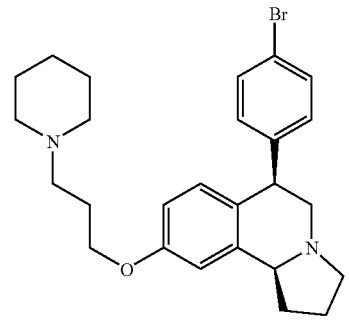

Cis-6-(4-Bromo-phenyl)-9-(3-piperidin-1-yl-propoxy)-1,2,3,5,6,10b-hexahydro-pyrrolo[2,1-a]isoquinoline Step 1. 2-(4-Bromo-phenyl)-2-hydroxy-1-[2-(3-methoxy-phenyl)-pyrrolidin-1-yl]-ethanone. A solution of 2-(3-methoxy-phenyl)-pyrrolidine (16.9 mmol, 1.0 equiv.) and hydroxy-(4-bromo-phenyl)-acetic acid (1.0 equiv.) in xylenes (0.2 M) was heated at reflux for 3 d under nitrogen. The bulk of the xylenes was removed by distillation and the residue was purified by chromatography (EtOAc/hexanes) to give the desired product as a mixture of diastereomers (3.66 g, 55%). MS: exact mass calcd for $C_{19}H_{20}BrNO_3$, 389.1; m/z found, 390.0 $[M+H]^+$, 392.0 $[M+H]^+$.

Step 2. A solution of 2-(4-bromo-phenyl)-2-hydroxy-1-[2-(3-methoxy-phenyl)-pyrrolidin-1-yl]-ethanone (3.6 g, 9.2 mmol) and PPA (15.0 g) was heated at 100° C. for 1 h. The mixture was cooled to rt, poured into water, and extracted with $CH_2Cl_2$. The combined organic layers were washed with brine, dried ($MgSO_4$), filtered and concentrated. Purification by normal phase column chromatography (EtOAc/hexanes) gave 87% combined yield of four isomeric products.

Cis-6-(4-Bromo-phenyl)-9-methoxy-2,3,6,10b-tetrahydro-1H-pyrrolo[2,1-a]isoquinolin-5-one. 500 mg (15%). MS: exact mass calcd for $C_{19}H_{18}BrNO_2$, 371.1 m/z found, 372.0

[M+H]+, 374.0 [M+H]+. 1H NMR (acetone-d6): 7.62 (d, J=8.4, 2H), 7.22 (d, J=8.4, 2H), 6.95 (m, 1H), 6.80 (dd, J=2.6, 8.6, 1H), 6.48 (m, 1H), 4.78 (m, 1H), 4.73 (s, 1H), 3.84 (s, 3H), 3.63 (m, 1H), 3.52 (m, 1H), 2.82 (m, 1H), 2.20 (m, 1H), 2.08 (m, 2H).

Trans-6-(4-Bromo-phenyl)-9-methoxy-2,3,6,10b-tetrahydro-1H-pyrrolo[2,1-a]isoquinolin-5-one. 170.0 mg (6%). MS: exact mass calcd for C19H18BrNO2, 371.1; m/z found, 372.0 [M+H]+, 374.0 [M+H]+. 1H NMR (acetone-d6): 7.41 (d, J=8.5, 2H), 7.22 (d, J=9.3, 1H), 7.08, (d, J=8.2, 2H), 6.95 (m, 2H), 4.77 (s, 1H), 4.57 (m, 1H), 3.84 (s, 3H), 3.48 (m, 2H), 2.69 (m, 1H), 2.04 (m, 1H), 1.86 (m, 2H).

Cis-6-(4-Bromo-phenyl)-7-methoxy-2,3,6,10b-tetrahydro-1H-pyrrolo[2,1-a]isoquinolin-5-one. 420 mg (14%). MS: exact mass calcd for C19H18BrNO2, 371.1; m/z found, 372.0 [M+H]+, 374.0 [M+H]+. 1H NMR (acetone-d6): 7.49 (d, J=8.5, 2H), 7.38 (m, 1H), 7.09 (d, J=8.5, J=2H), 7.06 (d, J=7.8, 1H), 6.88 (d, J=8.2, 1H), 4.74 (m, 1H), 4.70 (m, 1H), 3.82 (m, 1H), 3.58 (s, 3H), 3.36 (m, 1H), 2.73 (m, 1H), 2.10 (m, 2H), 1.87 (m, 1H).

Trans-6-(4-Bromo-phenyl)-7-methoxy-2,3,6,10b-tetrahydro-1H-pyrrolo[2,1-a]isoquinolin-5-one. The material obtained from the purification by normal phase column chromatography was recrystallized from acetone to give 48.3 mg (2%) of the desired product as white crystals. 1H NMR (acetone-d6): 7.45 (d, J=8.5, 2H), 7.37 (m, 1H), 7.02 (m, 3H), 6.96 (m, 1H), 4.89 (s, 1H), 4.58 (m, 1H), 3.74 (s, 3H), 3.41 (m, 2H), 2.65 (m, 1H), 2.00 (m, 1H), 1.88 (m, 1H), 1.73 (m, 1H).

Step 3. Cis-6-(4-Bromo-phenyl)-9-hydroxy-2,3,6,10b-tetrahydro-1H-pyrrolo[2,1-a]isoquinolin-5-one. Prepared from cis-6-(4-bromo-phenyl)-9-methoxy-2,3,6,10b-tetrahydro-1H-pyrrolo[2,1-a]isoquinolin-5-one (3.49 mmol) as described in Example 39, Step 5. The crude mixture was sonicated and extracted with diethyl ether. The organic layer was washed with brine, dried (MgSO4), and concentrated to give 1.08 g (86%) of crude product. A small amount was purified by reverse phase HPLC to give the product as the TFA salt. MS: exact mass calcd for C18H16BrNO2, 357.0; m/z found, 358.0 [M+H]+, 360.0 [M+H]+. 1H NMR (acetone-d6): 7.55 (d, J=8.4, 2H), 7.16 (d, J=8.4, 2H), 6.79 (m, 1H), 6.64 (dd, J=2.4, 8.5, 1H), 6.31 (m, 1H), 4.70 (m, 1H), 4.64 (s, 1H), 3.58 (m, 1H), 3.44 (m, 2H), 2.70 (m, 1H), 2.14 (m, 1H), 2.09 (m, 1H), 1.97 (m, 1H).

Step 4. Cis-6-(4-Bromo-phenyl)-9-(3-chloro-propoxy)-2,3,6,10b-tetrahydro-1H-pyrrolo[2,1-a]isoquinolin-5-one. Prepared as described in Example 39, Step 6, on a 0.56 mmol scale, to give 205 mg (84%) of the desired product. MS: exact mass calcd for C21H21BrClNO2, 433.0; m/z found, 434.0 [M+H]+, 436.0 [M+H]+. 1H NMR (acetone-d6): 7.27 (d, J=8.5, 2H), 7.09 (m, 1H), 6.95 (d, J=8.2, 2H), 6.82 (m, 2H), 4.58 (s, 1H), 4.42 (m, 1H), 4.04 (t, J=6.0, 2H), 3.66 (t, J=6.5, 2H), 3.32 (m, 2H), 2.56 (m, 1H), 2.10 (m, 2H), 1.92 (m, 1H), 1.81 (m, 1H), 1.70 (m, 1H).

Step 5. Cis-6-(4-Bromo-phenyl)-9-(3-piperidin-1-yl-propoxy)-2,3,6,10b-tetrahydro-1H-pyrrolo[2,1-a]isoquinolin-5-one. Prepared as described in Example 39, Step 7, on a 0.46 mmol scale, to give 190 mg (86%) of the desired product. MS: exact mass calcd for C26H31BrN2O2, 482.2; m/z found, 483.1 [M+H]+, 485.1 [M+H]+. 1H NMR (acetone-d6): 7.46 (d, J=8.5, 2H), 7.25 (d, J=8.2, 1H), 7.10 (d, J=7.0, 2H), 6.97 (m, 2H), 4.76 (s, 1H), 4.59 (m, 1H), 4.12 (t, J=6.5, 2H), 3.49 (m, 2H), 2.85 (m, 2H), 2.74 (m, 1H), 2.45 (t, J=7.0, 2H), 2.39 (m, 4H), 1.94 (3H), 1.57 (m, 4H), 1.39 (m, 2H).

Step 6. Prepared as described in Example 39, Step 8, on a 0.93 mmol scale, to give 88.0 mg (14%) of the desired product as the TFA salt. MS: exact mass calcd for C26H33BrN2O, 468.2; m/z found, 469.1 [M+H]+, 471.1 [M+H]+. 1H NMR (acetone-d6): 7.55 (d, J=8.4, 2H), 7.22 (d, J=8.4, 2H), 6.99 (br s, 1H), 6.85 (m, 2H), 5.15 (br s, 1H), 4.70 (m, 3H), 4.16 (m, 2H), 3.84 (br s, 1H), 3.66 (m, 3H), 3.58 (m, 1H), 3.36 (m, 2H), 3.00 (m, 2H), 2.77 (m, 1H), 2.33 (m, 2H), 2.20 (m, 2H), 1.92 (m, 4H), 1.85 (m, 1H), 1.53 (m, 1H).

Example 41-(A-B)

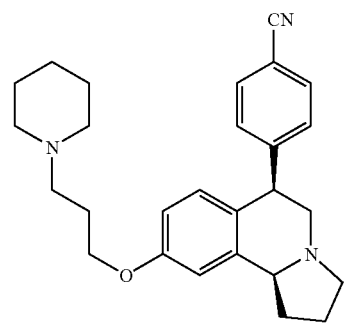

41A

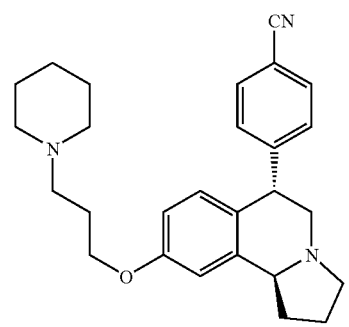

41B

41A: Cis-4-[9-(3-Piperidin-1-yl-propoxy)-1,2,3,5,6,10b-hexahydro-pyrrolo[2,1-a]isoquinolin-6-yl]-benzonitrile 41B: Trans-4-[9-(3-Piperidin-1-yl-propoxy)-1,2,3,5,6,10b-hexahydro-pyrrolo[2,1-a]isoquinolin-6-yl]-benzonitrile To a sealed tube reaction vessel were added cis-6-(4-bromo-phenyl)-9-(3-piperidin-1-yl-propoxy)-1,2,3,5,6,10b-hexahydro-pyrrolo[2,1-a]isoquinoline (0.21 mmol), CuCN (5.2 equiv.), and DMF (1.7 M). The tube was purged with nitrogen, sealed, and heated at 150° C. overnight. The reaction mixture was cooled to rt, diluted with aqueous NaCN, and extracted with diethyl ether. The organic layer was washed with water, satd. aq. NaHCO3, and brine, dried (Na2CO3), and concentrated to give the crude product. Chromatographic purification (NH3 in MeOH/CH2Cl2) followed by reverse-phase HPLC gave the desired product as a mixture with the 6-trans isomer (7% combined yield).

41A: Cis-4-[9-(3-Piperidin-1-yl-propoxy)-1,2,3,5,6,10b-hexahydro-pyrrolo[2,1-a]isoquinolin-6-yl]-benzonitrile. 5.2 mg (4%) as the TFA salt. MS: exact mass calcd for C27H33N3O, 415.3; m/z found, 416.2 [M+H]+. 1H NMR (acetone-d6): 7.74 (d, J=8.1, 2H), 7.46 (d, J=8.1, 2H), 7.00 (m, 1H), 6.85 (m, 2H), 6.80 (d, J=8.6, 1H), 5.07 (br s, 1H), 4.74 (m, 1H), 4.16 (m, 2H), 3.71 (m, 1H), 3.62 (m, 2H), 3.50 (m, 4H), 3.30 (m, 2H), 2.94 (m, 2H), 2.77 (m, 1H), 2.32 (m, 2H), 2.19 (m, 1H), 2.10 (m, 1H), 1.94 (m, 3H), 1.79 (m, 1H), 1.42 (m, 1H).

41B: Trans-4-[9-(3-Piperidin-1-yl-propoxy)-1,2,3,5,6,10b-hexahydro-pyrrolo[2,1-a]isoquinolin-6-yl]-benzonitrile. 4.6 mg (3%) as the TFA salt. MS: exact mass calcd for C27H33N3O, 415.3; m/z found, 416.2 [M+H]+. 1H NMR (acetone-d$_6$): 7.82 (d, J=8.2, 2H), 7.54 (d, J=8.0, 2H), 7.02 (s, 1H), 6.79 (dd, J=2.1, 8.7, 1H), 6.62 (d, J=8.7, 1H), 4.91 (m, 1H), 4.74 (m, 1H), 4.13 (m, 2H), 3.93 (m, 1H), 3.70 (m, 1H), 3.61 (m, 3H), 3.50 (t, J=11.7, 2H), 3.37 (m, 4H), 3.29 (m, 8H), 2.93 (m, 3H).

Example 42

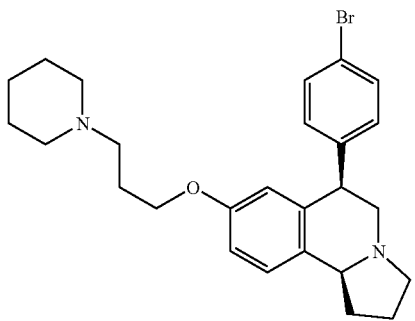

Trans-6-(4-Bromo-phenyl)-8-(3-piperidin-1-yl-propoxy)-1,2,3,5,6,10b-hexahydro-pyrrolo[2,1-a]isoquinoline. Step 1. 2-(4-Bromo-benzylidene)-malonic Acid Diethyl Ester A mixture of 4-bromobenzaldehyde (118.3 g, 0.639 mol), diethyl malonate (105.5 mL, 0.6243 mol), and p-toluic acid (9.40 g, 62.6 mmol), in toluene (220 mL) was stirred under nitrogen until homogeneous and then was treated with piperidine (7.50 mL, 75.8 mmol). The flask was fitted with a Dean-Stark trap and a condenser and was heated at between 128-135° C. overnight. The mixture was diluted with toluene, washed with 10% aq. HCl, 1 N NaOH, and brine (×2). The organic layer was dried (MgSO$_4$) and concentrated to give the crude product as a pale-red oil. Vacuum distillation (bp=159° C.@1 torr) of the crude material yielded 142.1 g (70%) of the desired product as a pale-yellow oil. $^1$H NMR (acetone-d$_6$): 7.67 (d, J=2.9, 1H), 7.62 (br s, 2H), 7.47 (br s, 2H), 4.29 (m, 4H), 1.26 (m, 6H).

Step 2. 2-[(4-Bromo-phenyl)-(3-methoxy-phenyl)-methyl]-malonic acid diethyl ester. A 0° C. solution of 3-methoxyphenyl magnesium bromide (1 M in THF; 414 mL, 0.414 mol) was treated with a solution of 2-(4-bromo-benzylidene)-malonic acid dimethyl ester (114.7 g, 0.3506 mol) in diethyl ether (250 mL), via cannula, over the course of 18 min. The mixture was stirred at 0° C. for 1 h and then was allowed to warm to rt. After 2 h, the reaction was quenched with satd. aq. NH$_4$Cl, and extracted with diethyl ether. The organic layer was washed with satd. aq. NH$_4$Cl and brine, dried (MgSO$_4$), and concentrated to give the crude product as a yellow oil (163.5 g, >100%). The bulk of the crude product was taken on to the next step without purification, but a small portion was purified by normal phase column chromatography (EtOAc/hexanes) for characterization. MS: exact mass calcd for C$_{21}$H$_{23}$BrO$_5$, 434.1; m/z found, 457.0 [M+Na]$^+$, 459.0 [M+Na]$^+$. $^1$H NMR (acetone-d$_6$): 7.42 (m, 4H), 7.17 (d, J=7.9, 1H), 6.98 (m, 2H), 6.35 (m, 1H), 4.67 (d, J=12.3, 1H), 4.47 (d, J=12.2, 1H), 3.98 (m, 4H), 3.95 (s, 3H), 1.00 (m, 6H).

Step 3. 2-[(4-Bromo-phenyl)-(3-methoxy-phenyl)-methyl]-malonic acid. A mixture of crude 2-[(4-bromo-phenyl)-(3-methoxy-phenyl)-methyl]-malonic acid diethyl ester (131.3 g, est. 0.3016 mol) in 150 mL hot ethanol was treated with a solution of KOH (85%; 99.6 g, 1.51 mol) in water (301 mL). The mixture was heated overnight at 105° C. and then was allowed to cool to rt. The mixture was diluted with water and extracted with diethyl ether (500 mL, ×3). The aqueous phase was acidified with 12 N HCl until the pH=1 and was extracted with diethyl ether (500 mL, ×3). The latter organic extracts were combined, dried (Na$_2$CO$_3$), and concentrated to give 107.97 g of a white-grey solid. The crude product was divided into two equal portions and each was suspended in 700 mL toluene. The toluene suspensions were heated at 105° C. for 3 h and then allowed to slowly cool to rt. The white solid was filtered off, rinsed with toluene, the portions combined and dried under high vacuum to give 68.8 g (60%) of the desired product as a white solid. MS (ESI, negative ionization): exact mass calcd for C$_{17}$H$_{15}$BrO$_5$, 378.0; m/z found, 377.9 [M−H]$^−$, 379.9 [M−H]$^−$. $^1$H NMR (DMSO-d$_6$): 12.68 (br s, 2H), 7.41 (m, 4H), 7.15 (m, 1H), 6.97 (m, 2H), 6.70 (m, 1H), 4.52 (d, J=12.4, 1H), 4.42 (d, J=12.3, 1H), 3.69 (s, 3H).

Step 4. 3-(4-Bromo-phenyl)-3-(3-methoxy-phenyl)-propionic acid. To a 1-L round bottomed flask was added 79.9 g (0.211 mol) 2-[(4-bromo-phenyl)-(3-methoxy-phenyl)-methyl]-malonic acid, the flask fitted with a septum, and the system subjected to a continuous stream of nitrogen (nitrogen line into septum and a needle as a bleed). The flask was then heated slowly in an oil bath to 160° C. for 2 h. Gas evolution was evident beginning at 140° C. The mixture was allowed to cool to rt to give 70.1 g (99%) of the desired product as a white solid. MS (ESI, negative ionization): exact mass calcd for C$_{16}$H$_{15}$BrO$_3$, 334.0; m/z found, 333.0 [M−H]$^−$, 335.0 [M−H]$^−$. $^1$H NMR (DMSO-d$_6$): 12.14 (br s, 1H), 7.42 (dd, J=1.8, 6.6, 2H), 7.28 (m, 2H), 7.17 (m, 1H), 6.88 (m, 2H), 6.73 (m, 1H), 4.38 (t, J=7.9, 1H), 3.70 (s, 3H), 3.00 (dd, J=3.6, 8.0, 2H).

Step 5. [2-(4-Bromo-phenyl)-2-(3-methoxy-phenyl)-ethyl]-carbamic acid tert-butyl ester. A mixture of 3-(4-bromo-phenyl)-3-(3-methoxy-phenyl)-propionic acid (24.99 g, 74.55 mmol), triethylamine (12.5 mL, 89.5 mmol) and diphenylphosphoryl azide (17.0 mL, 78.3 mmol) in tert-butanol (250 mL) was heated at 85° C. overnight. The reaction mixture was then concentrated and the residue was purified by normal phase column chromatography (EtOAc/hexanes) to give 24.19 g (80%) of the desired product as a viscous colorless oil. MS: exact mass calcd for C$_{20}$H$_{24}$BrNO$_3$, 405.1; m/z found, 428.1 [M+Na]$^+$, 430.1 [M+Na]$^+$. $^1$H NMR (acetone-d$_6$): 7.45 (d, J=8.4, 2H), 7.27 (d, J=8.4, 2H), 7.20 (m, 1H), 6.86 (m, 2H), 6.76 (dd, J=1.9, 7.8, 1H), 5.96 (br s, 1H), 4.25 (t, J=7.9, 1H), 3.76 (s, 3H), 3.70 (m, 1H), 1.34 (s, 9H).

Step 6. 2-(4-Bromo-phenyl)-2-(3-methoxy-phenyl)-ethylamine. Prepared as described in Example 29, Step 2, on a 59.5 mmol scale, to give 16.8 g (92%) product as the free base. MS: exact mass calcd for C$_{15}$H$_{16}$BrNO, 305.0; m/z found, 306.1 [M+H]$^+$, 308.1 [M+H]$^+$. $^1$H NMR (MeOH-d$_4$): 7.24 (m, 2H), 7.03 (m, 3H), 6.64 (m, 3H), 4.66 (br s, 2H), 3.76 (m, 1H), 3.57 (s, 3H), 3.01 (m, 2H).

Step 7. N-[2-(4-Bromo-phenyl)-2-(3-methoxy-phenyl)-ethyl]-succinamic acid. A solution of succinic anhydride (5.77 g, 57.6 mmol) in CH$_2$Cl$_2$ (55 mL) was stirred under nitrogen until homogeneous, cooled to 0° C., and then treated with a solution of 2-(4-bromo-phenyl)-2-(3-methoxy-phenyl)-ethylamine (16.8 g, 54.9 mmol) in CH$_2$Cl$_2$ (55 mL). Once the addition was complete, the ice bath was removed and the mixture was stirred at rt for 2.5 h. The mixture was concentrated to give the crude product. The crude material was immediately taken on to the next step without purification. MS: exact mass calcd for C$_{19}$H$_{20}$BrNO$_4$, 405.1; m/z found, 406.0 [M+H]$^+$, 408.0 [M+H]$^+$.

Step 8. 1-[2-(4-Bromo-phenyl)-2-(3-methoxy-phenyl)-ethyl]-pyrrolidine-2,5-dione. A solution of the crude product from Step 7 (54.9 mmol) in EtOAc (55 mL) was treated with acetyl chloride (14.0 mL) and then was heated at reflux overnight. The mixture was cooled, and a precipitate formed. The solid was filtered to provide 15.9 g (75%) of the desired product. The filtrate was purified by chromatography (EtOAc/hexanes) to give an additional 3.28 g, for a combined yield of 19.2 g (90%). MS: exact mass calcd for $C_{19}H_{18}BrNO_3$, 387.1; m/z found, 410.0 [M+Na]$^+$, 412.0 [M+Na]$^+$. $^1$H NMR (CDCl$_3$): 7.38 (m, 2H), 7.19 (m, 3H), 6.81 (d, J=7.6, 1H), 6.73 (m, 2H), 4.60 (t, J=8.4, 1H), 4.06 (m, 2H), 3.74 (s, 3H), 2.51 (s, 4H).

Step 9. 1-[2-(4-Bromo-phenyl)-2-(3-methoxy-phenyl)-ethyl]-5-ethoxy-pyrrolidin-2-one. A mixture of 1-[2-(4-bromo-phenyl)-2-(3-methoxy-phenyl)-ethyl]-pyrrolidine-2,5-dione (5.21 g, 13.4 mmol) in 1,4-dioxane (65 mL) was stirred until homogeneous and then was treated with ethanol (65 mL) and cooled to 0° C. Once cold, the mixture was treated with NaBH$_4$ (2.13 g, 56.4 mmol), followed by MSA (2 N in ethanol, 5 drops). Equivalent portions of MSA were added every 15 min over 5.5 h, after which time additional MSA was added to quench the NaBH$_4$ and to lower the pH to 1. The resulting viscous mixture was stirred for 3.5 h. The mixture was diluted with diethyl ether, washed with satd. aq. NaHCO$_3$, water, and brine, dried (MgSO$_4$), and concentrated to give the crude product.

Chromatographic purification (EtOAc/hexanes) yielded 4.30 g (76%) of the desired product. MS: exact mass calcd for $C_{21}H_{24}BrNO_3$, 417.1; m/z found, 440.0 [M+Na]$^+$, 442.0 [M+Na]$^+$. $^1$H NMR (acetone-d$_6$): 7.46 (m, 2H), 7.32 (m, 2H), 7.23 (m, 1H), 6.90 (m, 2H), 6.76 (m, 1H), 4.63 (m, 1H), 4.42 (m, 1H), 4.15 (m, 1H), 3.75 (m, 3H), 3.61 (m, 1H), 3.41 (m, 2H), 2.29 (m, 1H), 2.04 (m, 1H), 1.84 (m, 2H), 1.13 (m, 3H).

Step 10. A mixture of 1-[2-(4-bromo-phenyl)-2-(3-methoxy-phenyl)-ethyl]-5-ethoxy-pyrrolidin-2-one (472.2 mg, 1.13 mmol) and MSA (2 N in ethanol, 10 mL) was stirred for 2 h at rt. The mixture was diluted with EtOAc, washed with satd. aq. NaHCO$_3$ and brine, dried (MgSO$_4$), and concentrated to give a colorless oil. Chromatographic purification (EtOAc/hexanes) yielded 325.4 mg (78%) of the desired product as a mixture of cis and trans diastereomers. The diastereomers were separated by normal-phase HPLC.

Trans-6-(4-Bromo-phenyl)-8-methoxy-1,5,6,10b-tetrahydro-2H-pyrrolo[2,1-a]isoquinolin-3-one. MS: exact mass calcd for $C_{19}H_{18}BrNO_2$, 371.1; m/z found, 372.0 [M+H]$^+$, 374.0 [M+H]$^+$. $^1$H NMR (CDCl$_3$): 7.45 (m, 2H), 7.07 (m, 3H), 6.82 (m, 1H), 6.29 (d, J=1.9, 1H), 4.87 (m, 1H), 4.41 (m, 1H), 4.10 (m, 1H), 3.62 (s, 3H), 3.00 (m, 1H), 2.55 (m, 1H), 2.47 (m, 1H), 2.42 (m, 1H).

Cis-6-(4-Bromo-phenyl)-8-methoxy-1,5,6,10b-tetrahydro-2H-pyrrolo[2,1-a]isoquinolin-3-one. The cis isomer was processed as described in Example 43 below. MS: exact mass calcd for $C_{19}H_{18}BrNO_2$, 371.1; m/z found, 372.3 [M+H]$^+$, 374.3 [M+H]$^+$. $^1$H NMR (acetone-d$_6$): 7.36 (m, 2H), 6.98 (m, 3H), 6.70 (d, J=8.0, 1H), 6.24 (d, J=7.5, 1H), 4.89 (m, 1H), 4.34 (dd, J=6.0, 12.8, 1H), 3.98 (dd, J=5.5, 11.2, 1H), 3.79 (s, 3H), 2.89 (m, 1H), 2.83 (m, 1H), 2.48 (m, 1H), 2.33 (m, 1H), 1.64 (m, 1H).

Step 11. Trans-6-(4-Bromo-phenyl)-8-hydroxy-1,5,6,10b-tetrahydro-2H-pyrrolo[2,1-a]isoquinolin-3-one. A solution of the product from Step 10 (2.56 mmol, 1.0 equiv.) in CH$_2$Cl$_2$ (0.1 M) was treated with BBr$_3$ (1.0 M in CH$_2$Cl$_2$, 5 equiv.). The mixture was stirred overnight and then poured onto a mixture of crushed ice and CH$_2$Cl$_2$. The mixture was diluted with water and the layers were separated. The organic layer was washed with water (×2) and brine, dried (MgSO$_4$), and concentrated to give the crude product (776.0 mg) as a mixture of the desired product and the corresponding des-bromo material (trans-6-phenyl-8-hydroxy-1,5,6,10b-tetrahydro-2H-pyrrolo[2,1-a]isoquinolin-3-one). The crude product was taken on to the next step without purification. Brominated product: MS (ESI, negative ionization): exact mass calcd for $C_{18}H_{16}BrNO_2$, 357.0; m/z found, 355.9 [M–H]$^-$, 357.9 [M–H]$^-$. Des-bromo product: MS: exact mass calcd for $C_{18}H_{17}NO_2$, 279.1; m/z found, 278.0 [M–H]$^-$.

Step 12. Trans-6-(4-Bromo-phenyl)-8-(3-chloro-propoxy)-1,5,6,10b-tetrahydro-2H-pyrrolo[2,1-a]isoquinolin-3-one. A mixture of the crude material from Step 11 (2.43 mmol, 1.0 equiv.), K$_2$CO$_3$ (5 equiv.), and 1,3-bromochloropropane (5.12 mmol, 3 equiv.) in acetone (0.1 M) was heated at 60° C. overnight. The reaction mixture was diluted with CH$_2$Cl$_2$, filtered and concentrated. The crude product was purified by chromatography (EtOAc/hexanes) to provide a mixture of the desired product and trans-6-phenyl-8-methoxy-1,5,6,10b-tetrahydro-2H-pyrrolo[2,1-a]isoquinolin-3-one (637.6 mg). Brominated product: MS: exact mass calcd for $C_{21}H_{21}BrClNO_2$, 433.0; m/z found, 434.0 [M+H]$^+$, 436.0 [M+H]$^+$. Des-bromo product: MS: exact mass calcd for $C_{21}H_{22}ClNO_2$, 355.1; m/z found, 356.1 [M+H]$^+$.

Step 13. Trans-6-(4-Bromo-phenyl)-8-(3-piperidin-1-yl-propoxy)-1,5,6,10b-tetrahydro-2H-pyrrolo[2,1-a]isoquinolin-3-one. Prepared from the product mixture from Step 12 (est. 1.61 mmol), as described in Example 39, Step 7. The reaction was performed in a glass pressure tube. Chromatographic purification (NH$_3$ in MeOH/CH$_2$Cl$_2$) gave a mixture of the desired product and trans-6-phenyl-8-(3-piperidin-1-yl-propoxy)-1,5,6,10b-tetrahydro-2H-pyrrolo[2,1-a]isoquinolin-3-one (683.9 mg). The product mixture was taken on to the next step without characterization.

Step 14. Prepared as described in Example 39, Step 8, on a 1.54 mmol scale (est.). Purification of the crude mixture of bromo and des-bromo compounds by reverse-phase HPLC gave the desired product (25.6 mg, 2%) as the TFA salt as well as 45.4 mg (4%) of the des-brominated product (Example 49). MS: exact mass calcd for $C_{26}H_{33}N_2OBr$, 468.2; m/z found, 469.1 [M+H]$^+$, 471.1 [M+H]$^+$. $^1$H NMR (MeOH-d$_4$): 7.51 (d, J=8.2, 2H), 7.29 (br d, J=7.8, 1H), 7.11 (br s, 2H), 6.98 (br d, J=6.9, 1H), 6.52 (br s, 1H), 4.57 (br s, 1H), 3.99 (m, 2H), 3.75 (br d, 2H), 3.53 (d, J=11.7, 2H), 4.45 (br m, 1H), 3.22 (t, J=7.8, 2H), 2.72 (br s, 1H), 2.15 (m, 5H), 1.91 (m, 2H), 1.79 (m, 3H), 1.50 (m, 1H).

Example 43

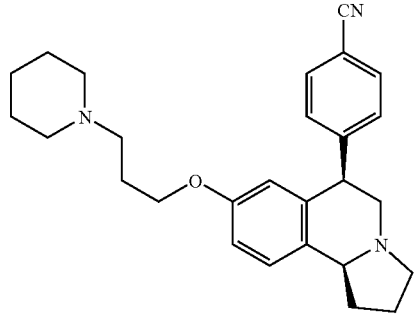

Cis-4-[8-(3-Piperidin-1-yl-propoxy)-1,2,3,5,6,10b-hexahydro-pyrrolo[2,1-a]isoquinolin-6-yl]-benzonitrile Step 1. Cis-6-(4-Bromo-phenyl)-8-hydroxy-1,5,6,10b-tetrahydro-2H-pyrrolo[2,1-a]isoquinolin-3-one. Prepared as described in Example 42, Step 11, on a 1.89 mmol scale, to yield 654.3 mg of a mixture of the desired product and cis-6-phenyl-8-hydroxy-1,5,6,10b-tetrahydro-2H-pyrrolo[2,1-a]

isoquinolin-3-one, the product of debromination under the reaction conditions. The crude product was taken on to the next step without purification or characterization.

Step 2. Cis-6-(4-Bromo-phenyl)-8-(3-chloro-propoxy)-1,5,6,10b-tetrahydro-2H-pyrrolo[2,1-a]isoquinolin-3-one. Prepared as described in Example 42, Step 12, on a 1.71 mmol scale, to yield 486.4 mg of a mixture of the desired product and cis-6-phenyl-8-methoxy-1,5,6,10b-tetrahydro-2H-pyrrolo[2,1-a]isoquinolin-3-one. Brominated product: MS: exact mass calcd for $C_{21}H_{21}BrClNO_2$, 433.0; m/z found, 434.0 $[M+H]^+$, 436.0 $[M+H]^+$. Des-bromo product: MS: exact mass calcd for $C_{21}H_{22}ClNO_2$, 355.1; m/z found, 356.0 $[M+H]^+$.

Step 3. Cis-6-(4-Bromo-phenyl)-8-(3-piperidin-1-yl-propoxy)-1,5,6,10b-tetrahydro-2H-pyrrolo[2,1-a]isoquinolin-3-one. Prepared as described in Example 42, Step 13, on a 1.23 mmol scale to yield 308.1 mg of a mixture of the desired product and cis-6-phenyl-8-(3-piperidin-1-yl-propoxy)-1,5,6,10b-tetrahydro-2H-pyrrolo[2,1-a]isoquinolin-3-one.

Step 4. Prepared as described in Example 42, Step 14, on a 0.694 mmol scale. The crude product was divided into two equal portions. One portion was carried forward to prepare the nitrile and the other portion was subjected to reverse-phase HPLC to yield pure des-bromo product (Example 50). The bromo-product was not isolated as a pure substance.

Step 5. Cis-4-[8-(3-Piperidin-1-yl-propoxy)-1,2,3,5,6,10b-hexahydro-pyrrolo[2,1-a]isoquinolin-6-yl]-benzonitrile. To a high-pressure reaction vial was added the product of Step 4 (1.06 mmol), CuCN (1.2 equiv.), and DMF (2.0 M). The sealed vial was heated at 150° C. for 2 d. The mixture was cooled to rt, diluted with aqueous NaCN, and extracted with diethyl ether. The combined organic extracts were combined, washed with water, satd. aq. $NaHCO_3$, and brine, dried ($Na_2CO_3$) and concentrated to give the crude product. The product was purified by reverse-phase HPLC to give 4.7 mg (0.7%) of the desired product as the TFA salt. MS: exact mass calcd for $C_{27}H_{33}N_3O$, 415.3; m/z found, 416.2 $[M+H]^+$. $^1H$ NMR (MeOH-$d_4$): 4.72 (d, J=8.4, 2H), 7.31 (m, 3H), 7.03 (d, J=8.3, 1H), 6.59 (d, J=7.7, 1H), 5.02 (br m, 1H), 4.69 (m, 1H), 4.24 (m, 1H), 4.18 (m, 1H), 3.66 (m, 6H), 3.33 (m, 1H), 3.00 (m, 2H), 2.90 (br s, 1H), 2.32 (m, 2H), 2.19 (m, 2H), 1.98 (m, 2H), 1.81 (m, 4H), 1.55 (m, 1H).

Example 44

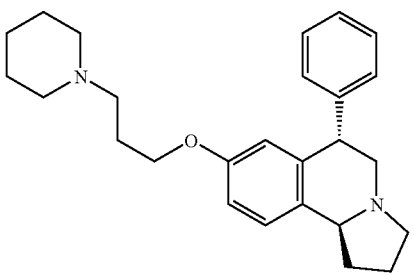

Trans-6-phenyl-8-(3-piperidin-1-yl-propoxy)-1,2,3,5,6,10b-hexahydro-pyrrolo[2,1-a]isoquinoline. Product was isolated by HPLC from the reaction described in Example 42, Step 14 (1.54 mmol scale), to yield 45.4 mg (4%) of the desired product as the TFA salt. MS: exact mass calcd for $C_{26}H_{34}N_2O$, 390.3; m/z found, 391.2 $[M+H]^+$. $^1H$ NMR (MeOH-$d_4$): 7.37 (m, 2H), 7.32 (m, 2H), 7.18 (br s, 1H), 6.98 (br s, 1H), 6.53 (br s, 1H), 4.56 (br s, 1H), 3.98 (br m, 2H), 3.77 (br s, 1H), 3.66 (br s, 1H), 3.53 (d, J=11.7, 2H), 3.48 (br s, 1H), 3.22 (m, 2H), 2.90 (t, J=12.2, 2H), 2.74 (br s, 1H), 2.15 (br m, 5H), 1.90 (d, J=14.0, 2H), 1.77 (m, 3H), 1.48 (m, 1H).

Example 45

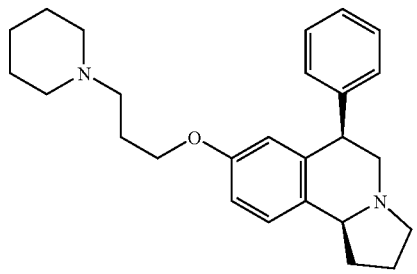

Cis-6-phenyl-8-(3-piperidin-1-yl-propoxy)-1,2,3,5,6,10b-hexahydro-pyrrolo[2,1-a]isoquinoline. Prepared as described in Example 42, Step 14, 0.694 mmol scale, to yield 15.3 mg (3%) of the desired product as the TFA salt. $^1H$ NMR (MeOH-$d_4$): 7.34 (m, 5H), 7.14 (d, J=7.2, 2H), 7.02 (d, J=8.2, 1H), 6.62 (d, J=7.7, 1H), 5.08 (m, 1H), 4.57 (m, 1H), 4.22 (m, 2H), 3.74 (m, 1H), 3.64 (m, 3H), 3.54 (m, 1H), 3.30 (m, 3H), 3.01 (m, 2H), 2.90 (m, 1H), 2.34 (m, 2H), 2.20 (m, 2H), 2.05 (m, 3H), 1.85 (m, 3H), 1.56 (m, 1H), 1.04 (m, 1H).

Example 46

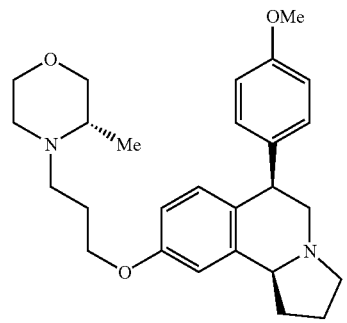

Cis-6-(4-Methoxy-phenyl)-9-[3-(3S-methyl-morpholin-4-yl)-propoxy]-1,2,3,5,6,10b-hexahydro-pyrrolo[2,1-a]isoquinoline Prepared as described in Example 38, Step 8, using (3S)-methylmorpholine, to give 62.0 mg (12%) of the desired product as the TFA salt. MS: exact mass calcd for $C_{27}H_{36}N_2O_3$, 436.3; m/z found, 437.5 $[M+H]^+$. $^1H$ NMR (MeOH-$d_4$): 7.15 (d, J=8.5, 2H), 6.94 (d, J=8.5, 2H), 6.87 (br d, J=2.0, 1H), 6.80 (dd, J=2.0, 8.8, 1H), 6.72 (d, J=8.5, 1H), 4.84 (m, 1H), 4.33 (dd, J=4.5, 12.0, 1H), 4.11 (t, J=5.5, 2H), 4.00 (m, 2H), 3.85 (m, 2H), 3.79 (s, 3H), 3.56 (m, 4H), 3.31 (m, 6H), 2.82 (m, 1H), 2.27 (m, 5H), 1.33 (d, J=6.5, 3H).

Example 47

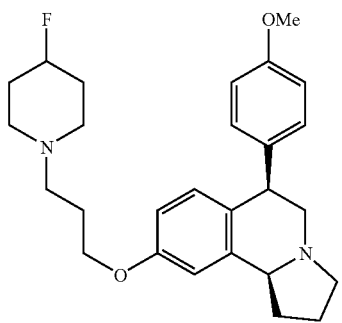

Cis-9-[3-(4-Fluoro-piperidin-1-yl)-propoxy]-6-(4-methoxy-phenyl)-1,2,3,5,6,10b-hexahydro-pyrrolo[2,1-a]isoquinoline Prepared as described in Example 38, Step 8, using 4-fluoropiperidine, to give 77.7 mg (14%) of the desired product as the TFA salt. MS: exact mass calcd for $C_{27}H_{35}FN_2O_2$, 438.3; m/z found, 439.3 [M+H]$^+$. $^1$H NMR (MeOH-d$_4$): 7.15 (d, J=8.5, 2H), 6.94 (d, J=9.0, 2H), 6.87 (d, J=2.5, 1H), 6.79 (dd, J=2.0, 8.8, 1H), 6.72 (d, J=9.0, 1H), 4.98 (m, 1H), 4.84 (m, 1H), 4.34 (dd, J=4.5, 12.0, 1H), 4.09 (t, J=6.0, 2H), 3.86 (m, 1H), 3.79 (s, 3H), 3.68 (m, 1H), 3.56 (m, 2H), 3.32 (m, 6H), 2.82 (m, 1H), 2.24 (m, 8H).

Example 48(A-B)

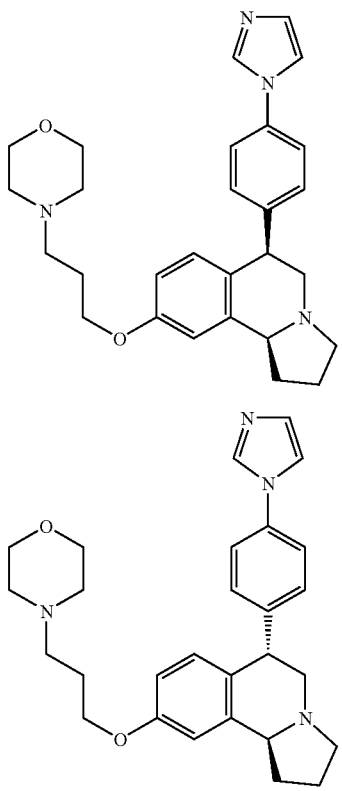

48A: Cis-6-(4-Imidazol-1-yl-phenyl)-9-(3-morpholin-4-yl-propoxy)-1,2,3,5,6,10b-hexahydro-pyrrolo[2,1-a]isoquinoline 48B: Trans-6-(4-Imidazol-1-yl-phenyl)-9-(3-morpholin-4-yl-propoxy)-1,2,3,5,6,10b-hexahydro-pyrrolo[2,1-a]isoquinoline Step 1. 1-(4-Imidazol-1-yl-phenyl)-2-{2-[3-(3-morpholin-4-yl-propoxy)-phenyl]-pyrrolidin-1-yl}-ethanone. Prepared as described in Example 8, Step 1, on a 3.44 mmol scale, to give 1.77 g (>100%) of crude product. MS: exact mass calcd for $C_{28}H_{34}N_4O_3$, 474.3; m/z found, 475.5 [M+H]$^+$.

Step 2. 6-(4-Imidazol-1-yl-phenyl)-9-(3-morpholin-4-yl-propoxy)-2,3-dihydro-1H-pyrrolo[2,1-a]isoquinolinylium. Prepared as described in Example 17, Step 2, on a 3.43 mmol scale, to give 1.60 g (95%) of crude product. MS: exact mass calcd for $C_{28}H_{31}N_4O_2^+$, 455.2; m/z found, 455.5 [M]$^+$.

Step 3. Prepared as described in Example 17, Step 3, on a 3.43 mmol scale, to give 579 mg (37%) of 48A and 63 mg (4%) of 48B after column chromatography and HPLC.

48A: Cis-6-(4-Imidazol-1-yl-phenyl)-9-(3-morpholin-4-yl-propoxy)-1,2,3,5,6,10b-hexahydro-pyrrolo[2,1-a]isoquinoline. MS: exact mass calcd for $C_{26}H_{33}N_4O_2$, 458.3; m/z found, 459.5 [M+H]$^+$. $^1$H NMR (MeOH-d$_4$): 9.52 (s, 1H), 8.10 (s, 1H), 7.79 (m, 3H), 7.57 (d, J=8.4, 2H), 6.93 (d, J=2.4, 1H), 6.82 (dd, J=1.8, 8.4, 1H), 6.71 (d, J=8.4, 1H), 4.92 (t, J=7.2, 1H), 4.61 (dd, J=4.2, 12.0, 1H), 4.12 (t, J=6.0, 2H), 4.05 (d, J=12.0, 2H), 3.92 (m, 1H), 3.82 (t, J=12.0, 2H), 3.69 (dd, J=4.8, 11.7, 1H), 3.57 (d, J=12.6, 2H), 3.51 (t, J=12.0, 1H), 3.45 (m, 1H), 3.39 (t, J=7.8, 2H), 3.18 (m, 2H), 2.87 (m, 1H), 2.30 (br m, 5H).

48B: Trans-6-(4-Imidazol-1-yl-phenyl)-9-(3-morpholin-4-yl-propoxy)-1,2,3,5,6,10b-hexahydro-pyrrolo[2,1-a]isoquinoline MS: exact mass calcd for $C_{26}H_{33}N_4O_2$, 458.3; m/z found, 459.5 [M+H]$^+$. $^1$H NMR (MeOH-d$_4$): 9.47 (s, 1H), 8.06 (s, 1H), 7.77 (s, 1H), 7.73 (d, J=6.0, 2H), 7.44 (br s, 2H), 6.93 (m, 3H), 4.71 (br s, 1H), 4.15 (t, J=5.4, 2H), 4.07 (d, J=12.0, 2H), 3.82 (m, 4H), 3.58 (d, J=11.4, 2H), 3.40 (t, J=7.8, 2H), 3.21 (br m, 2H), 2.82 (br s, 1H), 2.29 (m, 2H), 2.19 (br s, 2H).

Example 49

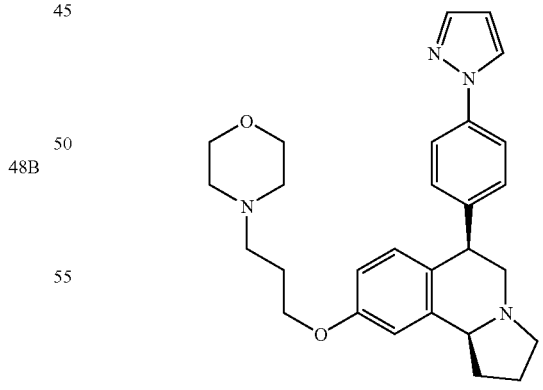

Cis-9-(3-Morpholin-4-yl-propoxy)-6-(4-pyrazol-1-yl-phenyl)-1,2,3,5,6,10b-hexahydro-pyrrolo[2,1-a]isoquinoline Step 1. 2-{2-[3-(3-Morpholin-4-yl-propoxy)-phenyl]-pyrrolidin-1-yl}-1-(4-pyrazol-1-yl-phenyl)-ethanone. Prepared as described in Example 8, Step 1, on a 3.44 mmol scale, to give 1.91 g (>100%) of crude product. MS: exact mass calcd for $C_{28}H_{34}N_4O_3$, 474.3; m/z found, 475.5 [M+H]$^+$.

Step 2. 9-(3-Morpholin-4-yl-propoxy)-6-(4-pyrazol-1-yl-phenyl)-2,3-dihydro-1H-pyrrolo[2,1-a]isoquinolinylium. Prepared as described in Example 17, Step 2, on a 3.44 mmol scale, to give 1.56 g (92%) of crude product. MS: exact mass calcd for $C_{28}H_{31}N_4O_2^+$, 455.2; m/z found, 455.5 [M]+.

Step 3. Prepared as described in Example 17, Step 3, on a 3.17 mmol scale, to give 135 mg (9%) of the desired product after column chromatography and recrystallization from hot IPA. 1H NMR (CDCl3): 7.86 (d, J=2.0, 1H), 7.69 (d, J=1.6, 1H), 7.56 (d, J=6.8, 2H), 7.30 (d, J=8.4, 2H), 6.81 (d, J=8.4, 1H), 6.69 (d, J=2.4, 1H), 6.65 (dd, J=2.8, 8.4, 1H), 6.42 (m, 1H), 4.15 (t, J=4.8, 1H), 3.99 (t, J=6.4, 2H), 3.72 (m, 4H), 3.46 (m, 1H), 3.02 (dd, J=4.8, 11.2, 1H), 2.96 (m, 1H), 2.86 (dd, J=4.8, 11.0, 1H), 2.61-2.46 (br m, 8H), 2.34 (m, 1H), 1.95 (m, 3H), 1.82 (m, 2H).

Example 50(A-B)

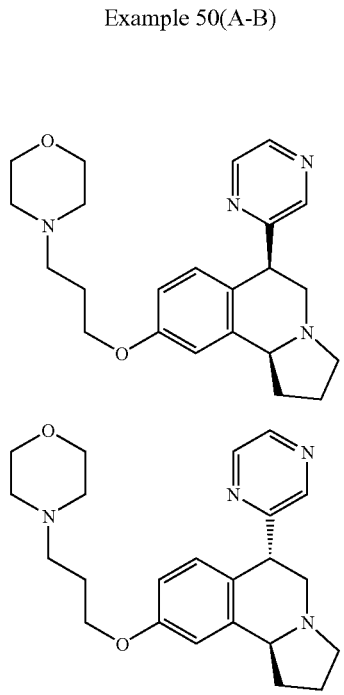

50A: Cis-9-(3-Morpholin-4-yl-propoxy)-6-pyrazin-2-yl-1,2,3,5,6,10b-hexahydro-pyrrolo[2,1-a]isoquinoline 50B: Trans-9-(3-Morpholin-4-yl-propoxy)-6-pyrazin-2-yl-1,2,3,5,6,10b-hexahydro-pyrrolo[2,1-a]isoquinoline Step 1. 2-{2-[3-(3-Morpholin-4-yl-propoxy)-phenyl]-pyrrolidin-1-yl}-1-pyrazin-2-yl-ethanone. Prepared as described in Example 8, Step 1, on a 3.43 mmol scale, to give 1.40 g (>100%) of crude product. MS: exact mass calcd for $C_{23}H_{30}N_4O_3$, 410.2; m/z found, 411.4 [M+H]+.

Step 2. 9-(3-Morpholin-4-yl-propoxy)-6-pyrazin-2-yl-2,3-dihydro-1H-pyrrolo[2,1-a]isoquinolinylium. Prepared as described in Example 17, Step 2, on a 3.43 mmol scale, to give the crude product. MS: exact mass calcd for $C_{23}H_{27}N_4O_2^+$, 391.2; m/z found, 391.5 [M]+.

Step 3. Prepared as described in Example 17, Step 3, on a 3.17 mmol scale, to give 155 mg (11%) of product A and 23 mg (2%) of product B after column chromatography and HPLC.

50A: Cis-9-(3-Morpholin-4-yl-propoxy)-6-pyrazin-2-yl-1,2,3,5,6,10b-hexahydro-pyrrolo[2,1-a]isoquinoline. MS: exact mass calcd for $C_{23}H_{30}N_4O_2$, 394.2; m/z found, 395.5 [M+H]+. 1H NMR (MeOH-d4): 8.48 (d, J=1.8, 1H), 8.37 (d, J=2.4, 1H), 8.32 (d, J=0.6, 1H), 6.77 (d, J=8.4, 1H), 6.73 (d, J=2.4, 1H), 6.67 (dd, J=2.4, 8.4, 1H), 4.31 (t, J=4.2, 1H), 3.97 (m, 2H), 3.65 (m, 4H), 3.37 (dd, J=7.2, 9.9, 1H), 3.21 (dd, J=4.2, 11.4, 1H), 2.89 (m, 2H), 2.49 (t, J=7.8, 2H), 2.43 (br s, 4H), 2.34 (m, 1H), 1.91 (m, 3H), 1.83-1.73 (m, 2H).

50B: Trans-9-(3-Morpholin-4-yl-propoxy)-6-pyrazin-2-yl-1,2,3,5,6,10b-hexahydro-pyrrolo[2,1-a]isoquinoline. MS: exact mass calcd for $C_{23}H_{30}N_4O_2$, 394.2; m/z found, 395.5 [M+H]+. 1H NMR (MeOH-d4): 8.53 (d, J=1.2, 1H), 8.36 (d, J=2.4, 1H), 7.97 (d, J=1.2, 1H), 7.25 (m, 1H), 6.84 (d, J=7.8, 1H), 6.78 (d, J=8.4, 1H), 4.40 (d, J=4.2, 1H), 4.03 (t, J=6.0, 1H), 3.91 (m, 1H), 3.70 (m, 2H), 3.62 (m, 4H), 3.29 (m, 1H), 3.25 (m, 1H), 2.84 (m, 2H), 2.53 (m, 1H), 2.47 (br s, 1H), 2.40 (m, 1H), 2.30 (m, 5H), 1.96 (m, 3H), 1.84 (m, 2H), 1.73 (m, 1H), 1.61 (m, 1H), 1.56 (m, 1H).

Example 51(A-B)

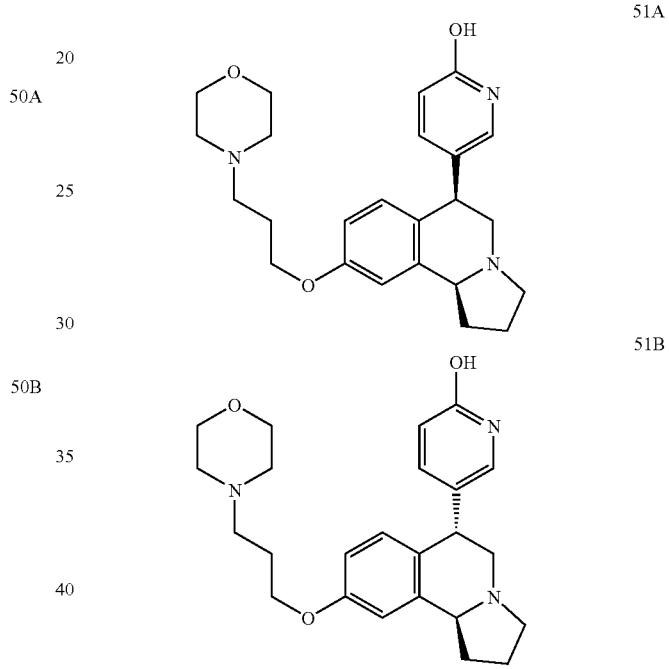

51A: Cis-5-[9-(3-Morpholin-4-yl-propoxy)-1,2,3,5,6,10b-hexahydro-pyrrolo[2,1-a]isoquinolin-6-yl]-pyridin-2-ol 51B: Trans-5-[9-(3-Morpholin-4-yl-propoxy)-1,2,3,5,6,10b-hexahydro-pyrrolo[2,1-a]isoquinolin-6-yl]-pyridin-2-ol Step 1. 1-(6-Hydroxy-pyridin-3-yl)-2-{2-[3-(3-morpholin-4-yl-propoxy)-phenyl]-pyrrolidin-1-yl}-ethanone. Prepared as described in Example 8, Step 1, on a 3.44 mmol scale, to give 590 mg (40%) of product after column chromatography. MS: exact mass calcd for $C_{24}H_{31}N_3O_4$, 425.2; m/z found, 426.5 [M+H]+. 1H NMR (acetone-d6): 8.37 (d, J=2.4, 1H), 7.82 (dd, J=3.0, 9.6, 1H), 7.22 (t, J=7.8, 1H), 6.96 (m, 2H), 6.79 (m, 1H), 6.34 (d, J=10.2, 1H), 4.03 (m, 2H), 3.78 (d, J=14.4, 1H), 3.60 (m, 4H), 3.41 (t, J=8.4, 1H), 3.27 (m, 1H), 3.25 (d, J=14.4, 1H), 2.47 (t, J=6.6, 2H), 2.38 (m, 5H), 2.19 (m, 1H), 1.92 (m, 3H), 1.84 (m, 1H), 1.73 (m, 1H).

Step 2. 6-(6-Hydroxy-pyridin-3-yl)-9-(3-morpholin-4-yl-propoxy)-2,3-dihydro-1H-pyrrolo[2,1-a]isoquinolinylium. Prepared as described in Example 17, Step 2, on a 1.32 mmol scale, to give 230 mg (40%) of crude product. MS: exact mass calcd for $C_{24}H_{28}N_3O_3^+$, 406.2; m/z found, 406.5 [M]+.

Step 3. Prepared as described in Example 17, Step 3, on a 0.453 mmol scale, to give 71.9 mg (25%) of 50A and 71.3 mg (25%) of 50B after column chromatography and HPLC.

51A: Cis-5-[9-(3-Morpholin-4-yl-propoxy)-1,2,3,5,6,10b-hexahydro-pyrrolo[2,1-a]isoquinolin-6-yl]-pyridin-2-ol.
MS: exact mass calcd for $C_{24}H_{31}N_3O_3$, 409.2; m/z found, 410.5 [M+H]$^+$. $^1$H NMR (MeOH-d$_4$): 7.37 (s, 1H), 7.21 (d, J=8.4, 1H), 6.68 (m, 3H), 6.40 (d, J=9.6, 1H), 4.67 (m, 1H), 4.11 (dd, J=4.2, 12.0, 1H), 3.91 (t, J=5.4, 2H), 3.86 (br d, J=12.6, 2H), 3.67 (m, 1H), 3.60 (t, J=12.0, 2H), 3.37 (m, 3H), 3.22 (m, 1H), 3.18 (m, 2H), 2.97 (m, 2H), 2.06 (m, 5H), 51B: Trans-5-[9-(3-Morpholin-4-yl-propoxy)-1,2,3,5,6,10b-hexahydro-pyrrolo[2,1-a]isoquinolin-6-yl]-pyridin-2-ol.
MS: exact mass calcd for $C_{24}H_{31}N_3O_3$, 409.2; m/z found, 410.5 [M+H]$^+$. $^1$H NMR (MeOH-d$_4$): 7.32 (br s, 1H), 6.84 (br s, 1H), 6.72 (m, 2H), 6.37 (d, J=9.6, 1H), 4.69 (br s, 1H), 4.18 (br s, 1H), 3.92 (t, J=5.4, 2H), 3.85 (d, J=12.6, 2H), 3.76 (s, 1H), 3.59 (t, J=12.0, 3H), 3.35 (d, J=12.0, 2H), 3.17 (m, 3H), 2.96 (br t, J=11.4, 2H), 2.55 (br s, 1H), 2.05 (m, 2H), 1.94 (br s, 3H).

Example 52

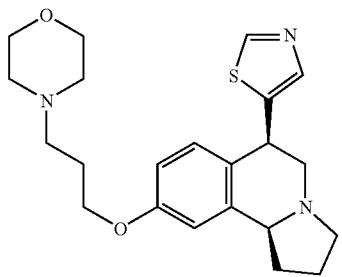

Cis-9-(3-Morpholin-4-yl-propoxy)-6-thiazol-5-yl-1,2,3,5,6,10b-hexahydro-pyrrolo[2,1-a]isoquinoline
Step 1. 2-{2-[3-(3-Morpholin-4-yl-propoxy)-phenyl]-pyrrolidin-1-yl}-1-thiazol-5-yl-ethanone. Prepared as described in Example 8, Step 1, on a 3.44 mmol scale, to give 1.18 g (81%) of product after column chromatography. MS: exact mass calcd for $C_{22}H_{29}N_3O_3S$, 415.2; m/z found, 416.4 [M+H]$^+$. $^1$H NMR (acetone-d$_6$): 9.21 (s, 1H), 8.57 (s, 1H), 7.22 (t, J=7.8, 1H), 7.03 (m, 1H), 6.98 (d, J=7.8, 1H), 6.81 (m, 1H), 5.62 (s, 1H), 4.02 (m, 3H), 3.89 (d, J=16.2, 1H), 3.60 (m, 5H), 3.52 (t, J=8.4, 1H), 3.38 (d, J=15.6, 1H), 3.30 (m, 1H), 2.45 (m, 9H), 2.22 (m, 1H), 1.90 (m, 5H), 1.78 (m, 1H).
Step 2. 9(3-Morpholin-4-yl-propoxy)-6-thiazol-5-yl-2,3-dihydro-1H-pyrrolo[2,1-a]isoquinolinylium. Prepared as described in Example 17, Step 2, on a 2.77 mmol scale, to give 680 mg (57%) of crude product. MS: exact mass calcd for $C_{22}H_{26}N_3O_2S^+$, 396.2; m/z found, 396.4 [M]$^+$.
Step 3. Prepared as described in Example 17, Step 3, on a 1.57 mmol scale, to give 538 mg (86%) of product after column chromatography. MS: exact mass calcd for $C_{22}H_{29}N_3O_2S$, 399.2; m/z found, 400.4 [M+H]$^+$. $^1$H NMR (MeOH-d$_4$): 8.63 (s, 1H), 7.72 (s, 1H), 6.90 (s, 1H), 6.62 (m, 2H), 4.39 (s, 1H), 3.90 (m, 2H), 3.61 (m, 4H), 3.24 (m, 1H), 2.97 (m, 2H), 2.75 (dd, J=4.2, 11.4, 1H), 2.38 (m, 7H), 2.30 (m, 1H), 1.80 (m, 4H), 1.66 (m, 1H).

Example 53

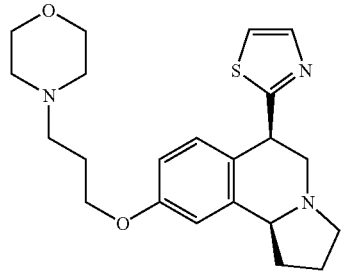

Cis-9-(3-Morpholin-4-yl-propoxy)-6-thiazol-2-yl-1,2,3,5,6,10b-hexahydro-pyrrolo[2,1-a]isoquinoline
Step 1. 2-{2-[3-(3-Morpholin-4-yl-propoxy)-phenyl]-pyrrolidin-1-yl}-1-thiazol-2-yl-ethanone. Prepared as described in Example 8, Step 1, on a 3.44 mmol scale, to give 680 mg (46%) of product after column chromatography. MS: exact mass calcd for $C_{22}H_{29}N_3O_3S$, 415.2; m/z found, 416.4 [M+H]$^+$.
Step 2. 9-(3-Morpholin-4-yl-propoxy)-6-thiazol-2-yl-2,3-dihydro-1H-pyrrolo[2,1-a]isoquinolinylium. Prepared as described in Example 17, Step 2, on a 1.64 mmol scale, to give 1.00 g (>100%) of crude product. MS: exact mass calcd for $C_{22}H_{26}N_3O_2S^+$, 396.2; m/z found, 396.4 [M]$^+$.
Step 3. Prepared as described in Example 17, Step 3, on a 1.64 mmol scale, to give 237 mg (38%) of product after column chromatography. MS: exact mass calcd for $C_{22}H_{29}N_3O_2S$, 399.2; m/z found, 400.4 [M+H]$^+$. $^1$H NMR (MeOH-d$_4$): 7.58 (d, J=3.6, 1H), 7.29 (d, J=3.6, 1H), 7.00 (m, 1H), 6.66 (m, 2H), 4.46 (m, 1H), 3.93 (m, 2H), 3.63 (m, 4H), 3.26 (m, 2H), 2.99 (m, 1H), 2.83 (dd, J=4.2, 11.4, 1H), 2.43 (m, 7H), 2.33 (m, 1H), 1.90 (m, 3H), 1.80 (m, 1H), 1.69 (m, 1H), Example 54

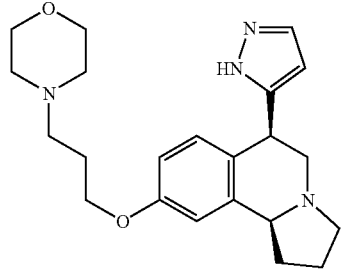

Cis-9-(3-Morpholin-4-yl-propoxy)-6-(2H-pyrazol-3-yl)-1,2,3,5,6,10b-hexahydro-pyrrolo[2,1-a]isoquinoline
Step 1. 2-{2-[3-(3-Morpholin-4-yl-propoxy)-phenyl]-pyrrolidin-1-yl}-1-(2H-pyrazol-3-yl)-ethanone. Prepared as described in Example 8, Step 1, on a 3.44 mmol scale, to give 940 mg (65%) of product after filtration and evaporation to dryness. MS: exact mass calcd for $C_{22}H_{30}N_4O_3$, 398.2; m/z found, 399.5 [M+H]$^+$.
Step 2. 9-(3-Morpholin-4-yl-propoxy)-6-(2H-pyrazol-3-yl)-2,3-dihydro-1H-pyrrolo[2,1-a]isoquinolinylium. Prepared as described in Example 17, Step 2, on a 2.36 mmol scale, to give the crude product. MS: exact mass calcd for $C_{22}H_{27}N_4O_2^+$, 379.2; m/z found, 379.5 [M]$^+$.
Step 3. Prepared as described in Example 17, Step 3, on a 2.36 mmol scale, to give 467 mg (52%) of product after column chromatography. MS: exact mass calcd for $C_{22}H_{30}N_4O_2$, 382.2; m/z found, 383.5 [M+H]$^+$. $^1$H NMR (acetone-d$_6$): 11.56 (br s, 1H), 7.35 (s, 1H), 7.00 (m, 1H), 6.68 (m, 2H), 6.06

(s, 1H), 4.22 (br s, 1H), 4.01 (m, 2H), 3.59 (m, 4H), 3.22 (m, 2H), 3.10 (br m, 1H), 2.76 (dd, J=4.2, 11.1, 1H), 2.45 (t, J=7.2, 2H), 2.37 (m, 6H), 1.98 (m, 1H), 1.90 (t, J=7.2, 2H), 1.88 (m, 1H), 1.75 (m, 1H).

Example 55

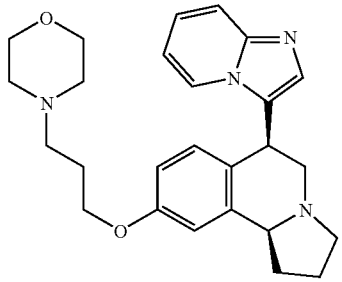

Cis-6-Imidazo[1,2-a]pyridin-3-yl-9-(3-morpholin-4-yl-propoxy)-1,2,3,5,6,10b-hexahydro-pyrrolo[2,1-a]isoquinoline Step 1. 1-Imidazo[1,2-a]pyridin-3-yl-2-{2-[3-(3-morpholin-4-yl-propoxy)-phenyl]-pyrrolidin-1-yl}-ethanone. Prepared as described in Example 8, Step 1, on a 3.44 mmol scale, to give 1.38 g (85%) of product after chromatography. MS: exact mass calcd for $C_{26}H_{32}N_4O_3$, 448.2; m/z found, 449.5 [M+H]$^+$. $^1$H NMR (acetone-d$_6$): 9.55 (d, J=7.0, 1H), 8.44 (s, 1H), 7.73 (d, J=9.0, 1H), 7.60 (m, 1H), 7.21 (m, 2H), 7.02 (d, J=1.5, 1H), 6.97 (d, J=7.5, 1H), 6.77 (dd, J=2.0, 8.2, 1H), 5.62 (s, 1H), 3.99 (m, 2H), 3.92 (d, J=15.0, 1H), 3.58 (m, 4H), 3.52 (t, J=8.5, 1H), 3.38 (m, 1H), 3.37 (d, J=14.5, 1H), 2.49 (m, 1H), 2.45 (t, J=7.0, 2H), 2.38 (br s, 4H), 2.20 (m, 1H), 1.89 (m, 4H), 1.75 (m, 1H).

Step 2. 6-Imidazo[1,2-a]pyridin-3-yl-9-(3-morpholin-4-yl-propoxy)-2,3-dihydro-1H-pyrrolo[2,1-a]isoquinolinylium. Prepared as described in Example 17, Step 2, on a 2.94 mmol scale, to give 1.74 g (>100%) of the crude product. MS: exact mass calcd for $C_{26}H_{29}N_4O_2^+$, 429.2; m/z found, 429.3 [M]$^+$.

Step 3. Prepared as described in Example 17, Step 3, on a 2.94 mmol scale, to give 652 mg (51%) of product after column chromatography. MS: exact mass calcd for $C_{26}H_{35}N_4O_2$, 432.2; m/z found, 433.3 [M+H]$^+$. $^1$H NMR (acetone-d$_6$): 8.57 (m, 1H), 7.48 (m, 1H), 7.23 (s, 1H), 7.12 (m, 1H), 6.87 (d, J=9.0, 1H), 6.70 (m, 3H), 4.67 (m, 1H), 4.02 (m, 2H), 3.59 (m, 4H), 3.26 (m, 2H), 2.97 (m, 1H), 2.87 (m, 2H), 2.46 (t, J=6.6, 2H), 2.37 (m, 6H), 1.85 (m, 6H).

Example 56

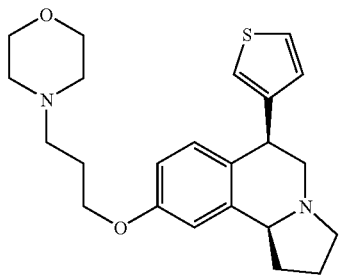

Cis-9-(3-Morpholin-4-yl-propoxy)-6-thiophen-3-yl-1,2,3,5,6,10b-hexahydro-pyrrolo[2,1-a]isoquinoline Step 1. 2-{2-[3-(3-Morpholin-4-yl-propoxy)-phenyl]-pyrrolidin-1-yl}-1-thiophen-3-yl-ethanone. Prepared as described in Example 8, Step 1, on a 3.44 mmol scale, to give 1.58 g (>100%) of the crude product. MS: exact mass calcd for $C_{23}H_{30}N_2O_3S$, 414.2; m/z found, 415.4 [M+H]$^+$.

Step 2. 9-(3-Morpholin-4-yl-propoxy)-6-thiophen-3-yl-2,3-dihydro-1H-pyrrolo[2,1-a]isoquinolinylium. Prepared as described in Example 17, Step 2, on a 3.44 mmol scale, to give 1.34 g (99%) of the crude product. MS: exact mass calcd for $C_{23}H_{30}N_2O_3S^+$, 395.2; m/z found, 395.4 [M+H]$^+$.

Step 3. Prepared as described in Example 17, Step 3, on a 3.39 mmol scale, to give 612 mg (38%) of product after column chromatography. MS: exact mass calcd for $C_{23}H_{30}N_2O_2S$, 398.2; m/z found, 399.4 [M+H]$^+$. $^1$H NMR (500 MHz, MeOH-d$_4$): 7.47 (m, 1H), 7.39 (m, 1H), 6.94 (m, 1H), 6.91 (m, 1H), 6.80 (m, 2H), 4.60 (m, 1H), 4.11 (m, 2H), 4.05 (m, 2H), 3.83 (m, 3H), 3.57 (m, 3H), 3.49 (m, 1H), 3.37 (m, 4H), 3.18 (m, 2H), 2.84 (m, 1H), 2.26 (m, 5H).

Example 57

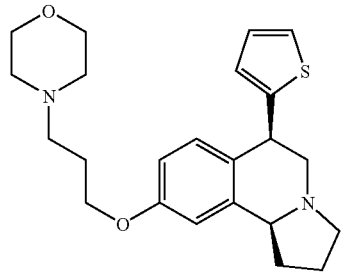

Cis-9-(3-Morpholin-4-yl-propoxy)-6-thiophen-2-yl-1,2,3,5,6,10b-hexahydro-pyrrolo[2,1-a]isoquinoline Step 1. 2-{2-[3-(3-Morpholin-4-yl-propoxy)-phenyl]-pyrrolidin-1-yl}-1-thiophen-2-yl-ethanone. Prepared as described in Example 8, Step 1, on a 3.44 mmol scale, to give 1.83 g (>100%%) of the crude product. MS: exact mass calcd for $C_{23}H_{30}N_2O_3S$, 414.2; m/z found, 415.4 [M+H]$^+$.

Step 2. 9-(3-Morpholin-4-yl-propoxy)-6-thiophen-2-yl-2,3-dihydro-1H-pyrrolo[2,1-a]isoquinolinylium. Prepared as described in Example 17, Step 2, on a 3.44 mmol scale, to give 1.50 g (>100%) of the crude product. MS: exact mass calcd for $C_{23}H_{30}N_2O_3S^+$, 395.2; m/z found, 395.4 [M+H]$^+$.

Step 3. Prepared as described in Example 17, Step 3, on a 3.44 mmol scale, to give 370 mg (17% over 3 steps) of product after column chromatography. MS: exact mass calcd for $C_{23}H_{30}N_2O_2S$, 398.2; m/z found, 399.5 [M+H]$^+$. $^1$H NMR (500 MHz, acetone-d$_6$): 7.50 (m, 1H), 7.16 (m, 1H), 7.11 (m, 1H), 6.93 (d, J=2.5, 1H), 6.87 (d, J=8.7, 1H), 6.82 (dd, J=2.5, 8.7, 1H), 4.93 (m, 2H), 4.13 (t, J=6.0, 2H), 3.96 (m, 5H), 3.78 (dd, J=4.6, 12.0, 1H), 3.61 (d, J=12.2, 2H), 3.44 (m, 4H), 3.19 (m, 2H), 2.89 (m, 1H), 2.30 (m, 5H).

Example 58

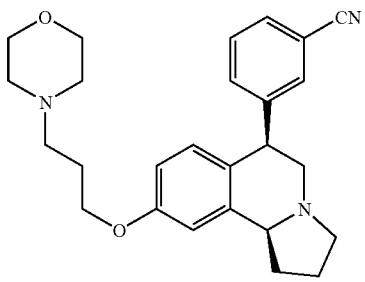

Cis-3-[9-(3-Morpholin-4-yl-propoxy)-1,2,3,5,6,10b-hexahydro-pyrrolo[2,1-a]isoquinolin-6-yl]-benzonitrile Step 1. 3-(2-{2-[3-(3-Morpholin-4-yl-propoxy)-phenyl]-pyrrolidin-1-yl}-acetyl)-benzonitrile. Prepared as described in Example 8, Step 1, on a 1.72 mmol scale, to give 0.86 g (>100%) of the crude product. MS: exact mass calcd for $C_{26}H_{31}N_3O_3$, 433.2; m/z found, 434.5 [M+H]$^+$.

Step 2. 6-(3-Cyano-phenyl)-9-(3-morpholin-4-yl-propoxy)-2,3-dihydro-1H-pyrrolo[2,1-a]isoquinolinylium. Prepared as described in Example 17, Step 2, on a 1.72 mmol scale, to give 0.81 g (>100%) of the crude product. MS: exact mass calcd for $C_{26}H_{28}N_3O_2^+$, 414.2; m/z found, 414.5 [M+H]$^+$.

Step 3. Prepared as described in Example 17, Step 3, on a 1.72 mmol scale, to give 70 mg (6% over 3 steps) of product after column chromatography. MS: exact mass calcd for $C_{26}H_{31}N_3O_2$, 417.2; m/z found, 418.5 [M+H]$^+$. $^1$H NMR (500 MHz, acetone-d$_6$): 7.77 (m, 1H), 7.67 (m, 3H), 6.96 (m, 1H), 6.79 (dd, J=2.5, 8.7, 1H) 6.62 (d, J=8.6, 1H), 4.93 (m, 1H), 4.73 (m, 1H), 4.13 (t, J=6.0, 2H), 3.94 (m, 5H), 3.72 (m, 1H), 3.59 (m, 3H), 3.40 (m, 3H), 3.14 (m, 2H), 2.89 (m, 1H), 2.33 (m, 5H).

Example 59

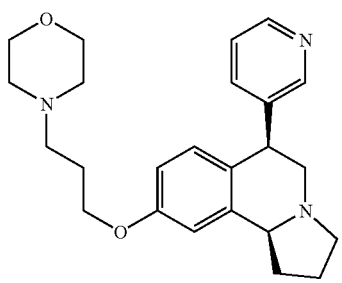

Cis-9-(3-Morpholin-4-yl-propoxy)-6-pyridin-3-yl-1,2,3,5,6,10b-hexahydro-pyrrolo[2,1-a]isoquinoline Step 1. 2-{2-[3-(3-Morpholin-4-yl-propoxy)-phenyl]-pyrrolidin-1-yl}-1-pyridin-3-yl-ethanone. Prepared as described in Example 8, Step 1, on a 3.44 mmol scale, to give 1.52 g (>100%) of the crude product. MS: exact mass calcd for $C_{24}H_{31}N_3O_3$, 409.2; m/z found, 410.5 [M+H]$^+$.

Step 2. 9-(3-Morpholin-4-yl-propoxy)-6-pyridin-3-yl-2,3-dihydro-1H-pyrrolo[2,1-a]isoquinolinylium. Prepared as described in Example 17, Step 2, on a 3.44 mmol scale, to give 1.00 g (75%) of the crude product. MS: exact mass calcd for $C_{24}H_{28}N_3O_2^+$, 390.2; m/z found, 390.4 [M+H]$^+$.

Step 3. Prepared as described in Example 17, Step 3, on a 2.56 mmol scale, to give 285 mg (18%) of product after column chromatography. MS: exact mass calcd for $C_{24}H_{31}N_3O_2$, 393.2; m/z found, 394.5 [M+H]$^+$. $^1$H NMR (500 MHz, acetone-d$_6$): 8.50 (m, 1H), 8.34 (dd, J=1.6, 4.7, 1H), 7.59 (m, 1H), 7.17 (m, 1H), 6.81 (d, J=8.5, 1H), 6.72 (m, 1H), 6.67 (dd, J=2.6, 8.5, 1H), 4.13 (m, 1H), 4.01 (m, 2H), 3.58 (m, 4H), 3.15 (m, 1H), 3.07 (m, 1H), 2.92 (m, 1H), 2.80 (m, 1H), 2.38 (m, 8H), 1.88 (m, 4H), 1.74 (m, 1H).

Example 60

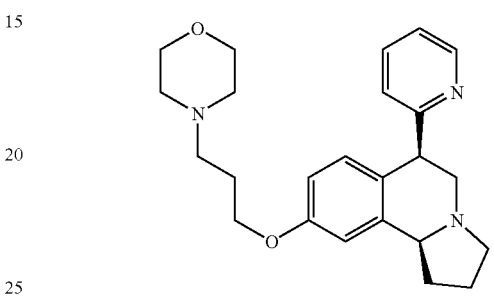

Cis-9-(3-Morpholin-4-yl-propoxy)-6-pyridin-2-yl-1,2,3,5,6,10b-hexahydro-pyrrolo[2,1-a]isoquinoline Step 1. 2-{2-[3-(3-Morpholin-4-yl-propoxy)-phenyl]-pyrrolidin-1-yl}-1-pyridin-2-yl-ethanone. Prepared as described in Example 8, Step 1, on a 3.44 mmol scale, to give 1.61 g (>100%) of the crude product. MS: exact mass calcd for $C_{24}H_{31}N_3O_3$, 409.2; m/z found, 410.5 [M+H]$^+$.

Step 2. 9-(3-Morpholin-4-yl-propoxy)-6-pyridin-2-yl-2,3-dihydro-1H-pyrrolo[2,1-a]isoquinolinylium. Prepared as described in Example 17, Step 2, on a 3.44 mmol scale, to give 1.34 g (>100%) of the crude product. MS: exact mass calcd for $C_{24}H_{28}N_3O_2^+$, 390.2; m/z found, 390.5 [M+H]$^+$.

Step 3. Prepared as described in Example 17, Step 3, on a 3.44 mmol scale, to give 200 mg (13% over 3 steps) of product after column chromatography. MS: exact mass calcd for $C_{24}H_{31}N_3O_2$, 393.2; m/z found, 394.5 [M+H]$^+$. $^1$H NMR (500 MHz, acetone-d$_6$): 8.47 (m, 1H), 7.53 (m, 1H), 7.10 (m, 2H), 6.88 (d, J=11.3, 1H), 6.70 (m, 2H), 4.22 (m, 1H), 4.02 (m, 2H), 3.58 (m, 4H), 3.28 (dd, J=2.2, 11.2, 1H), 3.16 (m, 1H), 2.91 (m, 1H), 2.79 (m, 1H), 2.39 (m, 8H), 1.85 (m, 4H), 1.69 (m, 1H).

Example 61

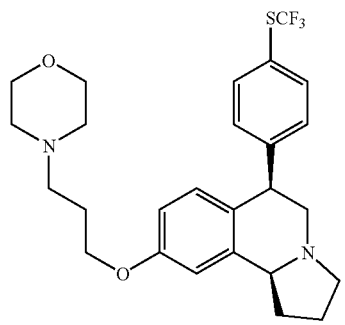

Cis-9-(3-Morpholin-4-yl-propoxy)-6-(4-trifluoromethylsulfanyl-phenyl)-1,2,3,5,6,10b-hexahydro-pyrrolo[2,1-a]isoquinoline Step 1. 2-{2-[3-(3-Morpholin-4-yl-propoxy)-phenyl]-pyrrolidin-1-yl}-1-(4-trifluoromethylsulfanyl-phenyl)-ethanone. Prepared as described in Example 8, Step 1, on a 3.44 mmol scale, to give 2.10 g (>100%) of the crude product. MS: exact mass calcd for $C_{26}H_{28}F_3N_2O_3S$, 508.2; m/z found, 509.4 $[M+H]^+$.

Step 2. 9-(3-Morpholin-4-yl-propoxy)-6-(4-trifluoromethylsulfanyl-phenyl)-2,3-dihydro-1H-pyrrolo[2,1-a]isoquinolinylium. Prepared as described in Example 17, Step 2, on a 3.34 mmol scale, to give 2.30 g (>100%) of the crude product. MS: exact mass calcd for $C_{26}H_{28}F_3N_2O_2S^+$, 489.2; m/z found, 489.4 $[M+H]^+$.

Step 3. Prepared as described in Example 17, Step 3, on a 3.34 mmol scale, to give 568 mg (24% over 3 steps) of product after column chromatography. MS: exact mass calcd for $C_{26}H_{31}F_3N_2O_2S$, 492.2; m/z found, 493.4 $[M+H]^+$. $^1$H NMR (500 MHz, acetone-$d_6$): 7.75 (d, J=8.1, 2H), 7.47 (d, J=8.1, 2H), 6.96 (m, 1H), 6.80 (dd, J=2.5, 8.6, 1H), 6.61 (d, J=10.9, 1H), 4.93 (m, 1H), 4.69 (dd, J=4.6, 12.0, 1H), 4.14 (t, J=6.0, 2H), 3.95 (m, 5H), 3.72 (m, 1H), 3.61 (m, 2H), 3.51 (m, 1H), 3.41 (m, 3H), 3.18 (m, 2H), 2.88 (m, 1H), 2.30 (m, 5H).

Example 62

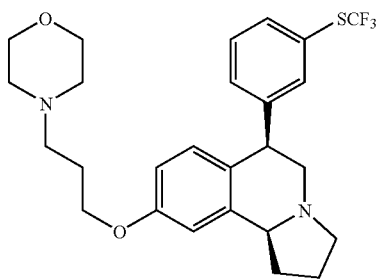

Cis-9-(3-Morpholin-4-yl-propoxy)-6-(3-trifluoromethylsulfanyl-phenyl)-1,2,3,5,6,10b-hexahydro-pyrrolo[2,1-a]isoquinoline Step 1. 2-{2-[3-(3-Morpholin-4-yl-propoxy)-phenyl]-pyrrolidin-1-yl}-1-(3-trifluoromethylsulfanyl-phenyl)-ethanone. Prepared as described in Example 8, Step 1, on a 3.44 mmol scale, to give 2.00 g (>100%) of the crude product. MS: exact mass calcd for $C_{26}H_{31}F_3N_2O_3S$, 508.2; m/z found, 509.4 $[M+H]^+$.

Step 2. 9-(3-Morpholin-4-yl-propoxy)-6-(3-trifluoromethylsulfanyl-phenyl)-2,3-dihydro-1H-pyrrolo[2,1-a]isoquinolinylium. Prepared as described in Example 17, Step 2, on a 3.44 mmol scale, to give 1.80 g (>100%) of the crude product. MS: exact mass calcd for $C_{26}H_{28}F_3N_2O_2S^+$, 489.2; m/z found, 489.4 $[M+H]^+$.

Step 3. Prepared as described in Example 17, Step 3, on a 3.44 mmol scale, to give 247 mg (10% over 3 steps) of product after column chromatography. MS: exact mass calcd for $C_{26}H_{31}F_3N_2O_2S$, 492.2; m/z found, 493.5 $[M+H]^+$. $^1$H NMR (500 MHz, acetone-$d_6$): 7.83 (d, J=16.7, 1H), 7.66 (s, 1H), 7.58 (m, 2H), 6.97 (m, 1H), 6.79 (dd, J=2.6, 8.7, 1H), 6.62 (d, J=8.6, 1H), 4.92 (m, 1H), 4.70 (m, 1H), 4.14 (m, 2H), 3.95 (m, 5H), 3.74 (m, 1H), 3.59 (m, 3H), 3.41 (m, 3H), 3.17 (m, 2H), 2.90 (m, 1H), 2.31 (m, 5H).

Example 63

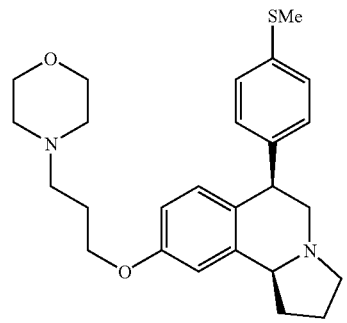

Cis-6-(4-Methylsulfanyl-phenyl)-9-(3-morpholin-4-yl-propoxy)-1,2,3,5,6,10b-hexahydro-pyrrolo[2,1-a]isoquinoline Step 1. 1-(4-Methylsulfanyl-phenyl)-2-{2-[3-(3-morpholin-4-yl-propoxy)-phenyl]-pyrrolidin-1-yl}-ethanone. Prepared as described in Example 8, Step 1, on a 3.44 mmol scale, to give 1.95 g (>100%) of the crude product. MS: exact mass calcd for $C_{26}H_{34}N_2O_3S$, 454.2; m/z found, 455.5 $[M+H]^+$.

Step 2. 6-(4-Methylsulfanyl-phenyl)-9-(3-morpholin-4-yl-propoxy)-2,3-dihydro-1H-pyrrolo[2,1-a]isoquinolinylium. Prepared as described in Example 17, Step 2, on a 3.44 mmol scale, to give 1.45 g (97%) of the crude product. MS: exact mass calcd for $C_{26}H_{31}N_2O_2S^+$, 435.2; m/z found, 435.4 $[M+H]^+$.

Step 3. Prepared as described in Example 17, Step 3, on a 3.33 mmol scale, to give 82 mg (4%) of product after column chromatography. MS: exact mass calcd for $C_{26}H_{34}N_2O_2S$, 438.2; m/z found, 439.5 $[M+H]^+$. $^1$H NMR (500 MHz, acetone-$d_6$): 7.29 (d, J=8.4, 2H), 7.21 (d, J=8.3, 2H), 6.94 (m, 1H), 6.78 (m, 1H), 6.66 (d, J=8.7, 1H), 4.92 (m, 1H), 4.53 (m, 1H), 4.13 (t, J=6.0, 2H), 3.94 (m, 5H), 3.63 (m, 3H), 3.43 (m, 4H), 3.16 (m, 2H), 2.89 (m, 1H), 2.49 (s, 3H), 2.30 (m, 5H).

Example 64

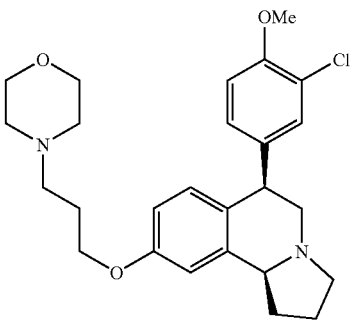

Cis-6-(3-Chloro-4-methoxy-phenyl)-9-(3-morpholin-4-yl-propoxy)-1,2,3,5,6,10b-hexahydro-pyrrolo[2,1-a]isoquinoline Step 1. 1-(3-Chloro-4-methoxy-phenyl)-2-{2-[3-(3-morpholin-4-yl-propoxy)-phenyl]-pyrrolidin-1-yl}-ethanone. Prepared as described in Example 8, Step 1, on a 3.44 mmol scale, to give 1.92 g (>100%) of the crude product. MS: exact mass calcd for $C_{26}H_{33}ClN_2O_4$, 472.2; m/z found, 473.5 $[M+H]^+$.

Step 2. 6-(3-Chloro-4-methoxy-phenyl)-9-(3-morpholin-4-yl-propoxy)-2,3-dihydro-1H-pyrrolo[2,1-a]isoquinolinylium. Prepared as described in Example 17, Step 2, on a 3.44 mmol scale, to give 1.85 g (>100%) of the crude product. MS: exact mass calcd for $C_{26}H_{30}ClN_2O_3^+$, 453.2; m/z found, 453.4 $[M+H]^+$.

Step 3. Prepared as described in Example 17, Step 3, on a 3.44 mmol scale, to give 340 mg (14% over 3 steps) of product after column chromatography. MS: exact mass calcd for $C_{26}H_{33}ClN_2O_3$, 456.2; m/z found, 457.5 $[M+H]^+$. $^1$H NMR (500 MHz, acetone-$d_6$): 7.26 (m, 2H), 7.14 (d, J=8.4, 1H), 6.94 (m, 1H), 6.79 (dd, J=2.5, 8.7, 1H), 6.68 (d, J=8.7, 1H), 4.91 (m, 1H), 4.53 (dd, J=4.6, 12.1, 1H), 4.13 (t, J=6.0, 2H), 3.99 (m, 2H), 3.90 (m, 7H), 3.64 (m, 3H), 3.50 (m, 1H), 3.40 (m, 3H), 3.17 (m, 2H), 2.88 (m, 1H), 2.34 (m, 5H), 2.25 (m, 1H).

Example 65

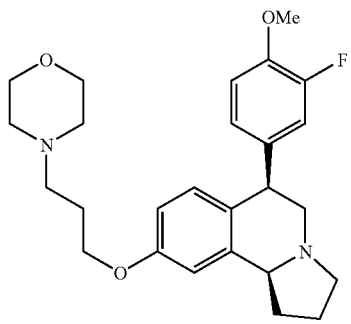

Cis-6-(3-Fluoro-4-methoxy-phenyl)-9-(3-morpholin-4-yl-propoxy)-1,2,3,5,6,10b-hexahydro-pyrrolo[2,1-a]isoquinoline Step 1. 1-(3-Chloro-4-fluoro-phenyl)-2-{2-[3-(3-morpholin-4-yl-propoxy)-phenyl]-pyrrolidin-1-yl}-ethanone. Prepared as described in Example 8, Step 1, on a 3.44 mmol scale, to give 1.80 g (>100%) of the crude product. MS: exact mass calcd for $C_{26}H_{33}FN_2O_4$, 456.2; m/z found, 457.5 $[M+H]^+$.

Step 2. 6-(3-Fluoro-4-methoxy-phenyl)-9-(3-morpholin-4-yl-propoxy)-2,3-dihydro-1H-pyrrolo[2,1-a]isoquinolinylium. Prepared as described in Example 17, Step 2, on a 3.44 mmol scale, to give 1.50 g (>100%) of the crude product. MS: exact mass calcd for $C_{26}H_{30}FN_2O_3^+$, 437.2; m/z found, 437.4 $[M+H]^+$.

Step 3. Prepared as described in Example 17, Step 3, on a 3.44 mmol scale, to give 415 mg (18% over 3 steps) of product after column chromatography. MS: exact mass calcd for $C_{26}H_{33}FN_2O_3$, 440.3; m/z found, 441.5 $[M+H]^+$. $^1$H NMR (500 MHz, acetone-$d_6$): 7.15 (m, 1H), 7.09 (m, 1H), 7.02 (dd, J=1.9, 12.4, 1H), 6.93 (m, 1H), 6.79 (dd, J=2.5, 8.7, 1H), 6.68 (d, J=8.7, 1H), 4.90 (m, 1H), 4.52 (dd, J=4.5, 12.0, 1H), 4.13 (t, J=6.0, 2H), 3.93 (m, 8H), 3.63 (m, 3H), 3.44 (m, 1H), 3.39 (m, 3H), 3.15 (m, 2H), 2.88 (m, 1H), 2.33 (m, 5H).

Example 66-(A-B)

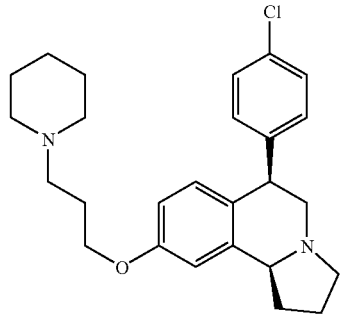

66A

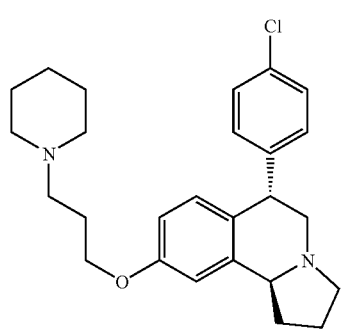

66B

66A: Cis-6-(4-Chloro-phenyl)-9-(3-piperidin-1-yl-propoxy)-1,2,3,5,6,10b-hexahydro-pyrrolo[2,1-a]isoquinoline 66B: Trans-6-(4-chloro-phenyl)-9-(3-piperidin-1-yl-propoxy)-1,2,3,5,6,10b-hexahydro-pyrrolo[2,1-a]isoquinoline Step 1. 1-(4-Chloro-phenyl)-2-{2-[3-(3-piperidin-1-yl-propoxy)-phenyl]-pyrrolidin-1-yl}-ethanol. Prepared as described in Example 1, Step 6, on a 3.47 mmol scale to give 1.70 g (>100%) of the desired product as a mixture of diastereomers. MS: exact mass calcd for $C_{26}H_{35}ClN_2O_2$, 476.3; m/z found, 477.4 $[M+H]^+$.

Step 2. Performed as described in Example 1, Step 7, on a 3.19 mmol scale, to give the desired products 66A and 66B, which were separated by HPLC.

66A: 6-(4-Chloro-phenyl)-9-(3-piperidin-1-yl-propoxy)-1,2,3,5,6,10b-hexahydro-pyrrolo[2,1-a]isoquinoline. 8.0 mg (0.4%) as the TFA salt. MS: exact mass calcd for $C_{26}H_{33}ClN_2O$, 424.2; m/z found, 425.4 $[M+H]^+$. $^1$H NMR (500 MHz, acetone-$d_6$): 7.44 (d, J=8.4, 2H), 7.33 (d, J=8.3, 2H), 6.96 (s, 1H), 6.80 (d, 8.7, 1H), 6.66 (d, J=8.7, 1H), 4.92 (m, 1H), 4.62 (m, 1H), 4.13 (m, 2H), 3.95 (m, 1H), 3.65 (m, 3H), 3.46 (m, 1H), 3.40 (m, 1H), 3.33 (m, 2H), 2.91 (m, 3H), 2.34 (m, 5H), 1.90 (m, 4H), 1.81 (m, 1H), 1.52 (m, 1H).

66B: 6-(4-Chloro-phenyl)-9-(3-piperidin-1-yl-propoxy)-1,2,3,5,6,10b-hexahydro-pyrrolo[2,1-a]isoquinoline. 205 mg (9%) as the TFA salt. MS: exact mass calcd for $C_{26}H_{33}ClN_2O$, 424.2; m/z found, 425.4 $[M+H]^+$. $^1$H NMR (500 MHz, acetone-$d_6$): 7.40 (d, J=8.8, 2H), 7.29 (d, J=8.4, 2H), 6.99 (br s, 1H), 6.86 (dd, J=2.5, 8.6, 1H), 6.82 (d, J=8.7, 1H), 5.14 (br s, 1H), 4.64 (br s, 1H), 4.17 (m, 2H), 3.81 (br s, 1H), 3.65 (m, 4H), 3.53 (br s, 1H), 3.34 (m, 2H), 2.99 (m, 2H), 2.77 (br s, 1H), 2.35-2.32 (m, 2H), 2.20 (m, 2H), 2.10 (m, 1H), 1.92 (m, 4H), 1.80 (m, 1H), 1.54 (m, 1H).

Example 67

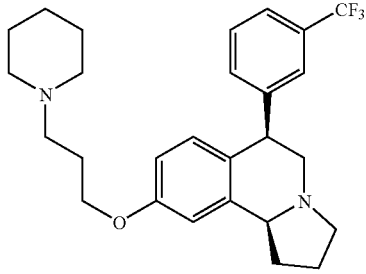

Cis-9-(3-Piperidin-1-yl-propoxy)-6-(3-trifluoromethyl-phenyl)-1,2,3,5,6,10b-hexahydro-pyrrolo[2,1-a]isoquinoline Step 1. 2-{2-[3-(3-Piperidin-1-yl-propoxy)-phenyl]-pyrrolidin-1-yl}-1-(3-trifluoromethyl-phenyl)-ethanol. Prepared as described in Example 1, Step 6, on a 3.47 mmol scale to give 1.52 g (92%) of product. MS: exact mass calcd for $C_{27}H_{35}F_3N_2O_2$, 476.3; m/z found, 477.4 [M+H]$^+$.

Step 2. Performed as described in Example 1, Step 7, on a 3.19 mmol scale to give 36.0 mg (2%) of product after chromatography. MS: exact mass calcd for $C_{27}H_{33}F_3N_2O$, 458.3; m/z found, 459.5 [M+H]$^+$. $^1$H NMR (500 MHz, acetone-d$_6$): 7.90 (m, 1H), 7.82 (m, 3H), 7.13 (s, 1H), 6.95 (d, J=8.6, 1H), 6.78 (d, 8.7, 1H), 5.09 (m, 1H), 4.91 (m, 1H), 4.28 (t, J=5.8, 2H), 3.90 (m, 1H), 3.88 (m, 1H), 3.76 (m, 3H), 3.57 (m, 1H), 3.48 (m, 2H), 3.14 (m, 2H), 3.05 (m, 1H), 2.46 (m, 4H), 2.21 (m, 1H), 2.05 (m, 4H), 1.95 (m, 1H), 1.66 (m, 1H).

The following compounds in Examples 68-87 may be prepared according to the methods described above.

Example 68

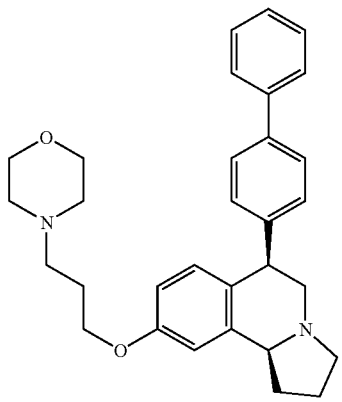

6-Biphenyl-4-yl-9-(3-morpholin-4-yl-propoxy)-1,2,3,5,6,10b-hexahydro-pyrrolo[2,1-a]isoquinoline

Example 69

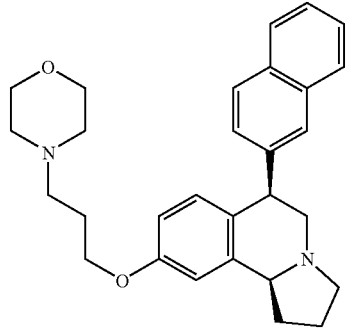

9-(3-Morpholin-4-yl-propoxy)-6-naphthalen-2-yl-1,2,3,5,6,10b-hexahydro-pyrrolo[2,1-a]isoquinoline

Example 70

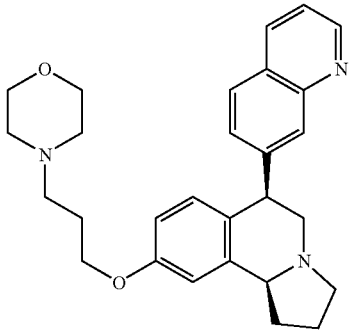

9-(3-Morpholin-4-yl-propoxy)-6-quinolin-7-yl-1,2,3,5,6,10b-hexahydro-pyrrolo[2,1-a]isoquinoline

Example 71

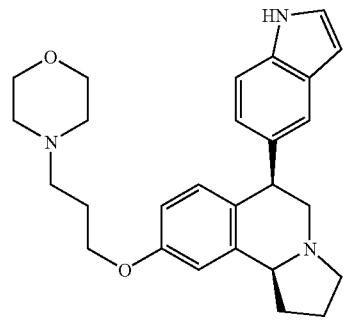

6-(1H-Indol-5-yl)-9-(3-morpholin-4-yl-propoxy)-1,2,3,5,6,10b-hexahydro-pyrrolo[2,1-a]isoquinoline

101
Example 72

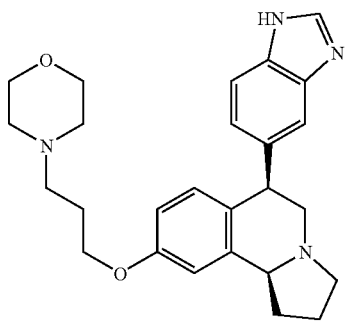

6-(1H-Benzoimidazol-5-yl)-9-(3-morpholin-4-yl-propoxy)-1,2,3,5,6,10b-hexahydro-pyrrolo[2,1-a]isoquinoline

Example 73

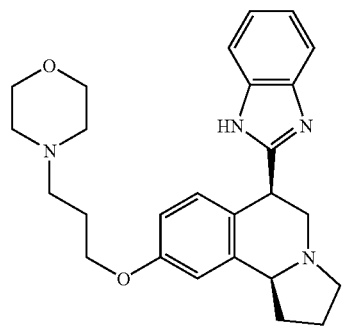

6-(1H-Benzoimidazol-2-yl)-9-(3-morpholin-4-yl-propoxy)-1,2,3,5,6,10b-hexahydro-pyrrolo[2,1-a]isoquinoline

Example 74

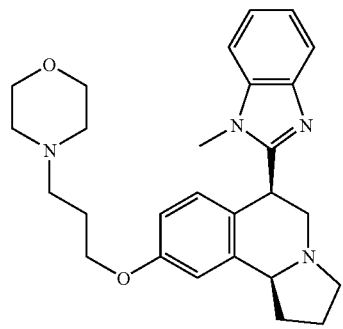

6-(1-Methyl-1H-benzoimidazol-2-yl)-9-(3-morpholin-4-yl-propoxy)-1,2,3,5,6,10b-hexahydro-pyrrolo[2,1-a]isoquinoline

102
Example 75

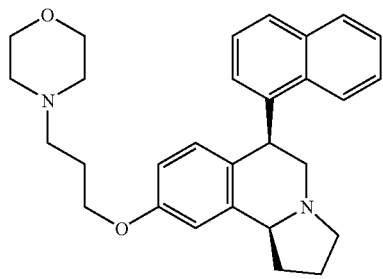

9-(3-Morpholin-4-yl-propoxy)-6-naphthalen-1-yl-1,2,3,5,6,10b-hexahydro-pyrrolo[2,1-a]isoquinoline

Example 76

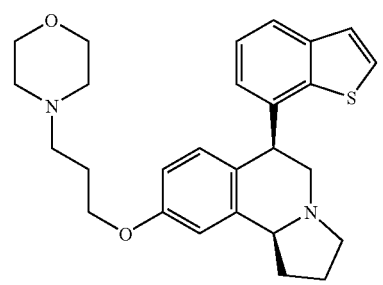

6-Benzo[b]thiophen-7-yl-9-(3-morpholin-4-yl-propoxy)-1,2,3,5,6,10b-hexahydro-pyrrolo[2,1-a]isoquinoline

Example 77

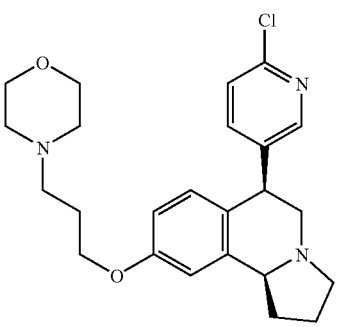

6-(6-Chloro-pyridin-3-yl)-9-(3-morpholin-4-yl-propoxy)-1,2,3,5,6,10b-hexahydro-pyrrolo[2,1-a]isoquinoline Example 78

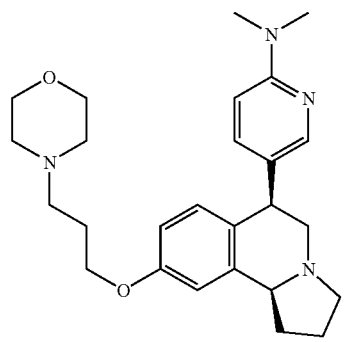

Dimethyl-{5-[9-(3-morpholin-4-yl-propoxy)-1,2,3,5,6,10b-hexahydro-pyrrolo[2,1-a]isoquinolin-6-yl]-pyridin-2-yl}-amine Example 79

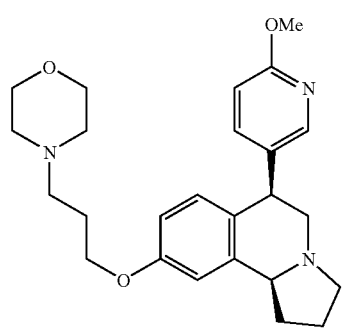

6-(6-Methoxy-pyridin-3-yl)-9-(3-morpholin-4-yl-propoxy)-1,2,3,5,6,10b-hexahydro-pyrrolo[2,1-a]isoquinoline Example 80

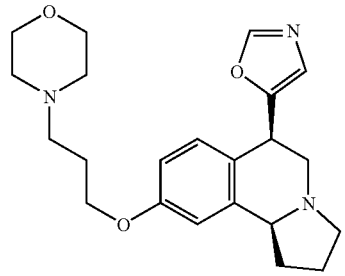

9-(3-Morpholin-4-yl-propoxy)-6-oxazol-5-yl-1,2,3,5,6,10b-hexahydro-pyrrolo[2,1-a]isoquinoline Example 81

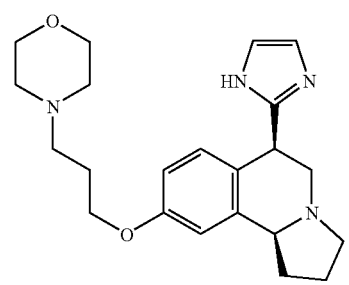

6-(1H-Imidazol-2-yl)-9-(3-morpholin-4-yl-propoxy)-1,2,3,5,6,10b-hexahydro-pyrrolo[2,1-a]isoquinoline Example 82

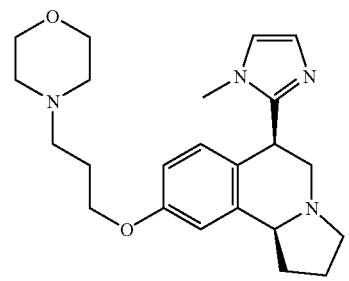

6-(1-Methyl-1H-imidazol-2-yl)-9-(3-morpholin-4-yl-propoxy)-1,2,3,5,6,10b-hexahydro-pyrrolo[2,1-a]isoquinoline Example 83

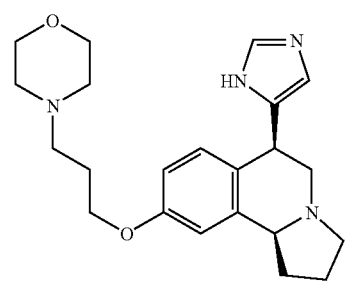

6-(3H-Imidazol-4-yl)-9-(3-morpholin-4-yl-propoxy)-1,2,3,5,6,10b-hexahydro-pyrrolo[2,1-a]isoquinoline

Example 84

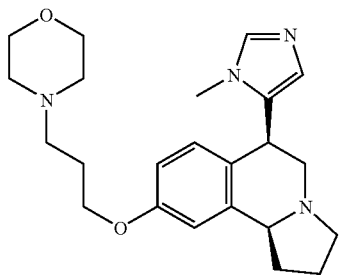

6-(3-Methyl-3H-imidazol-4-yl)-9-(3-morpholin-4-yl-propoxy)-1,2,3,5,6,10b-hexahydro-pyrrolo[2,1-a]isoquinoline

Example 85

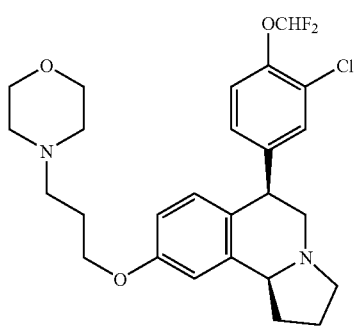

6-(3-Chloro-4-difluoromethoxy-phenyl)-9-(3-morpholin-4-yl-propoxy)-1,2,3,5,6,10b-hexahydro-pyrrolo[2,1-a]isoquinoline

Example 86

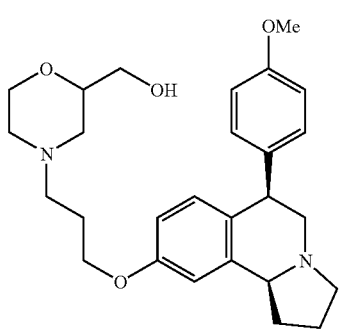

(4-{3-[6-(4-Methoxy-phenyl)-1,2,3,5,6,10b-hexahydro-pyrrolo[2,1-a]isoquinolin-9-yloxy]-propyl}-morpholin-2-yl)-methanol

Example 87

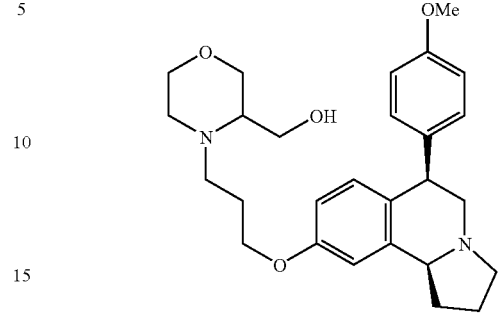

(4-{3-[6-(4-Methoxy-phenyl)-1,2,3,5,6,10b-hexahydro-pyrrolo[2,1-a]isoquinolin-9-yloxy]-propyl}-morpholin-3-yl)-methanol

Example 88

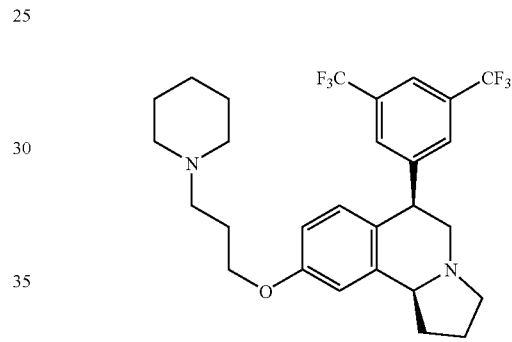

6-(3,5-Bis-trifluoromethyl-phenyl)-9-(3-piperidin-1-yl-propoxy)-1,2,3,5,6,10b-hexahydro-pyrrolo[2,1-a]isoquinoline

Example 89

(1R,6S)-6-(4-Methylsulfanyl-phenyl)-9-(3-morpholin-4-yl-propoxy)-1,2,3,5,6,10b-hexahydro-pyrrolo[2,1-a]isoquinoline Separation of the enantiomers from racemic cis-6-(4-methylsulfanyl-phenyl)-9-(3-morpholin-4-yl-propoxy)-1,2,3,5,6,10b-hexahydro-pyrrolo[2,1-a]isoquinoline gave the title

Example 90

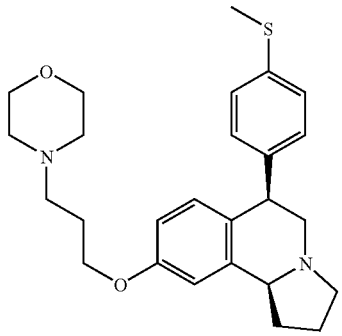

(1S,6R)-6-(4-Methylsulfanyl-phenyl)-9-(3-morpholin-4-yl-propoxy)-1,2,3,5,6,10b-hexahydro-pyrrolo[2,1-a]isoquinoline MS: exact mass calcd for $C_{26}H_{34}N_2O_2S$, 438.23; m/z found, 439.2 [M+H]$^+$.

Example 91

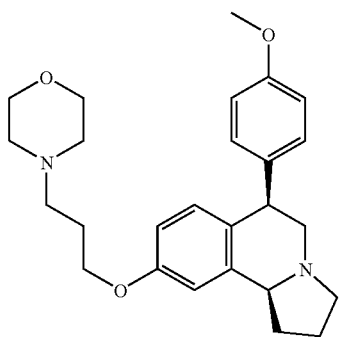

(1S,6R)-6-(4-Methoxy-phenyl)-9-(3-morpholin-4-yl-propoxy)-1,2,3,5,6,10b-hexahydro-pyrrolo[2,1-a]isoquinoline Separation of the enantiomers from racemic cis-6-(4-methoxy-phenyl)-9-(3-morpholin-4-yl-propoxy)-1,2,3,5,6,10b-hexahydro-pyrrolo[2,1-a]isoquinoline gave the title compound and Example 92. MS: exact mass calcd for $C_{26}H_{34}N_2O_3$, 422.26; m/z found, 423.5 [M+H]$^+$.

Example 92

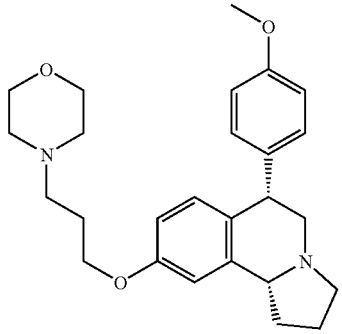

(1R,6S)-6-(4-Methoxy-phenyl)-9-(3-morpholin-4-yl-propoxy)-1,2,3,5,6,10b-hexahydro-pyrrolo[2,1-a]isoquinoline MS: exact mass calcd for $C_{26}H_{34}N_2O_3$, 422.26; m/z found, 423.5 [M+H]$^+$.

Example 93

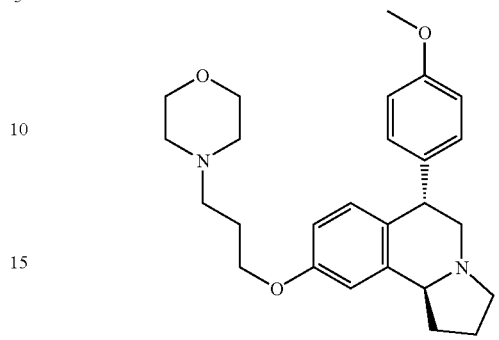

Trans-6-(4-Methoxy-phenyl)-9-(3-morpholin-4-yl-propoxy)-1,2,3,5,6,10b-hexahydro-pyrrolo[2,1-a]isoquinoline The title compound was prepared as described in the preceding examples. The racemic material was separated by chiral HPLC to provide Examples 94 and 95.

MS: exact mass calcd for $C_{26}H_{34}N_2O_3$, 422.26; m/z found, 423.5 [M+H]$^+$.

Example 94

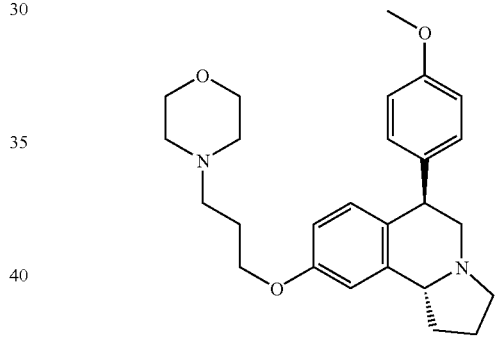

(1R,6R)-6-(4-Methoxy-phenyl)-9-(3-morpholin-4-yl-propoxy)-1,2,3,5,6,10b-hexahydro-pyrrolo[2,1-a]isoquinoline MS: exact mass calcd for $C_{26}H_{34}N_2O_3$, 422.26; m/z found, 423.5 [M+H]$^+$.

Example 95

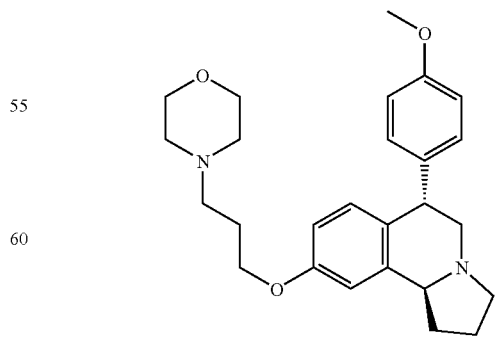

(1S,6S)-6-(4-Methoxy-phenyl)-9-(3-morpholin-4-yl-propoxy)-1,2,3,5,6,10b-hexahydro-pyrrolo[2,1-a]isoquinoline MS: exact mass calcd for $C_{26}H_{34}N_2O_3$, 422.26; m/z found, 423.5 $[M+H]^+$.

Example 96-(A-B)

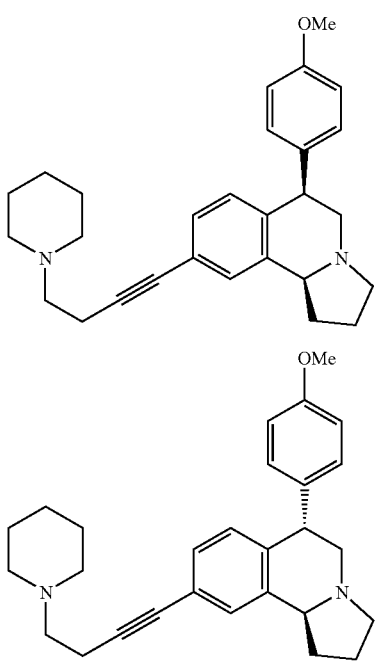

96A: Cis-6-(4-methoxy-phenyl)-9-(4-piperidin-1-yl-but-1-ynyl)-1,2,3,5,6,10b-hexahydro-pyrrolo[2,1-a]isoquinoline 96B: Trans-6-(4-methoxy-phenyl)-9-(4-piperidin-1-yl-but-1-ynyl)-1,2,3,5,6,10b-hexahydro-pyrrolo[2,1-a]isoquinoline Step 1. 5-(3-Bromo-phenyl)-3,4-dihydro-2H-pyrrole. Prepared as described in Example 1, Step 4, on a 0.19 mol scale, using 3 N HCl in place of 12 N HCl during the workup procedure, to give 47.4 g of the desired product. MS (ESI): exact mass calcd for $C_{10}H_{10}BrN$, 223.0; m/z found, 224.0 $[M+H]^+$, 226.0 $[M+H]^+$. $^1$H NMR (500 MHz, DMSO-$d_6$): 8.00 (m, 1H), 7.80 (d, J=7.8 Hz, 1H), 7.65 (m, 1H), 7.41 (m, 1H), 3.97 (t, J=6.9 Hz, 2H), 2.91 (t, J=7.7 Hz, 2H), 1.93 (m, 2H).

Step 2. 2-(3-Bromo-phenyl)-pyrrolidine. A solution of 5-(3-bromo-phenyl)-3,4-dihydro-2H-pyrrole (0.21 mol) in absolute ethanol (1.2 M) was treated portionwise with NaBH$_4$ (1.0 equiv.). The resultant mixture was stirred at room temperature overnight. The mixture was cooled to 0° C. and slowly quenched with 1 N HCl. The mixture was acidified to a pH of 1 with 3 N HCl and was stirred at room temperature for 45 min. The resulting mixture was again cooled to 0° C., and was treated with 1 N NaOH until basic. The aqueous mixture was extracted with CH$_2$Cl$_2$ (×3). The combined extracts were washed with brine, dried (MgSO$_4$), filtered and concentrated to give the crude product. Chromatography (EtOAc/hexanes) gave 39.8 g (84%) of the desired product. MS (ESI): exact mass calcd for $C_{10}H_{12}BrN$, 225.1; m/z found, 226.0 $[M+H]^+$, 228.0 $[M+H]^+$. $^1$H NMR (500 MHz, DMSO-$d_6$): 7.74 (m, 1H), 7.57 (m, 1H), 7.53 (m, 1H), 7.40 (m, 1H), 4.37 (m, 1H), 3.24 (m, 1H), 3.16 (m, 1H), 2.32 (m, 1H), 2.00 (m, 1H), 1.94 (m, 1H), 1.81 (m, 1H).

Step 3. 2-[2-(3-Bromo-phenyl)-pyrrolidin-1-yl]-1-(4-methoxy-phenyl)-ethanone. To a solution of 2-(3-bromo-phenyl)-pyrrolidine (3.8 g, 16.8 mmol) and Hunig's base (5.9 mL, 33.6 mmol) in THF (170 mL) was added 2-bromo-1-(4-methoxy-phenyl)-ethanone (4.6 g, 20.2 mmol). The mixture was stirred at room temperature for 5 h, concentrated, and purified by normal phase column chromatography (NH$_3$ in MeOH/CH$_2$Cl$_2$) to give 4.75 g (75%) of the product as a yellow oil. MS (ESI): exact mass calcd for $C_{19}H_{20}BrNO_2$, 373.1; m/z found, 374.3 $[M+H]^+$, 376.3 $[M+H]^+$. $^1$H NMR (500 MHz, CDCl$_3$): 7.84 (d, J=9.0 Hz, 2H), 7.58 (m, 1H), 7.38 (m, 1H), 7.31 (m, 1H), 7.18 (m, 1H), 6.87 (d, J=9.0 Hz, 2H), 3.99 (d, J=15.6 Hz, 1H), 3.85 (s, 3H), 3.50 (t, J=8.1 Hz, 1H), 3.39 (m, 1H), 2.42 (m, 1H), 2.21 (m, 1H), 1.97 (m, 1H), 1.86 (m, 1H), 1.73 (m, 1H), 1.61 (s, 1H).

Step 4. 2-[2-(3-Bromo-phenyl)-pyrrolidin-1-yl]-1-(4-methoxy-phenyl)-ethanol. Prepared as described in Example 8, Step 2, on a 6.68 mmol scale, to give 2.26 g (90%) of the crude product as a mixture of diastereomers. MS (ESI): exact mass calcd for $C_{19}H_{22}BrNO_2$, 375.1; m/z found, 376.3 $[M+H]^+$, 378.3 $[M+H]^+$.

Step 5. 9-Bromo-6-(4-methoxy-phenyl)-1,2,3,5,6,10b-hexahydro-pyrrolo[2,1-a]isoquinoline and 7-Bromo-6-(4-methoxy-phenyl)-1,2,3,5,6,10b-hexahydro-pyrrolo[2,1-a]isoquinoline. Prepared as described in Example 1, Step 7, to give a 48% combined yield (over 2 steps) of the two regioisomers, each as a set of two diastereomers. MS (ESI): exact mass calcd for $C_{19}H_{20}BrNO$, 357.1, m/z found, 358.3 $[M+H]^+$, 360.3 $[M+H]^+$.

Step 6. Performed on the mixture of isomers from Step 5 as described in Example 33, on a 1.73 mmol scale, using 1-but-3-ynylpiperidine, to give a 20% combined yield of two diastereomers. After HPLC purification, the products were converted from their TFA salts to their corresponding HCl salts by azeotrope (3×) with HCl in dioxane.

96A: Cis-6-(4-methoxy-phenyl)-9-(4-piperidin-1-yl-but-1-ynyl)-1,2,3,5,6,10b-hexahydro-pyrrolo[2,1-a]isoquinoline. 15.0 mg (2%) as the HCl salt. MS (ESI): exact mass calcd for $C_{26}H_{34}N_2O$, 414.3; m/z found, 415.5 $[M+H]^+$. $^1$H NMR (500 MHz, acetone-$d_6$): 7.45 (br s, 1H), 7.26 (d, J=7.8 Hz, 1H), 7.21 (d, J=8.0 Hz, 2H), 6.98 (d, J=8.0 Hz, 2H), 6.80 (d, J=7.9 Hz, 1H), 4.46 (d, 1H), 3.90 (m, 1H, 3.81 (s, 3H), 3.76 (m, 1H), 3.44 (m, 4H), 3.04 (m, 5H), 2.87 (br s, 1H), 2.22 (m, 3H), 2.00 (m, 3H), 1.86 (m, 4H), 1.56 (m, 1H).

96B: Trans-6-(4-methoxy-phenyl)-9-(4-piperidin-1-yl-but-1-ynyl)-1,2,3,5,6,10b-hexahydro-pyrrolo[2,1-a]isoquinoline. 31.0 mg (4% yield) as the HCl salt. MS (ESI): exact mass calcd for $C_{26}H_{34}N_2O$, 414.3; m/z found, 415.5 $[M+H]^+$.

Example 97-(A-B)

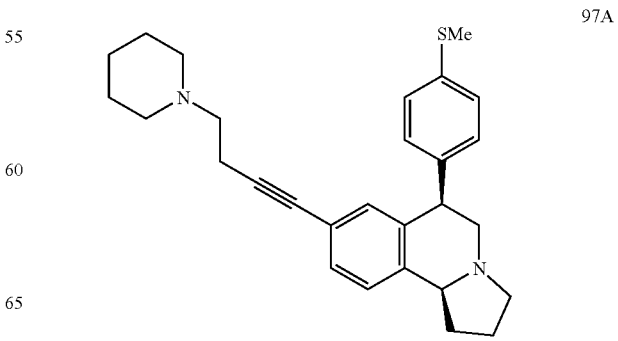

-continued

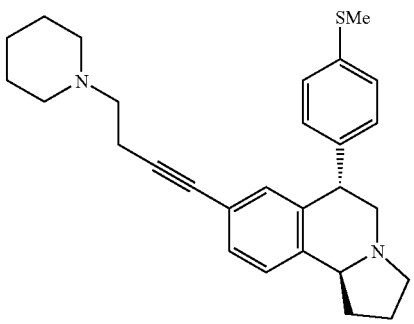

97B

97A: Cis-6-(4-methylsulfanyl-phenyl)-8-(4-piperidin-1-yl-but-1-ynyl)-1,2,3,5,6,10b-hexahydro-pyrrolo[2,1-a]isoquinoline 97B: Trans-6-(4-methylsulfanyl-phenyl)-8-(4-piperidin-1-yl-but-1-ynyl)-1,2,3,5,6,10b-hexahydro-pyrrolo[2,1-a]isoquinoline Step 1. 5-(4-Bromo-phenyl)-3,4-dihydro-2H-pyrrole Prepared as described in Example 39, Step 1, on a 93.0 mmol scale, to give 14.1 g (68%) of the desired product. MS (ESI): exact mass calcd for $C_{10}H_{10}BrN$, 223.0; m/z found, 224.0, 226.0 [M+H]$^+$. $^1$H NMR (400 MHz, DMSO-d$_6$): 7.73 (d, J=8.5 Hz, 2H), 7.60 (d, J=8.5 Hz, 2H), 3.91 (2H), 2.86 (m, 2H), 1.91 (m, 2H).

Step 2. 2-(4-Bromo-phenyl)-pyrrolidine. Prepared as described in Example 39, Step 2, on a 87.2 mmol scale, to give 12.9 g (65%) of the desired product. MS (ESI): exact mass calcd for $C_{10}H_{12}BrN$, 225.0; m/z found, 226.1 [M+H]$^+$, 228.1 [M+H]$^+$. $^1$H NMR (500 MHz, DMSO-d$_6$): 7.44 (m, 2H), 7.30 (d, J=6.6 Hz, 2H), 3.99 (m, 1H), 2.96 (m, 1H), 2.88 (m, 1H), 2.31 (br s, 1H), 2.07 (m, 1H), 1.70 (m, 2H), 1.40 (m, 1H).

Step 3. 1-[2-(4-Bromo-phenyl)-pyrrolidin-1-yl]-2-hydroxy-2-(4-methylsulfanyl-phenyl)-ethanone. A solution of 2-(4-bromo-phenyl)-pyrrolidine (16.8 mmol, 1.0 equiv.) and hydroxy-(4-methylsulfanyl-phenyl)-acetic acid (1.0 equiv.) in xylenes (0.2 M) was heated at reflux for 3 d under nitrogen. The bulk of the xylenes was removed by distillation and the residue was purified by chromatography to give the desired product as a mixture of diastereomers (5.22 g, 77%). MS (ESI): exact mass calcd for $C_{19}H_{20}BrNO_2S$, 405.0; m/z found, 406.0 [M+H]$^+$, 408.0 [M+H]$^+$.

Step 4. Cis- and Trans-8-bromo-6-(4-methylsulfanyl-phenyl)-2,3,6,10b-tetrahydro-1H-pyrrolo[2,1-a]isoquinolin-5-one. A solution of amide from Step 3 (12.1 mmol) and polyphosphoric acid (5 g/g amide) was heated at 105° C. under nitrogen until the starting material was consumed (2 h). The reaction mixture was poured into water and extracted with CH$_2$Cl$_2$ (×2). The combined extracts were washed with satd. aq. NaHCO$_3$ and brine, dried (MgSO$_4$), and concentrated to provide the crude product. The diastereomers were separated by chromatographic purification (EtOAc/Hexanes).

Cis-8-bromo-6-(4-methylsulfanyl-phenyl)-2,3,6,10b-tetrahydro-1H-pyrrolo[2,1-a]isoquinolin-5-one. 1.39 g (30%). MS (ESI): exact mass calcd for $C_{19}H_{18}BrNOS$, 387.0; m/z found, 388.0 [M+H]$^+$, 390.0 [M+H]$^+$. $^1$H NMR (500 MHz, acetone-d$_6$): 7.40 (m, 2H), 7.18 (d, J=8.0 Hz, 1H), 7.02 (m, 2H), 6.93 (d, J=8.2 Hz, 2H), 4.61 (s, 1H), 4.44 (m, 1H), 3.34 (m, 2H), 2.56 (m, 1H), 2.28 (s, 3H), 1.92 (m, 2H), 1.81 (m, 1H), 1.68 (m, 1H).

Trans-8-bromo-6-(4-methylsulfanyl-phenyl)-2,3,6,10b-tetrahydro-1H-pyrrolo[2,1-a]isoquinolin-5-one. 849.4 mg (18%). MS (ESI): exact mass calcd for $C_{19}H_{18}BrNOS$, 387.0; m/z found, 388.0 [M+H]$^+$, 390.0 [M+H]$^+$. $^1$H NMR (500 MHz, acetone-d$_6$): 7.36 (m, 1H), 7.21 (m, 3H), 7.07 (m, 2H), 6.60 (m, 1H), 4.62 (m, 1H), 3.49 (m, 1H), 3.37 (m, 1H), 2.66 (m, 1H), 2.44 (s, 3H), 1.97 (m, 4H).

Step 5. Cis- and Trans-8-bromo-6-(4-methylsulfanyl-phenyl)-1,2,3,5,6,10b-hexahydro-pyrrolo[2,1-a]isoquinoline.

To a 0° C. solution of BH$_3$.THF (1 M in THF, 2.5 equiv.) was added a solution of cis-amino-ketone (Step 4, 3.45 mmol, 1 equiv.) in THF (2 M) and the resulting solution was heated at reflux for 1 h. The mixture was cooled to room temperature, quenched with water, and acidified with 12 N HCl. The THF was removed in vacuo and the aqueous mixture was heated at reflux for 15 min. The reaction mixture was again cooled to room temperature, made basic with 3 N NaOH, and extracted with CH$_2$Cl$_2$. The organic extract was washed with brine, dried (MgSO$_4$), and concentrated to give the crude products. A small portion of the crude product was purified by Gilson to give analytically pure products. The bulk of the material was carried forward without purification.

Cis-8-bromo-6-(4-methylsulfanyl-phenyl)-1,2,3,5,6,10b-hexahydro-pyrrolo[2,1-a]isoquinoline. 1.21 g (94%) as the TFA salt. MS (ESI): exact mass calcd for $C_{19}H_{20}BrNS$, 373.1; m/z found, 374.0 [M+H]$^+$, 376.0 [M+H]$^+$. $^1$H NMR (500 MHz, MeOH-d$_4$): 7.54 (d, J=8.0 Hz, 1H), 7.28 (m, 3H), 7.17 (br s, 1H), 7.09 (br s, 2H), 4.56 (br s, 1H), 3.70 (br m, 3H), 3.43 (br s, 1H), 2.76 (br s, 1H), 2.49 (s, 3H), 2.16 (br s, 3H).

Trans-8-bromo-6-(4-methylsulfanyl-phenyl)-1,2,3,5,6,10b-hexahydro-pyrrolo[2,1-a]isoquinoline. Prepared as described for the cis isomer, on a 0.856 mmol scale, to give 119.5 mg (37%) of the desired product as the TFA salt. MS (ESI): exact mass calcd for $C_{19}H_{20}BrNS$, 373.1; m/z found, 374.0 [M+H]$^+$, 376.0 [M+H]$^+$.

Step 6. Prepared on the cis-isomer from Step 5, as described in Example 33, on a 0.267 mmol scale. After the reaction was complete, the reaction mixture was diluted with diethyl ether, washed with water (×2), and filtered through a pad of diatomaceous earth. The filtrate was dried (Na$_2$CO$_3$) and concentrated to provide the crude product. Purification by reverse-phase HPLC afforded 22.1 mg (12%) of the desired product as the TFA salt.

97A: Cis-6-(4-methylsulfanyl-phenyl)-8-(4-piperidin-1-yl-but-1-ynyl)-1,2,3,5,6,10b-hexahydro-pyrrolo[2,1-a]isoquinoline. MS (ESI): exact mass calcd for $C_{28}H_{34}N_2S$, 430.2; m/z found, 431.2 [M+H]$^+$. $^1$H NMR (500 MHz, MeOH-d$_4$): 7.40 (d, J=7.8 Hz, 1H), 7.33 (d, J=8.1 Hz, 1H), 7.27 (d, J=8.4 Hz, 2H), 7.10 (br s, 2H), 7.02 (br s, 1H), 4.54 (br s, 1H), 3.74 (br s, 3H), 3.56 (d, J=12.1 Hz, 2H), 3.30 (m, 3H), 2.96 (m, 2H), 2.90 (m, 2H), 2.78 (br s, 1H), 2.47 (s, 3H), 2.15 (br s, 3H), 1.92 (d, J=14.6 Hz, 2H), 1.80 (m, 3H), 1.49 (m, 1H).

97B: Trans-6-(4-methylsulfanyl-phenyl)-8-(4-piperidin-1-yl-but-1-ynyl)-1,2,3,5,6,10b-hexahydro-pyrrolo[2,1-a]isoquinoline. Prepared as described for the cis-isomer above, on a 0.0751 mmol scale, to give 34.4 mg (66%) of the desired product as the TFA salt. MS (ESI): exact mass calcd for $C_{28}H_{34}N_2S$, 430.2; m/z found, 431.2 [M+H]$^+$. $^1$H NMR (400 MHz, MeOH-d$_4$): 7.33 (d, J=8.1 Hz, 1H), 7.29 (m, 3H), 7.17 (d, J=8.2 Hz, 2H), 6.79 (s, 1H), 4.36 (m, 1H), 3.86 (m, 1H), 3.44 (m, 5H), 3.26 (m, 3H), 2.90 (m, 5H), 2.47 (s, 3H), 2.25 (m, 3H), 1.87 (d, J=14.6 Hz, 2H), 1.68 (m, 3H), 1.44 (m, 1H).

Example 98-(A-B)

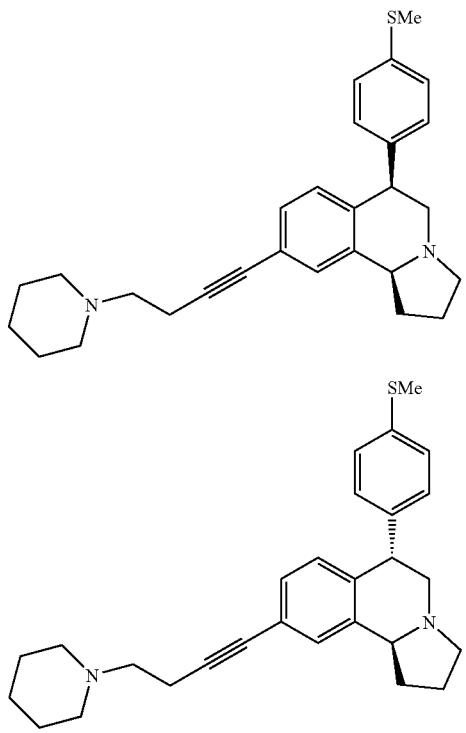

98A: Cis-6-(4-methylsulfanyl-phenyl)-9-(4-piperidin-1-yl-but-1-ynyl)-1,2,3,5,6,10b-hexahydro-pyrrolo[2,1-a]isoquinoline 98B: Trans-6-(4-methylsulfanyl-phenyl)-9-(4-piperidin-1-yl-but-1-ynyl)-1,2,3,5,6,10b-hexahydro-pyrrolo[2,1-a]isoquinoline Step 1. 1-[2-(3-Bromo-phenyl)-pyrrolidin-1-yl]-2-hydroxy-2-(4-methylsulfanyl-phenyl)-ethanone. A mixture of 2-(3-bromo-phenyl)-pyrrolidine (1.01 mmol, 1.0 equiv.), hydroxy-(4-methylsulfanyl-phenyl)-acetic acid (1.05 equiv.), O-benzotriazol-1-yl-N,N,N',N'-tetramethyluronium hexafluorophosphate (HATU, 1.2 equiv.), and Hunig's base (1.5 equiv.) in $CH_2Cl_2$ (0.2 M) was stirred at room temperature overnight under nitrogen. The reaction mixture was filtered to remove a white precipitate and the filtrate was washed with 1 N HCl, water, 1 N NaOH, water, and brine, dried ($MgSO_4$), and concentrated to give the crude product as a mixture of diastereomers. The crude product was purified by normal phase column chromatography (EtOAc/hexanes) to give 220 mg (56%) of the desired product as a mixture of diastereomers. MS (ESI): exact mass calcd for $C_{19}H_{20}BrNO_2S$, 405.0; m/z found, 406.0, 408.0 [M+H]$^+$.

Step 2. Prepared as described in Example 1, Step 7, on a 1.23 mmol scale. Purification by column chromatography (EtOAc/Hexanes) gave a 75% combined yield of two diastereomers, which were separated by reverse phase HPLC.

Cis-9-bromo-6-(4-methylsulfanyl-phenyl)-2,3,6,10b-tetrahydro-1H-pyrrolo[2,1-a]isoquinolin-5-one. 140 mg (29%) as the TFA salt. MS (ESI): exact mass calcd for $C_{19}H_{18}BrNOS$, 387.0; m/z found, 388.0, 390.0 [M+H]$^+$. $^1$H NMR (500 MHz, MeOH-d$_4$): 7.48 (m, 1H), 7.30 (m, 3H), 7.11 (d, J=8.3 Hz, 2H), 6.47 (m, 1H), 4.76 (m, 1H), 4.73 (m, 1H), 3.68 (m, 1H), 3.51 (m, 1H), 2.77 (m, 1H), 2.49 (s, 3H), 2.20 (m, 1H), 2.12 (m, 1H), 2.10 (m, 1H).

Trans-9-bromo-6-(4-methylsulfanyl-phenyl)-2,3,6,10b-tetrahydro-1H-pyrrolo[2,1-a]isoquinolin-5-one. 220 mg (46%) as the TFA. MS (ESI): exact mass calcd for $C_{19}H_{18}BrNOS$, 387.0; m/z found, 387.9, 390.0 [M+H]$^+$. $^1$H NMR (500 MHz, MeOH-d$_4$): 7.54 (s, 1H), 7.50 (m, 1H), 7.21 (d, J=8.1 Hz, 1H), 7.17 (d, J=8.5 Hz, 2H), 7.02 (d, J=8.3 Hz, 2H), 4.79 (s, 1H), 4.63 (m, 1H), 3.55 (m, 2H), 2.71 (m, 1H), 2.41 (s, 3H), 2.12 (m, 1H), 1.99 (m, 1H), 1.86 (m, 1H).

Step 3. Performed as described in Example 97, Step 5, on a 7.7 mmol scale, to give a 78% combined yield of a 1:1 mixture of diastereomers. MS (ESI): exact mass calcd for $C_{19}H_{20}BrNS$, 374.3; m/z found, 374.0, 376.0 [M+H]$^+$. The cis diastereomer was isolated by column chromatography and an analytical sample further purified by reverse phase HPLC.

Cis-9-bromo-6-(4-methylsulfanyl-phenyl)-1,2,3,5,6,10b-hexahydro-pyrrolo[2,1-a]isoquinoline. 1.13 g (39%) as the TFA salt. MS (ESI): exact mass calcd for $C_{19}H_{20}BrNS$, 373.1; m/z found, 374.0, 376.0 [M+H]$^+$. $^1$H NMR (500 MHz, acetone-d$_6$): 7.60 (m, 1H), 7.40 (m, 1H), 7.31 (d, J=8.5 Hz, 2H), 7.23 (d, J=6.6 Hz, 2H), 7.98 (m, 1H), 4.59 (m, 1H), 3.96 (m, 1H), 3.71 (m, 2H), 3.50 (m, 1H), 3.41 (m, 1H), 2.95 (m, 1H), 2.49 (s, 3H), 2.37 (m, 2H), 2.28 (m, 1H).

Step 4. Prepared as described in Example 97, Step 6, on a 1.47 mmol scale, to give a 15% combined yield of a mixture of diastereomers. The diastereomers were isolated by reverse-phase HPLC.

98A: Cis-6-(4-methylsulfanyl-phenyl)-9-(4-piperidin-1-yl-but-1-ynyl)-1,2,3,5,6,10b-hexahydro-pyrrolo[2,1-a]isoquinoline. 45.0 mg (5%) as the TFA salt. MS (ESI): exact mass calcd for $C_{28}H_{34}N_2S$, 430.2; m/z found, 431.2 [M+H]$^+$. $^1$H NMR (500 MHz, acetone-d$_6$): 7.44 (s, 1H), 7.31 (d, J=8.4 Hz, 2H), 7.24 (d, J=8.2 Hz, 2H), 6.75 (d, J=8.1 Hz, 1H), 4.95 (m, 1H), 4.63 (m, 1H), 3.94 (m, 2H), 3.70 (m, 3H), 3.50 (m, 1H), 3.40 (m, 3H), 3.06 (m, 4H), 2.91 (m, 1H), 2.51 (s, 3H), 2.35 (m, 2H), 2.27 (m, 1H), 1.90 (m, 4H), 1.79 (m, 1H), 1.52 (m, 1H).

98B: Trans-6-(4-methylsulfanyl-phenyl)-9-(4-piperidin-1-yl-but-1-ynyl)-1,2,3,5,6,10b-hexahydro-pyrrolo[2,1-a]isoquinoline. 103 mg (11%) as the TFA salt. MS (ESI): exact mass calcd for $C_{28}H_{34}N_2S$, 430.2; m/z found, 431.2 [M+H]$^+$. $^1$H NMR (500 MHz, acetone-d$_6$): 7.47 (br s, 1H), 7.30 (m, 3H), 7.21 (d, J=8.4 Hz, 2H), 6.88 (d, J=8.1 Hz, 1H), 5.13 (br s, 1H), 4.67 (br s, 1H), 3.70 (m, 5H), 3.43 (t, J=7.5 Hz, 2H), 3.07 (m, 4H), 2.79 (br s, 1H), 2.49 (s, 3H), 2.18 (m, 3H), 1.90 (m, H), 1.82 (m, 1H), 1.52 (m, 1H).

Biological Method 1. In Vitro Screening

H$_3$ Receptor Binding

Binding of compounds to the cloned human H$_3$ receptor, stably expressed in SK-N-MC cells, was performed (Lovenberg, T. W. et al. *J. Pharmacol. Exp. Ther.* 2000, 293, 771-778). Briefly, cell pellets from SK-N-MC cells expressing the human H$_3$ receptor were homogenized in 50 mM Tris-HCl/5 mM EDTA and re-centrifuged at 30,000 g for 30 min. Pellets were re-homogenized in 50 mM Tris/5 mM EDTA (pH 7.4). Membranes were incubated with 0.8 nM N-[$^3$H]-α-methylhistamine plus/minus test compounds for 60 min at 25° C. and harvested by rapid filtration over GF/C glass fiber filters (pretreated with 0.3% polyethylenimine) followed by four washes with ice-cold buffer. Nonspecific binding was defined in the presence of 10 μM histamine. IC$_{50}$ values were determined by a single site curve-fitting program (GraphPad, San Diego, Calif.) and converted to K$_i$ values based on a N-[$^3$H]-α-methylhistamine K$_d$ of 800 pM and a ligand concentration of 800 pM (Cheng & Prusoff, *Biochem. Pharmacol.* 1973, 22, 3099-3108). Data for compounds testing in this assay are presented in Table 1.

Rat Brain SERT

A rat brain without cerebellum (Zivic Laboratories, Inc.—Pittsburgh, Pa.) was homogenized in a 52.6 mM Tris pH 8/126.4 mM NaCl/5.26 mM KCl mixture and centrifuged at 1,000 rpm for 5 min. The supernatant was removed and re-centrifuged at 15,000 rpm for 30 min. Pellets were re-homogenized in a 52.6 mM Tris pH8/126.4 mM NaCl/5.26 mM KCl mixture. Membranes were incubated with 0.6 nM [$^3$H]-Citalopram plus/minus test compounds for 60 min at 25° C. and harvested by rapid filtration over GF/C glass fiber filters (pre-treated with 0.3% polyethylenimine) followed by four washes with ice-cold buffer. Nonspecific binding was defined in the presence of 100 μM fluoxetine. $IC_{50}$ values were determined by a single site curve-fitting program (GraphPad, San Diego, Calif.) and converted to $K_i$ values based on a [$^3$H]-Citalopram $K_d$ of 0.6 nM and a ligand concentration of 0.6 nM. Data for compounds tested in this assay are presented in Table 1.

TABLE 1

| EX | Rat SERT $K_i$ (nM) | Human $H_3$ $K_i$ (nM) | EX | Rat SERT $K_i$ (nM) | Human $H_3$ $K_i$ (nM) |
|---|---|---|---|---|---|
| 1A | 2 | 0.9 | 24B | 36 | 0.3 |
| 1B | 138 | 0.2 | 25 | 3 | 0.8 |
| 1C | 4000 | 68 | 26 | 2 | 0.8 |
| 2A | 5 | 1 | 27A | 20 | 1 |
| 2B | 544 | 31 | 27B | 26 | 0.3 |
| 2C | 4000 | 29 | 28 | 4 | 0.4 |
| 3 | 3 | 0.5 | 29 | 2 | 0.9 |
| 4A | 15 | 1 | 30 | 3 | 2 |
| 4B | 151 | 1 | 31 | 163 | 12 |
| 4C | 471 | 98 | 32 | 20 | 1 |
| 4D | 154 | 1 | 33 | 33 | 7 |
| 5A | 3 | 2 | 34 | 9 | 2 |
| 5B | 37 | 1 | 35A | 15 | 4 |
| 5C | 3000 | 85 | 35B | 4 | 2 |
| 6A | 1 | 3 | 36 | 15 | 4 |
| 6B | 14 | 1 | 37 | 7 | 4 |
| 6C | 291 | 76 | 38 | 10 | 6 |
| 7A | 27 | 5 | 39A | 3 | 2 |
| 7B | 25 | 2 | 39B | 3 | 1 |
| 7C | 630 | 31 | 39C | 69 | 36 |
| 8A | 2 | 0.7 | 40 | 12 | 3 |
| 8B | 50 | 0.75 | 41A | 25 | 1 |
| 8C | 2 | 2 | 41B | 6 | 1 |
| 8D | 3 | 1 | 42 | 221 | 2 |
| 8E | 477 | 226 | 43 | 6000 | 30 |
| 8F | 4000 | 482 | 44 | 4000 | 1 |
| 9A | 9 | 2 | 45 | 6000 | 16 |
| 9B | 6000 | 1000 | 46 | 14 | 4 |
| 10A | 5 | 2 | 47 | 9 | 3 |
| 10B | 37 | 2 | 48A | 7 | 6 |
| 10C | 2000 | 82 | 48B | 20 | 5 |
| 11A | 4 | 1 | 49 | 6 | 5 |
| 11B | 91 | 1 | 50A | 23 | 4 |
| 11C | 1000 | 136 | 50B | 363 | 181 |
| 12A | 11 | 2 | 51A | 130 | 3 |
| 12B | 52 | 1 | 51B | 161 | 5 |
| 12C | 2000 | 91 | 52 | 6 | 4 |
| 12D | 280 | 74 | 53 | 53 | 3 |
| 13A | 14 | 1 | 54 | 24 | 4 |
| 13B | 2000 | 129 | 55 | 39 | 2 |
| 14A | 4 | 2 | 56 | 2 | 3 |
| 14B | 67 | 1 | 57 | 3 | 3 |
| 14C | 3000 | 200 | 58 | 8 | 2 |
| 15 | 1 | 0.7 | 59 | 4 | 2 |
| 16 | 21 | 4 | 60 | 8 | 3 |
| 17 | 11 | 4 | 61 | 10 | 29 |
| 18 | 12 | 0.9 | 62 | 15 | 6 |
| 19 | 12 | 1 | 63 | 5 | 16 |
| 20 | 21 | 1 | 64 | 3 | 3 |
| 21 | 7 | 1 | 65 | 4 | 4 |
| 22 | 64 | 0.8 | 66A | 6 | 2 |
| 23 | 1 | 1 | 66B | 18 | 1 |
| 24A | 0.7 | 0.7 | 67 | 22 | 2 |
| 89 | 3 | 16 | 95 | 11 | 6 |
| 90 | 24 | 10 | 96A | 10 | 1 |
| 91 | 60 | 64 | 97A | 51 | 3 |
| 92 | 2.2 | 16 | 97B | 407 | 12 |
| 93 | 13 | 5 | 98A | 10 | 4 |
| 94 | 53 | 4 | 98B | 7 | 3 |

Human SERT

Homogenized HEK293 (Human Embryonic Kidney) membranes expressing the human SERT (Perkin-Elmer) were incubated with $^3$H-citalopram (SERT) at rt for 1 h in 50 mM Tris, 120 mM NaCl, 5 mM KCl (pH 7.4). Nonspecific binding was determined in the presence of 10 μM fluoxetine for the SERT. The membranes were washed and the radioactivity was counted as above. Calculations for $K_i$ at the SERT were based on a $K_d$ value for $^3$H-citalopram and a ligand concentration of 3.1 nM. Data for compounds testing in this assay are presented in Table 2.

TABLE 2

| EX | Human SERT $K_i$ (nM) | EX | Human SERT $K_i$ (nM) | EX | Human SERT $K_i$ (nM) |
|---|---|---|---|---|---|
| 1A | 4 | 15 | 3 | 29 | 2 |
| 2A | 6 | 16 | 112 | 30 | 2 |
| 3 | 8 | 17 | 7 | 31 | 28 |
| 4A | 4 | 18 | 13 | 32 | 11 |
| 5A | 4 | 19 | 5 | 34 | 3 |
| 6A | 4 | 20 | 43 | 35A | 7 |
| 7A | 12 | 21 | 5 | 37 | 0.8 |
| 8A | 2 | 22 | 220 | 38 | 7 |
| 8B | 128 | 23 | 2 | 39A | 4 |
| 8C | 1 | 24A | 1 | 40 | 18 |
| 9A | 58 | 25 | 18 | 41A | 59 |
| 10A | 2 | 26 | 6 | 46 | 9 |
| 11A | 0.6 | 27A | 15 | 47 | 5 |
| 12A | 8 | 27B | 112 | 66A | 6 |
| 13A | 21 | 28 | 5 | 67 | 9 |
| 14A | 3 | 94 | 111 | 96A | 9 |
| 92 | 4 | 95 | 13 | 97A | 2000 |
|  |  |  |  | 98A | 2 |

Cyclic AMP Accumulation

Sublines of SK-N-MC cells were created that expressed a reporter construct and the human $H_3$ receptor. The reporter gene (β-galactosidase) is under the control of multiple cyclic AMP responsive elements. In 96-well plates, histamine was added directly to the cell media followed 5 min later by an addition of forskolin (5 μM final concentration). When appropriate, antagonists were added 10 min prior to agonist addition. After a 6-h incubation at 37° C., the media was aspirated and the cells washed with 200 μL of phosphate-buffered saline followed by a second aspiration. Cells were lysed with 25 μL 0.1× assay buffer (10 mM Na-phosphate, pH 8, 0.2 mM $MgSO_4$, 0.01 mM $MnCl_2$) and incubated at rt for 10 min. Cells were then incubated for 10 min with 100 μL of 1× assay buffer containing 0.5% Triton and 40 mM β-mercaptoethanol. Color was developed using 25 μL of 1 mg/mL substrate solution (chlorophenolred β-D galactopyranoside; Roche Molecular Biochemicals, Indianapolis, Ind.). Color was quantitated on a microplate reader at absorbance 570 nM. The $pA_2$ values were calculated by Schild regression analysis of the $pEC_{50}$ values and are presented in Table 3.

TABLE 3

| EX | H₃ pA₂ | EX | H₃ pA₂ | EX | H₃ pA₂ |
|---|---|---|---|---|---|
| 1A | 9.7 | 10A | 9.8 | 23 | 9.7 |
| 1B | 9.6 | 10B | 9.6 | 24A | 9.9 |
| 2A | 9.4 | 11A | 9.5 | 24B | 10.0 |
| 2B | 8.8 | 11B | 9.3 | 25 | 10.0 |
| 3 | 10.1 | 12A | 8.9 | 26 | 10.1 |
| 4A | 9.9 | 12B | 9.2 | 32 | 9.5 |
| 4B | 9.8 | 14A | 9.0 | 33 | 8.1 |
| 5A | 8.6 | 14B | 9.1 | 34 | 9.0 |
| 6A | 8.2 | 15 | 9.9 | 35A | 8.4 |
| 7A | 8.2 | 16 | 8.9 | 35B | 8.5 |
| 7B | 8.2 | 17 | 8.2 | 36 | 8.0 |
| 8A | 8.8 | 18 | 9.3 | 37 | 8.8 |
| 8B | 9.2 | 19 | 9.4 | 41A | 9.1 |
| 8C | 8.8 | 20 | 9.0 | 41B | 9.1 |
| 8D | 8.8 | 21 | 9.1 | 67 | 9.3 |
| 9A | 9.5 | 22 | 9.2 | 97B | 8.0 |
| 91 | 8.5 | 96A | 8.2 | 98A | 8.0 |
| 92 | 7.8 | 97A | 8.8 | 98B | 8.6 |

Biological Method 2. In Vivo Screening.

Animal experiments were performed to illustrate that 6-(4-methoxy-phenyl)-9-(3-piperidin-1-yl-propoxy)-1,2,3,5,6,10b-hexahydro-pyrrolo[2,1-a]isoquinoline (Example 8A) is both an H₃ receptor antagonist and a blocker of serotonin reuptake in vivo.

A. Imetit-Induced Drinking Model

Histamine H₃ receptors play an important role in the regulation of drinking behavior. For instance, it is known that administration of H₃ antagonists can decrease the drinking response to histamine by about 40% (Kraly, F. S. et al. Pharmacol., Biochem. Behav. 1996, 53, 347-354). Indeed, it is possible to induce drinking behavior in rodents by administering a selective agonist for the H₃ receptor, such as R-α-methylhistamine (Fox, G. B. et al. Pharmacol., Biochem. Behav. 2002b, 72, 741-750) or imetit.

The imetit-induced drinking model was used to provide evidence of in vivo antagonism of an H₃ mediated behavior. In this model, animals were introduced into a cage containing a fully-automated water drinking monitoring system. The animals were injected i.p. with Example 8A. After 24 h, 1 mg/kg imetit, which was shown during preliminary experiments to induce a robust drinking response, was administered i.p., and drinking was measured for a period of 60 min (imetit-induced drinking). Example 8A inhibited imetit-induced drinking with a statistically significant effect at 10 mg/kg i.p. Data are presented in Table 4. Results are shown as averages ±s.e.m. of n=8-13 animals.

TABLE 4

| Treatment | Water Consumed (mL) | n |
|---|---|---|
| Vehicle (saline) | 1.05 ± 0.34 | 10 |
| Imetit (1 mg/kg) | 2.53 ± 0.60 | 13 |
| Example 8A (1 mg/kg) + Imetit (1 mg/kg) | 1.99 ± 0.68 | 10 |
| Example 8A (3 mg/kg) + Imetit (1 mg/kg) | 1.65 ± 0.51 | 8 |
| Example 8A (10 mg/kg) + Imetit (1 mg/kg) | *0.25 ± 0.15 | 10 |

*p = 0.022 compared to imetit-treated animals

B. 5-HTP Potentiation Test

The co-administration of the 5-HT precursor 5-HTP (5-hydroxytryptophan) and a decarboxylase inhibitor, carbidopa (Darmani, N. A. and S. L. Reeves. Pharmacol., Biochem. Behav. 1996, 55, 1-10) is known to induce a mild serotoninergic syndrome, mainly characterized by head twitches. In the presence of a compound blocking the synaptic reuptake of 5-HT, the syndrome will be potentiated.

Mice were injected with Example 8A (3 mg/kg and 10 mg/kg). Group 1 (1 h): 1) at t=0, mice were injected with carbidopa (10 mg/kg) and Example 8A (3 mg/kg or 10 mg/kg); 2) at t=20 min, mice were injected with 5-HTP (40 mg/kg); 3) at t=55 min, head twitch frequency was measured for a 5 min interval. Group 2 (24 h): 1) at t=0, mice were injected with Example 8A (3 mg/kg or 10 mg/kg); 2) at t=23 h, mice were injected with carbidopa (10 mg/kg); 3) at t=23 h, 20 min, mice were injected with 5-HTP (40 mg/kg); 4) at t=24 h, 25 min, head twitch frequency was measured for a 5 min interval. The data are presented in Table 5 as an average ±s.e.m. The n value is given between brackets.

TABLE 5

|  | Group 1 (1 h) | Group 2 (24 h) |
|---|---|---|
| Vehicle | 3.5 ± 0.6 (5) | 6.2 ± 1.2 (4) |
| 3 mg/kg Example 8A | 6.0 ± 1.2 (3) | 24.0 ± 2.1 (4) |
| 10 mg/kg Example 8A | 2.0 ± 0.6 (3) | 41.3 ± 5.2 (3) |

C. Microdialysis

Microdialysis is used to measure the concentration of small biological molecules in the extracellular fluid of the brain (Parent, M. et al. Methods 2001, 23, 11-20). A small probe, containing a fine microdialysis membrane at its tip, is introduced into the brain of an animal. A buffered solution is infused through the catheter. Small molecules, such as monoamine neurotransmitters, diffuse through the pores in the microdialysis membrane and are captured in the solution. The samples are then analyzed by analytical techniques to quantitate the amount of neurotransmitter in the brain extracellular fluid. This technique has been used extensively to measure the effects of SERT inhibitors on levels of extracellular serotonin.

Microdialysis was used to measure the levels of serotonin and dopamine in the brain of freely moving rats after subcutaneous injection of Example 8A. FIG. 1 shows the results of microdialysis of dopamine (DA) and serotonin (5-HT) in the cortex of freely moving rats after subcutaneous injection of 1 mg/kg of Example 8A at t=0. As shown in FIG. 1, injection of Example 8A caused a slow, persistent increase in serotonin and dopamine levels. Results are represented as the average ±s.d. of n=2-4 rats.

What is claimed is:

1. A compound of formula (I):

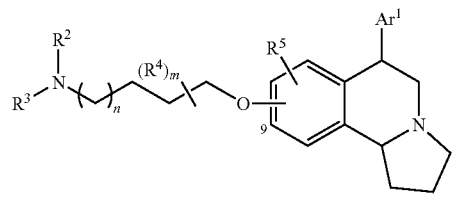

(I)

wherein n is 0 or 1;

m is 0;

$R^2$ and $R^3$ may be taken together with the nitrogen to which they are attached to form a 4-8 membered heterocyclic ring, said heterocyclic ring having 0 or 1 additional heteroatom members separated from the nitrogen of attachment by at least one carbon member and selected from >O, >S(O)$_{0-2}$, and >NH, having 0 or 1 double bonds, having 0, 1, or 2 carbon members separated from the nitrogen of attachment by at least one carbon member which is a carbonyl, optionally benzo or pyrido fused, optionally having one carbon member that forms a bridge, and having 0-1 substituents R$^f$, R$^f$ is selected from the group consisting of —C$_{1-6}$alkyl halo, and —C$_{1-6}$alkylOH;

R$^5$ is selected from the group consisting of —H, —C$_{1-6}$alkyl, —OH, —OC$_{1-6}$alkyl, —SC$_{1-6}$alkyl, and halo;

Ar$^1$ is a heteroaryl ring selected from the group consisting of:
- d) a monocyclic aromatic hydrocarbon group having five ring atoms, having a carbon atom which is the point of attachment, having one carbon atom replaced by >O, >S, >NH, or >N(C$_{1-4}$alkyl), having up to one additional carbon atom optionally replaced by —N=, optionally mono- or di-substituted with R$^t$
  R$^t$ is a substituent independently selected from the group consisting of: —OH, —C$_{1-6}$alkyl, —OC$_{1-6}$alkyl, phenyl, —CN, —NO$_2$, —N(R$^u$)R$^v$ (wherein R$^u$ and R$^v$ are independently —H or —C$_{1-6}$alkyl), —C(O)N(R$^u$)R$^v$, —N(R$^u$)C(O)R$^v$, —N(R$^u$)SO$_2$C$_{1-6}$alkyl, —C(O)C$_{1-6}$alkyl, —S(O)$_{0-2}$-C$_{1-6}$alkyl, —SO$_2$N(R$^u$)R$^v$, —SCF$_3$, halo, —CF$_3$, —OCF$_3$, —OCHF$_2$, —COOH, and —COOC$_{1-6}$alkyl;
- e) a monocyclic aromatic hydrocarbon group having six ring atoms, having a carbon atom which is the point of attachment, having one or two carbon atoms replaced by —N=, optionally mono- or di-substituted with R$^t$;

and enantiomers, diastereomers thereof, and pharmaceutically acceptable salts, esters and amides thereof.

2. The compound of claim 1 wherein n is 0 or 1.

3. The compound of claim 1 wherein R$^2$ and R$^3$, optionally substituted, are taken together with the nitrogen to which they are attached to form a ring selected from the group consisting of azetidinyl, pyrrolidinyl, piperidinyl, morpholinyl, thiomorpholinyl, piperazinyl, homopiperidinyl, 1,3-dihydro-isoindol-2-yl, 5,6-dihydro-4H-pyrimidin-1-yl, and 1,1-dioxo-1λ$^6$-thiomorpholin-4-yl.

4. The compound of claim 1 wherein R$^2$ and R$^3$ are taken together with the nitrogen to which they are attached to form a 4-8 membered heterocyclic ring, said heterocyclic ring selected from piperidine, pyrrolidine, and morpholine, said ring substituted with 1 substituent R$^f$.

5. The compound of claim 1 wherein R$^f$ is selected from the group consisting of methyl, ethyl, isopropyl, butyl, hexyl, bromo, chloro, fluoro, iodo, hydroxymethyl, and hydroxyethyl.

6. The compound of claim 1 wherein R$^f$ is selected from the group consisting of methyl, fluoro, and hydroxymethyl.

7. The compound of claim 1 wherein R$^2$ and R$^3$ are taken together with the nitrogen to which they are attached to form azetidinyl, 2-methylpyrrolidinyl, 2-hydroxymethylpyrrolidinyl, piperidinyl, 4-fluoropiperidinyl, 1,4-dioxa-8-aza-spiro[4.5]dec-8-yl, morpholinyl, 2-hydroxymethylpiperidinyl, 3-hydroxymethylpiperidinyl, 4-hydroxymethylpiperidinyl, 4-hydroxyethylpiperidinyl, 3-methylmorpholin-4-yl, 3-hydroxymethylmorpholin-4-yl, 2-hydroxymethylmorpholin-4-yl, 1,3-dihydro-isoindol-2-yl, 5,6-dihydro-4H-pyrimidin-1-yl, 1,1-dioxo-1λ$^6$-thiomorpholin-4-yl, or 2-methylmorpholin-4-yl.

8. The compound of claim 1 wherein R$^2$ and R$^3$ are taken together with the nitrogen to which they are attached to form 4-fluoropiperidinyl, morpholinyl, or 3-methylmorpholin-4-yl.

9. The compound of claim 1 wherein R$^5$ is hydrogen, methyl, ethyl, isopropyl, hexyl, hydroxyl, methoxy, ethoxy, isopropoxy, methylsulfanyl, bromo, chloro, fluoro, or iodo.

10. The compound of claim 1 wherein R$^5$ is hydrogen.

11. The compound of claim 1 wherein Ar$^1$, optionally substituted, is selected from the group consisting of:
- d) thiophenyl, imidazolyl, and
- e) pyridinyl, pyridinyl-N-oxide, or pyrazinyl.

12. The compound of claim 1 wherein Ar$^1$, optionally substituted, is selected from the group consisting of pyridyl, pyrazinyl, and thiophenyl.

13. The compound of claim 1 wherein Ar$^1$ is selected from the group consisting of thiophen-2-yl, thiophen-3-yl, 2-pyridinyl, 3-pyridinyl, 4-pyridinyl, 2-chloro-5-pyridinyl, 2-dimethylamino-5-pyridinyl, 2-methoxy-5-pyridinyl, 2-thiomethyl-5-pyridinyl, 2-hydroxy-5-pyridinyl, and pyrazin 2-yl.

14. The compound of claim 1 wherein Ar$^1$ is cis to the pyrrolidine ring of formula (I).

15. The compound of claim 1 wherein the R$^3$R$^2$N-containing ether substituent of formula (I) is at the 9-position.

16. A compound selected from the group consisting of:
Cis-9-(3-Piperidin-1-yl-propoxy)-6-thiophen-2-yl-1,2,3,5,6,10b-hexahydro-pyrrolo[2,1-a]isoquinoline;
Cis-9-(3-Piperidin-1-yl-propoxy)-6-thiophen-3-yl-1,2,3,5,6,10b-hexahydro-pyrrolo[2,1-a]isoquinoline;
Trans-9-(3-piperidin-1-yl-propoxy)-6-thiophen-3-yl-1,2,3,5,6,10b-hexahydro-pyrrolo[2,1-a]isoquinoline;
Cis-9-(3-Piperidin-1-yl-propoxy)-6-pyridin-2-yl-1,2,3,5,6,10b-hexahydro-pyrrolo[2,1-a]isoquinoline;
Cis-9-(3-Piperidin-1-yl-propoxy)-6-pyridin-3-yl-1,2,3,5,6,10b-hexahydro-pyrrolo[2,1-a]isoquinoline;
Cis-9-(3-Piperidin-1-yl-propoxy)-6-pyridin-4-yl-1,2,3,5,6,10b-hexahydro-pyrrolo[2,1-a]isoquinoline;
Trans-9-(3-Piperidin-1-yl-propoxy)-6-pyridin-4-yl-1,2,3,5,6,10b-hexahydro-pyrrolo[2,1-a]isoquinoline;
Cis-9-(3-Morpholin-4-yl-propoxy)-6-pyrazin-2-yl-1,2,3,5,6,10b-hexahydro-pyrrolo[2,1-a]isoquinoline;
Trans-9-(3-Morpholin-4-yl-propoxy)-6-pyrazin-2-yl-1,2,3,5,6,10b-hexahydro-pyrrolo[2,1-a]isoquinoline;
Cis-5-[9-(3-Morpholin-4-yl-propoxy)-1,2,3,5,6,10b-hexahydro-pyrrolo[2,1-a]isoquinolin-6-yl]-pyridin-2-ol;
Trans-5-[9-(3-Morpholin-4-yl-propoxy)-1,2,3,5,6,10b-hexahydro-pyrrolo[2,1-a]isoquinolin-6-yl]-pyridin-2-ol;
Cis-9-(3-Morpholin-4-yl-propoxy)-6-thiophen-3-yl-1,2,3,5,6,10b-hexahydro-pyrrolo[2,1-a]isoquinoline;
Cis-9-(3-Morpholin-4-yl-propoxy)-6-thiophen-2-yl-1,2,3,5,6,10b-hexahydro-pyrrolo[2,1-a]isoquinoline;
Cis-9-(3-Morpholin-4-yl-propoxy)-6-pyridin-3-yl-1,2,3,5,6,10b-hexahydro-pyrrolo[2,1-a]isoquinoline;
Cis-9-(3-Morpholin-4-yl-propoxy)-6-pyridin-2-yl-1,2,3,5,6,10b-hexahydro-pyrrolo[2,1-a]isoquinoline;
6-(6-Chloro-pyridin-3-yl)-9-(3-morpholin-4-yl-propoxy)-1,2,3,5,6,10b-hexahydro-pyrrolo[2,1-a]isoquinoline;
Dimethyl-{5-[9-(3-morpholin-4-yl-propoxy)-1,2,3,5,6,10b-hexahydro-pyrrolo[2,1-a]isoquinolin-6-yl]-pyridin-2-yl}-amine;
6-(6-Methoxy-pyridin-3-yl)-9-(3-morpholin-4-yl-propoxy)-1,2,3,5,6,10b-hexahydro-pyrrolo[2,1-a]isoquinoline;

6-(1H-Imidazol-2-yl)-9-(3-morpholin-4-yl-propoxy)-1,2,3,5,6,10b-hexahydro-pyrrolo[2,1-a]isoquinoline;

6-(1-Methyl-1H-imidazol-2-yl)-9-(3-morpholin-4-yl-propoxy)-1,2,3,5,6,10b-hexahydro-pyrrolo[2,1-a]isoquinoline;

6-(3H-Imidazol-4-yl)-9-(3-morpholin-4-yl-propoxy)-1,2,3,5,6,10b-hexahydro-pyrrolo[2,1-a]isoquinoline; and 6-(3-Methyl-3H-imidazol-4-yl)-9-(3-morpholin-4-yl-propoxy)-1,2,3,5,6,10b-hexahydro-pyrrolo[2,1-a]isoquinoline.

17. A pharmaceutical composition comprising a pharmaceutically acceptable carrier and at least one compound of formula (I).

* * * * *